US007667005B2

(12) United States Patent
Nabeshima et al.

(10) Patent No.: US 7,667,005 B2
(45) Date of Patent: Feb. 23, 2010

(54) POLYPEPTIDE, NOVEL DNA AND NOVEL ANTIBODY

(75) Inventors: Youichi Nabeshima, Kyoto (JP);
Makoto Kuroo, Dallas, TX (US);
Susumu Sekine, Kanagawa (JP);
Akihiro Iida, Tokyo (JP)

(73) Assignee: Shirankai Kyoto University Faculty Of Medicine Alumni Association Inc., Kyoto-fu (JP)

( * ) Notice: Subject to any disclaimer, the term of this patent is extended or adjusted under 35 U.S.C. 154(b) by 0 days.

(21) Appl. No.: 12/046,718

(22) Filed: Mar. 12, 2008

(65) Prior Publication Data

US 2008/0227158 A1     Sep. 18, 2008

Related U.S. Application Data

(60) Division of application No. 10/411,253, filed on Apr. 11, 2003, which is a division of application No. 09/344,510, filed on Jun. 25, 1999, now Pat. No. 6,579,850, which is a continuation-in-part of application No. PCT/JP97/04585, filed on Dec. 12, 1997.

(30) Foreign Application Priority Data

Dec. 26, 1996   (JP)   ............................. P. 8-347871
Jul. 31, 1997    (JP)   ............................. P. 9-205815

(51) Int. Cl.
*C07K 16/28* (2006.01)
(52) U.S. Cl. .................................. 530/388.1; 530/389.1
(58) Field of Classification Search ........................ None
See application file for complete search history.

(56) References Cited

U.S. PATENT DOCUMENTS 5,302,706 A    4/1994   Smith
5,783,680 A    7/1998   Brunner et al.

FOREIGN PATENT DOCUMENTS

JP    5-506148    9/1993
JP    7-502651    3/1995
WO    91/15226    10/1991

OTHER PUBLICATIONS

Nabeshima Y. Toward a better understanding of Klotho. Sci Aging Knowledge Environ. May 3, 2006;2006(8):pe11, 6 pages [online], [retrieved on Feb. 14, 2009]. Retrieved from the Internet:<URL:http://sageke.sciencemag.org/cgi/content/full/2006/8/pe11>.*
Nature, vol. 390 (1997) 45-51.
Science, vol. 272 (1996) 258-62.
Science, vol. 269 (1995) 1236-41.
Nature, vol. 366 (1993) 701-04.
Experimental Cell Research, vol. 199 (1992) 355-62.
Database Accession No. H28389 XP-002213894, Hillier, et al., "y152e03.r1 Soares Breast 3NbHBst *Homo sapiens* . . . " (1995).
Database Accession No. AAT27160 XP-002213952, Kakizuka, et al., "Human Machado-Joseph Disease Gene Probe" (1996).
Database Accession No. AAQ69624 XP-002213953, Andrews, et al., "Human bc1-2 proto-oncogene, target region".
Database Accession No. R63458 XP-002214179, Hillier, et al., "yi08a10.r1 Soares placenta Nb2HP *Homo sapiens* . . . " (1995).
Database Accession No. P09848 XP-002213895, Mantei, et al., "Lactase-phlorizin hydrolase precursor" (1989).
Database Accession No. AB005141 XP-002213896, Kuro-O, et al., "Mus musculus klotho mRNA, complete cds." (1997).
Database Accession No. AB005142 XP-002213897, Kuro-O, et al., "Homosapients klotho mRNA, complete cds." (1997).
Martin, et al., "Ageing: New mice for old Questions", Nature, vol. 390 (1997) 18-19.
Bowie, et al., "Deciphering the message in protein sequences: tolerance to amino acid substitutions", Science (1990), vol. 247 (4948) 1306-10.
Ngo, et al., "The Protein Folding Problem and Tertiary Structure . . . ", Merz and Le Grand (Eds) (1994), Springer Verlag, 433 and 492-95.
Roush W., "Fast-forward aging in a mutant mouse?", Science (1997), vol. 278 (5340) 1013.
Henikoff et al., "Gene Families: the taxonomy of protein paralogs and chimeras", Science (1997), vol. 278 (5338) 609-14.
Wu et al., "Naturalization of heparin activity by neutrophil lactoferrin", Blood (1995), vol. 85 (2) 421-8.
Tomasetto et al., "hSP, the domain-duplicated homolog of pS2 protein, . . . " EMBO J, vol. 9 (2) (1990) 407-14.
Playford et al., "Human Spasmolytic Polypeptide is a cytoprotective agent that stimulates cell migration", Gastroenterology, vol. 108, No. 1 (1995) 108-16.
Mian IS, "Sequence, Structural, Functional, and Phylogenetic Analyses of . . . ", Blood Cells Mol. Dis., vol. 24, No. 1 (1998) 83-100.
Sambrook, et al., "Molecular Cloning: A Laboratory", Cold Spring Harbor Lab. Press (1989) 9.50.

* cited by examiner

*Primary Examiner*—David S Romeo
(74) *Attorney, Agent, or Firm*—Fitzpatrick, Cella, Harper & Scinto

(57) ABSTRACT

The present invention relates to a polypeptide having an activity of suppressing aging; DNA encoding the polypeptide; a method for improving livestock, using the DNA; a recombinant DNA prepared by inserting the DNA into a vector; a transformant harboring the recombinant; a method for preparing the polypeptide of the present invention, using the transformant; an antibody which recognizes the polypeptide; a ligand for the polypeptide of the present invention; a compound inhibiting specific binding between the polypeptide and ligand of the present invention; a compound enhancing the expression of an aging-suppressing gene encoding the aging-suppressing polypeptide of the present invention; an oligonucleotide comprising a sequence of 10 to 50 nucleotides in the nucleotide sequence of the DNA; and a therapeutic agent for a syndrome resembling premature aging, a therapeutic agent for adult diseases or an aging-suppressing agent, using the same.

3 Claims, 40 Drawing Sheets

FIG. 2
Introduction Gene
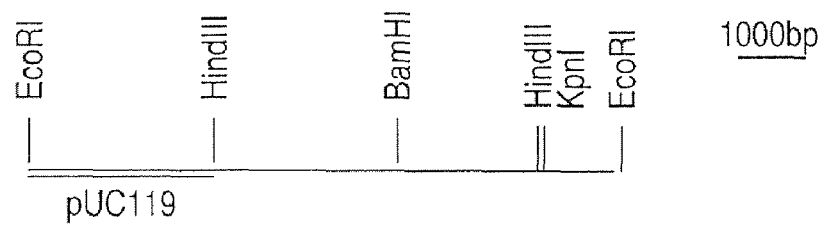
Plasmid 50
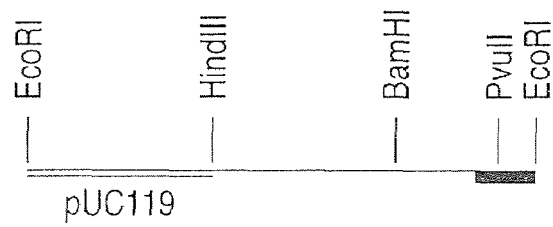
Plasmid E70
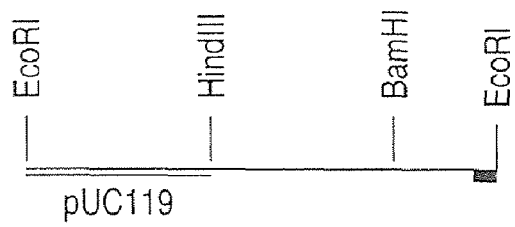
Plasmid K8
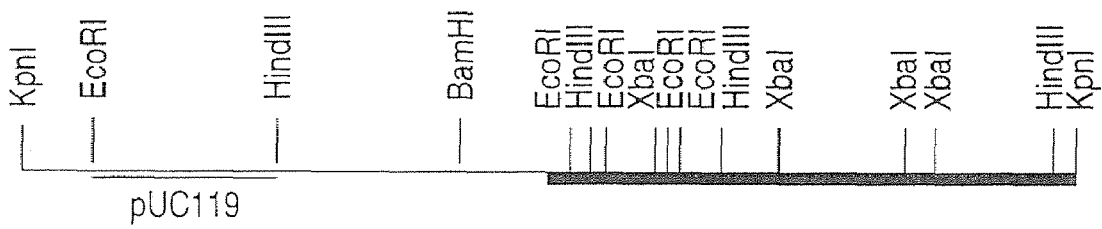

A: wild-type mouse - no administration
B: wild-type mouse - administration of virus
C: homozygote mouse showing a syndrome resembling premature aging - administration of virus
D: homozygote mouse showing a syndrome resembling premature aging - no administration

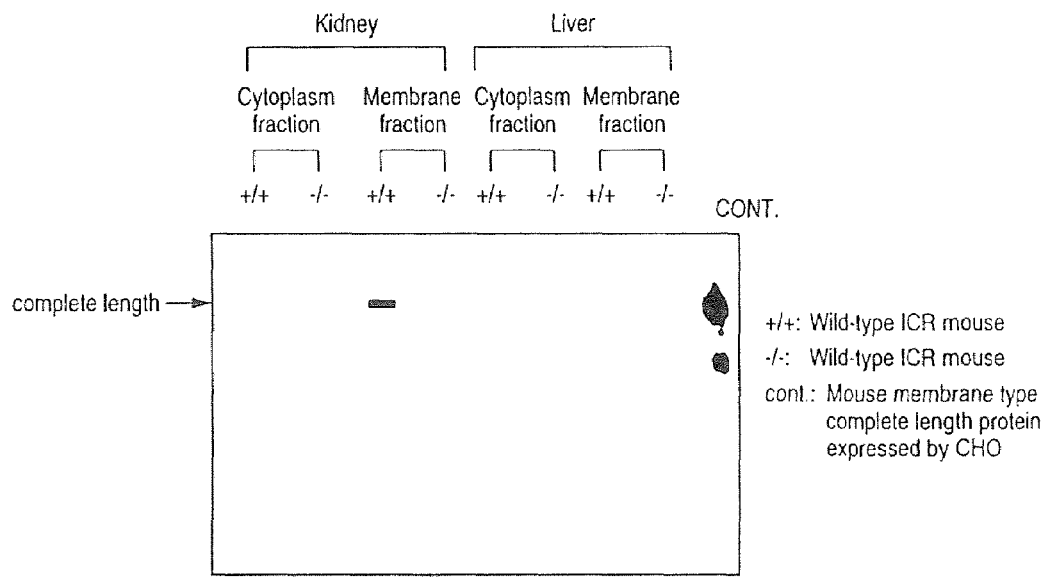
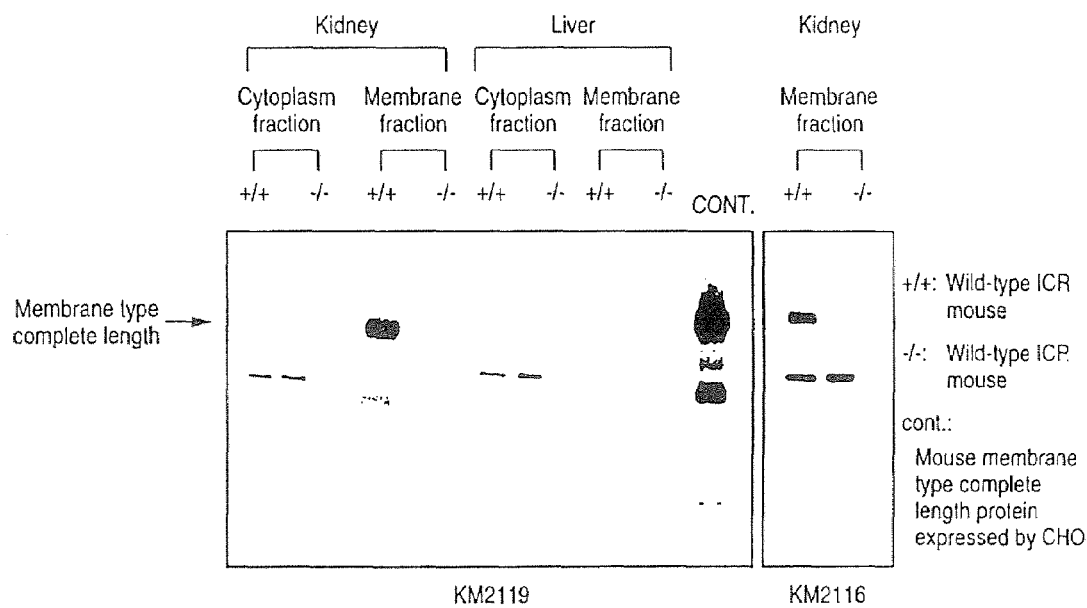

SEQUENCE LISTING (1) GENERAL INFORMATION:

(iii) NUMBER OF SEQUENCES: 38

(2) INFORMATION FOR SEQ ID NO: 1:

(i) SEQUENCE CHARACTERISTICS:
      (A) LENGTH: 1012
      (B) TYPE: amino acid
      (C) STRANDEDNESS: single
      (D) TOPOLOGY: linear (ii) MOLECULE TYPE: peptide (vi) ORIGINAL SOURCE:
      (A) ORGANISM: human (vii) IMMEDIATE SOURCE:
      (A) LIBRARY: kidney (xi) SEQUENCE DESCRIPTION: SEQ ID NO: 1:

```
Met Pro Ala Ser Ala Pro Pro Arg Arg Pro Arg Pro Pro Pro Ser
 1               5                  10                  15

Leu Ser Leu Leu Leu Val Leu Leu Gly Leu Gly Gly Arg Arg Leu Arg
                20                  25                  30

Ala Glu Pro Gly Asp Gly Ala Gln Thr Trp Ala Arg Phe Ser Arg Pro
            35                  40                  45

Pro Ala Pro Glu Ala Ala Gly Leu Phe Gln Gly Thr Phe Pro Asp Gly
        50                  55                  60

Phe Leu Trp Ala Val Gly Ser Ala Ala Tyr Gln Thr Glu Gly Gly Trp
65                  70                  75                  80

Gln Gln His Gly Lys Gly Ala Ser Ile Trp Asp Thr Phe Thr His His
                85                  90                  95

Pro Leu Ala Pro Pro Gly Asp Ser Arg Asn Ala Ser Leu Pro Leu Gly
            100                 105                 110

Ala Pro Ser Pro Leu Gln Pro Ala Thr Gly Asp Val Ala Ser Asp Ser
        115                 120                 125

Tyr Asn Asn Val Phe Arg Asp Thr Glu Ala Leu Arg Glu Leu Gly Val
    130                 135                 140

Thr His Tyr Arg Phe Ser Ile Ser Trp Ala Arg Val Leu Pro Asn Gly
145                 150                 155                 160

Ser Ala Gly Val Pro Asn Arg Glu Gly Leu Arg Tyr Tyr Arg Arg Leu
```

```
                    165                 170                 175
Leu Glu Arg Leu Arg Glu Leu Gly Val Gln Pro Val Thr Leu Tyr
                180                 185                 190

His Trp Asp Leu Pro Gln Arg Leu Gln Asp Ala Tyr Gly Gly Trp Ala
                195                 200                 205

Asn Arg Ala Leu Ala Asp His Phe Arg Asp Tyr Ala Glu Leu Cys Phe
            210                 215                 220

Arg His Phe Gly Gly Gln Val Lys Tyr Trp Ile Thr Ile Asp Asn Pro
225                 230                 235                 240

Tyr Val Val Ala Trp His Gly Tyr Ala Thr Gly Arg Leu Ala Pro Gly
                245                 250                 255

Ile Arg Gly Ser Pro Arg Leu Gly Tyr Leu Val Ala His Asn Leu Leu
                260                 265                 270

Leu Ala His Ala Lys Val Trp His Leu Tyr Asn Thr Ser Phe Arg Pro
            275                 280                 285

Thr Gln Gly Gly Gln Val Ser Ile Ala Leu Ser Ser His Trp Ile Asn
290                 295                 300

Pro Arg Arg Met Thr Asp His Ser Ile Lys Glu Cys Gln Lys Ser Leu
305                 310                 315                 320

Asp Phe Val Leu Gly Trp Phe Ala Lys Pro Val Phe Ile Asp Gly Asp
                325                 330                 335

Tyr Pro Glu Ser Met Lys Asn Asn Leu Ser Ser Ile Leu Pro Asp Phe
                340                 345                 350

Thr Glu Ser Glu Lys Lys Phe Ile Lys Gly Thr Ala Asp Phe Phe Ala
            355                 360                 365

Leu Cys Phe Gly Pro Thr Leu Ser Phe Gln Leu Leu Asp Pro His Met
370                 375                 380

Lys Phe Arg Gln Leu Glu Ser Pro Asn Leu Arg Gln Leu Leu Ser Trp
385                 390                 395                 400

Ile Asp Leu Glu Phe Asn His Pro Gln Ile Phe Ile Val Glu Asn Gly
                405                 410                 415

Trp Phe Val Ser Gly Thr Thr Lys Arg Asp Asp Ala Lys Tyr Met Tyr
                420                 425                 430

Tyr Leu Lys Lys Phe Ile Met Glu Thr Leu Lys Ala Ile Lys Leu Asp
            435                 440                 445

Gly Val Asp Val Ile Gly Tyr Thr Ala Trp Ser Leu Met Asp Gly Phe
450                 455                 460

Glu Trp His Arg Gly Tyr Ser Ile Arg Arg Gly Leu Phe Tyr Val Asp
465                 470                 475                 480

Phe Leu Ser Gln Asp Lys Met Leu Leu Pro Lys Ser Ser Ala Leu Phe
                485                 490                 495

Tyr Gln Lys Leu Ile Glu Lys Asn Gly Phe Pro Pro Leu Pro Glu Asn
            500                 505                 510

Gln Pro Leu Glu Gly Thr Phe Pro Cys Asp Phe Ala Trp Gly Val Val
            515                 520                 525

Asp Asn Tyr Ile Gln Val Asp Thr Thr Leu Ser Gln Phe Thr Asp Leu
530                 535                 540

Asn Val Tyr Leu Trp Asp Val His His Ser Lys Arg Leu Ile Lys Val
545                 550                 555                 560

Asp Gly Val Val Thr Lys Lys Arg Lys Ser Tyr Cys Val Asp Phe Ala
                565                 570                 575

Ala Ile Gln Pro Gln Ile Ala Leu Leu Gln Glu Met His Val Thr His
            580                 585                 590
```

```
Phe Arg Phe Ser Leu Asp Trp Ala Leu Ile Leu Pro Leu Gly Asn Gln
            595                 600                 605

Ser Gln Val Asn His Thr Ile Leu Gln Tyr Tyr Arg Cys Met Ala Ser
    610                 615                 620

Glu Leu Val Arg Val Asn Ile Thr Pro Val Val Ala Leu Trp Gln Pro
625                 630                 635                 640

Met Ala Pro Asn Gln Gly Leu Pro Arg Leu Leu Ala Arg Gln Gly Ala
                645                 650                 655

Trp Glu Asn Pro Tyr Thr Ala Leu Ala Phe Ala Glu Tyr Ala Arg Leu
            660                 665                 670

Cys Phe Gln Glu Leu Gly His His Val Lys Leu Trp Ile Thr Met Asn
    675                 680                 685

Glu Pro Tyr Thr Arg Asn Met Thr Tyr Ser Ala Gly His Asn Leu Leu
690                 695                 700

Lys Ala His Ala Leu Ala Trp His Val Tyr Asn Glu Lys Phe Arg His
705                 710                 715                 720

Ala Gln Asn Gly Lys Ile Ser Ile Ala Leu Gln Ala Asp Trp Ile Glu
                725                 730                 735

Pro Ala Cys Pro Phe Ser Gln Lys Asp Lys Glu Val Ala Glu Arg Val
            740                 745                 750

Leu Glu Phe Asp Ile Gly Trp Leu Ala Glu Pro Ile Phe Gly Ser Gly
            755                 760                 765

Asp Tyr Pro Trp Val Met Arg Asp Trp Leu Asn Gln Arg Asn Asn Phe
    770                 775                 780

Leu Leu Pro Tyr Phe Thr Glu Asp Glu Lys Lys Leu Ile Gln Gly Thr
785                 790                 795                 800

Phe Asp Phe Leu Ala Leu Ser His Tyr Thr Thr Ile Leu Val Asp Ser
                805                 810                 815

Glu Lys Glu Asp Pro Ile Lys Tyr Asn Asp Tyr Leu Glu Val Gln Glu
            820                 825                 830

Met Thr Asp Ile Thr Trp Leu Asn Ser Pro Ser Gln Val Ala Val Val
            835                 840                 845

Pro Trp Gly Leu Arg Lys Val Leu Asn Trp Leu Lys Phe Lys Tyr Gly
850                 855                 860

Asp Leu Pro Met Tyr Ile Ile Ser Asn Gly Ile Asp Asp Gly Leu His
865                 870                 875                 880

Ala Glu Asp Asp Gln Leu Arg Val Tyr Tyr Met Gln Asn Tyr Ile Asn
                885                 890                 895

Glu Ala Leu Lys Ala His Ile Leu Asp Gly Ile Asn Leu Cys Gly Tyr
            900                 905                 910

Phe Ala Tyr Ser Phe Asn Asp Arg Thr Ala Pro Arg Phe Gly Leu Tyr
            915                 920                 925

Arg Tyr Ala Ala Asp Gln Phe Glu Pro Lys Ala Ser Met Lys His Tyr
    930                 935                 940

Arg Lys Ile Ile Asp Ser Asn Gly Phe Pro Gly Pro Glu Thr Leu Glu
945                 950                 955                 960

Arg Phe Cys Pro Glu Glu Phe Thr Val Cys Thr Glu Cys Ser Phe Phe
                965                 970                 975

His Thr Arg Lys Ser Leu Leu Ala Phe Ile Ala Phe Leu Phe Phe Ala
            980                 985                 990

Ser Ile Ile Ser Leu Ser Leu Ile Phe Tyr Tyr Ser Lys Lys Gly Arg
            995                 1000                1005
```

-continued

```
Arg Ser Tyr Lys
       1010

(2) INFORMATION FOR SEQ ID NO: 2:

(i) SEQUENCE CHARACTERISTICS:
        (A) LENGTH: 549
        (B) TYPE: amino acid
        (C) STRANDEDNESS: single
        (D) TOPOLOGY: linear (ii) MOLECULE TYPE: peptide (vi) ORIGINAL SOURCE:
        (A) ORGANISM: human (vii) IMMEDIATE SOURCE:
        (A) LIBRARY: kidney (xi) SEQUENCE DESCRIPTION: SEQ ID NO: 2:

Met Pro Ala Ser Ala Pro Pro Arg Arg Pro Arg Pro Pro Pro Ser
  1               5                  10                  15

Leu Ser Leu Leu Leu Val Leu Leu Gly Leu Gly Gly Arg Arg Leu Arg
             20                  25                  30

Ala Glu Pro Gly Asp Gly Ala Gln Thr Trp Ala Arg Phe Ser Arg Pro
            35                  40                  45

Pro Ala Pro Glu Ala Ala Gly Leu Phe Gln Gly Thr Phe Pro Asp Gly
        50                  55                  60

Phe Leu Trp Ala Val Gly Ser Ala Ala Tyr Gln Thr Glu Gly Gly Trp
 65                 70                  75                  80

Gln Gln His Gly Lys Gly Ala Ser Ile Trp Asp Thr Phe Thr His His
                85                  90                  95

Pro Leu Ala Pro Pro Gly Asp Ser Arg Asn Ala Ser Leu Pro Leu Gly
            100                 105                 110

Ala Pro Ser Pro Leu Gln Pro Ala Thr Gly Asp Val Ala Ser Asp Ser
        115                 120                 125

Tyr Asn Asn Val Phe Arg Asp Thr Glu Ala Leu Arg Glu Leu Gly Val
        130                 135                 140

Thr His Tyr Arg Phe Ser Ile Ser Trp Ala Arg Val Leu Pro Asn Gly
145                 150                 155                 160

Ser Ala Gly Val Pro Asn Arg Glu Gly Leu Arg Tyr Tyr Arg Arg Leu
                165                 170                 175

Leu Glu Arg Leu Arg Glu Leu Gly Val Gln Pro Val Val Thr Leu Tyr
            180                 185                 190

His Trp Asp Leu Pro Gln Arg Leu Gln Asp Ala Tyr Gly Gly Trp Ala
        195                 200                 205

Asn Arg Ala Leu Ala Asp His Phe Arg Asp Tyr Ala Glu Leu Cys Phe
    210                 215                 220

Arg His Phe Gly Gly Gln Val Lys Tyr Trp Ile Thr Ile Asp Asn Pro
225                 230                 235                 240

Tyr Val Val Ala Trp His Gly Tyr Ala Thr Gly Arg Leu Ala Pro Gly
                245                 250                 255

Ile Arg Gly Ser Pro Arg Leu Gly Tyr Leu Val Ala His Asn Leu Leu
            260                 265                 270

Leu Ala His Ala Lys Val Trp His Leu Tyr Asn Thr Ser Phe Arg Pro
        275                 280                 285

Thr Gln Gly Gly Gln Val Ser Ile Ala Leu Ser Ser His Trp Ile Asn
    290                 295                 300
```

-continued

```
Pro Arg Arg Met Thr Asp His Ser Ile Lys Glu Cys Gln Lys Ser Leu
305                 310                 315                 320

Asp Phe Val Leu Gly Trp Phe Ala Lys Pro Val Phe Ile Asp Gly Asp
                325                 330                 335

Tyr Pro Glu Ser Met Lys Asn Asn Leu Ser Ser Ile Leu Pro Asp Phe
            340                 345                 350

Thr Glu Ser Glu Lys Lys Phe Ile Lys Gly Thr Ala Asp Phe Phe Ala
        355                 360                 365

Leu Cys Phe Gly Pro Thr Leu Ser Phe Gln Leu Leu Asp Pro His Met
    370                 375                 380

Lys Phe Arg Gln Leu Glu Ser Pro Asn Leu Arg Gln Leu Leu Ser Trp
385                 390                 395                 400

Ile Asp Leu Glu Phe Asn His Pro Gln Ile Phe Ile Val Glu Asn Gly
                405                 410                 415

Trp Phe Val Ser Gly Thr Thr Lys Arg Asp Asp Ala Lys Tyr Met Tyr
                420                 425                 430

Tyr Leu Lys Lys Phe Ile Met Glu Thr Leu Lys Ala Ile Lys Leu Asp
            435                 440                 445

Gly Val Asp Val Ile Gly Tyr Thr Ala Trp Ser Leu Met Asp Gly Phe
        450                 455                 460

Glu Trp His Arg Gly Tyr Ser Ile Arg Arg Gly Leu Phe Tyr Val Asp
465                 470                 475                 480

Phe Leu Ser Gln Asp Lys Met Leu Leu Pro Lys Ser Ser Ala Leu Phe
                485                 490                 495

Tyr Gln Lys Leu Ile Glu Lys Asn Gly Phe Pro Pro Leu Pro Glu Asn
            500                 505                 510

Gln Pro Leu Glu Gly Thr Phe Pro Cys Asp Phe Ala Trp Gly Val Val
        515                 520                 525

Asp Asn Tyr Ile Gln Val Ser Gln Leu Thr Lys Pro Ile Ser Ser Leu
    530                 535                 540

Thr Lys Pro Tyr His
545

(2) INFORMATION FOR SEQ ID NO: 3:

(i) SEQUENCE CHARACTERISTICS:
        (A) LENGTH: 1014
        (B) TYPE: amino acid
        (C) STRANDEDNESS: single
        (D) TOPOLOGY: linear (ii) MOLECULE TYPE: peptide (vi) ORIGINAL SOURCE:
        (A) ORGANISM: mouse (vii) IMMEDIATE SOURCE:
        (A) LIBRARY: kidney (xi) SEQUENCE DESCRIPTION: SEQ ID NO: 3:

Met Leu Ala Arg Ala Pro Pro Arg Arg Pro Pro Arg Leu Val Leu Leu
1               5                   10                  15

Arg Leu Leu Leu Leu His Leu Leu Leu Ala Leu Arg Ala Arg Cys
            20                  25                  30

Leu Ser Ala Glu Pro Gly Gln Gly Ala Gln Thr Trp Ala Arg Phe Ala
        35                  40                  45

Arg Ala Pro Ala Pro Glu Ala Ala Gly Leu Leu His Asp Thr Phe Pro
    50                  55                  60
```

-continued

```
Asp Gly Phe Leu Trp Ala Val Gly Ser Ala Ala Tyr Gln Thr Glu Gly
 65                  70                  75                  80

Gly Trp Arg Gln His Gly Lys Gly Ala Ser Ile Trp Asp Thr Phe Thr
             85                  90                  95

His His Ser Gly Ala Ala Pro Ser Asp Ser Pro Ile Val Val Ala Pro
        100                 105                 110

Ser Gly Ala Pro Ser Pro Leu Ser Ser Thr Gly Asp Val Ala Ser
    115                 120                 125

Asp Ser Tyr Asn Asn Val Tyr Arg Asp Thr Glu Gly Leu Arg Glu Leu
130                 135                 140

Gly Val Thr His Tyr Arg Phe Ser Ile Ser Trp Ala Arg Val Leu Pro
145                 150                 155                 160

Asn Gly Thr Ala Gly Thr Pro Asn Arg Glu Gly Leu Arg Tyr Tyr Arg
                165                 170                 175

Arg Leu Leu Glu Arg Leu Arg Glu Leu Gly Val Gln Pro Val Val Thr
            180                 185                 190

Leu Tyr His Trp Asp Leu Pro Gln Arg Leu Gln Asp Thr Tyr Gly Gly
        195                 200                 205

Trp Ala Asn Arg Ala Leu Ala Asp His Phe Arg Asp Tyr Ala Glu Leu
210                 215                 220

Cys Phe Arg His Phe Gly Gly Gln Val Lys Tyr Trp Ile Thr Ile Asp
225                 230                 235                 240

Asn Pro Tyr Val Val Ala Trp His Gly Tyr Ala Thr Gly Arg Leu Ala
                245                 250                 255

Pro Gly Val Arg Gly Ser Ser Arg Leu Gly Tyr Leu Val Ala His Asn
            260                 265                 270

Leu Leu Leu Ala His Ala Lys Val Trp His Leu Tyr Asn Thr Ser Phe
        275                 280                 285

Arg Pro Thr Gln Gly Gly Arg Val Ser Ile Ala Leu Ser Ser His Trp
290                 295                 300

Ile Asn Pro Arg Arg Met Thr Asp Tyr Asn Ile Arg Glu Cys Gln Lys
305                 310                 315                 320

Ser Leu Asp Phe Val Leu Gly Trp Phe Ala Lys Pro Ile Phe Ile Asp
                325                 330                 335

Gly Asp Tyr Pro Glu Ser Met Lys Asn Asn Leu Ser Ser Leu Leu Pro
            340                 345                 350

Asp Phe Thr Glu Ser Glu Lys Arg Leu Ile Arg Gly Thr Ala Asp Phe
        355                 360                 365

Phe Ala Leu Ser Phe Gly Pro Thr Leu Ser Phe Gln Leu Leu Asp Pro
370                 375                 380

Asn Met Lys Phe Arg Gln Leu Glu Ser Pro Asn Leu Arg Gln Leu Leu
385                 390                 395                 400

Ser Trp Ile Asp Leu Glu Tyr Asn His Pro Pro Ile Phe Ile Val Glu
                405                 410                 415

Asn Gly Trp Phe Val Ser Gly Thr Thr Lys Arg Asp Asp Ala Lys Tyr
            420                 425                 430

Met Tyr Tyr Leu Lys Lys Phe Ile Met Glu Thr Leu Lys Ala Ile Arg
        435                 440                 445

Leu Asp Gly Val Asp Val Ile Gly Tyr Thr Ala Trp Ser Leu Met Asp
450                 455                 460

Gly Phe Glu Trp His Arg Gly Tyr Ser Ile Arg Arg Gly Leu Phe Tyr
465                 470                 475                 480

Val Asp Phe Leu Ser Gln Asp Lys Glu Leu Leu Pro Lys Ser Ser Ala
```

```
                    485                 490                 495
Leu Phe Tyr Gln Lys Leu Ile Glu Asp Asn Gly Phe Pro Pro Leu Pro
                500                 505                 510
Glu Asn Gln Pro Leu Glu Gly Thr Phe Pro Cys Asp Phe Ala Trp Gly
                515                 520                 525
Val Val Asp Asn Tyr Val Gln Val Asp Thr Thr Leu Ser Gln Phe Thr
                530                 535                 540
Asp Pro Asn Val Tyr Leu Trp Asp Val His Ser Lys Arg Leu Ile
545                 550                 555                 560
Lys Val Asp Gly Val Val Ala Lys Lys Arg Lys Pro Tyr Cys Val Asp
                565                 570                 575
Phe Ser Ala Ile Arg Pro Gln Ile Thr Leu Leu Arg Glu Met Arg Val
                580                 585                 590
Thr His Phe Arg Phe Ser Leu Asp Trp Ala Leu Ile Leu Pro Leu Gly
                595                 600                 605
Asn Gln Thr Gln Val Asn His Thr Val Leu His Phe Tyr Arg Cys Met
                610                 615                 620
Ile Ser Glu Leu Val His Ala Asn Ile Thr Pro Val Val Ala Leu Trp
625                 630                 635                 640
Gln Pro Ala Ala Pro His Gln Gly Leu Pro His Ala Leu Ala Lys His
                645                 650                 655
Gly Ala Trp Glu Asn Pro His Thr Ala Leu Ala Phe Ala Asp Tyr Ala
                660                 665                 670
Asn Leu Cys Phe Lys Glu Leu Gly His Trp Val Asn Leu Trp Ile Thr
                675                 680                 685
Met Asn Glu Pro Asn Thr Arg Asn Met Thr Tyr Arg Ala Gly His His
                690                 695                 700
Leu Leu Arg Ala His Ala Leu Ala Trp His Leu Tyr Asp Asp Lys Phe
705                 710                 715                 720
Arg Ala Ala Gln Lys Gly Lys Ile Ser Ile Ala Leu Gln Ala Asp Trp
                725                 730                 735
Ile Glu Pro Ala Cys Pro Phe Ser Gln Asn Asp Lys Glu Val Ala Glu
                740                 745                 750
Arg Val Leu Glu Phe Asp Ile Gly Trp Leu Ala Glu Pro Ile Phe Gly
                755                 760                 765
Ser Gly Asp Tyr Pro Arg Val Met Arg Asp Trp Leu Asn Gln Lys Asn
                770                 775                 780
Asn Phe Leu Leu Pro Tyr Phe Thr Glu Asp Glu Lys Lys Leu Val Arg
785                 790                 795                 800
Gly Ser Phe Asp Phe Leu Ala Val Ser His Tyr Thr Thr Ile Leu Val
                805                 810                 815
Asp Trp Glu Lys Glu Asp Pro Met Lys Tyr Asn Asp Tyr Leu Glu Val
                820                 825                 830
Gln Glu Met Thr Asp Ile Thr Trp Leu Asn Ser Pro Ser Gln Val Ala
                835                 840                 845
Val Val Pro Trp Gly Leu Arg Lys Val Leu Asn Trp Leu Arg Phe Lys
                850                 855                 860
Tyr Gly Asp Leu Pro Met Tyr Val Thr Ala Asn Gly Ile Asp Asp Asp
865                 870                 875                 880
Pro His Ala Glu Gln Asp Ser Leu Arg Ile Tyr Tyr Ile Lys Asn Tyr
                885                 890                 895
Val Asn Glu Ala Leu Lys Ala Tyr Val Leu Asp Asp Ile Asn Leu Cys
                900                 905                 910
```

-continued

```
Gly Tyr Phe Ala Tyr Ser Leu Ser Asp Arg Ser Ala Pro Lys Ser Gly
            915                 920                 925

Phe Tyr Arg Tyr Ala Ala Asn Gln Phe Glu Pro Lys Pro Ser Met Lys
        930                 935                 940

His Tyr Arg Arg Ile Ile Asp Ser Asn Gly Phe Leu Gly Ser Gly Thr
945                 950                 955                 960

Leu Gly Arg Phe Cys Pro Glu Glu Tyr Thr Val Cys Thr Glu Cys Gly
            965                 970                 975

Phe Phe Gln Thr Arg Lys Ser Leu Leu Val Phe Ile Ser Phe Leu Val
        980                 985                 990

Phe Thr Phe Ile Ile Ser Leu Ala Leu Ile Phe His Tyr Ser Lys Lys
        995                1000                1005

Gly Gln Arg Ser Tyr Lys
   1010

(2) INFORMATION FOR SEQ ID NO: 4:

(i) SEQUENCE CHARACTERISTICS:
        (A) LENGTH: 550
        (B) TYPE: amino acid
        (C) STRANDEDNESS: single
        (D) TOPOLOGY: linear (ii) MOLECULE TYPE: peptide (vi) ORIGINAL SOURCE:
        (A) ORGANISM: mouse (vii) IMMEDIATE SOURCE:
        (A) LIBRARY: kidney (xi) SEQUENCE DESCRIPTION: SEQ ID NO: 4:

Met Leu Ala Arg Ala Pro Pro Arg Arg Pro Pro Arg Leu Val Leu Leu
  1               5                  10                  15

Arg Leu Leu Leu Leu His Leu Leu Leu Ala Leu Arg Ala Arg Cys
             20                  25                  30

Leu Ser Ala Glu Pro Gly Gln Gly Ala Gln Thr Trp Ala Arg Phe Ala
         35                  40                  45

Arg Ala Pro Ala Pro Glu Ala Ala Gly Leu Leu His Asp Thr Phe Pro
     50                  55                  60

Asp Gly Phe Leu Trp Ala Val Gly Ser Ala Ala Tyr Gln Thr Glu Gly
 65                  70                  75                  80

Gly Trp Arg Gln His Gly Lys Gly Ala Ser Ile Trp Asp Thr Phe Thr
             85                  90                  95

His His Ser Gly Ala Ala Pro Ser Asp Ser Pro Ile Val Val Ala Pro
            100                 105                 110

Ser Gly Ala Pro Ser Pro Leu Ser Ser Thr Gly Asp Val Ala Ser
            115                 120                 125

Asp Ser Tyr Asn Asn Val Tyr Arg Asp Thr Glu Gly Leu Arg Glu Leu
        130                 135                 140

Gly Val Thr His Tyr Arg Phe Ser Ile Ser Trp Ala Arg Val Leu Pro
145                 150                 155                 160

Asn Gly Thr Ala Gly Thr Pro Asn Arg Glu Gly Leu Arg Tyr Tyr Arg
            165                 170                 175

Arg Leu Leu Glu Arg Leu Arg Glu Leu Gly Val Gln Pro Val Val Thr
        180                 185                 190

Leu Tyr His Trp Asp Leu Pro Gln Arg Leu Gln Asp Thr Tyr Gly Gly
        195                 200                 205
```

```
Trp Ala Asn Arg Ala Leu Ala Asp His Phe Arg Asp Tyr Ala Glu Leu
    210                 215                 220
Cys Phe Arg His Phe Gly Gly Gln Val Lys Tyr Trp Ile Thr Ile Asp
225                 230                 235                 240
Asn Pro Tyr Val Val Ala Trp His Gly Tyr Ala Thr Gly Arg Leu Ala
                245                 250                 255
Pro Gly Val Arg Gly Ser Ser Arg Leu Gly Tyr Leu Val Ala His Asn
                260                 265                 270
Leu Leu Leu Ala His Ala Lys Val Trp His Leu Tyr Asn Thr Ser Phe
            275                 280                 285
Arg Pro Thr Gln Gly Gly Arg Val Ser Ile Ala Leu Ser Ser His Trp
    290                 295                 300
Ile Asn Pro Arg Arg Met Thr Asp Tyr Asn Ile Arg Glu Cys Gln Lys
305                 310                 315                 320
Ser Leu Asp Phe Val Leu Gly Trp Phe Ala Lys Pro Ile Phe Ile Asp
                325                 330                 335
Gly Asp Tyr Pro Glu Ser Met Lys Asn Asn Leu Ser Ser Leu Leu Pro
                340                 345                 350
Asp Phe Thr Glu Ser Glu Lys Arg Leu Ile Arg Gly Thr Ala Asp Phe
            355                 360                 365
Phe Ala Leu Cys Phe Gly Pro Thr Leu Ser Phe Gln Leu Leu Asp Pro
    370                 375                 380
Asn Met Lys Phe Arg Gln Leu Glu Ser Pro Asn Leu Arg Gln Leu Leu
385                 390                 395                 400
Ser Trp Ile Asp Leu Glu Tyr Asn His Pro Pro Ile Phe Ile Val Glu
                405                 410                 415
Asn Gly Trp Phe Val Ser Gly Thr Thr Lys Arg Asp Asp Ala Lys Tyr
                420                 425                 430
Met Tyr Tyr Leu Lys Lys Phe Ile Met Glu Thr Leu Lys Ala Ile Arg
            435                 440                 445
Leu Asp Gly Val Asp Val Ile Gly Tyr Thr Ala Trp Ser Leu Met Asp
    450                 455                 460
Gly Phe Glu Trp His Arg Gly Tyr Ser Ile Arg Arg Gly Leu Phe Tyr
465                 470                 475                 480
Val Asp Phe Leu Ser Gln Asp Lys Glu Leu Leu Pro Lys Ser Ser Ala
                485                 490                 495
Leu Phe Tyr Gln Lys Leu Ile Glu Asp Asn Gly Phe Pro Pro Leu Pro
            500                 505                 510
Glu Asn Gln Pro Leu Glu Gly Thr Phe Pro Cys Asp Phe Ala Trp Gly
            515                 520                 525
Val Val Asp Asn Tyr Val Gln Val Ser Pro Leu Thr Lys Pro Ser Val
    530                 535                 540
Gly Leu Leu Leu Pro His
545                 550
```

(2) INFORMATION FOR SEQ ID NO: 5:

(i) SEQUENCE CHARACTERISTICS:
        (A) LENGTH: 1015
        (B) TYPE: amino acid
        (C) STRANDEDNESS: single
        (D) TOPOLOGY: linear (ii) MOLECULE TYPE: peptide (vi) ORIGINAL SOURCE:

(A) ORGANISM: human (vii) IMMEDIATE SOURCE:
  (A) LIBRARY: pancreas (xi) SEQUENCE DESCRIPTION: SEQ ID NO: 5:

```
Met Ser Asn Gly Gly Leu Gln Arg Ser Val Ile Leu Ser Ala Leu Ile
 1               5                  10                  15
Leu Leu Arg Ala Val Thr Gly Phe Ser Gly Asp Gly Arg Ala Ile Trp
             20                  25                  30
Ser Lys Asn Pro Asn Phe Thr Pro Val Asn Glu Ser Gln Leu Phe Leu
         35                  40                  45
Tyr Gly Thr Phe Pro Lys Asn Phe Phe Trp Gly Ile Gly Thr Gly Ala
 50                  55                  60
Leu Gln Val Glu Gly Ser Trp Lys Lys Asp Gly Lys Gly Pro Ser Ile
 65                  70                  75                  80
Trp Asp His Phe Ile His Thr His Leu Lys Asn Val Ser Ser Thr Asn
             85                  90                  95
Gly Ser Ser Asp Ser Tyr Ile Phe Leu Glu Lys Asp Leu Ser Ala Leu
            100                 105                 110
Asp Phe Ile Gly Val Ser Phe Tyr Gln Phe Ser Ile Ser Trp Pro Arg
            115                 120                 125
Leu Phe Pro Asp Gly Ile Val Thr Val Ala Asn Ala Lys Gly Leu Gln
130                 135                 140
Tyr Tyr Ser Thr Leu Leu Asp Ala Leu Val Leu Arg Asn Ile Glu Pro
145                 150                 155                 160
Ile Val Thr Leu Tyr His Trp Asp Leu Pro Leu Ala Leu Gln Glu Lys
                165                 170                 175
Tyr Gly Gly Trp Lys Asn Asp Thr Ile Ile Asp Ile Phe Asn Asp Tyr
            180                 185                 190
Ala Thr Tyr Cys Phe Gln Met Phe Gly Asp Arg Val Lys Tyr Trp Ile
            195                 200                 205
Thr Ile His Asn Pro Tyr Leu Val Ala Trp His Gly Tyr Gly Thr Gly
210                 215                 220
Met His Ala Pro Gly Glu Lys Gly Asn Leu Ala Ala Val Tyr Thr Val
225                 230                 235                 240
Gly His Asn Leu Ile Lys Ala His Ser Lys Val Trp His Asn Tyr Asn
                245                 250                 255
Thr His Phe Arg Pro His Gln Lys Gly Trp Leu Ser Ile Thr Leu Gly
            260                 265                 270
Ser His Trp Ile Glu Pro Asn Arg Ser Glu Asn Thr Met Asp Ile Phe
            275                 280                 285
Lys Cys Gln Gln Ser Met Val Ser Val Leu Gly Trp Phe Ala Asn Pro
290                 295                 300
Ile His Gly Asp Gly Asp Tyr Pro Glu Gly Met Arg Lys Lys Leu Phe
305                 310                 315                 320
Ser Val Leu Pro Ile Phe Ser Glu Ala Glu Lys His Glu Met Arg Gly
                325                 330                 335
Thr Ala Asp Phe Phe Ala Phe Ser Phe Gly Pro Asn Asn Phe Lys Pro
            340                 345                 350
Leu Asn Thr Met Ala Lys Met Gly Gln Asn Val Ser Leu Asn Leu Arg
            355                 360                 365
Glu Ala Leu Asn Trp Ile Lys Leu Glu Tyr Asn Asn Pro Arg Ile Leu
370                 375                 380
```

-continued

```
Ile Ala Glu Asn Gly Trp Phe Thr Asp Ser Arg Val Lys Thr Glu Asp
385                 390                 395                 400

Thr Thr Ala Ile Tyr Met Met Lys Asn Phe Leu Ser Gln Val Leu Gln
            405                 410                 415

Ala Ile Arg Leu Asp Glu Ile Arg Val Phe Gly Tyr Thr Ala Trp Ser
        420                 425                 430

Leu Leu Asp Gly Phe Glu Trp Gln Asp Ala Tyr Thr Ile Arg Arg Gly
    435                 440                 445

Leu Phe Tyr Val Asp Phe Asn Ser Lys Gln Lys Glu Arg Lys Pro Lys
    450                 455                 460

Ser Ser Ala His Tyr Tyr Lys Gln Ile Ile Arg Glu Asn Gly Phe Ser
465                 470                 475                 480

Leu Lys Glu Ser Thr Pro Asp Val Gln Gly Gln Phe Pro Cys Asp Phe
                485                 490                 495

Ser Trp Gly Val Thr Glu Ser Val Leu Lys Pro Glu Ser Val Ala Ser
            500                 505                 510

Ser Pro Gln Phe Ser Asp Pro His Leu Tyr Val Trp Asn Ala Thr Gly
        515                 520                 525

Asn Arg Leu Leu His Arg Val Glu Gly Val Arg Leu Lys Thr Arg Pro
    530                 535                 540

Ala Gln Cys Thr Asp Phe Val Asn Ile Lys Lys Gln Leu Glu Met Leu
545                 550                 555                 560

Ala Arg Met Lys Val Thr His Tyr Arg Phe Ala Leu Asp Trp Ala Ser
                565                 570                 575

Val Leu Pro Thr Gly Asn Leu Ser Ala Val Asn Arg Gln Ala Leu Arg
            580                 585                 590

Tyr Tyr Arg Cys Val Val Ser Glu Gly Leu Lys Leu Gly Ile Ser Ala
        595                 600                 605

Met Val Thr Leu Tyr Tyr Pro Thr His Ala His Leu Gly Leu Pro Glu
    610                 615                 620

Pro Leu Leu His Ala Asp Gly Trp Leu Asn Pro Ser Thr Ala Glu Ala
625                 630                 635                 640

Phe Gln Ala Tyr Ala Gly Leu Cys Phe Gln Glu Leu Gly Asp Leu Val
                645                 650                 655

Lys Leu Trp Ile Thr Ile Asn Glu Pro Asn Arg Leu Ser Asp Ile Tyr
            660                 665                 670

Asn Arg Ser Gly Asn Asp Thr Tyr Gly Ala Ala His Asn Leu Leu Val
        675                 680                 685

Ala His Ala Leu Ala Trp Arg Leu Tyr Asp Gln Gln Phe Arg Pro Ser
    690                 695                 700

Gln Arg Gly Ala Val Ser Leu Ser Leu His Ala Asp Trp Ala Glu Pro
705                 710                 715                 720

Ala Asn Pro Tyr Ala Asp Ser His Trp Arg Ala Ala Glu Arg Phe Leu
                725                 730                 735

Gln Phe Glu Ile Ala Trp Phe Ala Glu Pro Leu Phe Lys Thr Gly Asp
            740                 745                 750

Tyr Pro Ala Ala Met Arg Glu Tyr Ile Ala Ser Lys His Arg Arg Gly
        755                 760                 765

Leu Ser Ser Ser Ala Leu Pro Arg Leu Thr Glu Ala Glu Arg Arg Leu
    770                 775                 780

Leu Lys Gly Thr Val Asp Phe Cys Ala Leu Asn His Phe Thr Thr Arg
785                 790                 795                 800

Phe Val Met His Glu Gln Leu Ala Gly Ser Arg Tyr Asp Ser Asp Arg
```

```
                805             810             815
Asp Ile Gln Phe Leu Gln Asp Ile Thr Arg Leu Ser Ser Pro Thr Arg
        820             825             830

Leu Ala Val Ile Pro Trp Gly Val Arg Lys Leu Leu Arg Trp Val Arg
        835             840             845

Arg Asn Tyr Gly Asp Met Asp Ile Tyr Ile Thr Ala Ser Gly Ile Asp
    850             855             860

Asp Gln Ala Leu Glu Asp Asp Arg Leu Arg Lys Tyr Tyr Leu Gly Lys
865             870             875             880

Tyr Leu Gln Glu Val Leu Lys Ala Tyr Leu Ile Asp Lys Val Arg Ile
            885             890             895

Lys Gly Tyr Tyr Ala Phe Lys Leu Ala Glu Glu Lys Ser Lys Pro Arg
        900             905             910

Phe Gly Phe Phe Thr Ser Asp Phe Lys Ala Lys Ser Ser Ile Gln Phe
        915             920             925

Tyr Asn Lys Val Ile Ser Ser Arg Gly Phe Pro Phe Glu Asn Ser Ser
    930             935             940

Ser Arg Cys Ser Gln Thr Gln Glu Asn Thr Glu Cys Thr Val Cys Leu
945             950             955             960

Phe Leu Val Gln Lys Lys Pro Leu Ile Phe Leu Gly Cys Cys Phe Phe
            965             970             975

Ser Thr Leu Val Leu Leu Leu Ser Ile Ala Ile Phe Gln Arg Gln Lys
        980             985             990

Arg Arg Lys Phe Trp Lys Ala Lys Asn Leu Gln His Ile Pro Leu Lys
        995             1000            1005

Lys Gly Lys Arg Val Val Ser
   1010            1015

(2) INFORMATION FOR SEQ ID NO: 6:

(i) SEQUENCE CHARACTERISTICS:
        (A) LENGTH: 3163
        (B) TYPE: nucleic acid
        (C) STRANDEDNESS: double
        (D) TOPOLOGY: linear (ii) MOLECULE TYPE: cDNA to mRNA (vi) ORIGINAL SOURCE:
        (A) ORGANISM: human (vii) IMMEDIATE SOURCE:
        (A) LIBRARY: kidney (ix) FEATURE:
        (A) NAME/KEY: CDS
        (B) LOCATION: 9..3047
        (C) IDENTIFICATION METHOD: E (xi) SEQUENCE DESCRIPTION: SEQ ID NO: 6:

CGCGCAGC ATG CCC GCC AGC GCC CCG CCG CGC CGC CCG CGG CCG CCG CCG        50
         Met Pro Ala Ser Ala Pro Pro Arg Arg Pro Arg Pro Pro Pro
         1               5                   10

CCG TCG CTG TCG CTG CTG CTG GTG CTG CTG GGC CTG GGC GGC CGC CGC        98
Pro Ser Leu Ser Leu Leu Leu Val Leu Leu Gly Leu Gly Gly Arg Arg
15                  20                  25                  30

CTG CGT GCG GAG CCG GGC GAC GGC GCG CAG ACC TGG GCC CGT GTC TCG       146
Leu Arg Ala Glu Pro Gly Asp Gly Ala Gln Thr Trp Ala Arg Val Ser
            35                  40                  45

CGG CCT CCT GCC CCC GAG GCC GCG GGC CTC TTC CAG GGC ACC TTC CCC       194
Arg Pro Pro Ala Pro Glu Ala Ala Gly Leu Phe Gln Gly Thr Phe Pro
```

```
                50                    55                    60
GAC GGC TTC CTC TGG GCC GTG GGC AGC GCC GCC TAC CAG ACC GAG GGC          242
Asp Gly Phe Leu Trp Ala Val Gly Ser Ala Ala Tyr Gln Thr Glu Gly
            65                    70                    75

GGC TGG CAG CAG CAC GGC AAG GGT GCG TCC ATC TGG GAC ACG TTC ACC          290
Gly Trp Gln Gln His Gly Lys Gly Ala Ser Ile Trp Asp Thr Phe Thr
    80                    85                    90

CAC CAC CCC CTG GCA CCC CCG GGA GAC TCC CGG AAC GCC AGT CTG CCG          338
His His Pro Leu Ala Pro Pro Gly Asp Ser Arg Asn Ala Ser Leu Pro
95                    100                   105                   110

TTG GGC GCC CCG TCG CCG CTG CAG CCC GCC ACC GGG GAC GTA GCC AGC          386
Leu Gly Ala Pro Ser Pro Leu Gln Pro Ala Thr Gly Asp Val Ala Ser
                    115                   120                   125

GAC AGC TAC AAC AAC GTC TTC CGC GAC ACG GAG GCG CTG CGC GAG CTC          434
Asp Ser Tyr Asn Asn Val Phe Arg Asp Thr Glu Ala Leu Arg Glu Leu
            130                   135                   140

GGG GTC ACT CAC TAC CGC TTC TCC ATC TCG TGG GCG CGA GTG CTC CCC          482
Gly Val Thr His Tyr Arg Phe Ser Ile Ser Trp Ala Arg Val Leu Pro
    145                   150                   155

AAT GGC AGC GCG GGC GTC CCC AAC CGC GAG GGG CTG CGC TAC TAC CGG          530
Asn Gly Ser Ala Gly Val Pro Asn Arg Glu Gly Leu Arg Tyr Tyr Arg
160                   165                   170

CGC CTG CTG GAG CGG CTG CGG GAG CTG GGC GTG CAG CCC GTG GTC ACC          578
Arg Leu Leu Glu Arg Leu Arg Glu Leu Gly Val Gln Pro Val Val Thr
175                   180                   185                   190

CTG TAC CAC TGG GAC CTG CCC CAG CGC CTG CAG GAC GCC TAC GGC GGC          626
Leu Tyr His Trp Asp Leu Pro Gln Arg Leu Gln Asp Ala Tyr Gly Gly
            195                   200                   205

TGG GCC AAC CGC GCC CTG GCC GAC CAC TTC AGG GAT TAC GCG GAG CTC          674
Trp Ala Asn Arg Ala Leu Ala Asp His Phe Arg Asp Tyr Ala Glu Leu
            210                   215                   220

TGC TTC CGC CAC TTC GGC GGT CAG GTC AAG TAC TGG ATC ACC ATC GAC          722
Cys Phe Arg His Phe Gly Gly Gln Val Lys Tyr Trp Ile Thr Ile Asp
    225                   230                   235

AAC CCC TAC GTG GTG GCC TGG CAC GGC TAC GCC ACC GGG CGC CTG GCC          770
Asn Pro Tyr Val Val Ala Trp His Gly Tyr Ala Thr Gly Arg Leu Ala
240                   245                   250

CCC GGC ATC CGG GGC AGC CCG CGG CTC GGG TAC CTG GTG GCG CAC AAC          818
Pro Gly Ile Arg Gly Ser Pro Arg Leu Gly Tyr Leu Val Ala His Asn
255                   260                   265                   270

CTC CTC CTG GCT CAT GCC AAA GTC TGG CAT CTC TAC AAT ACT TCT TTC          866
Leu Leu Leu Ala His Ala Lys Val Trp His Leu Tyr Asn Thr Ser Phe
                    275                   280                   285

CGT CCC ACT CAG GGA GGT CAG GTG TCC ATT GCC CTA AGC TCT CAC TGG          914
Arg Pro Thr Gln Gly Gly Gln Val Ser Ile Ala Leu Ser Ser His Trp
            290                   295                   300

ATC AAT CCT CGA AGA ATG ACC GAC CAC AGC ATC AAA GAA TGT CAA AAA          962
Ile Asn Pro Arg Arg Met Thr Asp His Ser Ile Lys Glu Cys Gln Lys
            305                   310                   315

TCT CTG GAC TTT GTA CTA GGT TGG TTT GCC AAA CCC GTA TTT ATT GAT         1010
Ser Leu Asp Phe Val Leu Gly Trp Phe Ala Lys Pro Val Phe Ile Asp
    320                   325                   330

GGT GAC TAT CCC GAG AGC ATG AAG AAT AAC CTT TCA TCT ATT CTG CCT         1058
Gly Asp Tyr Pro Glu Ser Met Lys Asn Asn Leu Ser Ser Ile Leu Pro
335                   340                   345                   350

GAT TTT ACT GAA TCT GAG AAA AAG TTC ATC AAA GGA ACT GCT GAC TTT         1106
Asp Phe Thr Glu Ser Glu Lys Lys Phe Ile Lys Gly Thr Ala Asp Phe
            355                   360                   365

TTT GCT CTT TGC TTT GGA CCC ACC TTG AGT TTT CAA CTT TTG GAC CCT         1154
```

```
        Phe Ala Leu Cys Phe Gly Pro Thr Leu Ser Phe Gln Leu Leu Asp Pro
                        370                 375                 380

CAC ATG AAG TTC CGC CAA TTG GAA TCT CCC AAC CTG AGG CAA CTG CTT              1202
His Met Lys Phe Arg Gln Leu Glu Ser Pro Asn Leu Arg Gln Leu Leu
            385                 390                 395

TCC TGG ATT GAC CTT GAA TTT AAC CAT CCT CAA ATA TTT ATT GTG GAA              1250
Ser Trp Ile Asp Leu Glu Phe Asn His Pro Gln Ile Phe Ile Val Glu
        400                 405                 410

AAT GGC TGG TTT GTC TCA GGG ACC ACC AAG AGA GAT GAT GCC AAA TAT              1298
Asn Gly Trp Phe Val Ser Gly Thr Thr Lys Arg Asp Asp Ala Lys Tyr
415                 420                 425                 430

ATG TAT TAC CTC AAA AAG TTC ATC ATG GAA ACC TTA AAA GCC ATC AAG              1346
Met Tyr Tyr Leu Lys Lys Phe Ile Met Glu Thr Leu Lys Ala Ile Lys
                435                 440                 445

CTG GAT GGG GTG GAT GTC ATC GGG TAT ACC GCA TGG TCC CTC ATG GAT              1394
Leu Asp Gly Val Asp Val Ile Gly Tyr Thr Ala Trp Ser Leu Met Asp
            450                 455                 460

GGT TTC GAG TGG CAC AGA GGT TAC AGC ATC AGG CGT GGA CTC TTC TAT              1442
Gly Phe Glu Trp His Arg Gly Tyr Ser Ile Arg Arg Gly Leu Phe Tyr
        465                 470                 475

GTT GAC TTT CTA AGC CAG GAC AAG ATG TTG TTG CCA AAG TCT TCA GCC              1490
Val Asp Phe Leu Ser Gln Asp Lys Met Leu Leu Pro Lys Ser Ser Ala
480                 485                 490

TTG TTC TAC CAA AAG CTG ATA GAG AAA AAT GGC TTC CCT CCT TTA CCT              1538
Leu Phe Tyr Gln Lys Leu Ile Glu Lys Asn Gly Phe Pro Pro Leu Pro
495                 500                 505                 510

GAA AAT CAG CCC CTA GAA GGG ACA TTT CCC TGT GAC TTT GCT TGG GGA              1586
Glu Asn Gln Pro Leu Glu Gly Thr Phe Pro Cys Asp Phe Ala Trp Gly
                515                 520                 525

GTT GTT GAC AAC TAC ATT CAA GTA GAT ACC ACT CTG TCT CAG TTT ACC              1634
Val Val Asp Asn Tyr Ile Gln Val Asp Thr Thr Leu Ser Gln Phe Thr
            530                 535                 540

GAC CTG AAT GTT TAC CTG TGG GAT GTC CAC CAC AGT AAA AGG CTT ATT              1682
Asp Leu Asn Val Tyr Leu Trp Asp Val His His Ser Lys Arg Leu Ile
        545                 550                 555

AAA GTG GAT GGG GTT GTG ACC AAG AAG AGG AAA TCC TAC TGT GTT GAC              1730
Lys Val Asp Gly Val Val Thr Lys Lys Arg Lys Ser Tyr Cys Val Asp
560                 565                 570

TTT GCT GCC ATC CAG CCC CAG ATC GCT TTA CTC CAG GAA ATG CAC GTT              1778
Phe Ala Ala Ile Gln Pro Gln Ile Ala Leu Leu Gln Glu Met His Val
575                 580                 585                 590

ACA CAT TTT CGC TTC TCC CTG GAC TGG GCC CTG ATT CTC CCT CTG GGT              1826
Thr His Phe Arg Phe Ser Leu Asp Trp Ala Leu Ile Leu Pro Leu Gly
                595                 600                 605

AAC CAG TCC CAG GTG AAC CAC ACC ATC CTG CAG TAC TAT CGC TGC ATG              1874
Asn Gln Ser Gln Val Asn His Thr Ile Leu Gln Tyr Tyr Arg Cys Met
            610                 615                 620

GCC AGC GAG CTT GTC CGT GTC AAC ATC ACC CCA GTG GTG GCC CTG TGG              1922
Ala Ser Glu Leu Val Arg Val Asn Ile Thr Pro Val Val Ala Leu Trp
        625                 630                 635

CAG CCT ATG GCC CCG AAC CAA GGA CTG CCG CGC CTC CTG GCC AGG CAG              1970
Gln Pro Met Ala Pro Asn Gln Gly Leu Pro Arg Leu Leu Ala Arg Gln
640                 645                 650

GGC GCC TGG GAG AAC CCC TAC ACT GCC CTG GCC TTT GCA GAG TAT GCC              2018
Gly Ala Trp Glu Asn Pro Tyr Thr Ala Leu Ala Phe Ala Glu Tyr Ala
655                 660                 665                 670

CGA CTG TGC TTT CAA GAG CTC GGC CAT CAC GTC AAG CTT TGG ATA ACG              2066
Arg Leu Cys Phe Gln Glu Leu Gly His His Val Lys Leu Trp Ile Thr
                675                 680                 685
```

```
ATG AAT GAG CCG TAT ACA AGG AAT ATG ACA TAC AGT GCT GGC CAC AAC      2114
Met Asn Glu Pro Tyr Thr Arg Asn Met Thr Tyr Ser Ala Gly His Asn
            690                 695                 700

CTT CTG AAG GCC CAT GCC CTG GCT TGG CAT GTG TAC AAT GAA AAG TTT      2162
Leu Leu Lys Ala His Ala Leu Ala Trp His Val Tyr Asn Glu Lys Phe
                705                 710                 715

AGG CAT GCT CAG AAT GGG AAA ATA TCC ATA GCC TTG CAG GCT GAT TGG      2210
Arg His Ala Gln Asn Gly Lys Ile Ser Ile Ala Leu Gln Ala Asp Trp
720                 725                 730

ATA GAA CCT GCC TGC CCT TTC TCC CAA AAG GAC AAA GAG GTG GCC GAG      2258
Ile Glu Pro Ala Cys Pro Phe Ser Gln Lys Asp Lys Glu Val Ala Glu
735                 740                 745                 750

AGA GTT TTG GAA TTT GAC ATT GGC TGG CTG GCT GAG CCC ATT TTC GGC      2306
Arg Val Leu Glu Phe Asp Ile Gly Trp Leu Ala Glu Pro Ile Phe Gly
                755                 760                 765

TCT GGA GAT TAT CCA TGG GTG ATG AGG GAC TGG CTG AAC CAA AGA AAC      2354
Ser Gly Asp Tyr Pro Trp Val Met Arg Asp Trp Leu Asn Gln Arg Asn
                770                 775                 780

AAT TTT CTT CTT CCT TAT TTC ACT GAA GAT GAA AAA AAG CTA ATC CAG      2402
Asn Phe Leu Leu Pro Tyr Phe Thr Glu Asp Glu Lys Lys Leu Ile Gln
                785                 790                 795

GGT ACC TTT GAC TTT TTG GCT TTA AGC CAT TAT ACC ACC ATC CTT GTA      2450
Gly Thr Phe Asp Phe Leu Ala Leu Ser His Tyr Thr Thr Ile Leu Val
800                 805                 810

GAC TCA GAA AAA GAA GAT CCA ATA AAA TAC AAT GAT TAC CTA GAA GTG      2498
Asp Ser Glu Lys Glu Asp Pro Ile Lys Tyr Asn Asp Tyr Leu Glu Val
815                 820                 825                 830

CAA GAA ATG ACC GAC ATC ACG TGG CTC AAC TCC CCC AGT CAG GTG GCG      2546
Gln Glu Met Thr Asp Ile Thr Trp Leu Asn Ser Pro Ser Gln Val Ala
                835                 840                 845

GTA GTG CCC TGG GGG TTG CGC AAA GTG CTG AAC TGG CTG AAG TTC AAG      2594
Val Val Pro Trp Gly Leu Arg Lys Val Leu Asn Trp Leu Lys Phe Lys
                850                 855                 860

TAC GGA GAC CTC CCC ATG TAC ATA ATA TCC AAC GGA ATC GAT GAC GGG      2642
Tyr Gly Asp Leu Pro Met Tyr Ile Ile Ser Asn Gly Ile Asp Asp Gly
                865                 870                 875

CTG CAT GCT GAG GAC GAC CAG CTG AGG GTG TAT TAT ATG CAG AAT TAC      2690
Leu His Ala Glu Asp Asp Gln Leu Arg Val Tyr Tyr Met Gln Asn Tyr
            880                 885                 890

ATA AAC GAA GCT CTC AAA GCC CAC ATA CTG GAT GGT ATC AAT CTT TGC      2738
Ile Asn Glu Ala Leu Lys Ala His Ile Leu Asp Gly Ile Asn Leu Cys
895                 900                 905                 910

GGA TAC TTT GCT TAT TCG TTT AAC GAC CGC ACA GCT CCG AGG TTT GGC      2786
Gly Tyr Phe Ala Tyr Ser Phe Asn Asp Arg Thr Ala Pro Arg Phe Gly
                915                 920                 925

CTC TAT CGT TAT GCT GCA GAT CAG TTT GAG CCC AAG GCA TCC ATG AAA      2834
Leu Tyr Arg Tyr Ala Ala Asp Gln Phe Glu Pro Lys Ala Ser Met Lys
            930                 935                 940

CAT TAC AGG AAA ATT ATT GAC AGC AAT GGT TTC CCG GGC CCA GAA ACT      2882
His Tyr Arg Lys Ile Ile Asp Ser Asn Gly Phe Pro Gly Pro Glu Thr
            945                 950                 955

CTG GAA AGA TTT TGT CCA GAA GAA TTC ACC GTG TGT ACT GAG TGC AGT      2930
Leu Glu Arg Phe Cys Pro Glu Glu Phe Thr Val Cys Thr Glu Cys Ser
960                 965                 970

TTT TTT CAC ACC CGA AAG TCT TTA CTG GCT TTC ATA GCT TTT CTA TTT      2978
Phe Phe His Thr Arg Lys Ser Leu Leu Ala Phe Ile Ala Phe Leu Phe
975                 980                 985                 990

TTT GCT TCT ATT ATT TCT CTC TCC CTT ATA TTT TAC TAC TCG AAG AAA      3026
Phe Ala Ser Ile Ile Ser Leu Ser Leu Ile Phe Tyr Tyr Ser Lys Lys
                995                 1000                1005
```

```
GGC AGA AGA AGT TAC AAA TAGTTCTGAA CATTTTTCTA TTCATTCATT        3074
Gly Arg Arg Ser Tyr Lys
            1010

TTGAAATAAT TATGCAGACA CATCAGCTGT TAACCATTTG CACCTCTAAG TGTTGTGAAA  3134

CTGTAAATTT CATACATTTG ACTTCTAGA                                    3163

(2) INFORMATION FOR SEQ ID NO: 7:

(i) SEQUENCE CHARACTERISTICS:
        (A) LENGTH: 3435
        (B) TYPE: nucleic acid
        (C) STRANDEDNESS: double
        (D) TOPOLOGY: linear (ii) MOLECULE TYPE: cDNA to mRNA (vi) ORIGINAL SOURCE:
        (A) ORGANISM: human (vii) IMMEDIATE SOURCE:
        (A) LIBRARY: kidney (ix) FEATURE:
        (A) NAME/KEY: CDS
        (B) LOCATION: 9..1655
        (C) IDENTIFICATION METHOD: E (xi) SEQUENCE DESCRIPTION: SEQ ID NO: 7:

CGCGCAGC ATG CCC GCC AGC GCC CCG CCG CGC CGC CCG CGG CCG CCG CCG   50
        Met Pro Ala Ser Ala Pro Pro Arg Arg Pro Arg Pro Pro Pro
        1               5                   10

CCG TCG CTG TCG CTG CTG CTG GTG CTG CTG GGC CTG GGC GGC CGC CGC    98
Pro Ser Leu Ser Leu Leu Leu Val Leu Leu Gly Leu Gly Gly Arg Arg
15                  20                  25                  30

CTG CGT GCG GAG CCG GGC GAC GGC GCG CAG ACC TGG GCC CGT GTC TCG   146
Leu Arg Ala Glu Pro Gly Asp Gly Ala Gln Thr Trp Ala Arg Val Ser
                35                  40                  45

CGG CCT CCT GCC CCC GAG GCC GCG GGC CTC TTC CAG GGC ACC TTC CCC   194
Arg Pro Pro Ala Pro Glu Ala Ala Gly Leu Phe Gln Gly Thr Phe Pro
            50                  55                  60

GAC GGC TTC CTC TGG GCC GTG GGC AGC GCC GCC TAC CAG ACC GAG GGC   242
Asp Gly Phe Leu Trp Ala Val Gly Ser Ala Ala Tyr Gln Thr Glu Gly
65                  70                  75

GGC TGG CAG CAG CAC GGC AAG GGT GCG TCC ATC TGG GAC ACG TTC ACC   290
Gly Trp Gln Gln His Gly Lys Gly Ala Ser Ile Trp Asp Thr Phe Thr
        80                  85                  90

CAC CAC CCC CTG GCA CCC CCG GGA GAC TCC CGG AAC GCC AGT CTG CCG   338
His His Pro Leu Ala Pro Pro Gly Asp Ser Arg Asn Ala Ser Leu Pro
95                  100                 105                 110

TTG GGC GCC CCG TCG CCG CTG CAG CCC GCC ACC GGG GAC GTA GCC AGC   386
Leu Gly Ala Pro Ser Pro Leu Gln Pro Ala Thr Gly Asp Val Ala Ser
                115                 120                 125

GAC AGC TAC AAC AAC GTC TTC CGC GAC ACG GAG GCG CTG CGC GAG CTC   434
Asp Ser Tyr Asn Asn Val Phe Arg Asp Thr Glu Ala Leu Arg Glu Leu
            130                 135                 140

GGG GTC ACT CAC TAC CGC TTC TCC ATC TCG TGG GCG CGA GTG CTC CCC   482
Gly Val Thr His Tyr Arg Phe Ser Ile Ser Trp Ala Arg Val Leu Pro
        145                 150                 155

AAT GGC AGC GCG GGC GTC CCC AAC CGC GAG GGG CTG CGC TAC TAC CGG   530
Asn Gly Ser Ala Gly Val Pro Asn Arg Glu Gly Leu Arg Tyr Tyr Arg
160                 165                 170

CGC CTG CTG GAG CGG CTG CGG GAG CTG GGC GTG CAG CCC GTG GTC ACC   578
Arg Leu Leu Glu Arg Leu Arg Glu Leu Gly Val Gln Pro Val Val Thr
```

```
                175                 180                 185                 190
CTG TAC CAC TGG GAC CTG CCC CAG CGC CTG CAG GAC GCC TAC GGC GGC      626
Leu Tyr His Trp Asp Leu Pro Gln Arg Leu Gln Asp Ala Tyr Gly Gly
                195                 200                 205

TGG GCC AAC CGC GCC CTG GCC GAC CAC TTC AGG GAT TAC GCG GAG CTC      674
Trp Ala Asn Arg Ala Leu Ala Asp His Phe Arg Asp Tyr Ala Glu Leu
            210                 215                 220

TGC TTC CGC CAC TTC GGC GGT CAG GTC AAG TAC TGG ATC ACC ATC GAC      722
Cys Phe Arg His Phe Gly Gly Gln Val Lys Tyr Trp Ile Thr Ile Asp
        225                 230                 235

AAC CCC TAC GTG GTG GCC TGG CAC GGC TAC GCC ACC GGG CGC CTG GCC      770
Asn Pro Tyr Val Val Ala Trp His Gly Tyr Ala Thr Gly Arg Leu Ala
    240                 245                 250

CCC GGC ATC CGG GGC AGC CCG CGG CTC GGG TAC CTG GTG GCG CAC AAC      818
Pro Gly Ile Arg Gly Ser Pro Arg Leu Gly Tyr Leu Val Ala His Asn
255                 260                 265                 270

CTC CTC CTG GCT CAT GCC AAA GTC TGG CAT CTC TAC AAT ACT TCT TTC      866
Leu Leu Leu Ala His Ala Lys Val Trp His Leu Tyr Asn Thr Ser Phe
                275                 280                 285

CGT CCC ACT CAG GGA GGT CAG GTG TCC ATT GCC CTA AGC TCT CAC TGG      914
Arg Pro Thr Gln Gly Gly Gln Val Ser Ile Ala Leu Ser Ser His Trp
            290                 295                 300

ATC AAT CCT CGA AGA ATG ACC GAC CAC AGC ATC AAA GAA TGT CAA AAA      962
Ile Asn Pro Arg Arg Met Thr Asp His Ser Ile Lys Glu Cys Gln Lys
        305                 310                 315

TCT CTG GAC TTT GTA CTA GGT TGG TTT GCC AAA CCC GTA TTT ATT GAT     1010
Ser Leu Asp Phe Val Leu Gly Trp Phe Ala Lys Pro Val Phe Ile Asp
    320                 325                 330

GGT GAC TAT CCC GAG AGC ATG AAG AAT AAC CTT TCA TCT ATT CTG CCT     1058
Gly Asp Tyr Pro Glu Ser Met Lys Asn Asn Leu Ser Ser Ile Leu Pro
335                 340                 345                 350

GAT TTT ACT GAA TCT GAG AAA AAG TTC ATC AAA GGA ACT GCT GAC TTT     1106
Asp Phe Thr Glu Ser Glu Lys Lys Phe Ile Lys Gly Thr Ala Asp Phe
                355                 360                 365

TTT GCT CTT TGC TTT GGA CCC ACC TTG AGT TTT CAA CTT TTG GAC CCT     1154
Phe Ala Leu Cys Phe Gly Pro Thr Leu Ser Phe Gln Leu Leu Asp Pro
            370                 375                 380

CAC ATG AAG TTC CGC CAA TTG GAA TCT CCC AAC CTG AGG CAA CTG CTT     1202
His Met Lys Phe Arg Gln Leu Glu Ser Pro Asn Leu Arg Gln Leu Leu
        385                 390                 395

TCC TGG ATT GAC CTT GAA TTT AAC CAT CCT CAA ATA TTT ATT GTG GAA     1250
Ser Trp Ile Asp Leu Glu Phe Asn His Pro Gln Ile Phe Ile Val Glu
    400                 405                 410

AAT GGC TGG TTT GTC TCA GGG ACC ACC AAG AGA GAT GAT GCC AAA TAT     1298
Asn Gly Trp Phe Val Ser Gly Thr Thr Lys Arg Asp Asp Ala Lys Tyr
415                 420                 425                 430

ATG TAT TAC CTC AAA AAG TTC ATC ATG GAA ACC TTA AAA GCC ATC AAG     1346
Met Tyr Tyr Leu Lys Lys Phe Ile Met Glu Thr Leu Lys Ala Ile Lys
                435                 440                 445

CTG GAT GGG GTG GAT GTC ATC GGG TAT ACC GCA TGG TCC CTC ATG GAT     1394
Leu Asp Gly Val Asp Val Ile Gly Tyr Thr Ala Trp Ser Leu Met Asp
            450                 455                 460

GGT TTC GAG TGG CAC AGA GGT TAC AGC ATC AGG CGT GGA CTC TTC TAT     1442
Gly Phe Glu Trp His Arg Gly Tyr Ser Ile Arg Arg Gly Leu Phe Tyr
        465                 470                 475

GTT GAC TTT CTA AGC CAG GAC AAG ATG TTG TTG CCA AAG TCT TCA GCC     1490
Val Asp Phe Leu Ser Gln Asp Lys Met Leu Leu Pro Lys Ser Ser Ala
    480                 485                 490

TTG TTC TAC CAA AAG CTG ATA GAG AAA AAT GGC TTC CCT CCT TTA CCT     1538
```

```
Leu Phe Tyr Gln Lys Leu Ile Glu Lys Asn Gly Phe Pro Pro Leu Pro
495                 500                 505                 510

GAA AAT CAG CCC CTA GAA GGG ACA TTT CCC TGT GAC TTT GCT TGG GGA     1586
Glu Asn Gln Pro Leu Glu Gly Thr Phe Pro Cys Asp Phe Ala Trp Gly
                515                 520                 525

GTT GTT GAC AAC TAC ATT CAA GTA AGT CAG CTG ACA AAA CCA ATC AGC     1634
Val Val Asp Asn Tyr Ile Gln Val Ser Gln Leu Thr Lys Pro Ile Ser
                530                 535                 540

AGT CTC ACC AAG CCC TAT CAC TAGTAGATAC CACTCTGTCT CAGTTTACCG         1685
Ser Leu Thr Lys Pro Tyr His
            545

ACCTGAATGT TTACCTGTGG GATGTCCACC ACAGTAAAAG GCTTATTAAA GTGGATGGGG    1745

TTGTGACCAA GAAGAGGAAA TCCTACTGTG TTGACTTTGC TGCCATCCAG CCCCAGATCG    1805

CTTTACTCCA GGAAATGCAC GTTACACATT TTCGCTTCTC CCTGGACTGG GCCCTGATTC    1865

TCCCTCTGGG TAACCAGTCC CAGGTGAACC ACACCATCCT GCAGTACTAT CGCTGCATGG    1925

CCAGCGAGCT TGTCCGTGTC AACATCACCC CAGTGGTGGC CCTGTGGCAG CCTATGGCCC    1985

CGAACCAAGG ACTGCCGCGC CTCCTGGCCA GGCAGGGCGC CTGGGAGAAC CCCTACACTG    2045

CCCTGGCCTT TGCAGAGTAT GCCCGACTGT GCTTTCAAGA GCTCGGCCAT CACGTCAAGC    2105

TTTGGATAAC GATGAATGAG CCGTATACAA GGAATATGAC ATACAGTGCT GGCCACAACC    2165

TTCTGAAGGC CCATGCCCTG GCTTGGCATG TGTACAATGA AAAGTTTAGG CATGCTCAGA    2225

ATGGGAAAAT ATCCATAGCC TTGCAGGCTG ATTGGATAGA ACCTGCCTGC CCTTTCTCCC    2285

AAAAGGACAA AGAGGTGGCC GAGAGAGTTT TGGAATTTGA CATTGGCTGG CTGGCTGAGC    2345

CCATTTTCGG CTCTGGAGAT TATCCATGGG TGATGAGGGA CTGGCTGAAC CAAAGAAACA    2405

ATTTTCTTCT TCCTTATTTC ACTGAAGATG AAAAAAAGCT AATCCAGGGT ACCTTTGACT    2465

TTTTGGCTTT AAGCCATTAT ACCACCATCC TTGTAGACTC AGAAAAAGAA GATCCAATAA    2525

AATACAATGA TTACCTAGAA GTGCAAGAAA TGACCGACAT CACGTGGCTC AACTCCCCCA    2585

GTCAGGTGGC GGTAGTGCCC TGGGGGTTGC GCAAAGTGCT GAACTGGCTG AAGTTCAAGT    2645

ACGGAGACCT CCCCATGTAC ATAATATCCA ACGGAATCGA TGACGGGCTG CATGCTGAGG    2705

ACGACCAGCT GAGGGTGTAT TATATGCAGA ATTACATAAA CGAAGCTCTC AAAGCCCACA    2765

TACTGGATGG TATCAATCTT TGCGGATACT TTGCTTATTC GTTTAACGAC CGCACAGCTC    2825

CGAGGTTTGG CCTCTATCGT TATGCTGCAG ATCAGTTTGA GCCCAAGGCA TCCATGAAAC    2885

ATTACAGGAA ATTATTGAC AGCAATGGTT TCCCGGGCCC AGAAACTCTG GAAAGATTTT     2945

GTCCAGAAGA ATTCACCGTG TGTACTGAGT GCAGTTTTTT TCACACCCGA AAGTCTTTAC    3005

TGGCTTTCAT AGCTTTTCTA TTTTTTGCTT CTATTATTTC TCTCTCCCTT ATATTTTACT    3065

ACTCGAAGAA AGGCAGAAGA AGTTACAAAT AGTTCTGAAC ATTTTTCTAT TCATTCATTT    3125

TGAAATAATT ATGCAGACAC ATCAGCTGTT AACCATTTGC ACCTCTAAGT GTTGTGAAAC    3185

TGTAAATTTC ATACATTTGA CTTCTAGAAA ACATTTTTGT GGCTTATGAC AGAGGTTTTG    3245

AAATGGGCAT AGGTGATCGT AAAATATTGA ATAATGCGAA TAGTGCCTGA ATTTGTTCTC    3305

TTTTTGGGTG ATTAAAAAAC TGACAGGCAC TATAATTTCT GTAACACACT AACAAAAGCA    3365

TGAAAAATAG GAACCACACC AATGCAACAT TTGTGCAGAA ATTTGAATGA CAAGATTAGG    3425

AATATTTTCT                                                            3435
```

(2) INFORMATION FOR SEQ ID NO: 8:

(i) SEQUENCE CHARACTERISTICS:

```
    (A) LENGTH: 5032
    (B) TYPE: nucleic acid
    (C) STRANDEDNESS: double
    (D) TOPOLOGY: linear (ii) MOLECULE TYPE: cDNA to mRNA (vi) ORIGINAL SOURCE:
    (A) ORGANISM: mouse (vii) IMMEDIATE SOURCE:
    (A) LIBRARY: kidney (ix) FEATURE:
    (A) NAME/KEY: CDS
    (B) LOCATION: 9..3060
    (C) IDENTIFICATION METHOD: E (xi) SEQUENCE DESCRIPTION: SEQ ID NO: 8:
```

| | | | | | | | | | | | | | | | | |
|---|---|---|---|---|---|---|---|---|---|---|---|---|---|---|---|---|
| CCTCCCGGCT | CCCGCAGC | ATG | CTA | GCC | CGC | GCC | CCT | CCT | CGC | CGC | CCG | CCG | | | | 51 |
| | | Met | Leu | Ala | Arg | Ala | Pro | Pro | Arg | Arg | Pro | Pro | | | | |
| | | 1 | | 5 | | | | | | 10 | | | | | | |
| CGG | CTG | GTG | CTG | CTC | CGT | TTG | CTG | TTG | CTG | CAT | CTG | CTG | CTC | GCC | | 99 |
| Arg | Leu | Val | Leu | Leu | Arg | Leu | Leu | Leu | Leu | His | Leu | Leu | Leu | Ala | | |
| | | | 15 | | | | 20 | | | | | 25 | | | | |
| CTG | CGC | GCC | CGC | TGC | CTG | AGC | GCT | GAG | CCG | GGT | CAG | GGC | GCG | CAG | ACC | 147 |
| Leu | Arg | Ala | Arg | Cys | Leu | Ser | Ala | Glu | Pro | Gly | Gln | Gly | Ala | Gln | Thr | |
| | | 30 | | | | | 35 | | | | | 40 | | | | |
| TGG | GCT | CGC | TTC | GCG | CGC | GCT | CCT | GCC | CCA | GAG | GCC | GCT | GGC | CTC | CTC | 195 |
| Trp | Ala | Arg | Phe | Ala | Arg | Ala | Pro | Ala | Pro | Glu | Ala | Ala | Gly | Leu | Leu | |
| | 45 | | | | | 50 | | | | | 55 | | | | | |
| CAC | GAC | ACC | TTC | CCC | GAC | GGT | TTC | CTC | TGG | GCG | GTA | GGC | AGC | GCC | GCC | 243 |
| His | Asp | Thr | Phe | Pro | Asp | Gly | Phe | Leu | Trp | Ala | Val | Gly | Ser | Ala | Ala | |
| 60 | | | | | 65 | | | | | 70 | | | | | 75 | |
| TAT | CAG | ACC | GAG | GGC | GGC | TGG | CGA | CAG | CAC | GGC | AAA | GGC | GCG | TCC | ATC | 291 |
| Tyr | Gln | Thr | Glu | Gly | Gly | Trp | Arg | Gln | His | Gly | Lys | Gly | Ala | Ser | Ile | |
| | | | | 80 | | | | | 85 | | | | | 90 | | |
| TGG | GAC | ACT | TTC | ACC | CAT | CAC | TCT | GGG | GCG | GCC | CCG | TCC | GAC | TCC | CCG | 339 |
| Trp | Asp | Thr | Phe | Thr | His | His | Ser | Gly | Ala | Ala | Pro | Ser | Asp | Ser | Pro | |
| | | | 95 | | | | | 100 | | | | | 105 | | | |
| ATC | GTC | GTG | GCG | CCG | TCG | GGT | GCC | CCG | TCG | CCT | CCC | CTG | TCC | TCC | ACT | 387 |
| Ile | Val | Val | Ala | Pro | Ser | Gly | Ala | Pro | Ser | Pro | Pro | Leu | Ser | Ser | Thr | |
| | | 110 | | | | | 115 | | | | | 120 | | | | |
| GGA | GAT | GTG | GCC | AGC | GAT | AGT | TAC | AAC | AAC | GTC | TAC | CGC | GAC | ACA | GAG | 435 |
| Gly | Asp | Val | Ala | Ser | Asp | Ser | Tyr | Asn | Asn | Val | Tyr | Arg | Asp | Thr | Glu | |
| | 125 | | | | | 130 | | | | | 135 | | | | | |
| GGG | CTG | CGC | GAA | CTG | GGG | GTC | ACC | CAC | TAC | CGC | TTC | TCC | ATA | TCG | TGG | 483 |
| Gly | Leu | Arg | Glu | Leu | Gly | Val | Thr | His | Tyr | Arg | Phe | Ser | Ile | Ser | Trp | |
| 140 | | | | | 145 | | | | | 150 | | | | | 155 | |
| GCG | CGG | GTG | CTC | CCC | AAT | GGC | ACC | GCG | GGC | ACT | CCC | AAC | CGC | GAG | GGG | 531 |
| Ala | Arg | Val | Leu | Pro | Asn | Gly | Thr | Ala | Gly | Thr | Pro | Asn | Arg | Glu | Gly | |
| | | | 160 | | | | | 165 | | | | | 170 | | | |
| CTG | CGC | TAC | TAC | CGG | CGG | CTG | CTG | GAG | CGG | CTG | CGG | GAG | CTG | GGC | GTG | 579 |
| Leu | Arg | Tyr | Tyr | Arg | Arg | Leu | Leu | Glu | Arg | Leu | Arg | Glu | Leu | Gly | Val | |
| | | 175 | | | | | 180 | | | | | 185 | | | | |
| CAG | CCG | GTG | GTT | ACC | CTG | TAC | CAT | TGG | GAC | CTG | CCA | CAG | CGC | CTG | CAG | 627 |
| Gln | Pro | Val | Val | Thr | Leu | Tyr | His | Trp | Asp | Leu | Pro | Gln | Arg | Leu | Gln | |
| | 190 | | | | | 195 | | | | | 200 | | | | | |
| GAC | ACC | TAT | GGC | GGA | TGG | GCC | AAT | CGC | GCC | CTG | GCC | GAC | CAT | TTC | AGG | 675 |
| Asp | Thr | Tyr | Gly | Gly | Trp | Ala | Asn | Arg | Ala | Leu | Ala | Asp | His | Phe | Arg | |
| 205 | | | | | 210 | | | | | 215 | | | | | | |
| GAT | TAT | GCC | GAG | CTC | TGC | TTC | CGC | CAC | TTC | GGT | GGT | CAG | GTC | AAG | TAC | 723 |
| Asp | Tyr | Ala | Glu | Leu | Cys | Phe | Arg | His | Phe | Gly | Gly | Gln | Val | Lys | Tyr | |
| 220 | | | | | 225 | | | | | 230 | | | | | 235 | |

```
TGG ATC ACC ATT GAC AAC CCC TAC GTG GTG GCC TGG CAC GGG TAT GCC    771
Trp Ile Thr Ile Asp Asn Pro Tyr Val Val Ala Trp His Gly Tyr Ala
            240                 245                 250

ACC GGG CGC CTG GCC CCG GGC GTG AGG GGC AGC TCC AGG CTC GGG TAC    819
Thr Gly Arg Leu Ala Pro Gly Val Arg Gly Ser Ser Arg Leu Gly Tyr
            255                 260                 265

CTG GTT GCC CAC AAC CTA CTT TTG GCT CAT GCC AAA GTC TGG CAT CTC    867
Leu Val Ala His Asn Leu Leu Leu Ala His Ala Lys Val Trp His Leu
            270                 275                 280

TAC AAC ACC TCT TTC CGC CCC ACA CAG GGA GGC CGG GTG TCT ATC GCC    915
Tyr Asn Thr Ser Phe Arg Pro Thr Gln Gly Gly Arg Val Ser Ile Ala
        285                 290                 295

TTA AGC TCC CAT TGG ATC AAT CCT CGA AGA ATG ACT GAC TAT AAT ATC    963
Leu Ser Ser His Trp Ile Asn Pro Arg Arg Met Thr Asp Tyr Asn Ile
300                 305                 310                 315

AGA GAA TGC CAG AAG TCT CTT GAC TTT GTG CTA GGC TGG TTT GCC AAA   1011
Arg Glu Cys Gln Lys Ser Leu Asp Phe Val Leu Gly Trp Phe Ala Lys
                320                 325                 330

CCC ATA TTT ATT GAT GGC GAC TAC CCA GAG AGT ATG AAG AAC AAC CTC   1059
Pro Ile Phe Ile Asp Gly Asp Tyr Pro Glu Ser Met Lys Asn Asn Leu
            335                 340                 345

TCG TCT CTT CTG CCT GAT TTT ACT GAA TCT GAG AAG AGG CTC ATC AGA   1107
Ser Ser Leu Leu Pro Asp Phe Thr Glu Ser Glu Lys Arg Leu Ile Arg
            350                 355                 360

GGA ACT GCT GAC TTT TTT GCT CTC TCC TTC GGA CCA ACC TTG AGC TTT   1155
Gly Thr Ala Asp Phe Phe Ala Leu Ser Phe Gly Pro Thr Leu Ser Phe
            365                 370                 375

CAG CTA TTG GAC CCT AAC ATG AAG TTC CGC CAA TTG GAG TCT CCC AAC   1203
Gln Leu Leu Asp Pro Asn Met Lys Phe Arg Gln Leu Glu Ser Pro Asn
380                 385                 390                 395

CTG AGG CAG CTT CTG TCT TGG ATA GAT CTG GAA TAT AAC CAC CCT CCA   1251
Leu Arg Gln Leu Leu Ser Trp Ile Asp Leu Glu Tyr Asn His Pro Pro
                400                 405                 410

ATA TTT ATT GTG GAA AAT GGC TGG TTT GTC TCG GGA ACC ACC AAA AGG   1299
Ile Phe Ile Val Glu Asn Gly Trp Phe Val Ser Gly Thr Thr Lys Arg
            415                 420                 425

GAT GAT GCC AAA TAT ATG TAT TAT CTC AAG AAG TTC ATA ATG GAA ACC   1347
Asp Asp Ala Lys Tyr Met Tyr Tyr Leu Lys Lys Phe Ile Met Glu Thr
            430                 435                 440

TTA AAA GCA ATC AGA CTG GAT GGG GTC GAC GTC ATT GGG TAC ACC GCG   1395
Leu Lys Ala Ile Arg Leu Asp Gly Val Asp Val Ile Gly Tyr Thr Ala
            445                 450                 455

TGG TCG CTC ATG GAC GGT TTC GAG TGG CAT AGG GGC TAC AGC ATC CGG   1443
Trp Ser Leu Met Asp Gly Phe Glu Trp His Arg Gly Tyr Ser Ile Arg
460                 465                 470                 475

CGA GGA CTC TTC TAC GTT GAC TTT CTG AGT CAG GAC AAG GAG CTG TTG   1491
Arg Gly Leu Phe Tyr Val Asp Phe Leu Ser Gln Asp Lys Glu Leu Leu
                480                 485                 490

CCA AAG TCT TCG GCC TTG TTC TAC CAA AAG CTG ATA GAG GAC AAT GGC   1539
Pro Lys Ser Ser Ala Leu Phe Tyr Gln Lys Leu Ile Glu Asp Asn Gly
            495                 500                 505

TTT CCT CCT TTA CCT GAA AAC CAG CCC CTT GAA GGG ACA TTT CCC TGT   1587
Phe Pro Pro Leu Pro Glu Asn Gln Pro Leu Glu Gly Thr Phe Pro Cys
            510                 515                 520

GAC TTT GCT TGG GGA GTT GTT GAC AAC TAC GTT CAA GTG GAC ACT ACT   1635
Asp Phe Ala Trp Gly Val Val Asp Asn Tyr Val Gln Val Asp Thr Thr
            525                 530                 535

CTC TCT CAG TTT ACT GAC CCG AAT GTC TAT CTG TGG GAT GTG CAT CAC   1683
Leu Ser Gln Phe Thr Asp Pro Asn Val Tyr Leu Trp Asp Val His His
```

```
540              545              550              555

AGT AAG AGG CTT ATT AAA GTA GAC GGG GTT GTA GCC AAG AAG AGA AAA         1731
Ser Lys Arg Leu Ile Lys Val Asp Gly Val Val Ala Lys Lys Arg Lys
            560              565              570

CCT TAC TGT GTT GAT TTC TCT GCC ATC CGG CCT CAG ATA ACC TTA CTT         1779
Pro Tyr Cys Val Asp Phe Ser Ala Ile Arg Pro Gln Ile Thr Leu Leu
        575              580              585

CGA GAA ATG CGG GTC ACC CAC TTT CGC TTC TCC CTG GAC TGG GCC CTG         1827
Arg Glu Met Arg Val Thr His Phe Arg Phe Ser Leu Asp Trp Ala Leu
            590              595              600

ATC TTG CCT CTG GGT AAC CAG ACC CAA GTG AAC CAC ACG GTT CTG CAC         1875
Ile Leu Pro Leu Gly Asn Gln Thr Gln Val Asn His Thr Val Leu His
        605              610              615

TTC TAC CGC TGC ATG ATC AGC GAG CTG GTG CAC GCC AAC ATC ACT CCA         1923
Phe Tyr Arg Cys Met Ile Ser Glu Leu Val His Ala Asn Ile Thr Pro
620              625              630              635

GTG GTG GCC CTG TGG CAG CCA GCA GCC CCG CAC CAA GGC CTG CCA CAT         1971
Val Val Ala Leu Trp Gln Pro Ala Ala Pro His Gln Gly Leu Pro His
            640              645              650

GCC CTT GCA AAA CAT GGG GCC TGG GAG AAC CCG CAC ACT GCT CTG GCG         2019
Ala Leu Ala Lys His Gly Ala Trp Glu Asn Pro His Thr Ala Leu Ala
        655              660              665

TTT GCA GAC TAC GCA AAC CTG TGT TTT AAA GAG TTG GGT CAC TGG GTC         2067
Phe Ala Asp Tyr Ala Asn Leu Cys Phe Lys Glu Leu Gly His Trp Val
            670              675              680

AAT CTC TGG ATC ACC ATG AAC GAG CCA AAC ACA CGG AAC ATG ACC TAT         2115
Asn Leu Trp Ile Thr Met Asn Glu Pro Asn Thr Arg Asn Met Thr Tyr
        685              690              695

CGT GCC GGG CAC CAC CTC CTG AGA GCC CAT GCC TTG GCT TGG CAT CTG         2163
Arg Ala Gly His His Leu Leu Arg Ala His Ala Leu Ala Trp His Leu
700              705              710              715

TAC GAT GAC AAG TTT AGG GCG GCT CAG AAA GGC AAA ATA TCC ATC GCC         2211
Tyr Asp Asp Lys Phe Arg Ala Ala Gln Lys Gly Lys Ile Ser Ile Ala
            720              725              730

TTG CAG GCT GAC TGG ATA GAA CCG GCC TGC CCT TTC TCT CAA AAT GAC         2259
Leu Gln Ala Asp Trp Ile Glu Pro Ala Cys Pro Phe Ser Gln Asn Asp
        735              740              745

AAA GAA GTG GCC GAG AGA GTT TTG GAA TTT GAT ATA GGC TGG CTG GCA         2307
Lys Glu Val Ala Glu Arg Val Leu Glu Phe Asp Ile Gly Trp Leu Ala
            750              755              760

GAG CCT ATT TTT GGT TCC GGA GAT TAT CCA CGT GTG ATG AGG GAC TGG         2355
Glu Pro Ile Phe Gly Ser Gly Asp Tyr Pro Arg Val Met Arg Asp Trp
        765              770              775

CTG AAC CAA AAA AAC AAT TTT CTT TTG CCC TAT TTC ACC GAA GAT GAA         2403
Leu Asn Gln Lys Asn Asn Phe Leu Leu Pro Tyr Phe Thr Glu Asp Glu
780              785              790              795

AAA AAG CTA GTC CGG GGT TCC TTT GAC TTC CTG GCG GTG AGT CAT TAC         2451
Lys Lys Leu Val Arg Gly Ser Phe Asp Phe Leu Ala Val Ser His Tyr
            800              805              810

ACC ACC ATT CTG GTA GAC TGG GAA AAG GAG GAT CCG ATG AAA TAC AAC         2499
Thr Thr Ile Leu Val Asp Trp Glu Lys Glu Asp Pro Met Lys Tyr Asn
        815              820              825

GAT TAC TTG GAG GTA CAG GAG ATG ACT GAC ATC ACA TGG CTC AAC TCT         2547
Asp Tyr Leu Glu Val Gln Glu Met Thr Asp Ile Thr Trp Leu Asn Ser
            830              835              840

CCC AGT CAG GTG GCA GTG GTG CCT TGG GGG CTG CGC AAA GTG CTC AAC         2595
Pro Ser Gln Val Ala Val Val Pro Trp Gly Leu Arg Lys Val Leu Asn
        845              850              855

TGG CTA AGG TTC AAG TAC GGA GAC CTC CCG ATG TAT GTG ACA GCC AAT         2643
```

-continued

```
Trp Leu Arg Phe Lys Tyr Gly Asp Leu Pro Met Tyr Val Thr Ala Asn
860                 865                 870                 875

GGA ATC GAT GAT GAC CCC CAC GCC GAG CAA GAC TCA CTG AGG ATC TAT    2691
Gly Ile Asp Asp Asp Pro His Ala Glu Gln Asp Ser Leu Arg Ile Tyr
                880                 885                 890

TAT ATT AAG AAT TAT GTG AAT GAG GCT CTG AAA GCC TAC GTG TTG GAC    2739
Tyr Ile Lys Asn Tyr Val Asn Glu Ala Leu Lys Ala Tyr Val Leu Asp
            895                 900                 905

GAC ATC AAC CTT TGT GGC TAC TTT GCG TAT TCA CTT AGT GAT CGC TCA    2787
Asp Ile Asn Leu Cys Gly Tyr Phe Ala Tyr Ser Leu Ser Asp Arg Ser
        910                 915                 920

GCT CCC AAG TCT GGC TTT TAT CGA TAT GCT GCG AAT CAG TTT GAG CCC    2835
Ala Pro Lys Ser Gly Phe Tyr Arg Tyr Ala Ala Asn Gln Phe Glu Pro
    925                 930                 935

AAA CCA TCT ATG AAA CAT TAC AGG AGA ATT ATT GAC AGC AAT GGC TTC    2883
Lys Pro Ser Met Lys His Tyr Arg Arg Ile Ile Asp Ser Asn Gly Phe
940                 945                 950                 955

CTG GGT TCT GGA ACA CTG GGA AGG TTT TGT CCA GAA GAA TAC ACT GTG    2931
Leu Gly Ser Gly Thr Leu Gly Arg Phe Cys Pro Glu Glu Tyr Thr Val
                960                 965                 970

TGC ACC GAA TGT GGA TTT TTT CAA ACC CGG AAG TCT TTG CTG GTC TTC    2979
Cys Thr Glu Cys Gly Phe Phe Gln Thr Arg Lys Ser Leu Leu Val Phe
            975                 980                 985

ATC TCG TTT CTT GTT TTT ACT TTT ATT ATT TCT CTT GCT CTC ATT TTT    3027
Ile Ser Phe Leu Val Phe Thr Phe Ile Ile Ser Leu Ala Leu Ile Phe
        990                 995                 1000

CAC TAC TCC AAG AAA GGC CAG AGA AGT TAT AAG TAATGTGAAC GTCTGCCTGG  3080
His Tyr Ser Lys Lys Gly Gln Arg Ser Tyr Lys
    1005                1010

CCATTCGCTT TGGGATCAAG ATGTACACGC CGTCAGCCGT TGCACCTCT CTGTGTTGTG   3140

AGCCGCATTC CACACATTTC GATTCTAGAA AACCCTTTTT GTCATGGGTG GTAGAGGTTT  3200

TAAACAGGAA TTGGTGAGAA TAAAATATTG CAGGGTGAAT GGTATCTGAA TCTGCTCTCT  3260

TTGGTGGCAA TTACGGAATT ATACTCACCA CAGTTTCTAC AGTGCCCCGG AATGGAAGGC  3320

ATAGAATACG GTAGGGATAA CAGTGCCAAG CAGACAGAAG TTTAAAGAAC AACTTTAGGG  3380

ACTTGTTTAT CCATGGCCAT TTTTAAATTC ACTCCTGTTG GGGAGTAACA CTCTCTCAAT  3440

TACCATCTTA ACACCTGGAC TTTACCTGAT CCAGTTTTAC AAGGTGAAGT AGAAAAATAT  3500

CCAGTAAAGG TGGCCAAGAG CCCTGAGTCC AGAGCAGCCC ATTAAGAAGC ACTATTCCTA  3560

CCAAATGCTG CTAATGTCAA TTTACAAATA TACTTAGAAA GCACATTATG GACATTTGTA  3620

TTCTTGTGAA TGTTTTTGAG GTGTGCCCTA AACCCCAGAT CCTTGAGGGC TTTCTCTTAC  3680

CAACTTTCCT TTCAGAGCCT GCTTGTTGGA GATTCTTCCC CAGCCCCCTT CCCCTTTCCC  3740

TCTTGCTCTG CCCCACCTCG CTCCACCCAG CTTGCTCCAG CCCAAAGATT CTTTATTTGT  3800

TTCTCATTAC CGAAGGTTGT GAGCCACCAT GTGGTTTCTG GGATTTGAAC TCATGACCTC  3860

CGGAGGAGCT GTCATGCTCT TAACCAGCCC ATGTTGAAGA TTCTTTTGAT AAATATTCAC  3920

AAAAAATAAA GATGAGCCAT GAGCTGTTGG CCTCTTCGGA AGCGGAAACT GAGTGATTTG  3980

ATTGAACATC CTTTTATCTT TGACCAGACC TTGGAATGAA TGCAATGACC TTTCCCACAG  4040

GAAGAAGGAG GAGCTCTCAG TCAAACTGTA AAGAATGCCT CTTCAGAATA TGCTGTCAGT  4100

GCTTGGATGC CATGATGTTC AACTTTCTTA GTCGATCCGG CAGCAATCAC AGTGTGAGCA  4160

CACTGGGAAC CTGTCCTTGC GGCCGCCGAG ATCTACCGTG TGCTTCTGTG AAGAGGCTTT  4220

GACGTAGCCC CTCTTTGAGC TCTTACACCA TGCTACTGAC TTCTAGAAAG GCTAATTAGG  4280
```

-continued

```
TCTTCTTCTA CACCTAATAC CCTAAGTCTT ACTGACTCTC ACGGGAGAAG TCTCTGTGCT      4340

ACACCTGAGT GGTCTTATTG ATAACCCTGA TACCAGATCA GGCAAGATAA ATCCGTCATA      4400

GCAGGCATGG CTACCCTTGC TGCCACAGGG TCACAGCACA TAGCTCATCA CCCTGTTATT      4460

CTTCATCTTG CAATGTGGTA TGGTTTTCCT GGTGAATGAT CAGCTTTTGC TGTGGTATTC      4520

TTTATACATC TGGACTTATT ATTGAAATCA AATGCTATAG AATCAATAGT TTATTTTATG      4580

TCTATTTTTC TTGATCGCAG AGTAATATAT ATTAATTGTA AAAATTTAA GAAACAAAAA       4640

CTATATGTAA AGAAAAAATT ATAATATAAT ACAGAGATGC TGCTGACAGT TCCTATGTGT      4700

TGTGTTTTGT ATACTGAGAT CATGTGATAC GTAGGCATAC ATCTTCTTGG GTTTTTTTGT     4760

TTTTGTTTTT TGTTTGTTT TGTTTTGTTT TGGTTTTTTG AGATAGGGTT TCTCTGTATA       4820

GCCCTGGCTG TCCTGGAACT CACTTTGCAG ACCAGGCTAG CCTCAAACTC TTATTCATTT      4880

TTACTGAAGT AATTTTTCTG TCATTAGTCT TCAAGAGCAA AACTTTAATA GTTATGGAGA     4940

ATATTGCCAG AACAGCTCAA AACTGTTTTA TTTGTTGGTC CAATTTCCCA TTAATTAGTT      5000

CAATAATAAA TATCATTTAG AAATAAAAAA AA                                    5032
```

(2) INFORMATION FOR SEQ ID NO: 9:

(i) SEQUENCE CHARACTERISTICS:
        (A) LENGTH: 1650
        (B) TYPE: nucleic acid
        (C) STRANDEDNESS: double
        (D) TOPOLOGY: linear (ii) MOLECULE TYPE: cDNA to mRNA (vi) ORIGINAL SOURCE:
        (A) ORGANISM: mouse (vii) IMMEDIATE SOURCE:
        (A) LIBRARY: kidney (ix) FEATURE:
        (A) NAME/KEY: CDS
        (B) LOCATION: 1..1650
        (C) IDENTIFICATION METHOD: E (xi) SEQUENCE DESCRIPTION: SEQ ID NO: 9:

```
ATG CTA GCC CGC GCC CCT CCT CGC CGC CCG CCG CGG CTG GTG CTG CTC        48
Met Leu Ala Arg Ala Pro Pro Arg Arg Pro Pro Arg Leu Val Leu Leu
 1               5                  10                  15

CGT TTG CTG TTG CTG CAT CTG CTG CTC GCC CTG CGC GCC CGC TGC            96
Arg Leu Leu Leu Leu His Leu Leu Leu Ala Leu Arg Ala Arg Cys
             20                  25                  30

CTG AGC GCT GAG CCG GGT CAG GGC GCG CAG ACC TGG GCT CGC TTC GCG       144
Leu Ser Ala Glu Pro Gly Gln Gly Ala Gln Thr Trp Ala Arg Phe Ala
         35                  40                  45

CGC GCT CCT GCC CCA GAG GCC GCT GGC CTC CTC CAC GAC ACC TTC CCC       192
Arg Ala Pro Ala Pro Glu Ala Ala Gly Leu Leu His Asp Thr Phe Pro
     50                  55                  60

GAC GGT TTC CTC TGG GCG GTA GGC AGC GCC GCC TAT CAG ACC GAG GGC       240
Asp Gly Phe Leu Trp Ala Val Gly Ser Ala Ala Tyr Gln Thr Glu Gly
 65                  70                  75                  80

GGC TGG CGA CAG CAC GGC AAA GGC GCG TCC ATC TGG GAC ACT TTC ACC       288
Gly Trp Arg Gln His Gly Lys Gly Ala Ser Ile Trp Asp Thr Phe Thr
                 85                  90                  95

CAT CAC TCT GGG GCG GCC CCG TCC GAC TCC CCG ATC GTC GTG GCG CCG       336
His His Ser Gly Ala Ala Pro Ser Asp Ser Pro Ile Val Val Ala Pro
            100                 105                 110

TCG GGT GCC CCG TCG CCT CCC CTG TCC TCC ACT GGA GAT GTG GCC AGC       384
```

```
Ser Gly Ala Pro Ser Pro Pro Leu Ser Ser Thr Gly Asp Val Ala Ser
        115                 120                 125

GAT AGT TAC AAC AAC GTC TAC CGC GAC ACA GAG GGG CTG CGC GAA CTG         432
Asp Ser Tyr Asn Asn Val Tyr Arg Asp Thr Glu Gly Leu Arg Glu Leu
    130                 135                 140

GGG GTC ACC CAC TAC CGC TTC TCC ATA TCG TGG GCG CGG GTG CTC CCC         480
Gly Val Thr His Tyr Arg Phe Ser Ile Ser Trp Ala Arg Val Leu Pro
145                 150                 155                 160

AAT GGC ACC GCG GGC ACT CCC AAC CGC GAG GGG CTG CGC TAC TAC CGG         528
Asn Gly Thr Ala Gly Thr Pro Asn Arg Glu Gly Leu Arg Tyr Tyr Arg
                165                 170                 175

CGG CTG CTG GAG CGG CTG CGG GAG CTG GGC GTG CAG CCG GTG GTT ACC         576
Arg Leu Leu Glu Arg Leu Arg Glu Leu Gly Val Gln Pro Val Val Thr
            180                 185                 190

CTG TAC CAT TGG GAC CTG CCA CAG CGC CTG CAG GAC ACC TAT GGC GGA         624
Leu Tyr His Trp Asp Leu Pro Gln Arg Leu Gln Asp Thr Tyr Gly Gly
        195                 200                 205

TGG GCC AAT CGC GCC CTG GCC GAC CAT TTC AGG GAT TAT GCC GAG CTC         672
Trp Ala Asn Arg Ala Leu Ala Asp His Phe Arg Asp Tyr Ala Glu Leu
    210                 215                 220

TGC TTC CGC CAC TTC GGT GGT CAG GTC AAG TAC TGG ATC ACC ATT GAC         720
Cys Phe Arg His Phe Gly Gly Gln Val Lys Tyr Trp Ile Thr Ile Asp
225                 230                 235                 240

AAC CCC TAC GTG GTG GCC TGG CAC GGG TAT GCC ACC GGG CGC CTG GCC         768
Asn Pro Tyr Val Val Ala Trp His Gly Tyr Ala Thr Gly Arg Leu Ala
                245                 250                 255

CCG GGC GTG AGG GGC AGC TCC AGG CTC GGG TAC CTG GTT GCC CAC AAC         816
Pro Gly Val Arg Gly Ser Ser Arg Leu Gly Tyr Leu Val Ala His Asn
            260                 265                 270

CTA CTT TTG GCT CAT GCC AAA GTC TGG CAT CTC TAC AAC ACC TCT TTC         864
Leu Leu Leu Ala His Ala Lys Val Trp His Leu Tyr Asn Thr Ser Phe
        275                 280                 285

CGC CCC ACA CAG GGA GGC CGG GTG TCT ATC GCC TTA AGC TCC CAT TGG         912
Arg Pro Thr Gln Gly Gly Arg Val Ser Ile Ala Leu Ser Ser His Trp
    290                 295                 300

ATC AAT CCT CGA AGA ATG ACT GAC TAT AAT ATC AGA GAA TGC CAG AAG         960
Ile Asn Pro Arg Arg Met Thr Asp Tyr Asn Ile Arg Glu Cys Gln Lys
305                 310                 315                 320

TCT CTT GAC TTT GTG CTA GGC TGG TTT GCC AAA CCC ATA TTT ATT GAT        1008
Ser Leu Asp Phe Val Leu Gly Trp Phe Ala Lys Pro Ile Phe Ile Asp
                325                 330                 335

GGC GAC TAC CCA GAG AGT ATG AAG AAC AAC CTC TCG TCT CTT CTG CCT        1056
Gly Asp Tyr Pro Glu Ser Met Lys Asn Asn Leu Ser Ser Leu Leu Pro
            340                 345                 350

GAT TTT ACT GAA TCT GAG AAG AGG CTC ATC AGA GGA ACT GCT GAC TTT        1104
Asp Phe Thr Glu Ser Glu Lys Arg Leu Ile Arg Gly Thr Ala Asp Phe
        355                 360                 365

TTT GCT CTC TGC TTC GGA CCA ACC TTG AGC TTT CAG CTA TTG GAC CCT        1152
Phe Ala Leu Cys Phe Gly Pro Thr Leu Ser Phe Gln Leu Leu Asp Pro
    370                 375                 380

AAC ATG AAG TTC GCC CAA TTG GAG TCT CCC AAC CTG AGG CAG CTT CTS        1200
Asn Met Lys Phe Arg Gln Leu Glu Ser Pro Asn Leu Arg Gln Leu Leu
385                 390                 395                 400

TCT TGG ATA GAT CTG GAA TAT AAC CAC CCT CCA ATA TTT ATT GTG GAA        1248
Ser Trp Ile Asp Leu Glu Tyr Asn His Pro Pro Ile Phe Ile Val Glu
                405                 410                 415

AAT GGC TGG TTT GTC TCG GGA ACC ACC AAA AGG GAT GAT GCC AAA TAT        1296
Asn Gly Trp Phe Val Ser Gly Thr Thr Lys Arg Asp Asp Ala Lys Tyr
            420                 425                 430
```

```
ATG TAT TAT CTC AAG AAG TTC ATA ATG GAA ACC TTA AAA GCA ATC AGA        1344
Met Tyr Tyr Leu Lys Lys Phe Ile Met Glu Thr Leu Lys Ala Ile Arg
        435                 440                 445

CTG GAT GGG GTC GAC GTC ATT GGG TAC ACC GCG TGG TCG CTC ATG GAC        1392
Leu Asp Gly Val Asp Val Ile Gly Tyr Thr Ala Trp Ser Leu Met Asp
450                 455                 460

GGT TTC GAG TGG CAT AGG GGC TAC AGC ATC CGG CGA GGA CTC TTC TAC        1440
Gly Phe Glu Trp His Arg Gly Tyr Ser Ile Arg Arg Gly Leu Phe Tyr
465                 470                 475                 480

GTT GAC TTT CTG AGT CAG GAC AAG GAG CTG TTG CCA AAG TCT TCG GCC        1488
Val Asp Phe Leu Ser Gln Asp Lys Glu Leu Leu Pro Lys Ser Ser Ala
                485                 490                 495

TTG TTC TAC CAA AAG CTG ATA GAG GAC AAT GGC TTT CCT CCT TTA CCT        1536
Leu Phe Tyr Gln Lys Leu Ile Glu Asp Asn Gly Phe Pro Pro Leu Pro
        500                 505                 510

GAA AAC CAG CCC CTT GAA GGG ACA TTT CCC TGT GAC TTT GCT TGG GGA        1584
Glu Asn Gln Pro Leu Glu Gly Thr Phe Pro Cys Asp Phe Ala Trp Gly
        515                 520                 525

GTT GTT GAC AAC TAC GTA CAA GTA AGT CCT TTG ACA AAA CCC AGT GTC        1632
Val Val Asp Asn Tyr Val Gln Val Ser Pro Leu Thr Lys Pro Ser Val
530                 535                 540

GGC CTC TTG CTT CCT CAC                                                1650
Gly Leu Leu Leu Pro His
545             550

(2) INFORMATION FOR SEQ ID NO: 10:

(i) SEQUENCE CHARACTERISTICS:
        (A) LENGTH: 3460
        (B) TYPE: nucleic acid
        (C) STRANDEDNESS: double
        (D) TOPOLOGY: linear (ii) MOLECULE TYPE: cDNA to mRNA (vi) ORIGINAL SOURCE:
        (A) ORGANISM: human (vii) IMMEDIATE SOURCE:
        (A) LIBRARY: pancreas (ix) FEATURE:
        (A) NAME/KEY: CDS
        (B) LOCATION: 60..3107
        (C) IDENTIFICATION METHOD: E (xi) SEQUENCE DESCRIPTION: SEQ ID NO: 10:

CAGGGAATGA ATGGATTTTC TTCAGCACTG ATGAAATAAC CACACGCTAT AGGAATACA      59

ATG TCC AAC GGG GGA TTG CAA AGA TCT GTC ATC CTG TCA GCA CTT ATT        107
Met Ser Asn Gly Gly Leu Gln Arg Ser Val Ile Leu Ser Ala Leu Ile
1               5                   10                  15

CTG CTA CGA GCT GTT ACT GGA TTC TCT GGA GAT GGA AGA GCT ATA TGG        155
Leu Leu Arg Ala Val Thr Gly Phe Ser Gly Asp Gly Arg Ala Ile Trp
                20                  25                  30

TCT AAA AAT CCT AAT TTT ACT CCG GTA AAT GAA AGT CAG CTG TTT CTC        203
Ser Lys Asn Pro Asn Phe Thr Pro Val Asn Glu Ser Gln Leu Phe Leu
            35                  40                  45

TAT GGC ACT TTC CCT AAA AAC TTT TTC TGG GGT ATT GGG ACT GGA GCA        251
Tyr Gly Thr Phe Pro Lys Asn Phe Phe Trp Gly Ile Gly Thr Gly Ala
        50                  55                  60

TTG CAA GTG GAA GGG AGT TGG AAG AAG GAT GGA AAA GGA CCT TCT ATA        299
Leu Gln Val Glu Gly Ser Trp Lys Lys Asp Gly Lys Gly Pro Ser Ile
65                  70                  75                  80

TGG GAT CAT TTC ATC CAC ACA CAC CTT AAA AAT GTC AGC AGC ACG AAT        347
```

-continued

```
                Trp Asp His Phe Ile His Thr His Leu Lys Asn Val Ser Ser Thr Asn
                                85                  90                  95

GGT TCC AGT GAC AGT TAT ATT TTT CTG GAA AAA GAC TTA TCA GCC CTG              395
Gly Ser Ser Asp Ser Tyr Ile Phe Leu Glu Lys Asp Leu Ser Ala Leu
            100                 105                 110

GAT TTT ATA GGA GTT TCT TTT TAT CAA TTT TCA ATT TCC TGG CCA AGG              443
Asp Phe Ile Gly Val Ser Phe Tyr Gln Phe Ser Ile Ser Trp Pro Arg
            115                 120                 125

CTT TTC CCC GAT GGA ATA GTA ACA GTT GCC AAC GCA AAA GGT CTG CAG              491
Leu Phe Pro Asp Gly Ile Val Thr Val Ala Asn Ala Lys Gly Leu Gln
            130                 135                 140

TAC TAC AGT ACT CTT CTG GAC GCT CTA GTG CTT AGA AAC ATT GAA CCT              539
Tyr Tyr Ser Thr Leu Leu Asp Ala Leu Val Leu Arg Asn Ile Glu Pro
145                 150                 155                 160

ATA GTT ACT TTA TAC CAC TGG GAT TTG CCT TTG GCA CTA CAA GAA AAA              587
Ile Val Thr Leu Tyr His Trp Asp Leu Pro Leu Ala Leu Gln Glu Lys
                165                 170                 175

TAT GGG GGG TGG AAA AAT GAT ACC ATA ATA GAT ATC TTC AAT GAC TAT              635
Tyr Gly Gly Trp Lys Asn Asp Thr Ile Ile Asp Ile Phe Asn Asp Tyr
            180                 185                 190

GCC ACA TAC TGT TTC CAG ATG TTT GGG GAC CGT GTC AAA TAT TGG ATT              683
Ala Thr Tyr Cys Phe Gln Met Phe Gly Asp Arg Val Lys Tyr Trp Ile
            195                 200                 205

ACA ATT CAC AAC CCA TAT CTA GTG GCT TGG CAT GGG TAT GGG ACA GGT              731
Thr Ile His Asn Pro Tyr Leu Val Ala Trp His Gly Tyr Gly Thr Gly
            210                 215                 220

ATG CAT GCC CCT GGA GAG AAG GGA AAT TTA GCA GCT GTC TAC ACT GTG              779
Met His Ala Pro Gly Glu Lys Gly Asn Leu Ala Ala Val Tyr Thr Val
225                 230                 235                 240

GGA CAC AAC TTG ATC AAG GCT CAC TCG AAA GTT TGG CAT AAC TAC AAC              827
Gly His Asn Leu Ile Lys Ala His Ser Lys Val Trp His Asn Tyr Asn
                245                 250                 255

ACA CAT TTC CGC CCA CAT CAG AAG GGT TGG TTA TCG ATC ACG TTG GGA              875
Thr His Phe Arg Pro His Gln Lys Gly Trp Leu Ser Ile Thr Leu Gly
            260                 265                 270

TCT CAT TGG ATC GAG CCA AAC CGG TCG GAA AAC ACG ATG GAT ATA TTC              923
Ser His Trp Ile Glu Pro Asn Arg Ser Glu Asn Thr Met Asp Ile Phe
            275                 280                 285

AAA TGT CAA CAA TCC ATG GTT TCT GTG CTT GGA TGG TTT GCC AAC CCT              971
Lys Cys Gln Gln Ser Met Val Ser Val Leu Gly Trp Phe Ala Asn Pro
            290                 295                 300

ATC CAT GGG GAT GGC GAC TAT CCA GAG GGG ATG AGA AAG AAG TTG TTC             1019
Ile His Gly Asp Gly Asp Tyr Pro Glu Gly Met Arg Lys Lys Leu Phe
305                 310                 315                 320

TCC GTT CTA CCC ATT TTC TCT GAA GCA GAG AAG CAT GAG ATG AGA GGC             1067
Ser Val Leu Pro Ile Phe Ser Glu Ala Glu Lys His Glu Met Arg Gly
                325                 330                 335

ACA GCT GAT TTC TTT GCC TTT TCT TTT GGA CCC AAC AAC TTC AAG CCC             1115
Thr Ala Asp Phe Phe Ala Phe Ser Phe Gly Pro Asn Asn Phe Lys Pro
            340                 345                 350

CTA AAC ACC ATG GCT AAA ATG GGA CAA AAT GTT TCA CTT AAT TTA AGA             1163
Leu Asn Thr Met Ala Lys Met Gly Gln Asn Val Ser Leu Asn Leu Arg
            355                 360                 365

GAA GCG CTG AAC TGG ATT AAA CTG GAA TAC AAC AAC CCT CGA ATC TTG             1211
Glu Ala Leu Asn Trp Ile Lys Leu Glu Tyr Asn Asn Pro Arg Ile Leu
            370                 375                 380

ATT GCT GAG AAT GGC TGG TTC ACA GAC AGT CGT GTG AAA ACA GAA GAC             1259
Ile Ala Glu Asn Gly Trp Phe Thr Asp Ser Arg Val Lys Thr Glu Asp
385                 390                 395                 400
```

-continued

```
ACC ACG GCC ATC TAC ATG ATG AAG AAT TTC CTC AGC CAG GTG CTT CAA         1307
Thr Thr Ala Ile Tyr Met Met Lys Asn Phe Leu Ser Gln Val Leu Gln
            405                 410                 415

GCA ATA AGG TTA GAT GAA ATA CGA GTG TTT GGT TAT ACT GCC TGG TCT         1355
Ala Ile Arg Leu Asp Glu Ile Arg Val Phe Gly Tyr Thr Ala Trp Ser
            420                 425                 430

CTC CTG GAT GGC TTT GAA TGG CAG GAT GCT TAC ACC ATC CGC CGA GGA         1403
Leu Leu Asp Gly Phe Glu Trp Gln Asp Ala Tyr Thr Ile Arg Arg Gly
            435                 440                 445

TTA TTT TAT GTG GAT TTT AAC AGT AAA CAG AAA GAG CGG AAA CCT AAG         1451
Leu Phe Tyr Val Asp Phe Asn Ser Lys Gln Lys Glu Arg Lys Pro Lys
            450                 455                 460

TCT TCA GCA CAC TAC TAC AAA CAG ATC ATA CGA GAA AAT GGT TTT TCT         1499
Ser Ser Ala His Tyr Tyr Lys Gln Ile Ile Arg Glu Asn Gly Phe Ser
465                 470                 475                 480

TTA AAA GAG TCC ACG CCA GAT GTG CAG GGC CAG TTT CCC TGT GAC TTC         1547
Leu Lys Glu Ser Thr Pro Asp Val Gln Gly Gln Phe Pro Cys Asp Phe
                485                 490                 495

TCC TGG GGT GTC ACT GAA TCT GTT CTT AAG CCC GAG TCT GTG GCT TCG         1595
Ser Trp Gly Val Thr Glu Ser Val Leu Lys Pro Glu Ser Val Ala Ser
                500                 505                 510

TCC CCA CAG TTC AGC GAT CCT CAT CTG TAC GTG TGG AAC GCC ACT GGC         1643
Ser Pro Gln Phe Ser Asp Pro His Leu Tyr Val Trp Asn Ala Thr Gly
                515                 520                 525

AAC AGA CTG TTG CAC CGA GTG GAA GGG GTG AGG CTG AAA ACA CGA CCC         1691
Asn Arg Leu Leu His Arg Val Glu Gly Val Arg Leu Lys Thr Arg Pro
            530                 535                 540

GCT CAA TGC ACA GAT TTT GTA AAC ATC AAA AAA CAA CTT GAG ATG TTG         1739
Ala Gln Cys Thr Asp Phe Val Asn Ile Lys Lys Gln Leu Glu Met Leu
545                 550                 555                 560

GCA AGA ATG AAA GTC ACC CAC TAC CGG TTT GCT CTG GAT TGG GCC TCG         1787
Ala Arg Met Lys Val Thr His Tyr Arg Phe Ala Leu Asp Trp Ala Ser
                565                 570                 575

GTC CTT CCC ACT GGC AAC CTG TCC GCG GTG AAC CGA CAG GCC CTG AGG         1835
Val Leu Pro Thr Gly Asn Leu Ser Ala Val Asn Arg Gln Ala Leu Arg
                580                 585                 590

TAC TAC AGG TGC GTG GTC AGT GAG GGG CTG AAG CTT GGC ATC TCC GCG         1883
Tyr Tyr Arg Cys Val Val Ser Glu Gly Leu Lys Leu Gly Ile Ser Ala
            595                 600                 605

ATG GTC ACC CTG TAT TAT CCG ACC CAC GCC CAC CTA GGC CTC CCC GAG         1931
Met Val Thr Leu Tyr Tyr Pro Thr His Ala His Leu Gly Leu Pro Glu
            610                 615                 620

CCT CTG TTG CAT GCC GAC GGG TGG CTG AAC CCA TCG ACG GCC GAG GCC         1979
Pro Leu Leu His Ala Asp Gly Trp Leu Asn Pro Ser Thr Ala Glu Ala
625                 630                 635                 640

TTC CAG GCC TAC GCT GGG CTG TGC TTC CAG GAG CTG GGG GAC CTG GTG         2027
Phe Gln Ala Tyr Ala Gly Leu Cys Phe Gln Glu Leu Gly Asp Leu Val
                645                 650                 655

AAG CTC TGG ATC ACC ATC AAC GAG CCT AAC CGG CTA AGT GAC ATC TAC         2075
Lys Leu Trp Ile Thr Ile Asn Glu Pro Asn Arg Leu Ser Asp Ile Tyr
                660                 665                 670

AAC CGC TCT GGC AAC GAC ACC TAC GGG GCG GCG CAC AAC CTG CTG GTG         2123
Asn Arg Ser Gly Asn Asp Thr Tyr Gly Ala Ala His Asn Leu Leu Val
            675                 680                 685

GCC CAC GCC CTG GCC TGG CGC CTC TAC GAC CAG CAG TTC AGG CCG TCA         2171
Ala His Ala Leu Ala Trp Arg Leu Tyr Asp Gln Gln Phe Arg Pro Ser
            690                 695                 700

CAG CGC GGG GCC GTG TCG CTG TCG CTG CAC GCG GAC TGG GCG GAA CCC         2219
Gln Arg Gly Ala Val Ser Leu Ser Leu His Ala Asp Trp Ala Glu Pro
705                 710                 715                 720
```

```
GCC AAC CCC TAT GCT GAC TCG CAC TGG AGG GCG GCC GAG CGC TTC CTG      2267
Ala Asn Pro Tyr Ala Asp Ser His Trp Arg Ala Ala Glu Arg Phe Leu
            725                 730                 735

CAG TTC GAG ATC GCC TGG TTC GCC GAG CCG CTC TTC AAG ACC GGG GAC      2315
Gln Phe Glu Ile Ala Trp Phe Ala Glu Pro Leu Phe Lys Thr Gly Asp
        740                 745                 750

TAC CCC GCG GCC ATG AGG GAA TAC ATT GCC TCC AAG CAC CGA CGG GGG      2363
Tyr Pro Ala Ala Met Arg Glu Tyr Ile Ala Ser Lys His Arg Arg Gly
    755                 760                 765

CTT TCC AGC TCG GCC CTG CCG CGC CTC ACC GAG GCC GAA AGG AGG CTG      2411
Leu Ser Ser Ser Ala Leu Pro Arg Leu Thr Glu Ala Glu Arg Arg Leu
770                 775                 780

CTC AAG GGC ACG GTC GAC TTC TGC GCG CTC AAC CAC TTC ACC ACT AGG      2459
Leu Lys Gly Thr Val Asp Phe Cys Ala Leu Asn His Phe Thr Thr Arg
785                 790                 795                 800

TTC GTG ATG CAC GAG CAG CTG GCC GGC AGC CGC TAC GAC TCG GAC AGG      2507
Phe Val Met His Glu Gln Leu Ala Gly Ser Arg Tyr Asp Ser Asp Arg
            805                 810                 815

GAC ATC CAG TTT CTG CAG GAC ATC ACC CGC CTG AGC TCC CCC ACG CGC      2555
Asp Ile Gln Phe Leu Gln Asp Ile Thr Arg Leu Ser Ser Pro Thr Arg
        820                 825                 830

CTG GCT GTG ATT CCC TGG GGG GTG CGC AAG CTG CTG CGG TGG GTC CGG      2603
Leu Ala Val Ile Pro Trp Gly Val Arg Lys Leu Leu Arg Trp Val Arg
    835                 840                 845

AGG AAC TAC GGC GAC ATG GAC ATT TAC ATC ACC GCC AGT GGC ATC GAC      2651
Arg Asn Tyr Gly Asp Met Asp Ile Tyr Ile Thr Ala Ser Gly Ile Asp
850                 855                 860

GAC CAG GCT CTG GAG GAT GAC CGG CTC CGG AAG TAC TAC CTA GGG AAG      2699
Asp Gln Ala Leu Glu Asp Asp Arg Leu Arg Lys Tyr Tyr Leu Gly Lys
865                 870                 875                 880

TAC CTT CAG GAG GTG CTG AAA GCA TAC CTG ATT GAT AAA GTC AGA ATC      2747
Tyr Leu Gln Glu Val Leu Lys Ala Tyr Leu Ile Asp Lys Val Arg Ile
            885                 890                 895

AAA GGC TAT TAT GCA TTC AAA CTG GCT GAA GAG AAA TCT AAA CCC AGA      2795
Lys Gly Tyr Tyr Ala Phe Lys Leu Ala Glu Glu Lys Ser Lys Pro Arg
        900                 905                 910

TTT GGA TTC TTC ACA TCT GAT TTT AAA GCT AAA TCC TCA ATA CAA TTT      2843
Phe Gly Phe Phe Thr Ser Asp Phe Lys Ala Lys Ser Ser Ile Gln Phe
    915                 920                 925

TAC AAC AAA GTG ATC AGC AGC AGG GGC TTC CCT TTT GAG AAC AGT AGT      2891
Tyr Asn Lys Val Ile Ser Ser Arg Gly Phe Pro Phe Glu Asn Ser Ser
930                 935                 940

TCT AGA TGC AGT CAG ACC CAA GAA AAT ACA GAG TGC ACT GTC TGC TTA      2939
Ser Arg Cys Ser Gln Thr Gln Glu Asn Thr Glu Cys Thr Val Cys Leu
945                 950                 955                 960

TTC CTT GTG CAG AAG AAA CCA CTG ATA TTC CTG GGT TGT TGC TTC TTC      2987
Phe Leu Val Gln Lys Lys Pro Leu Ile Phe Leu Gly Cys Cys Phe Phe
            965                 970                 975

TCC ACC CTG GTT CTA CTC TTA TCA ATT GCC ATT TTT CAA AGG CAG AAG      3035
Ser Thr Leu Val Leu Leu Leu Ser Ile Ala Ile Phe Gln Arg Gln Lys
        980                 985                 990

AGA AGA AAG TTT TGG AAA GCA AAA AAC TTA CAA CAC ATA CCA TTA AAG      3083
Arg Arg Lys Phe Trp Lys Ala Lys Asn Leu Gln His Ile Pro Leu Lys
    995                 1000                1005

AAA GGC AAG AGA GTT GTT AGC TAAACTGATC TGTCTGCATG ATAGACAGTT         3134
Lys Gly Lys Arg Val Val Ser
    1010            1015

TAAAAATTCA TCCCAGTTCC ATATGCTGGT AACTTACAGG AGATATACCT GTATTATAGA    3194
```

```
AAGACAATCT GAGATACAGC TGTAACCAAG GTGATGACAA TTGTCTCTGC TGTGTGGTTC      3254

AAAGAACATT CCCTTAGGTG TTGACATCAG TGAACTCAGT TCTTGGATGT AAACATAAAG      3314

GCTTCATCCT GACAGTAAGC TATGAGGATT ACATGCTACA TTGCTTCTTA AAGTTTCATC      3374

AACTGTATTC CATCATTCTG CTTTAGCTTT CATCTCTACC AATAGCTACT TGTGGTACAA      3434

TAAATTATTT TTAAGAAGAA AAAAAA                                          3460

(2) INFORMATION FOR SEQ ID NO: 11:

(i) SEQUENCE CHARACTERISTICS:
          (A) LENGTH: 20
          (B) TYPE: nucleic acid
          (C) STRANDEDNESS: single
          (D) TOPOLOGY: linear (ii) MOLECULE TYPE: other nucleic acid (xi) SEQUENCE DESCRIPTION: SEQ ID NO: 11:

AGGCTCATCA GAGGAACTGC                                                   20

(2) INFORMATION FOR SEQ ID NO: 12:

(i) SEQUENCE CHARACTERISTICS:
          (A) LENGTH: 20
          (B) TYPE: nucleic acid
          (C) STRANDEDNESS: single
          (D) TOPOLOGY: linear (ii) MOLECULE TYPE: other nucleic acid (xi) SEQUENCE DESCRIPTION: SEQ ID NO: 12:

AAGACAGAAG CTGCCTCAGG                                                   20

(2) INFORMATION FOR SEQ ID NO: 13:

(i) SEQUENCE CHARACTERISTICS:
          (A) LENGTH: 27
          (B) TYPE: nucleic acid
          (C) STRANDEDNESS: single
          (D) TOPOLOGY: linear (ii) MOLECULE TYPE: other nucleic acid (xi) SEQUENCE DESCRIPTION: SEQ ID NO: 13:

CCATCCTAAT ACGACTCACT ATAGGGC                                           27

(2) INFORMATION FOR SEQ ID NO: 14:

(i) SEQUENCE CHARACTERISTICS:
          (A) LENGTH: 21
          (B) TYPE: nucleic acid
          (C) STRANDEDNESS: single
          (D) TOPOLOGY: linear (ii) MOLECULE TYPE: other nucleic acid (xi) SEQUENCE DESCRIPTION: SEQ ID NO: 14:

TTAGTGAGGA AGCAAGAGGC C                                                 21

(2) INFORMATION FOR SEQ ID NO: 15:

(i) SEQUENCE CHARACTERISTICS:
          (A) LENGTH: 34
          (B) TYPE: nucleic acid
          (C) STRANDEDNESS: single
```

-continued (ii) MOLECULE TYPE: other nucleic acid (xi) SEQUENCE DESCRIPTION: SEQ ID NO: 15:

CAAAGCTTCC ACCATGCTAG CCCGCGCCCC TCCT                                    34

(2) INFORMATION FOR SEQ ID NO: 16:

(i) SEQUENCE CHARACTERISTICS:
        (A) LENGTH: 34
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 16:

CAGGATCCTT AGTGAGGAAG CAAGAGGCCG ACAC                                    34

(2) INFORMATION FOR SEQ ID NO: 17:

(i) SEQUENCE CHARACTERISTICS:
        (A) LENGTH: 21
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 17:

GGGTTTTGTC AAAGGACTTA C                                                              21

(2) INFORMATION FOR SEQ ID NO: 18:

(i) SEQUENCE CHARACTERISTICS:
        (A) LENGTH: 20
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 18:

AGGCTCATCA GAGGAACTGC                                                                20

(2) INFORMATION FOR SEQ ID NO: 19:

(i) SEQUENCE CHARACTERISTICS:
        (A) LENGTH: 22
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 19:

GACCAGGCTC TGGACGATGA CC                                                          22

(2) INFORMATION FOR SEQ ID NO: 20:

(i) SEQUENCE CHARACTERISTICS:
        (A) LENGTH: 24
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 20:

```
GTCTGACTGC ATCTAGAACT ACTG                                              24

(2) INFORMATION FOR SEQ ID NO: 21:

(i) SEQUENCE CHARACTERISTICS:
           (A) LENGTH: 43
           (B) TYPE: nucleic acid
           (C) STRANDEDNESS: single
           (D) TOPOLOGY: linear (ii) MOLECULE TYPE: other nucleic acid (xi) SEQUENCE DESCRIPTION: SEQ ID NO: 21:

CGATAAGCTA TGAAAACTAC AGCCTTGGAG GAAGCTTAAA TGG                          43

(2) INFORMATION FOR SEQ ID NO: 22:

(i) SEQUENCE CHARACTERISTICS:
           (A) LENGTH: 41
           (B) TYPE: nucleic acid
           (C) STRANDEDNESS: single
           (D) TOPOLOGY: linear (ii) MOLECULE TYPE: other nucleic acid (xi) SEQUENCE DESCRIPTION: SEQ ID NO: 22:

CCATTTAAGC TTCCTCCAAG GCTGTAGTTT TCATAGCTTA T                            41

(2) INFORMATION FOR SEQ ID NO: 23:

(i) SEQUENCE CHARACTERISTICS:
           (A) LENGTH: 44
           (B) TYPE: nucleic acid
           (C) STRANDEDNESS: single
           (D) TOPOLOGY: linear (ii) MOLECULE TYPE: other nucleic acid (xi) SEQUENCE DESCRIPTION: SEQ ID NO: 23:

AGCTTAAATG AGCTCGATAT CAAGGCCTAC CCGGGCGCCA TGCA                         44

(2) INFORMATION FOR SEQ ID NO: 24:

(i) SEQUENCE CHARACTERISTICS:
           (A) LENGTH: 36
           (B) TYPE: nucleic acid
           (C) STRANDEDNESS: single
           (D) TOPOLOGY: linear (ii) MOLECULE TYPE: other nucleic acid (xi) SEQUENCE DESCRIPTION: SEQ ID NO: 24:

TGGCGCCCGG GTAGGCCTTG ATATCGAGCT CATTTA                                  36

(2) INFORMATION FOR SEQ ID NO: 25:

(i) SEQUENCE CHARACTERISTICS:
           (A) LENGTH: 18
           (B) TYPE: nucleic acid
           (C) STRANDEDNESS: single
           (D) TOPOLOGY: linear (ii) MOLECULE TYPE: other nucleic acid (xi) SEQUENCE DESCRIPTION: SEQ ID NO: 25:

CCTGGTCGAC CATTTCAG                                                      18

(2) INFORMATION FOR SEQ ID NO: 26:
```

```
        (i) SEQUENCE CHARACTERISTICS:
            (A) LENGTH: 25
            (B) TYPE: nucleic acid
            (C) STRANDEDNESS: single
            (D) TOPOLOGY: linear (ii) MOLECULE TYPE: other nucleic acid (xi) SEQUENCE DESCRIPTION: SEQ ID NO: 26:

AGCACAAAGT CGACAGACTT CTGGC                                              25

(2) INFORMATION FOR SEQ ID NO: 27:

(i) SEQUENCE CHARACTERISTICS:
            (A) LENGTH: 19
            (B) TYPE: nucleic acid
            (C) STRANDEDNESS: single
            (D) TOPOLOGY: linear (ii) MOLECULE TYPE: other nucleic acid (xi) SEQUENCE DESCRIPTION: SEQ ID NO: 27:

TGGAGATTGG AAGTGGACG                                                     19

(2) INFORMATION FOR SEQ ID NO: 28:

(i) SEQUENCE CHARACTERISTICS:
            (A) LENGTH: 20
            (B) TYPE: nucleic acid
            (C) STRANDEDNESS: single
            (D) TOPOLOGY: linear (ii) MOLECULE TYPE: other nucleic acid (xi) SEQUENCE DESCRIPTION: SEQ ID NO: 28:

CAAGGACCAG TTCATCATCG                                                    20

(2) INFORMATION FOR SEQ ID NO: 29:

(i) SEQUENCE CHARACTERISTICS:
            (A) LENGTH: 20
            (B) TYPE: nucleic acid
            (C) STRANDEDNESS: single
            (D) TOPOLOGY: linear (ii) MOLECULE TYPE: other nucleic acid (xi) SEQUENCE DESCRIPTION: SEQ ID NO: 29:

TTAAGGACTC CTGCATCTGC                                                    20

(2) INFORMATION FOR SEQ ID NO: 30:

(i) SEQUENCE CHARACTERISTICS:
            (A) LENGTH: 20
            (B) TYPE: nucleic acid
            (C) STRANDEDNESS: single
            (D) TOPOLOGY: linear (ii) MOLECULE TYPE: other nucleic acid (xi) SEQUENCE DESCRIPTION: SEQ ID NO: 30:

GAAGATCTGA ACAAAAGCTG                                                    20

(2) INFORMATION FOR SEQ ID NO: 31:

(i) SEQUENCE CHARACTERISTICS:
            (A) LENGTH: 20
            (B) TYPE: nucleic acid
```

```
        (C) STRANDEDNESS: single
        (D) TOPOLOGY: linear (ii) MOLECULE TYPE: other nucleic acid (xi) SEQUENCE DESCRIPTION: SEQ ID NO: 31:

CGTAATACGA CTCACTATAG                                        20

(2) INFORMATION FOR SEQ ID NO: 32:

(i) SEQUENCE CHARACTERISTICS:
        (A) LENGTH: 58
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 32:

AGCTTGTTAA CGGATCCATA ACTTCGTATA ATGTATGCTA TACGAAGTTA TGAATTCC    58

(2) INFORMATION FOR SEQ ID NO: 33:

(i) SEQUENCE CHARACTERISTICS:
        (A) LENGTH: 58
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 33:

TCGAGGAATT CATAACTTCG TATAGCATAC ATTATACGAA GTTATGGATC CGTTAACA    58

(2) INFORMATION FOR SEQ ID NO: 34:

(i) SEQUENCE CHARACTERISTICS:
        (A) LENGTH: 51
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 34:

GGATAACTTC GTATAATGTA TGCTATACGA AGTTATGTCG ACGCGGCCGC G          51

(2) INFORMATION FOR SEQ ID NO: 35:

(i) SEQUENCE CHARACTERISTICS:
        (A) LENGTH: 57
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 35:

AATTCGCGGC CGCGTCGACA TAACTTCGTA TAGCATACAT TATACGAAGT TATCCGC     57

(2) INFORMATION FOR SEQ ID NO: 36:

(i) SEQUENCE CHARACTERISTICS:
        (A) LENGTH: 30
        (B) TYPE: nucleic acid
        (C) STRANDEDNESS: single
        (D) TOPOLOGY: linear (ii) MOLECULE TYPE: other nucleic acid
```

```
(xi) SEQUENCE DESCRIPTION: SEQ ID NO: 36:

GACCGCATGT ACTGGCGCGA CACGAACACC                                      30

(2) INFORMATION FOR SEQ ID NO: 37:

(i) SEQUENCE CHARACTERISTICS:
        (A) LENGTH: 24
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 37:

CAAAGCTCTC CTGGGATGTT CTCT                                            24

(2) INFORMATION FOR SEQ ID NO: 38:

(i) SEQUENCE CHARACTERISTICS:
        (A) LENGTH: 22
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 38:

ATATGGAGAA GCGGTAGTGG GT                                              22
```

POLYPEPTIDE, NOVEL DNA AND NOVEL ANTIBODY

CROSS-REFERENCE TO RELATED APPLICATION

This application is a division of application Ser. No. 10/411,253 filed Apr. 11, 2003, which in turn is a division of application Ser. No. 09/344,510 filed Jun. 25, 1999 (now U.S. Pat. No. 6,579,850), which in turn is a continuation-in-part of application PCT/JP97/04585 filed Dec. 12, 1997.

BACKGROUND OF THE INVENTION

1. Field of the Invention

The present invention relates to a novel aging-suppressing polypeptide in animals, DNA encoding the polypeptide, an antibody recognizing the polypeptide, a ligand for the polypeptide of the present invention, a compound inhibiting a specific binding between the polypeptide and ligand of the present invention, and a compound enhancing the expression of an aging-suppressing gene encoding the aging-suppressing polypeptide of the present invention.

2. Brief Description of the Background Art

The aging phenomenon refers to deterioration of individuals, in terms of change in their functions and appearances, which is generally promoted by the advance in aging. It is known that the frequency of the onset of various adult diseases increases with aging. Therefore, pharmaceutical agents capable of controlling aging in a certain form are expected to be developed as therapeutic agents or preventive agents of adult diseases and as protective agents or preventive agents against functional and apparent deterioration. However, no pharmaceutical agents having these scientifically verified effects have been reported.

Throughout the world, research directed to aging in individuals at the genetic level has just started, and no molecular genetics information relating to aging in individuals has been presented so far. However, several types of genetic premature aging syndromes are known, including Werner's syndrome, Hutchinson-Gilford syndrome (progeria), Down's syndrome, Turner's syndrome, Louis Barr's syndrome, Rothmond Thomson syndrome and the like (Daizabuzo Fujimoto, eds., *Mechanism and Control of Aging*, IPC, 1993).

The causative gene of Werner's syndrome has been identified as the gene encoding helicase [*Science*, 272: 258 (1996)]. Various mutations have been observed in the genes from the patients with Werner's syndrome. It is believed that no normal helicase protein is produced in the patients due to the mutation of the gene and, therefore, its function is not expressed so that a syndrome resembling premature aging may develop.

Based on the above, a suggestion has been presented that a gene relating to aging is present and that aging is promoted through the mutation of the gene. Because other causative genes are also present for other types of genetic premature aging syndromes, it is believed that a plurality of genes may be involved in aging.

If an aging syndrome occurs as a result of loss in function of a gene involved in aging, therapeutic treatment would be useful, such treatment comprising supplementing the function of the gene, i.e. administering a protein product encoded by the gene or expressing the protein product in genetic treatment fashion. Also, if aging can be controlled, except for a genetic premature aging syndrome, various adult diseases occurring in close relation to aging would be treated or prevented.

The gene of the present invention is different from the causative gene of Werner's syndrome.

SUMMARY OF THE INVENTION

No measure is known for treating, preventing or diagnosing adult diseases of which the frequency of the occurrence increases based on aging; for protecting, preventing or diagnosing functional and apparent deterioration based on aging; or for treating and diagnosing a premature aging syndrome. The present invention is useful for such a measure.

The present invention relates to a polypeptide having an activity of suppressing aging in animals including humans; a therapeutic agent for a syndrome resembling premature aging, a therapeutic agent for adult diseases or an aging-suppressing agent, each comprising the polypeptide; DNA encoding the polypeptide; a therapeutic agent for a syndrome resembling premature aging, a therapeutic agent for adult diseases or an aging-suppressing agent, each comprising the DNA; a method for improving livestock using the DNA; a recombinant DNA prepared by inserting the DNA into a vector; a transformant harboring the recombinant; a method for producing the polypeptide of the present invention using the transformant; an antibody recognizing the polypeptide; a method for detecting the polypeptide of the present invention or a method for diagnosing aging, each using the antibody; a method for screening a ligand for the polypeptide of the present invention; the ligand; a method for screening a compound inhibiting a specific binding between the polypeptide and ligand of the present invention; and a compound prepared by the screening method.

BRIEF DESCRIPTION OF THE DRAWINGS

The symbols used in the drawings are described below.

| | |
|---|---|
| bp: | base pairs |
| kb: | kilobase pairs |
| IFN-γ: | interferon-γ gene |
| Amp, Ap or Ap$^r$: | ampicillin resistant gene derived from pBR322 |
| rop$^+$: | rop gene |
| PletI: | letI promoter |
| Ptrp: | trp promoter |
| P$_{SE}$: | simian virus 40 (SV40) early gene promoter |
| P$_{MO}$: | long terminal repeat (LTR) promoter of Molony mouse leukemia virus |
| Hyg: | hygromycin resistant gene |
| G418$^r$: | G418 resistant gene |
| dhfr: | dihydrofolic acid reductase gene |
| P1: | P1 promoter derived from pBR322 |
| Ptk: | promoter of herpes simplex virus (HSV) thymidine kinase (tk) gene |
| Sp.βG: | rabbit β-globin gene splicing signal |
| A.βG: | rabbit β-globin gene poly(A) addition signal |
| A.SE: | simian virus 40 (SV40) early gene poly(A) addition signal |
| Atk: | poly(A) addition signal of herpes simplex virus (HSV) thymidine kinase (tk) gene |

The drawings are simply described below.

Figure 1:
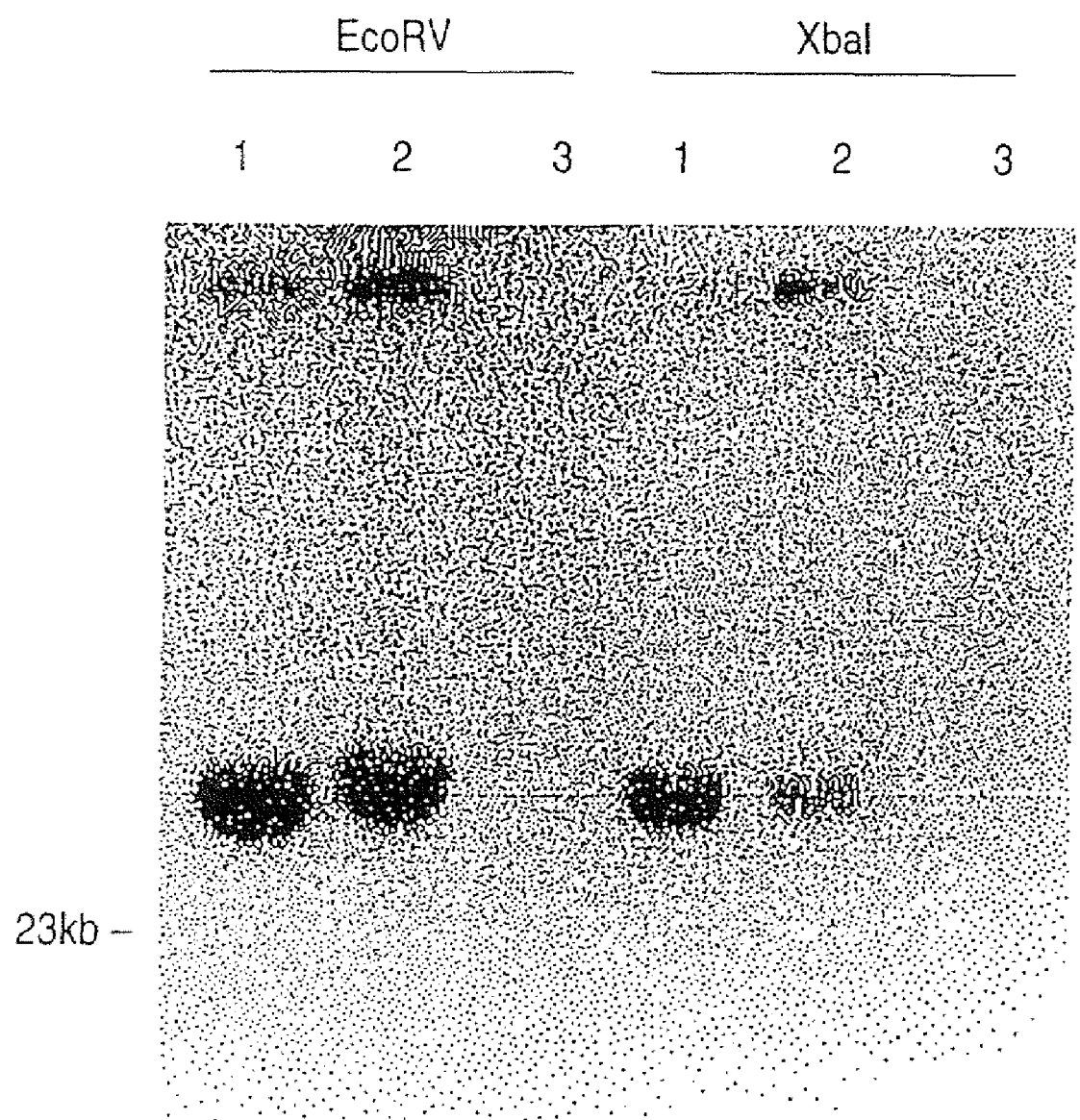

FIG. 1 is an electrophoretic pattern depicting the results of chromosomal Southern blot hybridization with the full length of an introduction gene as the probe; lane 1 shows the results from a homozygote; lane 2 shows the results from a heterozygote; and lane 3 shows the results from a wild-type mouse.

FIG. 2 depicts restriction maps of the introduction gene and plasmids practically rescued.

Figure 3:
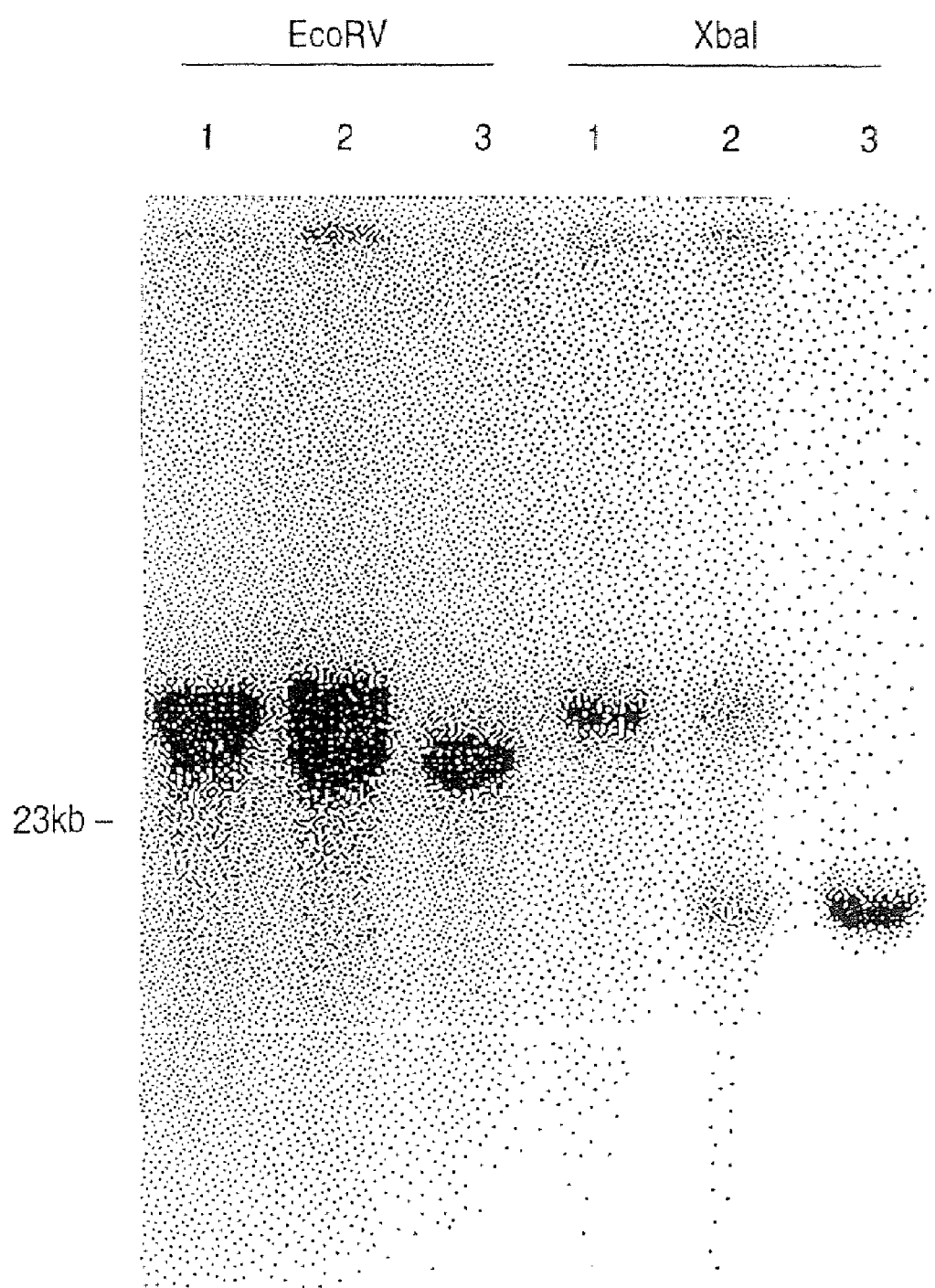

FIG. 3 is an electrophoretic pattern depicting the outcome of chromosomal Southern blot hybridization with a chromosome fragment contained in the rescued plasmid as the probe; lane 1 shows the results from a homozygote; lane 2 shows the results from a heterozygote; and lane 3 shows the results from a wild-type mouse.

Figure 4:
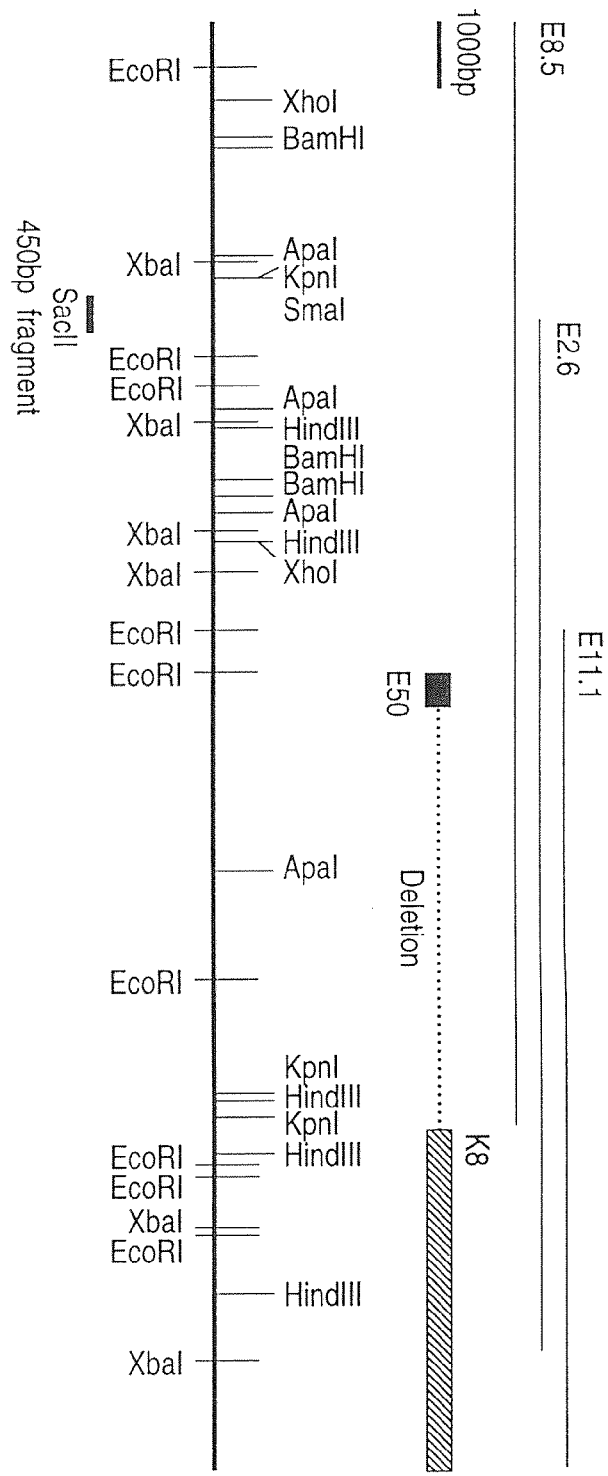

FIG. 4 depicts a restriction map of a phage clone with the chromosomal DNA in the proximity of the introduction gene to be inserted.

Figure 5:
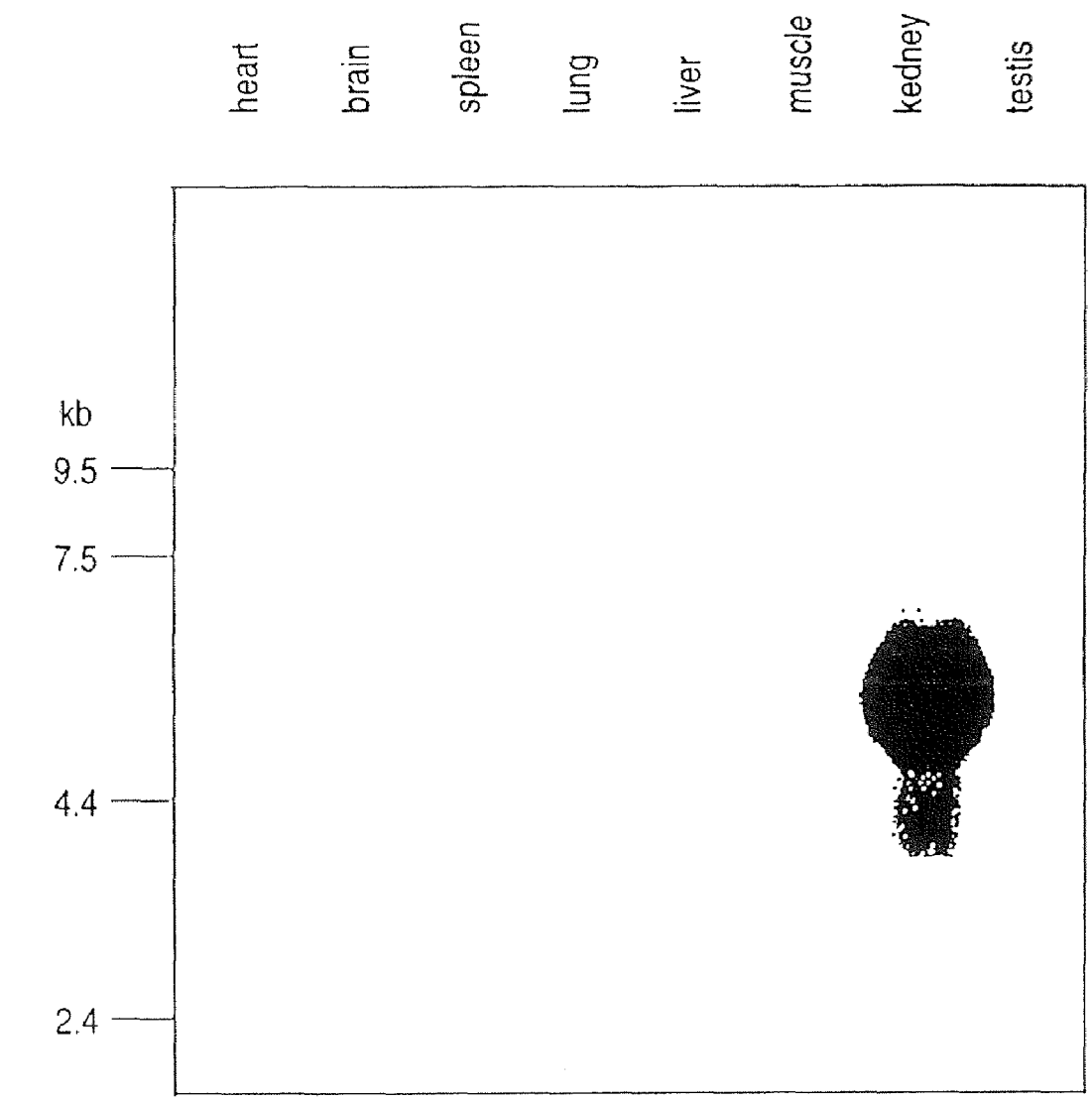

FIG. 5 is an electrophoresis pattern depicting the results of the Northern blot hybridization on poly(A)$^+$ RNAs of murine individual organs and SacII 450 bp as the probe.

Figure 6:
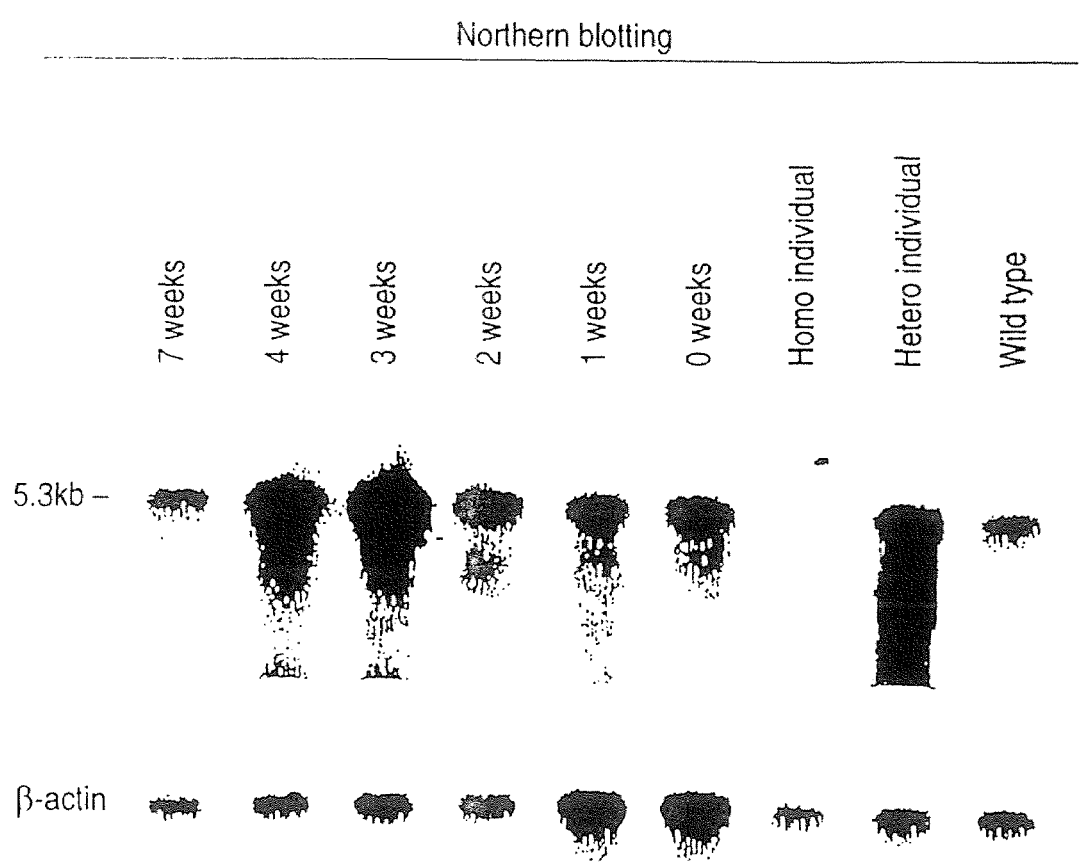

FIG. 6 is an electrophoresis pattern depicting the results of the Northern blot hybridization on poly(A)$^+$ RNA prepared from the kidney of each of a wild-type mouse, a heterozygote, a homozygote (mouse showing a syndrome resembling premature aging), and wild-type mice at individual stages from the birth (0 W) to 7 weeks, together with SacII 450 bp as the probe.

Figure 7:
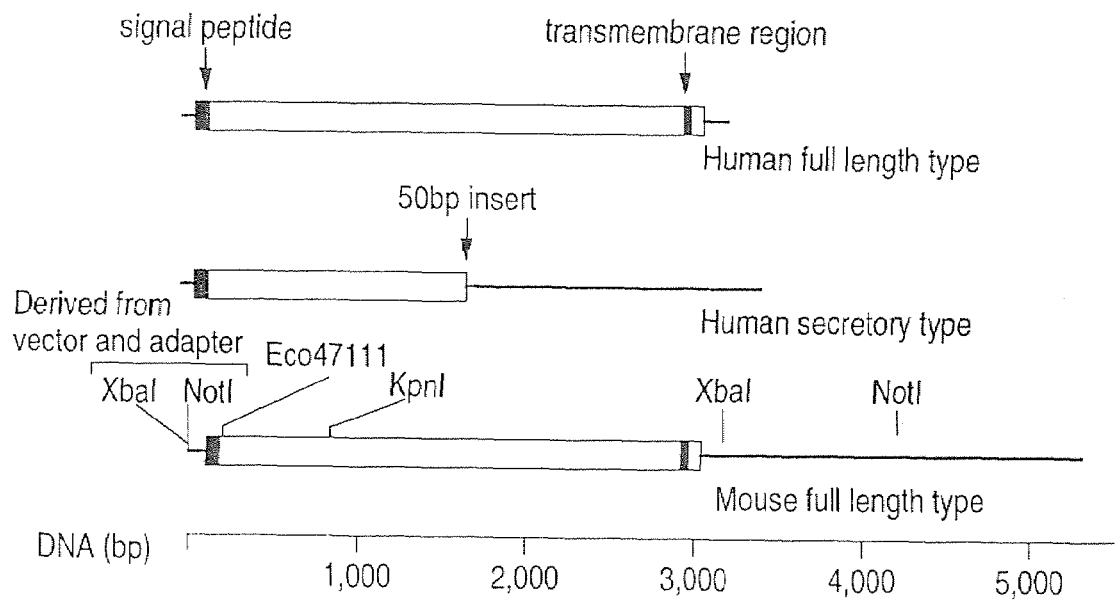

FIG. 7 schematically depicts the cDNAs of the aging-suppressing polypeptides of human full length (upper), human secretory type (center) and murine full-length (lower), and the proteins encoded by the cDNAs.

Figure 8:
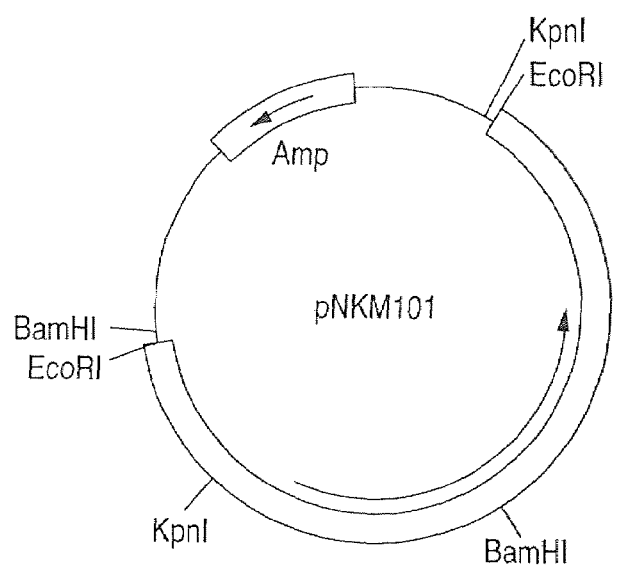

FIG. 8 is a view depicting the restriction map of plasmid pNKM101; the longer arrow represents the mouse-derived aging-suppressing gene and the direction of transfer.

Figure 9:
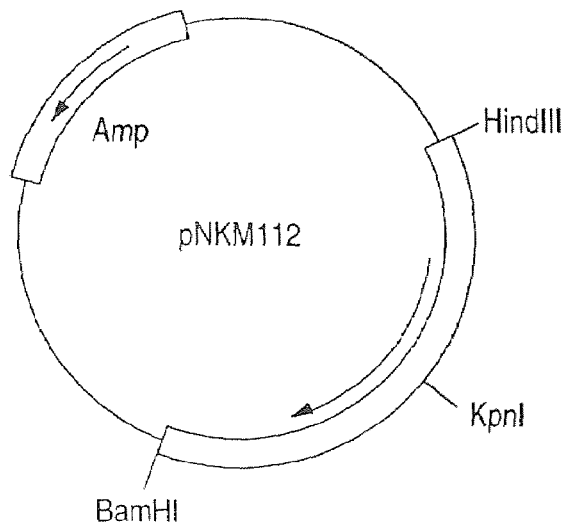

FIG. 9 is a view depicting the restriction map of plasmid pNKM112; the longer arrow represents the mouse-derived aging-suppressing gene derived and the direction of transfer.

Figure 10:
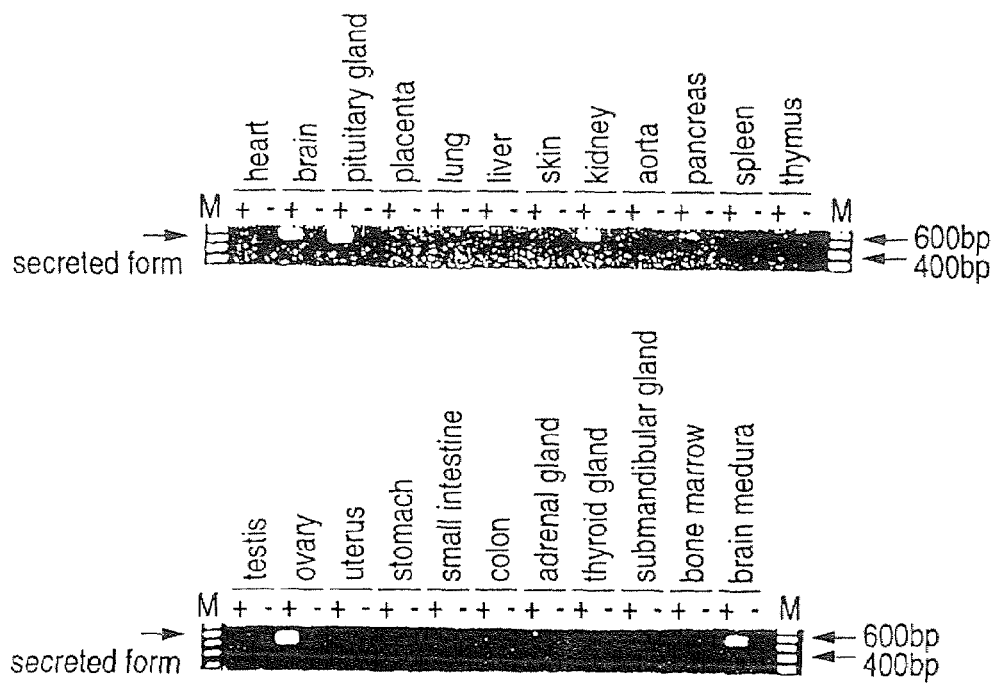

FIG. 10 is an electrophoresis pattern showing the results of examining the expression of the murine secretory aging-suppressing gene toward the poly(A)$^+$ RNA of each of mouse organs by RT-PCR.

Figure 11:
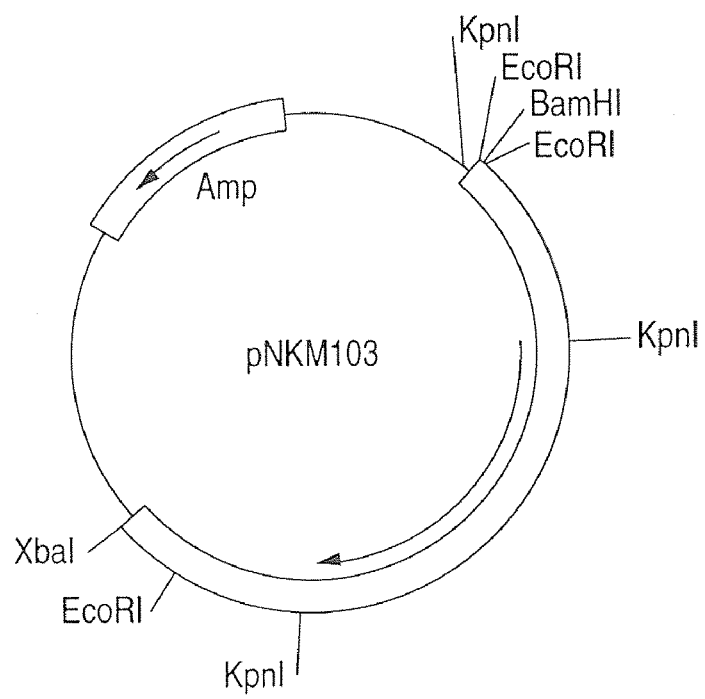

FIG. 11 is a view depicting the restriction map of plasmid pNKM103; the longer arrow represents the human-derived aging-suppressing gene and the direction of transfer.

Figure 12:
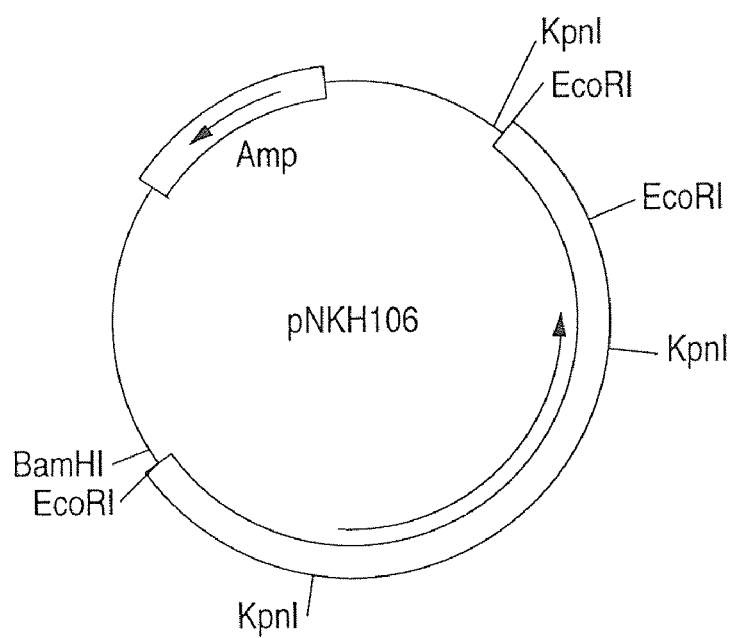

FIG. 12 is a view depicting the restriction map of plasmid pNKH106; the longer arrow represents the human-derived secretory aging-suppressing gene and the direction of transfer.

Figure 13:
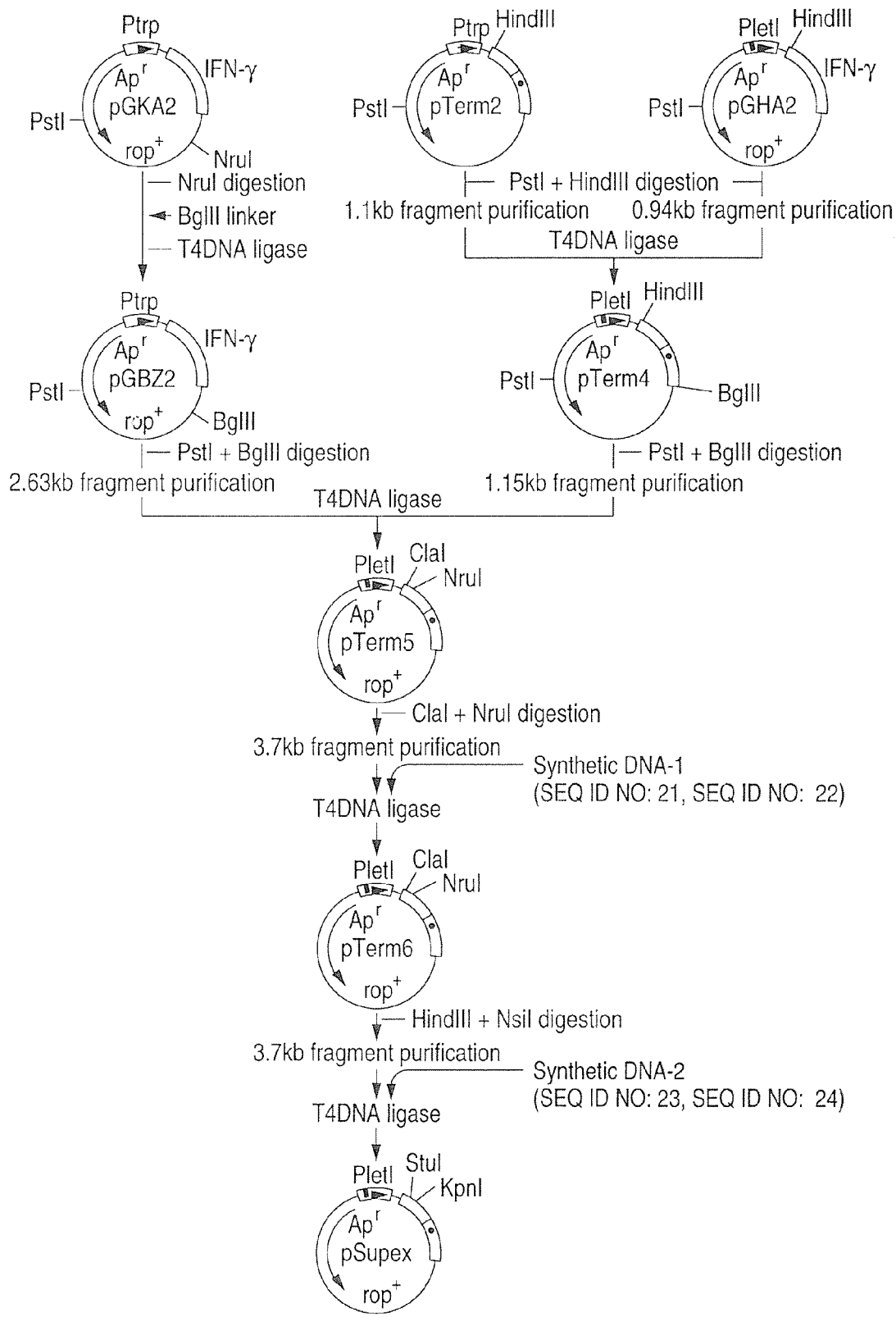

FIG. 13 is a view showing the construction process of plasmid pSupex.

Figure 14:
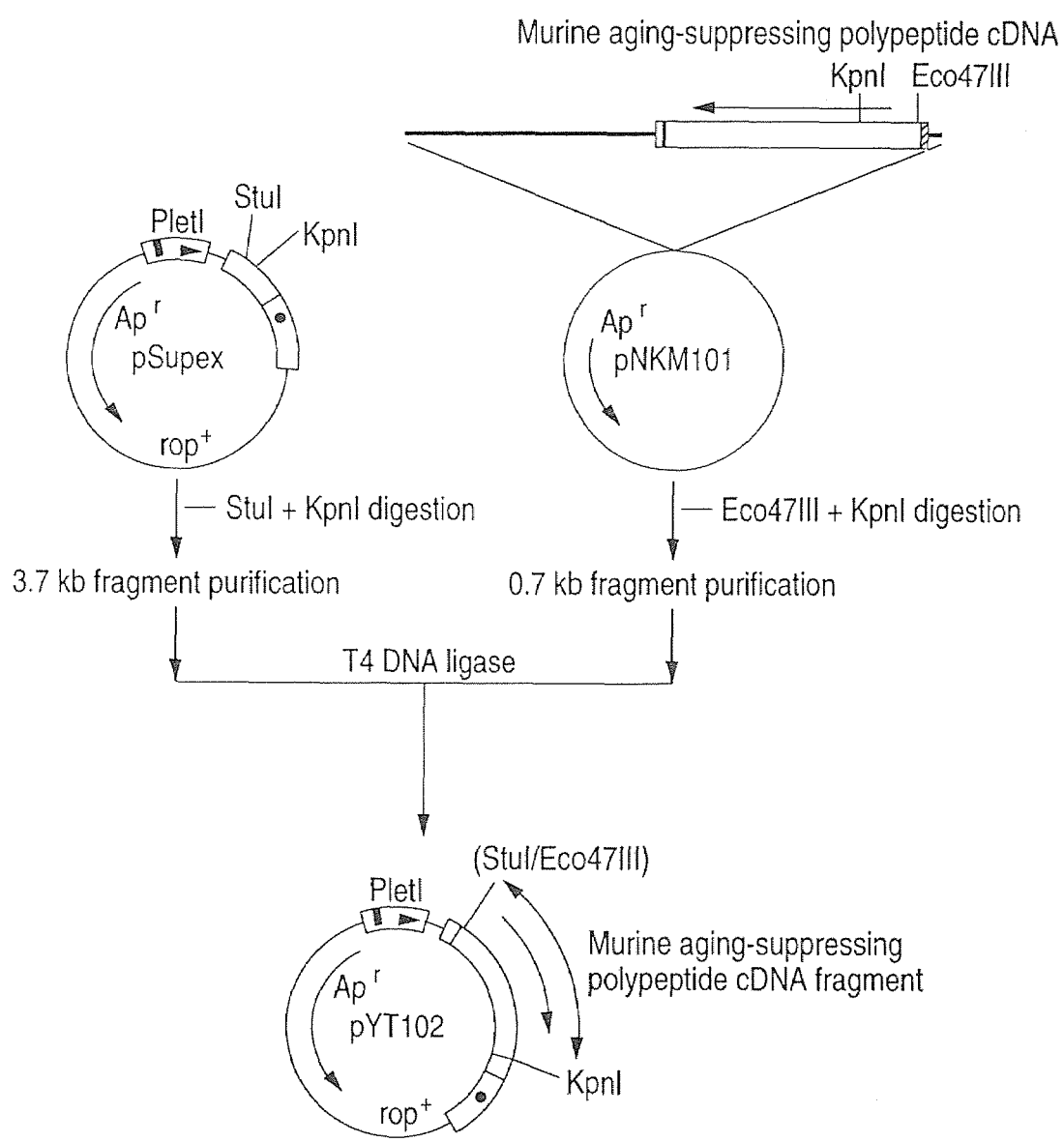

FIG. 14 is a view showing the construction process of plasmid pYT102.

Figure 15:
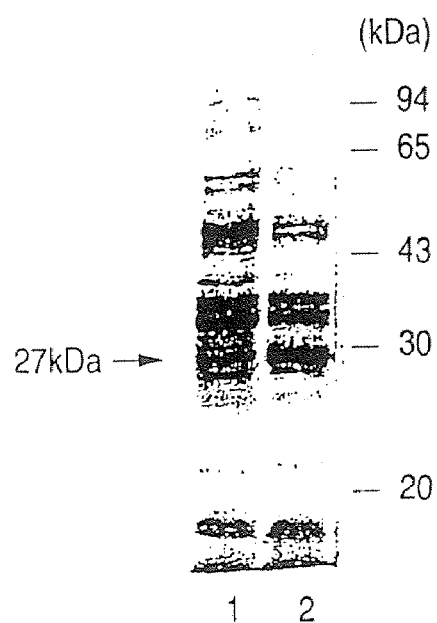

FIG. 15 is a SDS-polyacrylamide gel electrophoresis pattern for confirming the presence of an aging-suppressing polypeptide fragment produced in *Escherichia coli* harboring pYT102; lane 1 represents the production of an aging-suppressing polypeptide fragment in *Escherichia coli* NY49 harboring pYT102, with no addition of IAA, and lane 2 represents the production thereof with addition of IAA.

Figure 16:
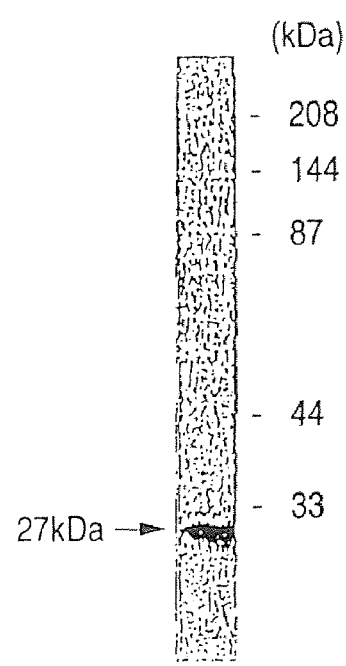

FIG. 16 is an electrophoresis pattern confirming the expression of an aging-suppressing polypeptide fragment in *Escherichia coli* using a polyclonal antibody against the aging-suppressing polypeptide fragment by Western blotting.

Figure 17:
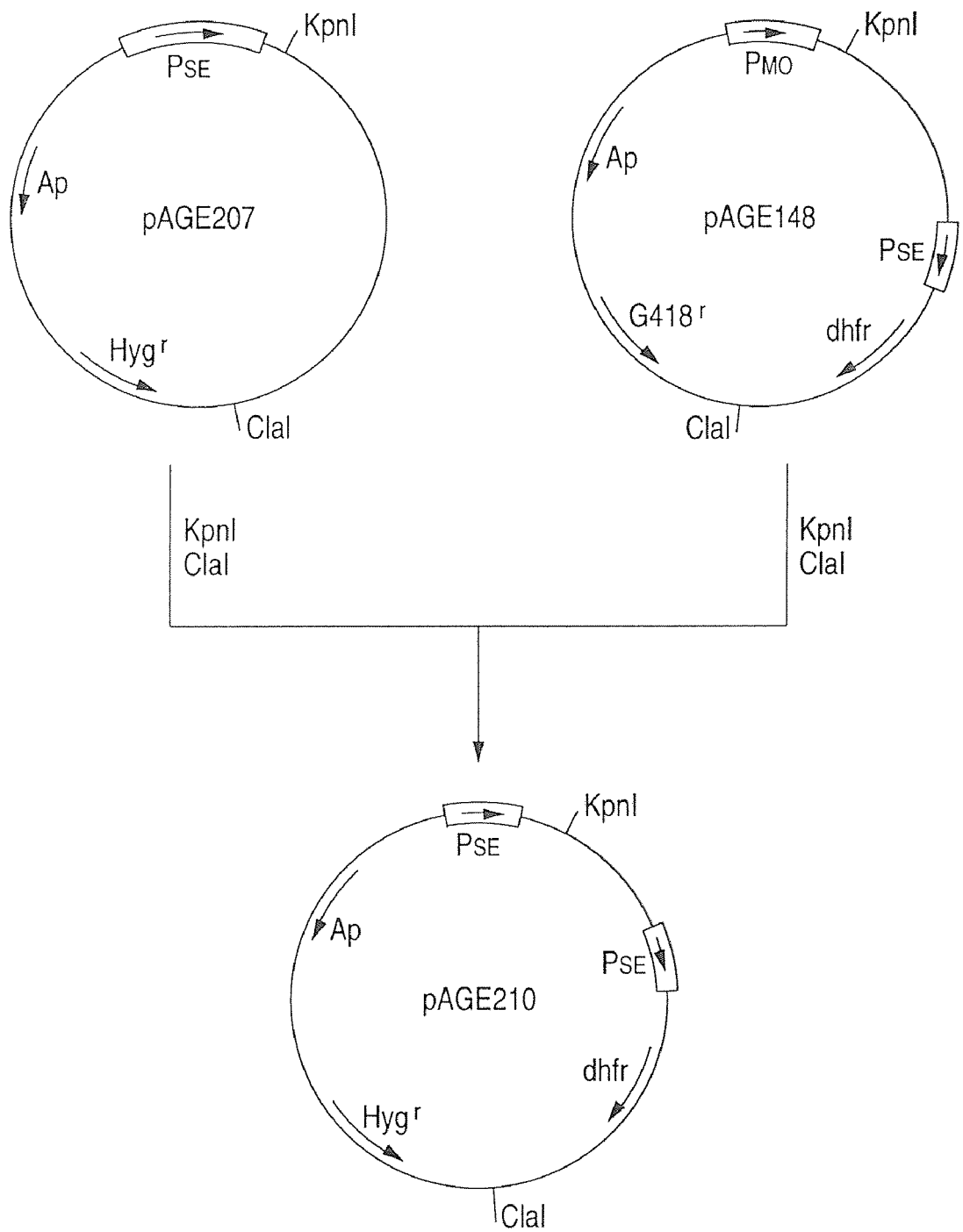

FIG. 17 is a view showing the construction process of pAGE210.

Figure 18:
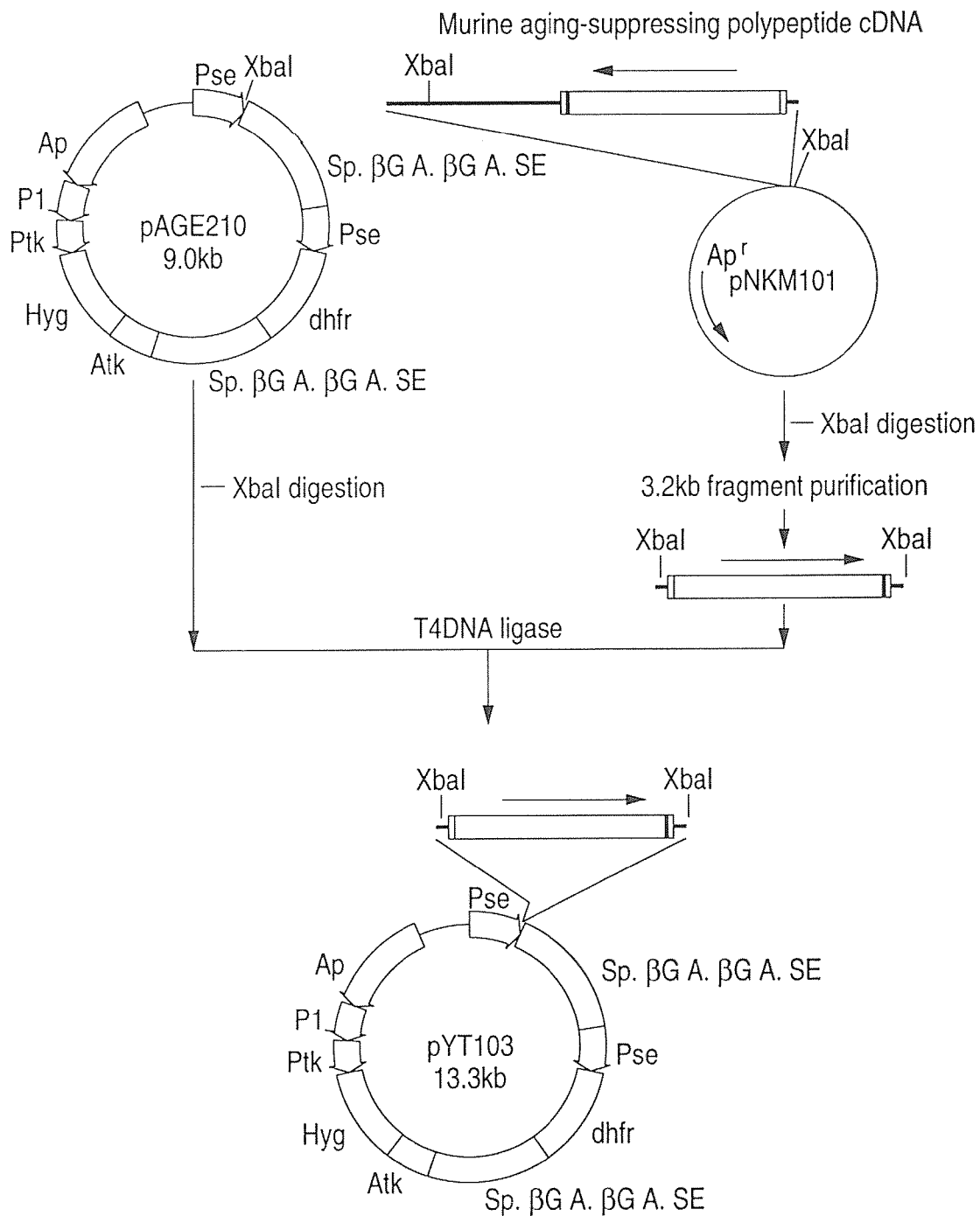

FIG. 18 is a view showing the construction process of PYT103.

Figure 19:
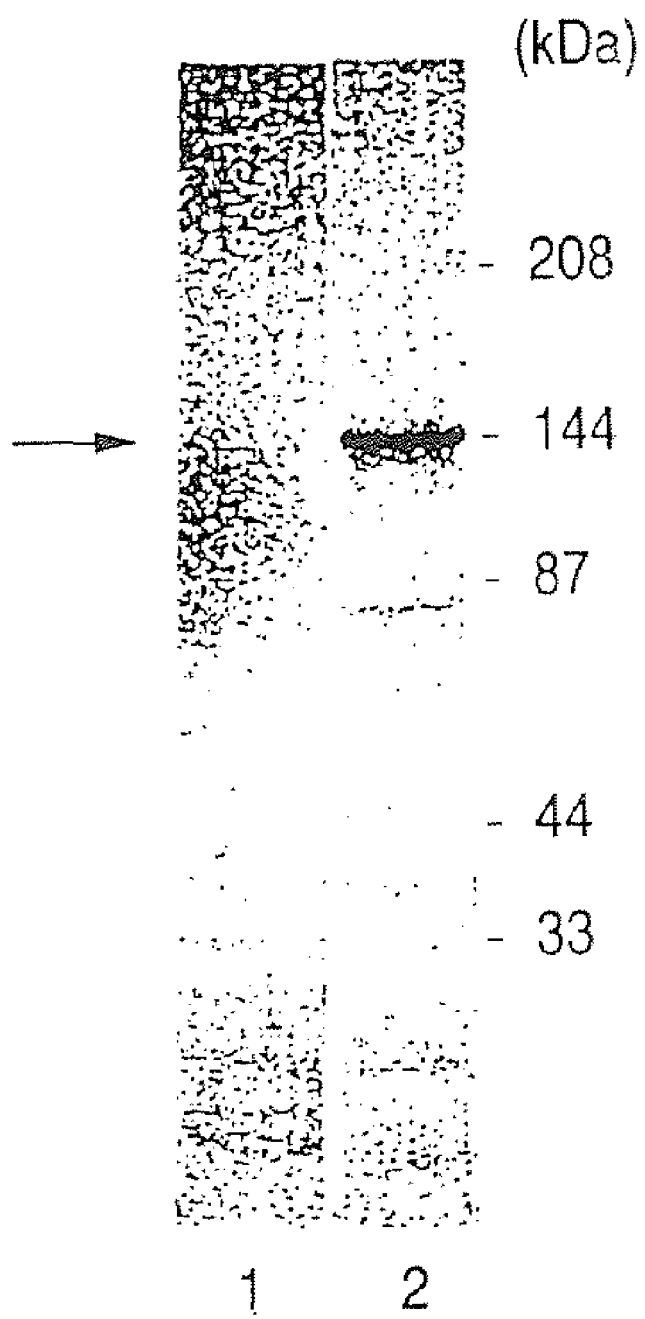

FIG. 19 is an electrophoresis pattern confirming the expression of the full length of the aging-suppressing polypeptide in animal cells using a polyclonal antibody against the aging-suppressing polypeptide fragment by Western blotting; lane 1 represents the results using CHO dhfr$^-$ cells (as control of a host alone); and lane 2 represents the results using CHO dhfr$^-$/pYT103 MTX amplified cells.

Figure 20:
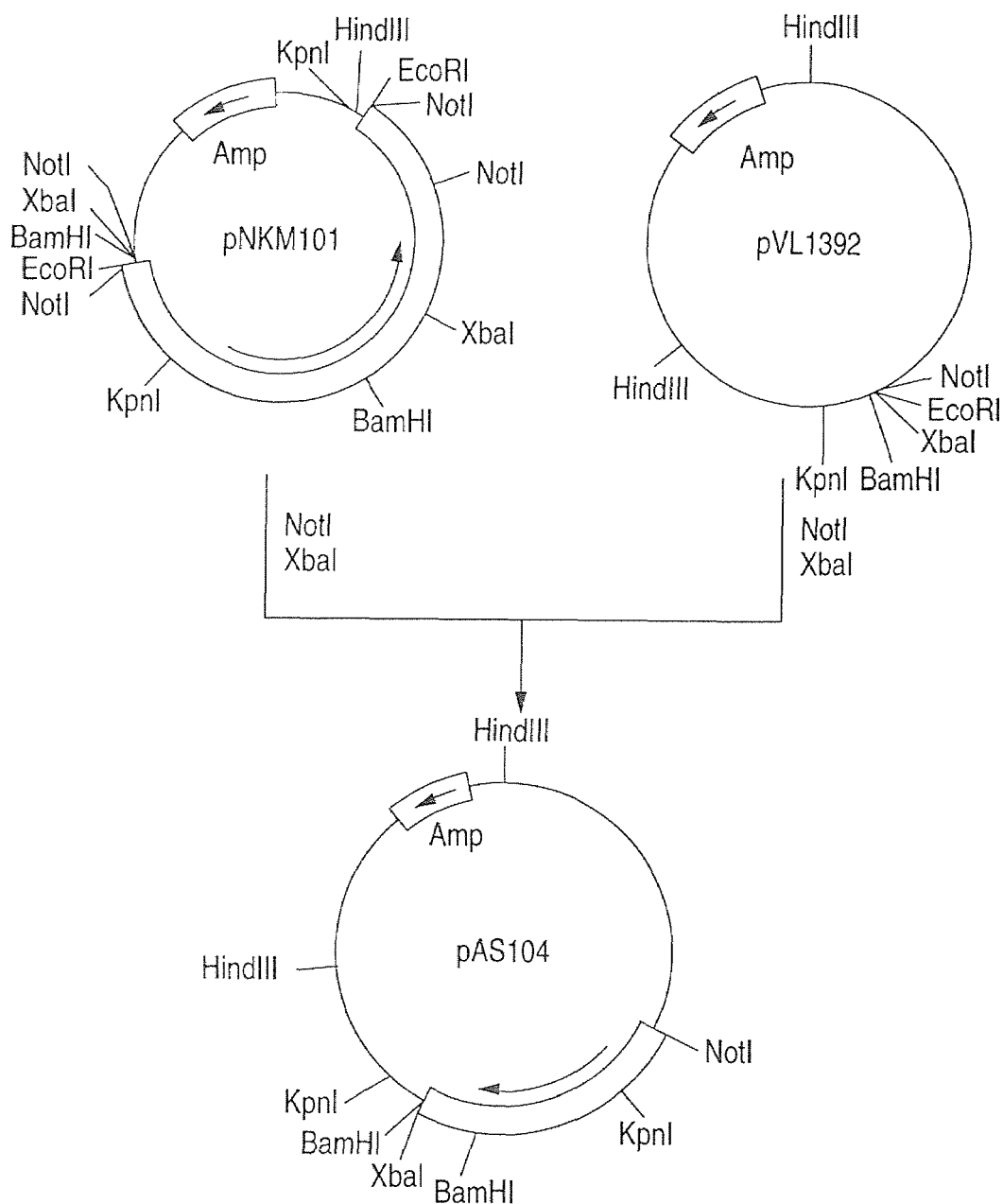

FIG. 20 is a view showing the construction process of pAS104.

Figure 21:
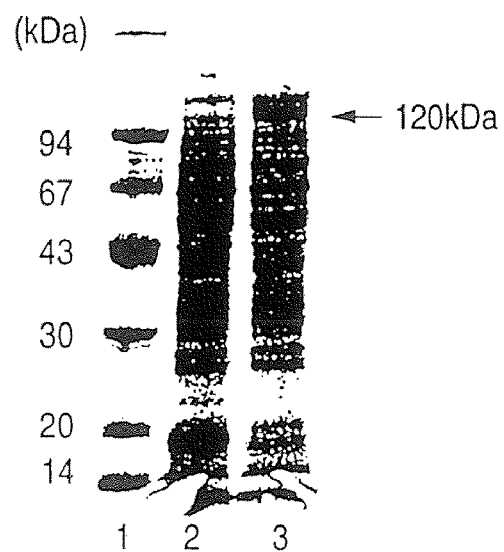

FIG. 21 is a SDS-polyacrylamide electrophoresis pattern confirming the expression of the full length of the aging-suppressing polypeptide in insect cells; lane 1 represents the results using molecular weight markers; lane 2 represents the results using Sf9 cells; and lane 3 represents the results using Sf9 cells infected with a virus expressing the aging-suppressing polypeptide.

Figure 22:
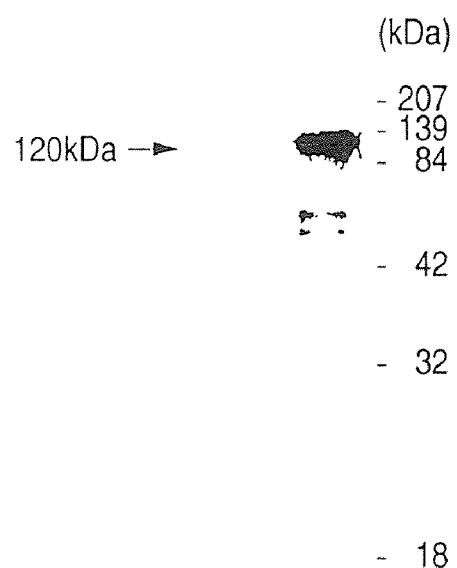

FIG. 22 is an electrophoresis pattern confirming the expression of the full length of the aging-suppressing polypeptide in insect cells using a polyclonal antibody against the aging-suppressing polypeptide fragment by Western blotting; lane 1 represents the results using Sf9 cells; and lane 2 represents the results using Sf9 cells infected with a virus expressing the aging-suppressing polypeptide.

Figure 23:
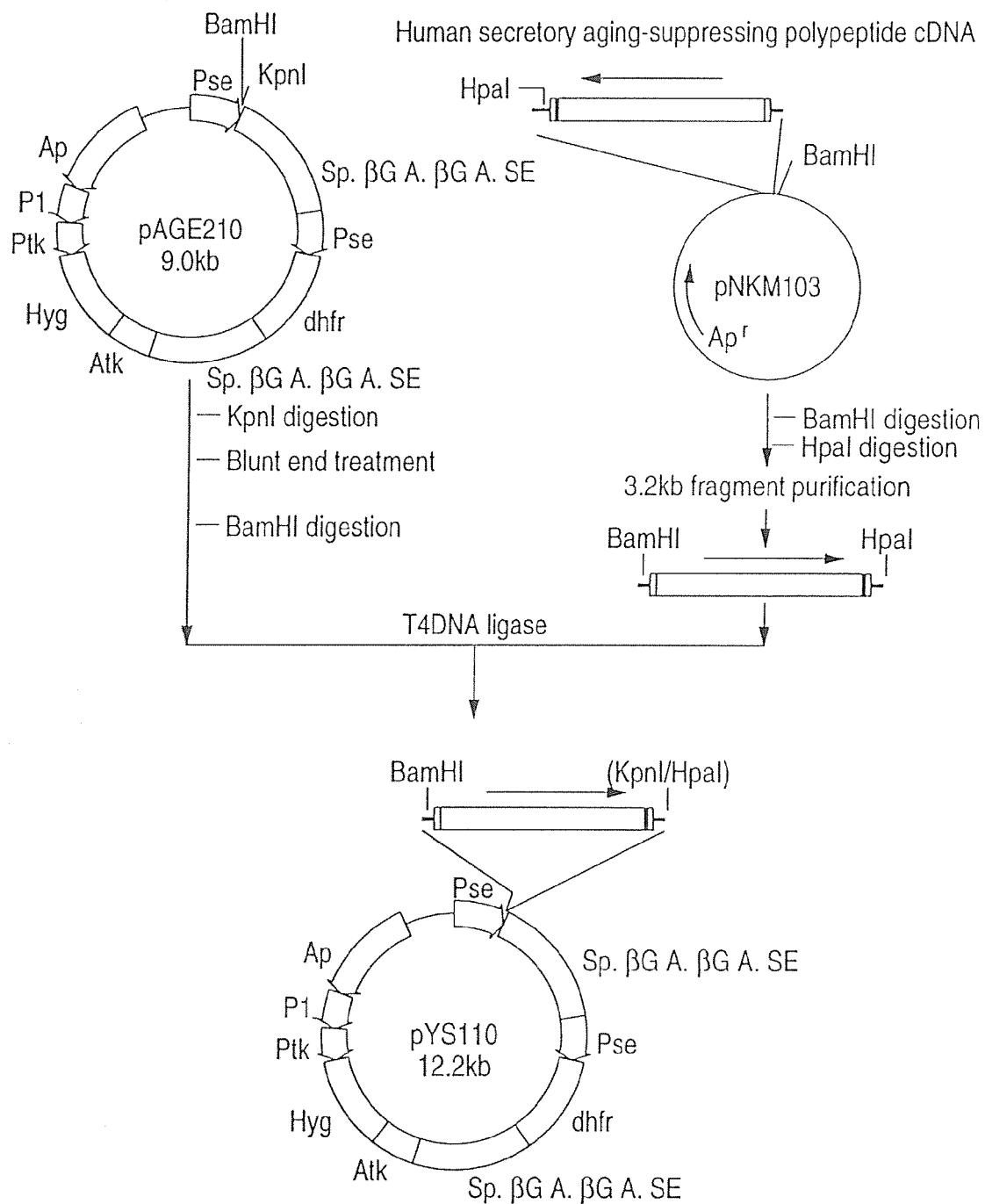

FIG. 23 is a view depicting the construction process of plasmid pYS110.

Figure 24:
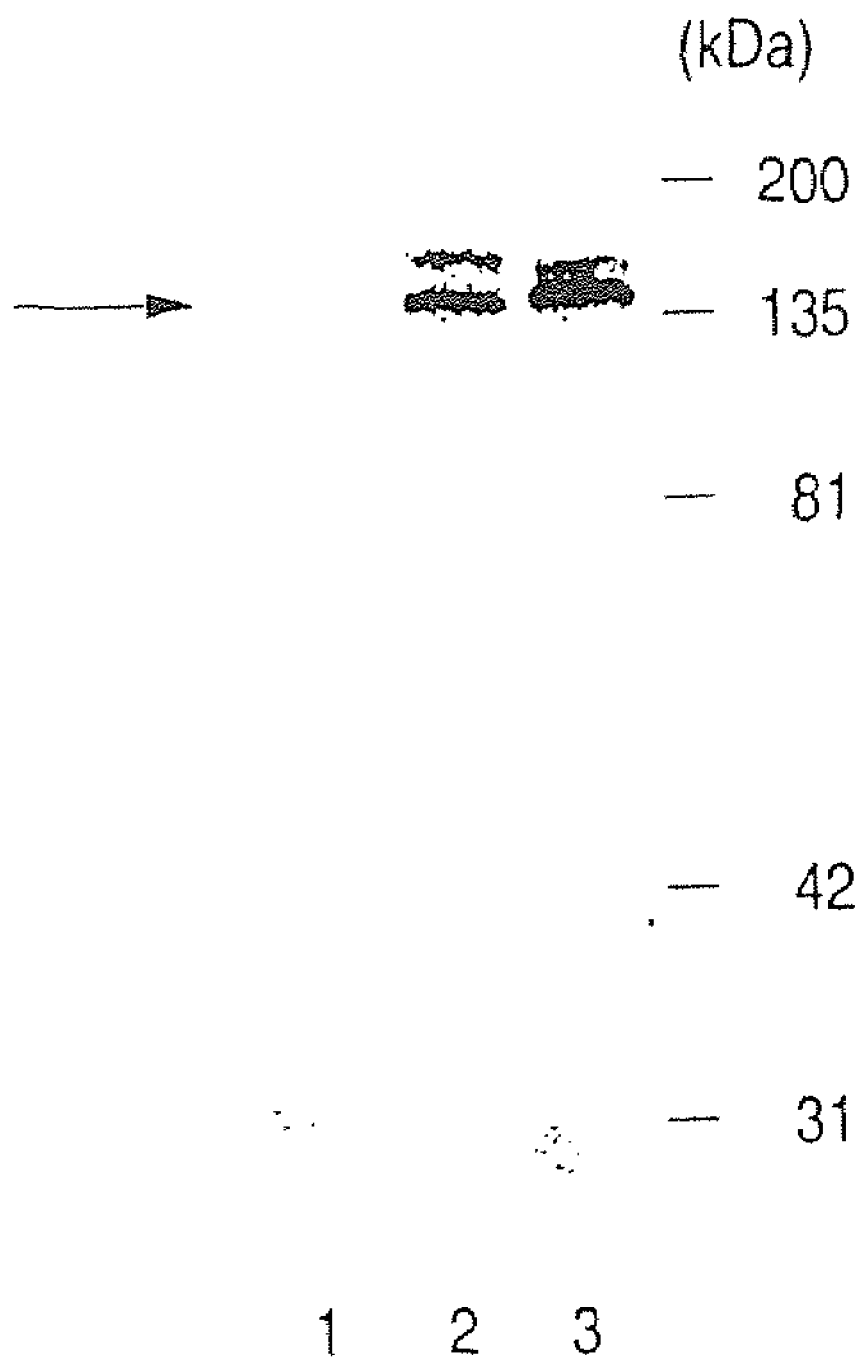

FIG. 24 is an electrophoresis pattern confirming the expression of the full length of the aging-suppressing polypeptide in CHO cells (CHO dhfr–) using the monoclonal antibody KM1902 against the aging-suppressing polypeptide fragment by Western blotting; lane 1 represents the results of Western reaction using CHO cells; lane 2 represents the results of Western reaction using CHO cells (CHO dhfr$^-$/pYS110) expressing the human-derived aging-suppressing polypeptide; and lane 3 represents the results using CHO cells (CHO dhfr$^-$/pYT103) expressing the mouse-derived aging-suppressing polypeptide.

Figure 25:
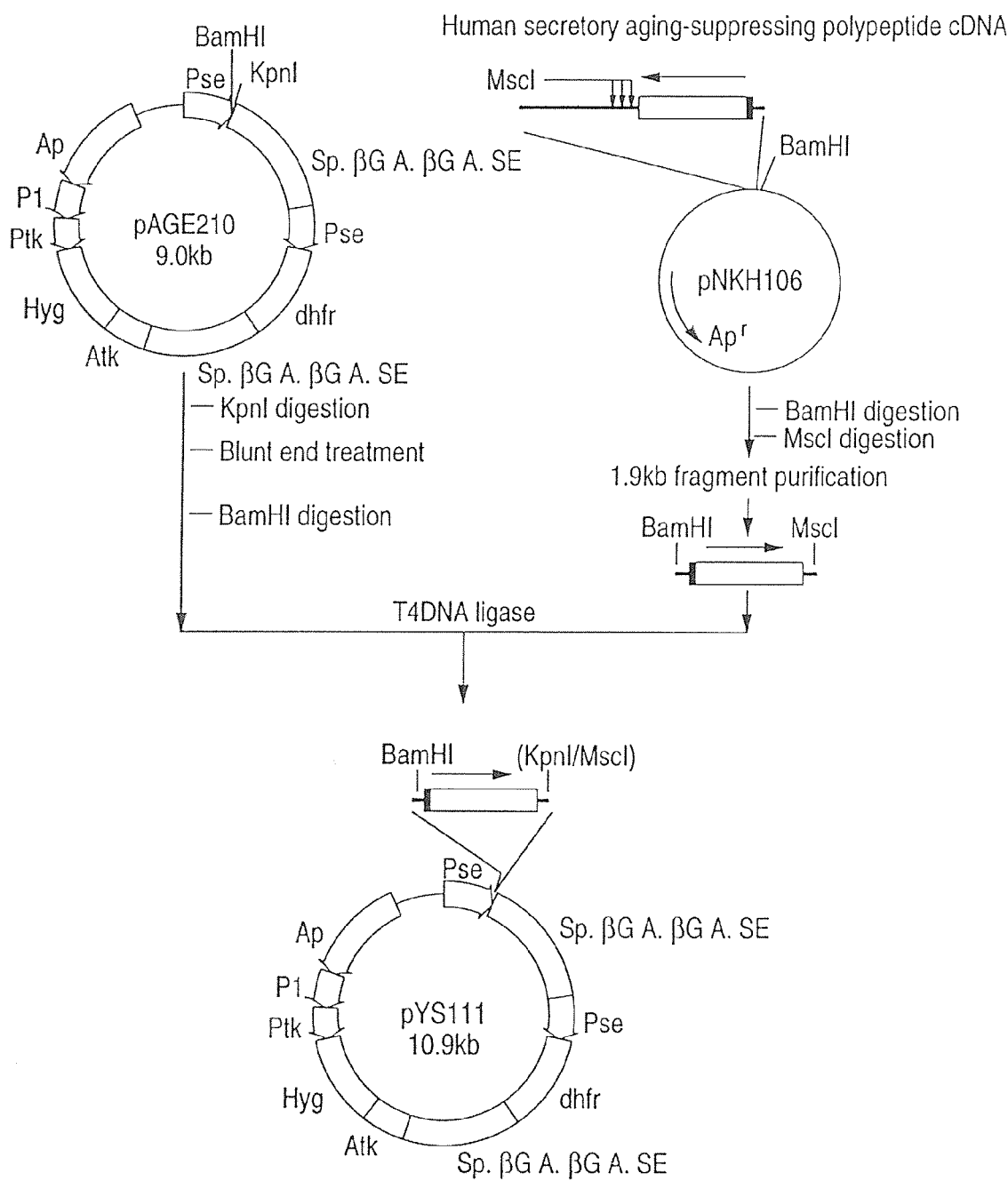

FIG. 25 is a view of the construction process of plasmid pYS111.

Figure 26:
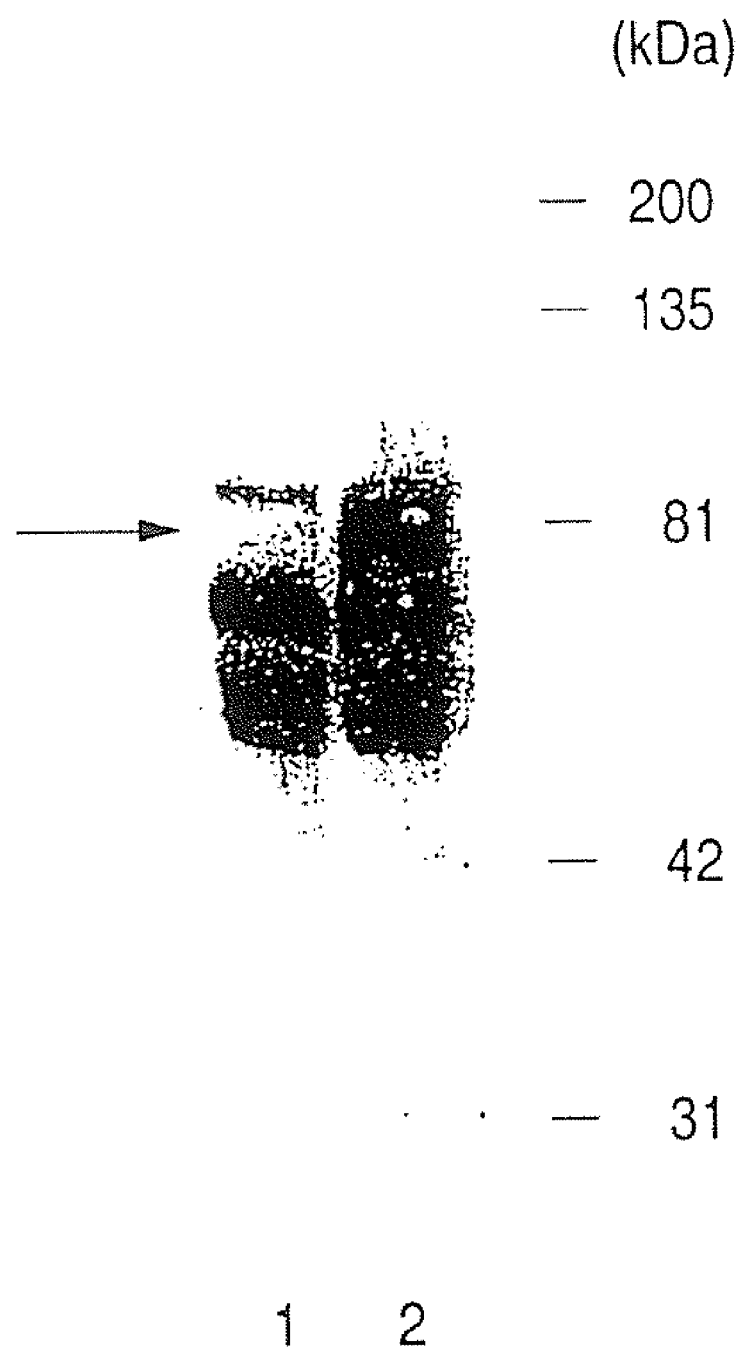

FIG. 26 is an electrophoresis pattern confirming the expression of the full length of the human-derived secretory aging-suppressing polypeptide in CHO cells (CHO dhfr–) using the monoclonal antibody KM1902 against the aging-suppressing polypeptide fragment by Western blotting; lane 1 represents the results of Western reaction using CHO cells (CHO dhfr$^-$); and lane 2 represents the results of Western reaction using CHO cells (CHO dhfr$^-$/pYS111) expressing the human-derived secretory aging-suppressing polypeptide.

Figure 27:
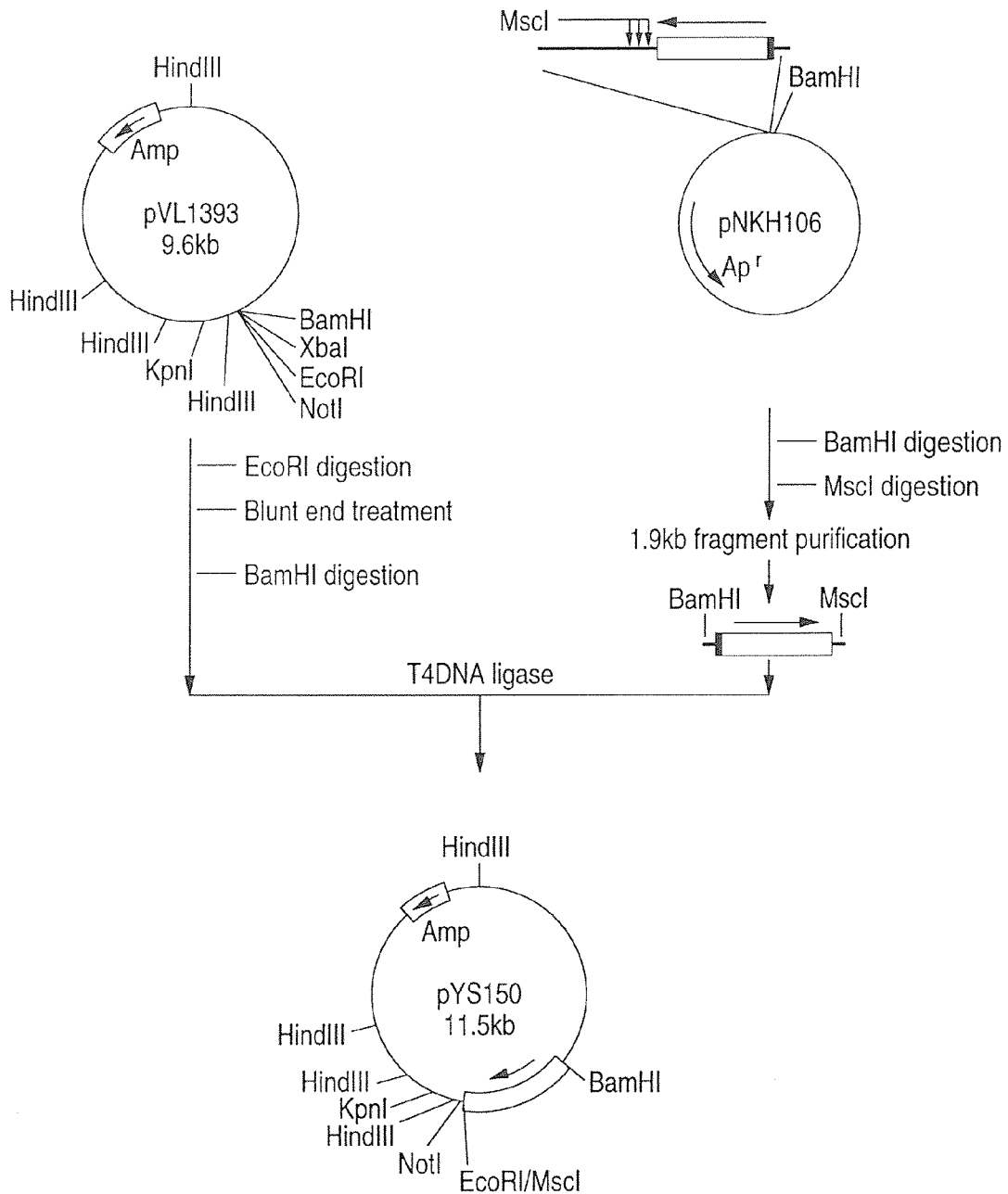

FIG. 27 is a view of the construction process of plasmid pYS150.

Figure 28:
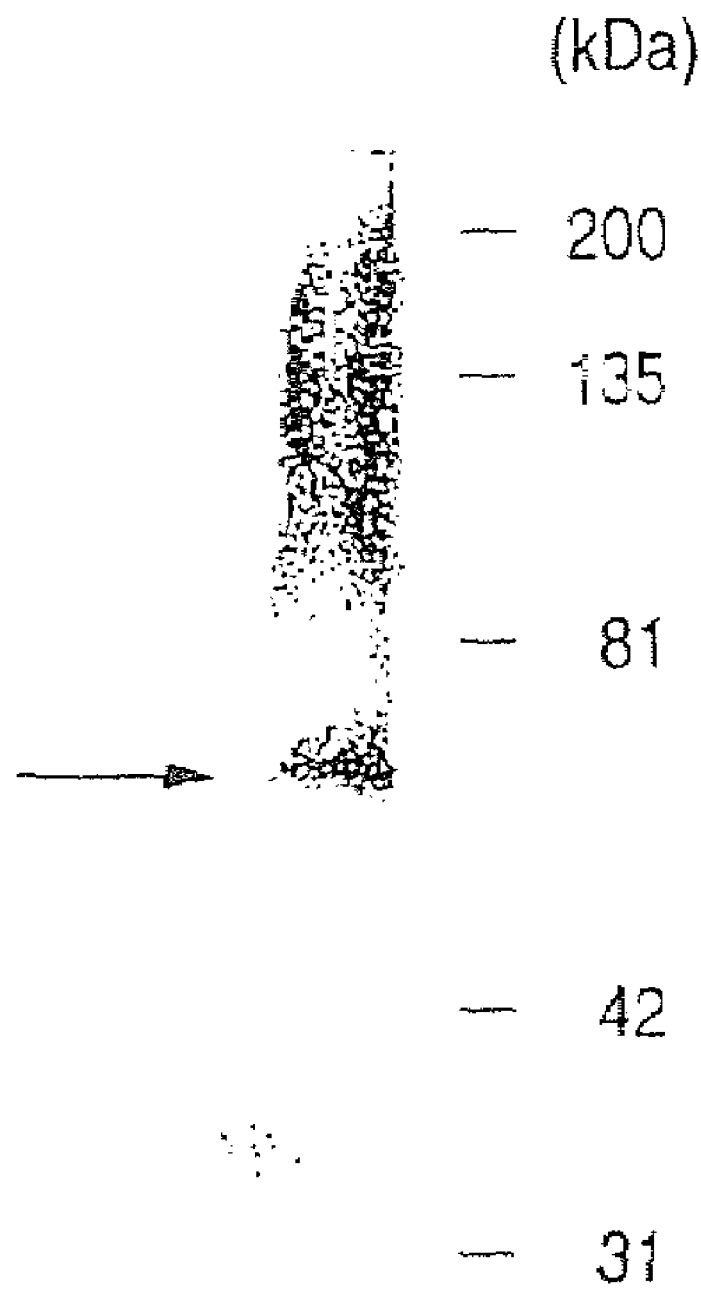

FIG. 28 is an electrophoresis pattern confirming the expression of the full length of the human-derived secretory aging-suppressing polypeptide in insect cells using the monoclonal antibody KM1902 against the aging-suppressing polypeptide fragment by Western blotting. The results in which Sf21 cells infected with a virus expressing the human-derived secretory aging-suppressing polypeptide were used are shown.

Figure 29:
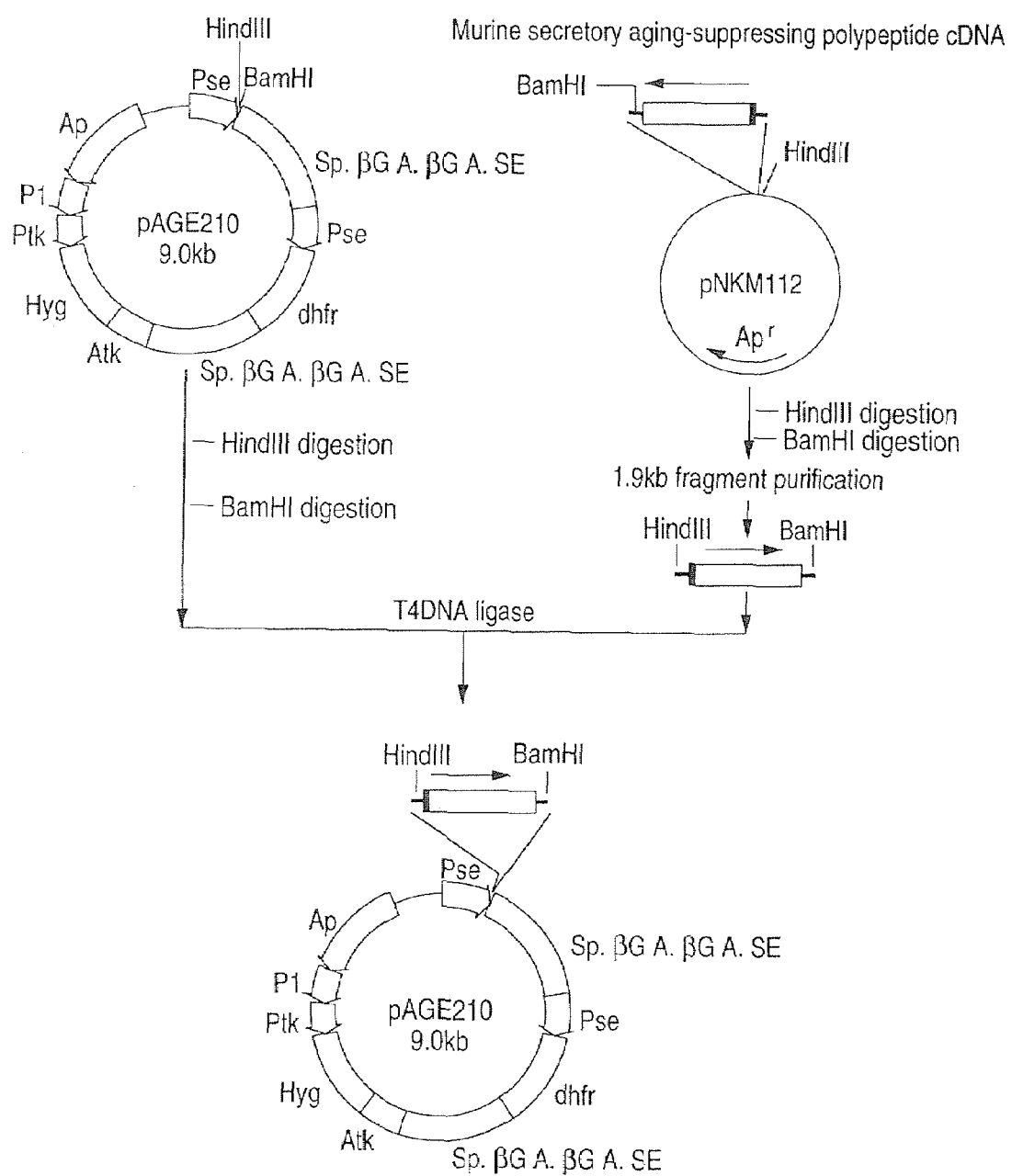

FIG. 29 is a view of the construction process of plasmid pYS112.

Figure 30:
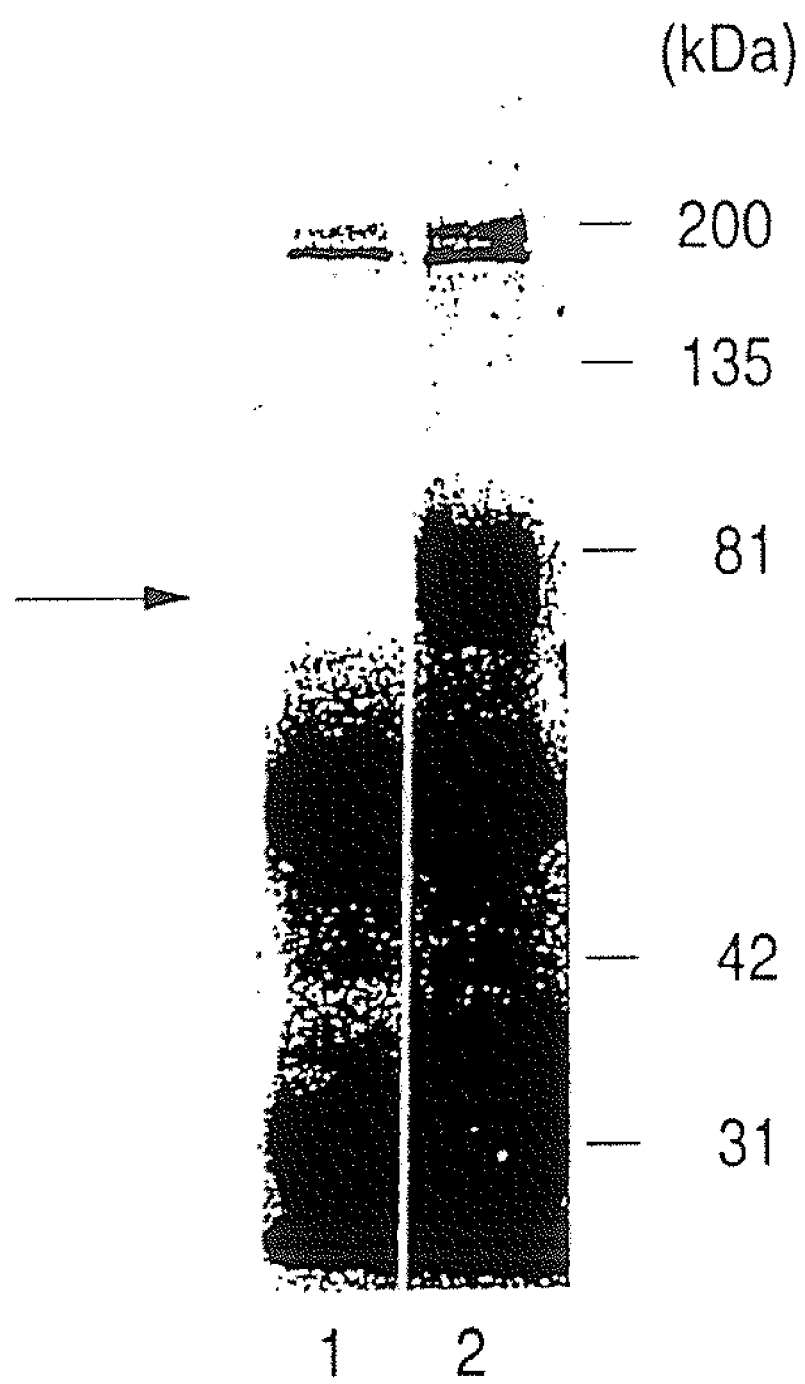

FIG. 30 is an electrophoresis pattern confirming the expression of the full length of the mouse-derived secretory aging-suppressing polypeptide in CHO cells (CHO dhfr$^-$) using the monoclonal antibody KM1902 against the aging-suppressing polypeptide fragment by immunoprecipitation; lane 1 represents the results of Western reaction using CHO cells; and lane 2 represents the results of Western reaction using CHO cells (CHO dhfr$^-$/pYS112) expressing the mouse-derived secretory aging-suppressing polypeptide.

Figure 31:
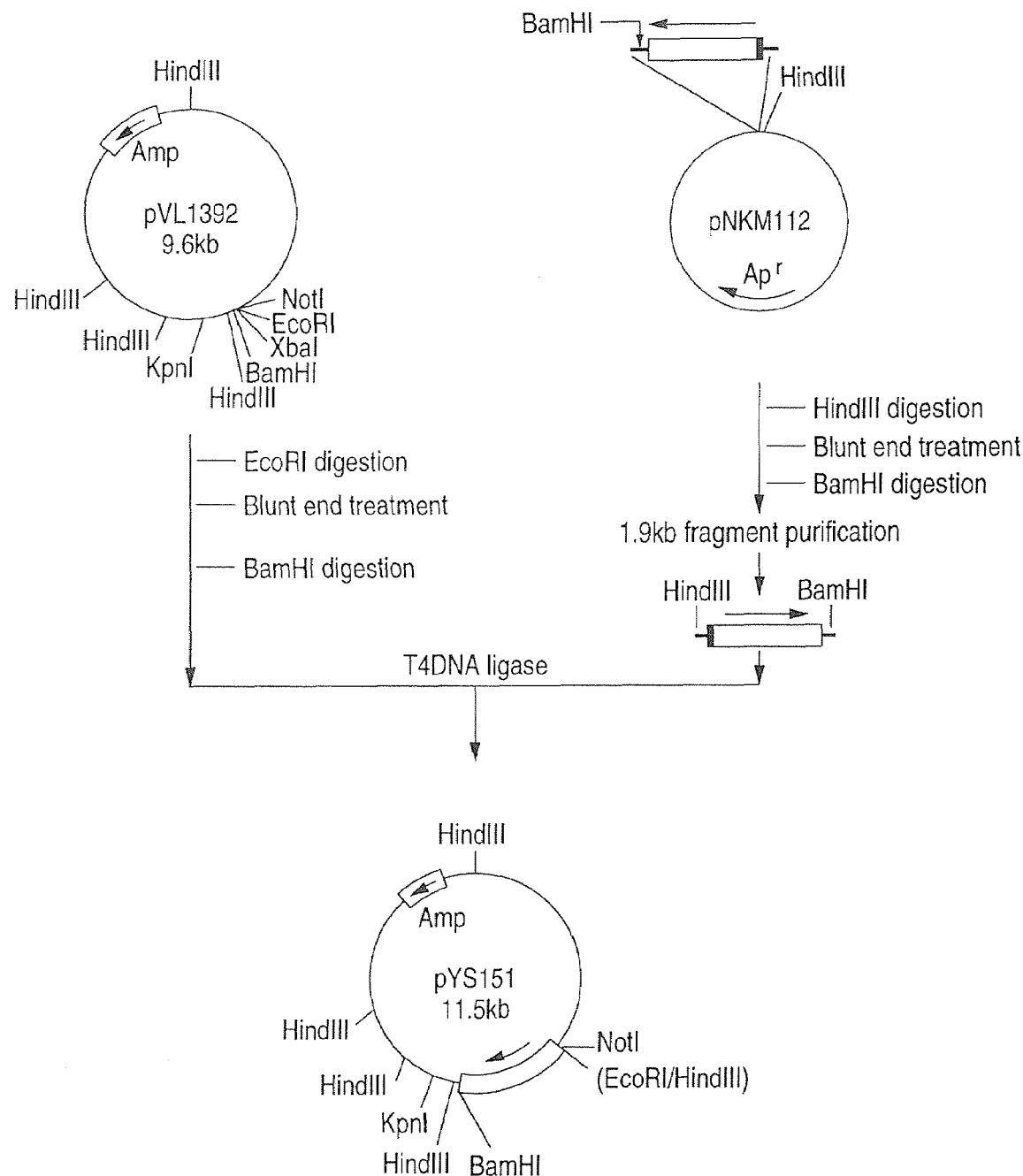

FIG. 31 is a view of the construction process of plasmid pYS151.

Figure 32:

FIG. 32 is an electrophoresis pattern confirming the expression of the full length of the mouse-derived secretory aging-suppressing polypeptide in insect cells using the monoclonal antibody KM1902 against the aging-suppressing polypeptide fragment by immunoprecipitation; lane 1 represents the results using Sf21 cells; and lane 2 represents the results using Sf21 cells infected with a virus expressing the mouse-derived secretory aging-suppressing polypeptide.

Figure 33:
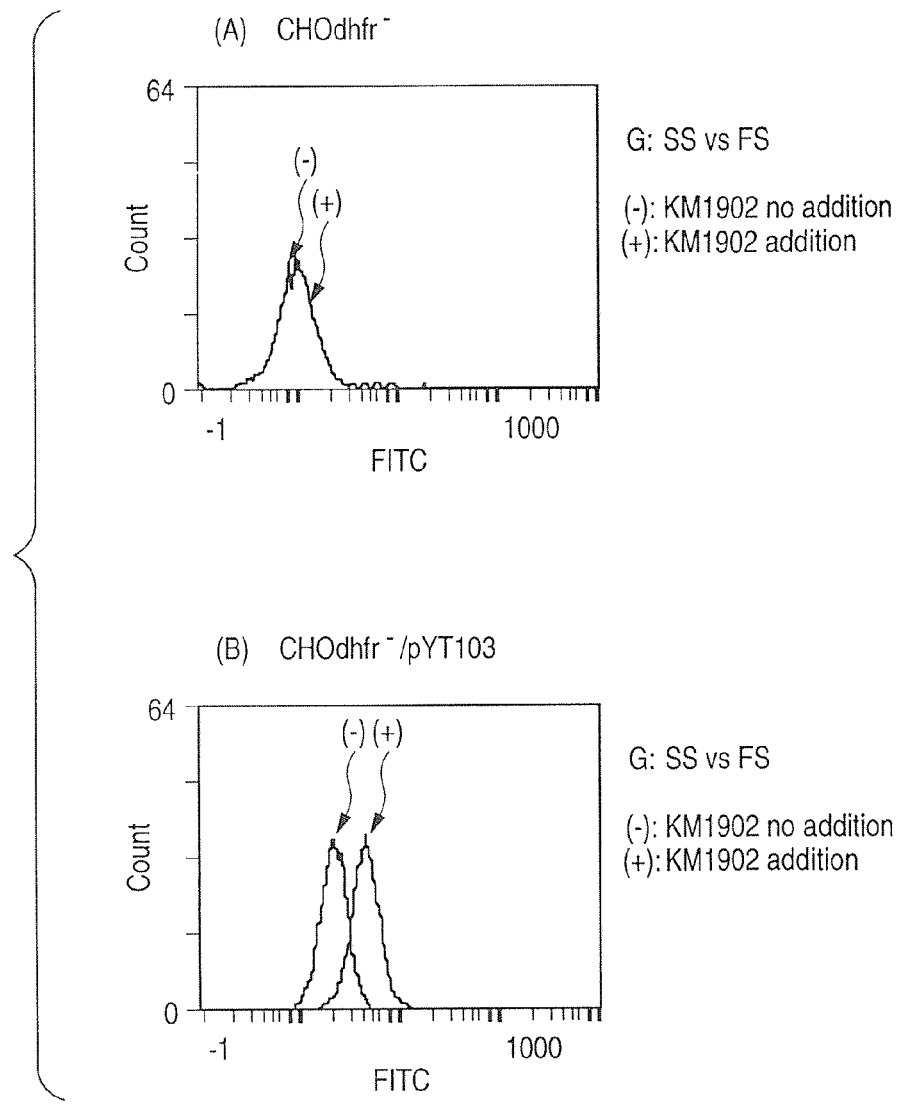

FIG. 33 is a view showing the analysis of the reactivity of the monoclonal antibody KM1902 by a flow cytometer; (A) represents the results of the comparison between the addition of the monoclonal antibody KM1902 and no addition of the antibody into CHO cells (CHO dhfr⁻); (B) represents the results of the comparison between the addition of the monoclonal antibody KM1902 and no addition of the antibody into CHO cells (CHO dhfr⁻/pYT103) expressing the aging-suppressing polypeptide.

Figure 34:
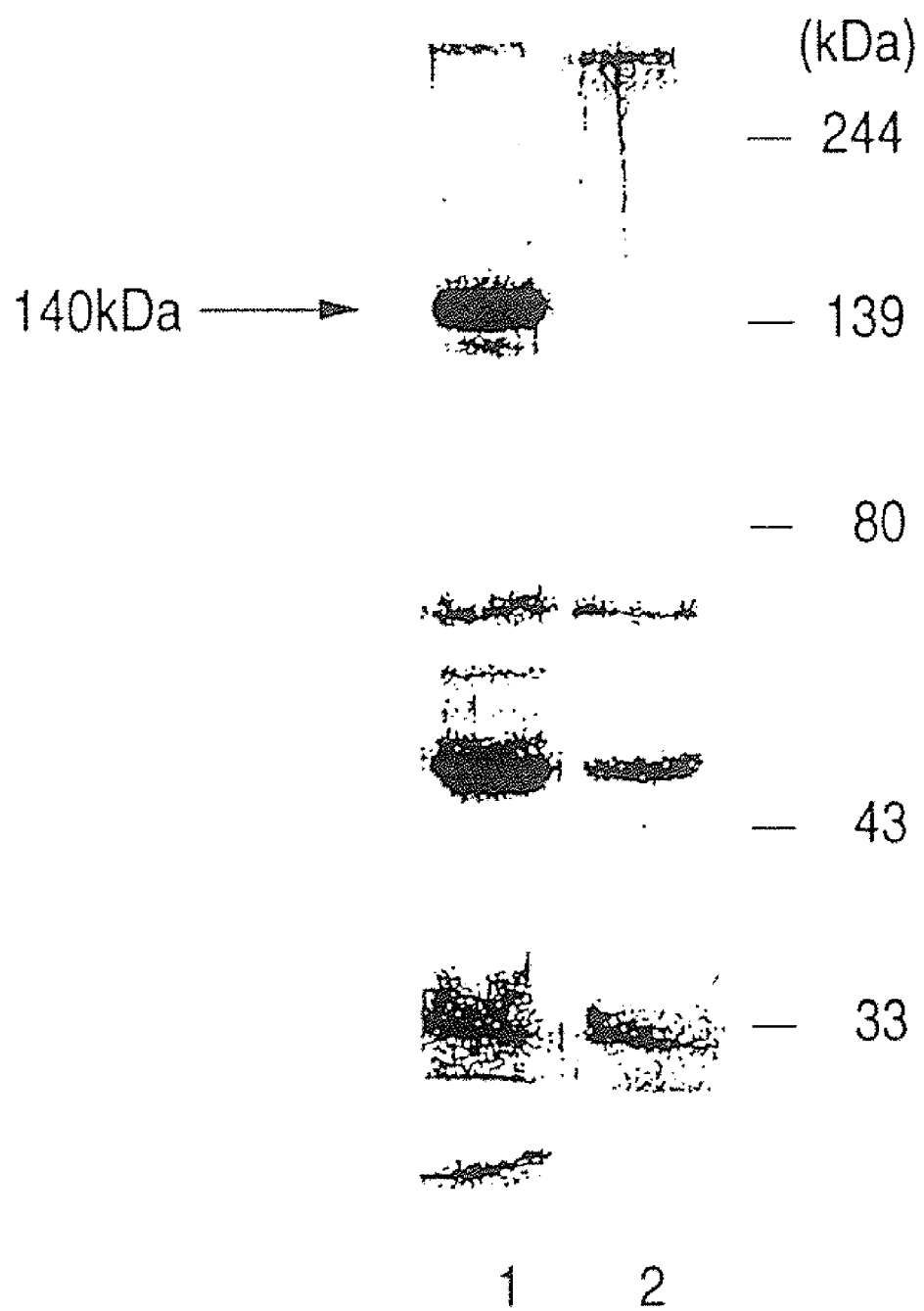

FIG. 34 depicts a Western blotting pattern showing the results of immunoprecipitation with the monoclonal antibody KM1902 using the aging-suppressing polypeptide expressing CHO cells (CHO dhfr⁻/pYT103); on lane 1, the results of immunoprecipitation with the monoclonal antibody KM1902 using the aging-suppressing polypeptide expressing CHO cells (CHO dhfr⁻/pYT103); and on lane 2, the results of immunoprecipitation with no addition of the monoclonal antibody KM1902 using the aging-suppressing polypeptide expressing CHO cells (CHO dhfr⁻/pYT103).

Figure 35:
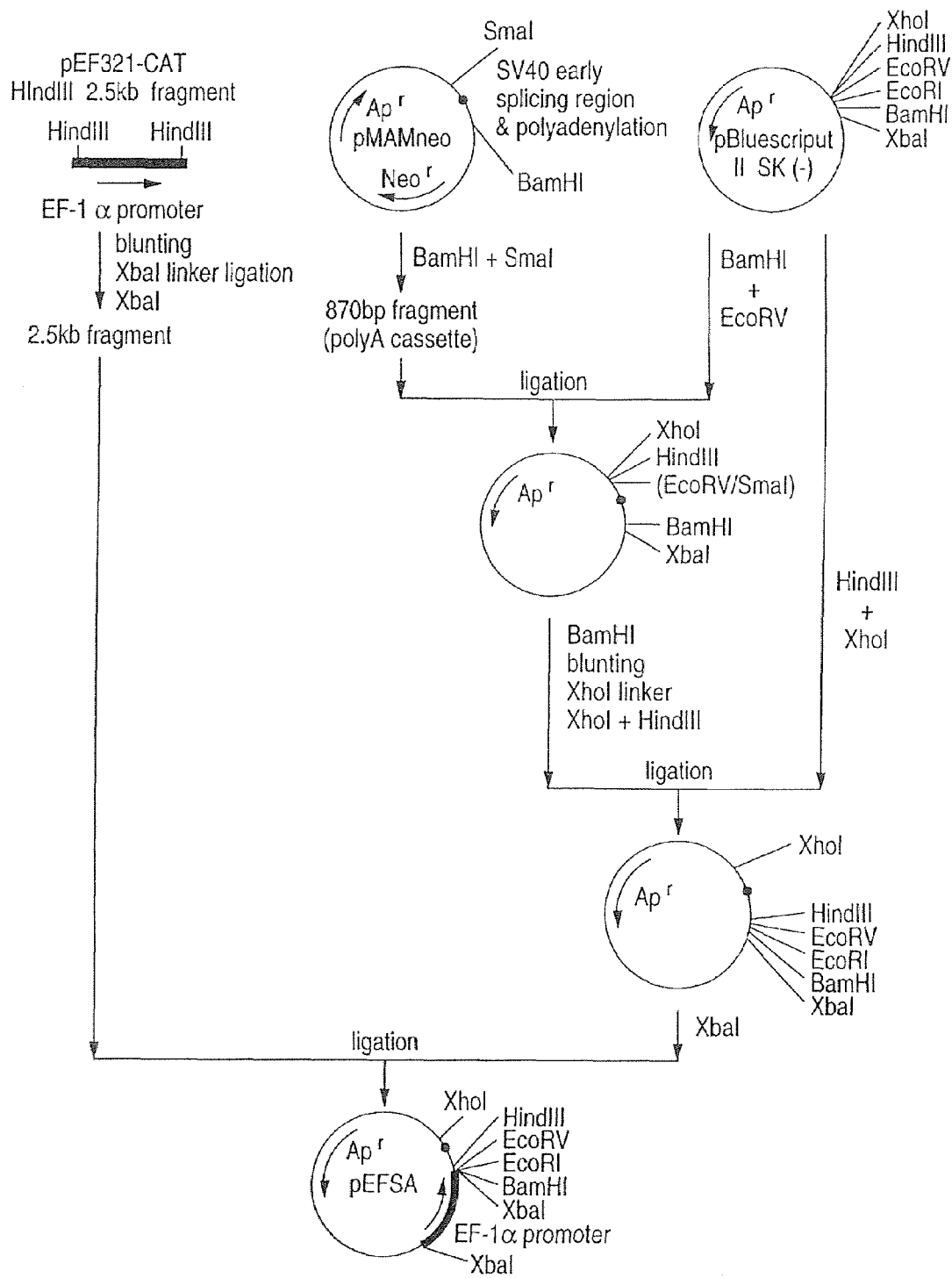

FIG. 35 depicts a scheme of the construction process of plasmid pEFSA.

Figure 36:
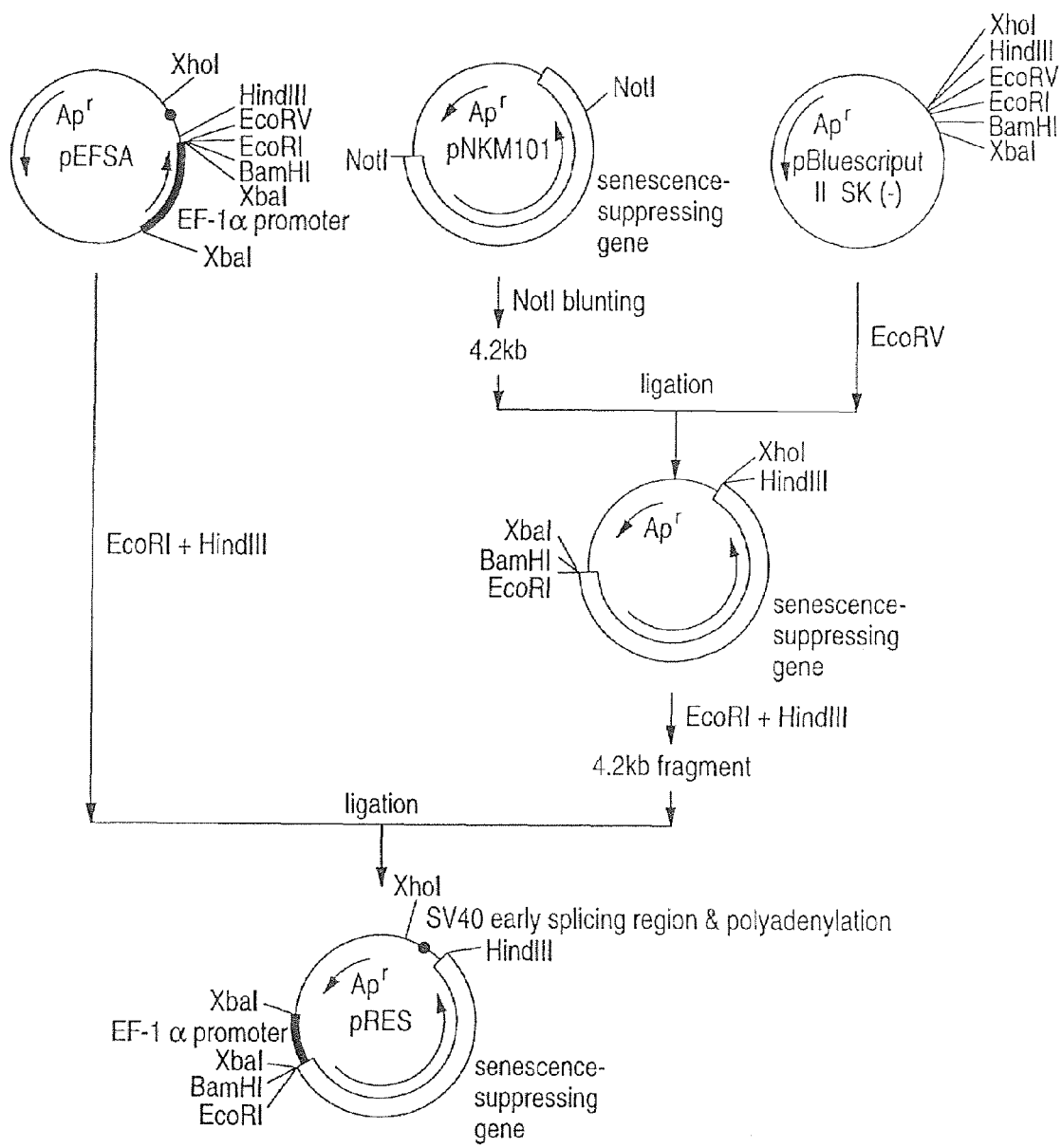

FIG. 36 depicts a scheme of the construction process of plasmid pRES.

Figure 37:
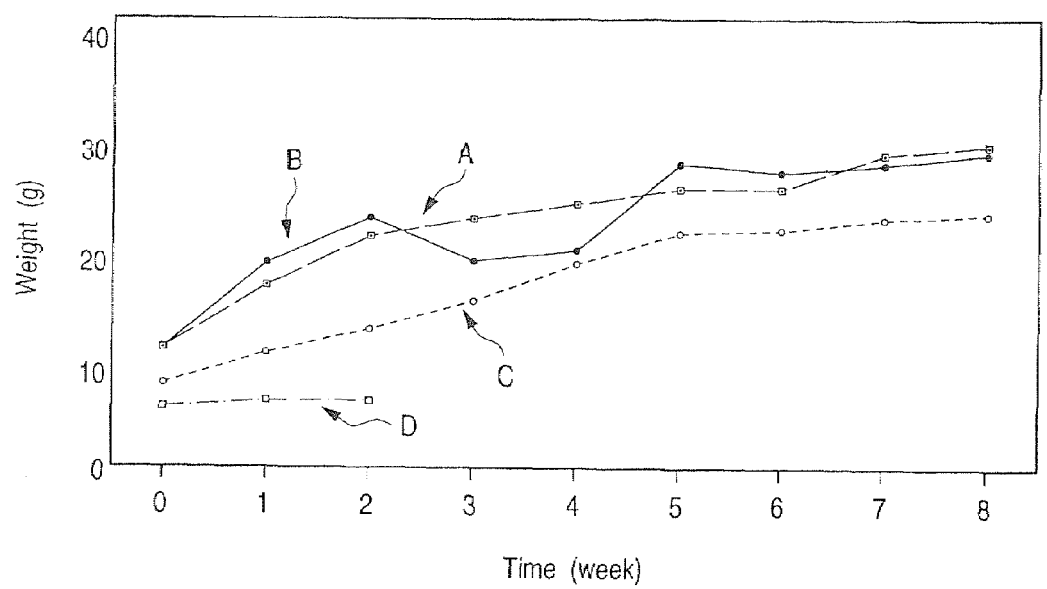

FIG. 37 depicts the results of the administration of a recombinant adenovirus harboring the murine aging-suppressing gene; A, wild-type with no administration; B, wild-type with administration of virus; C, homozygote (mouse showing a syndrome resembling premature aging) with administration of virus; D, homozygote (mouse showing a syndrome resembling premature aging) with no administration.

Figure 38:
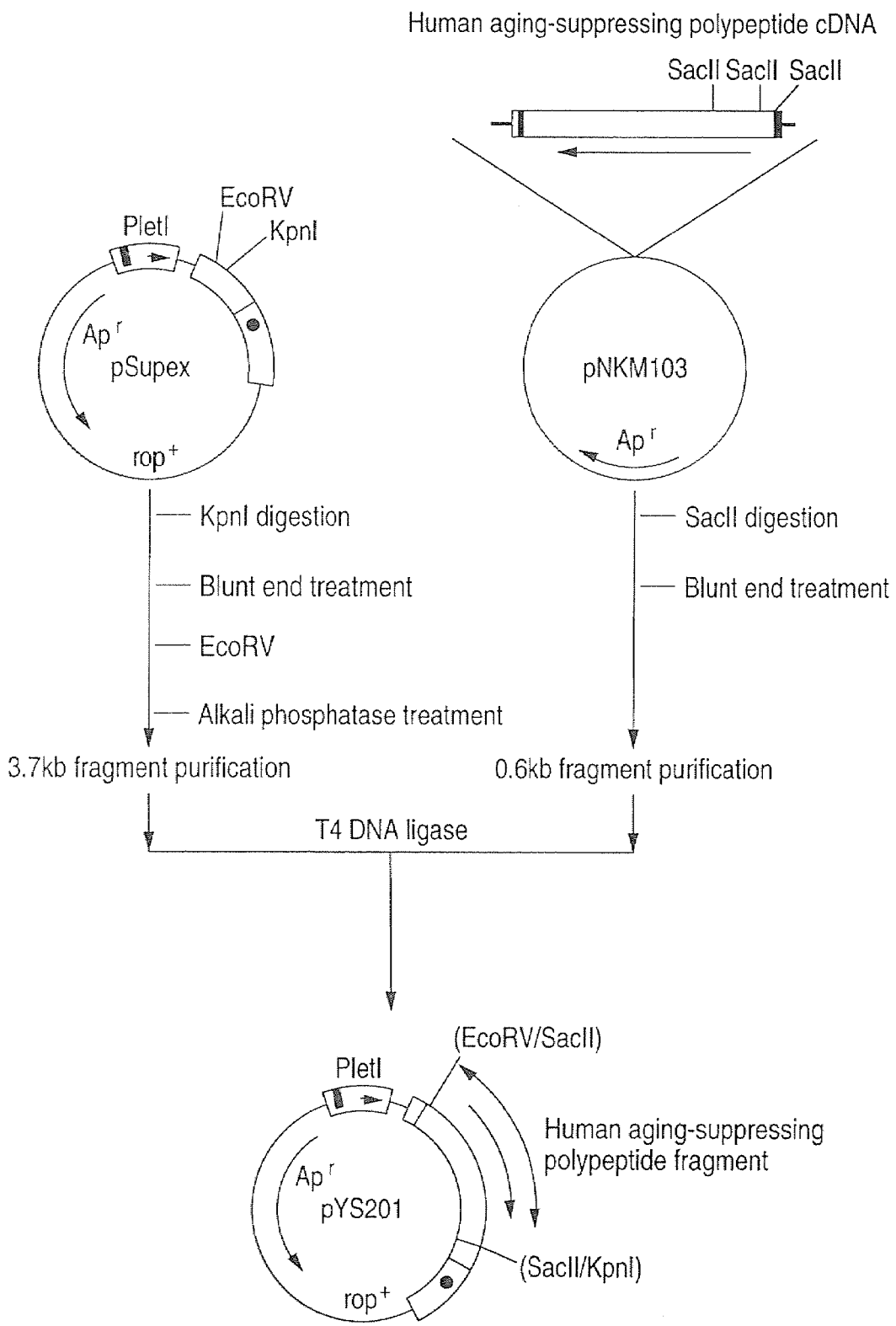

FIG. 38 depicts a scheme of the construction process of plasmid pYS201.

Figure 39:
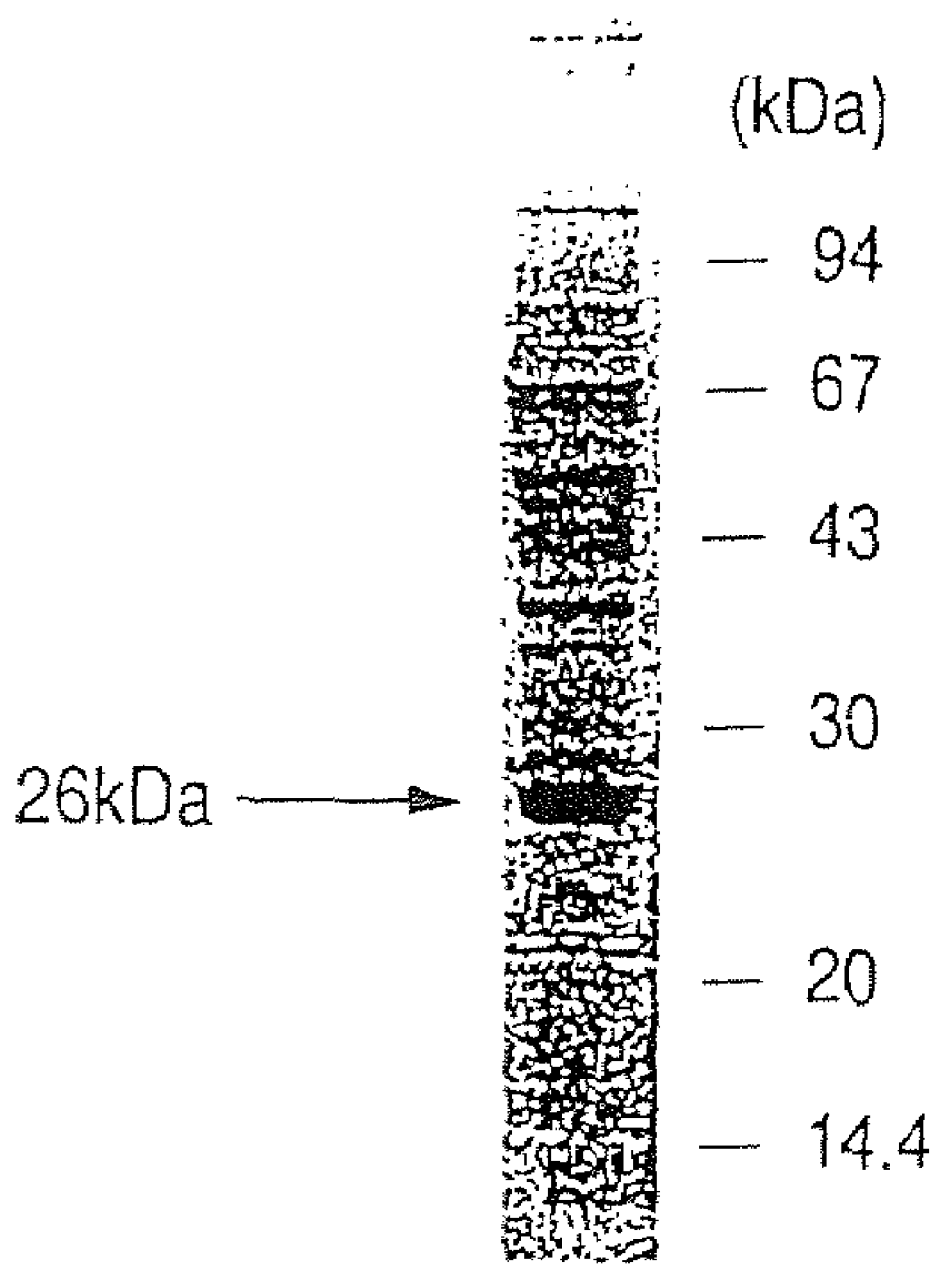

FIG. 39 is an SDS-polyacrylamide electrophoresis pattern of the human-derived aging-suppressing polypeptide N-terminal region (peptide SUHN) produced in *Escherichia coli* harboring pYS201.

Figure 40:
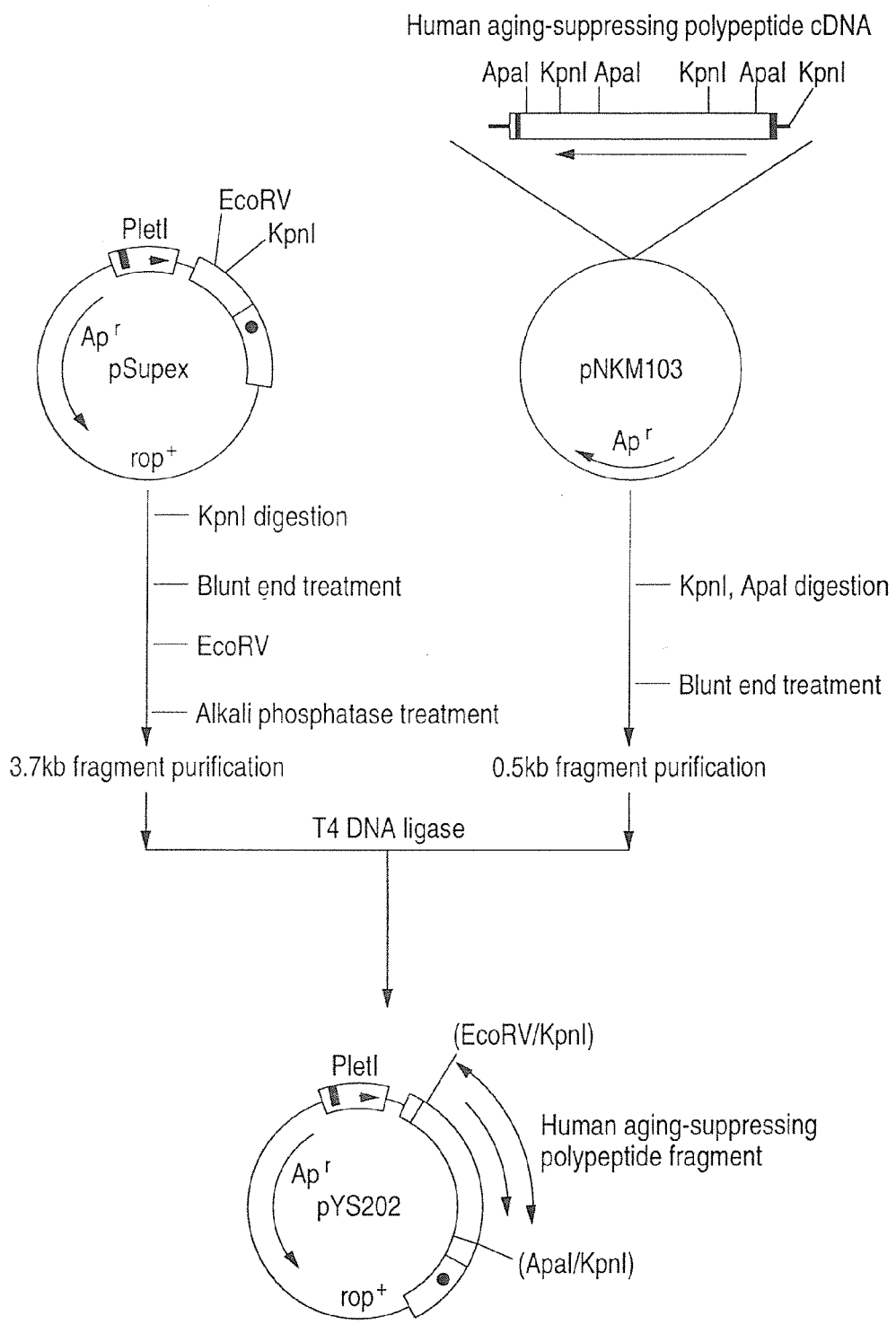

FIG. 40 depicts a scheme of the construction process of plasmid pYS202.

Figure 41:
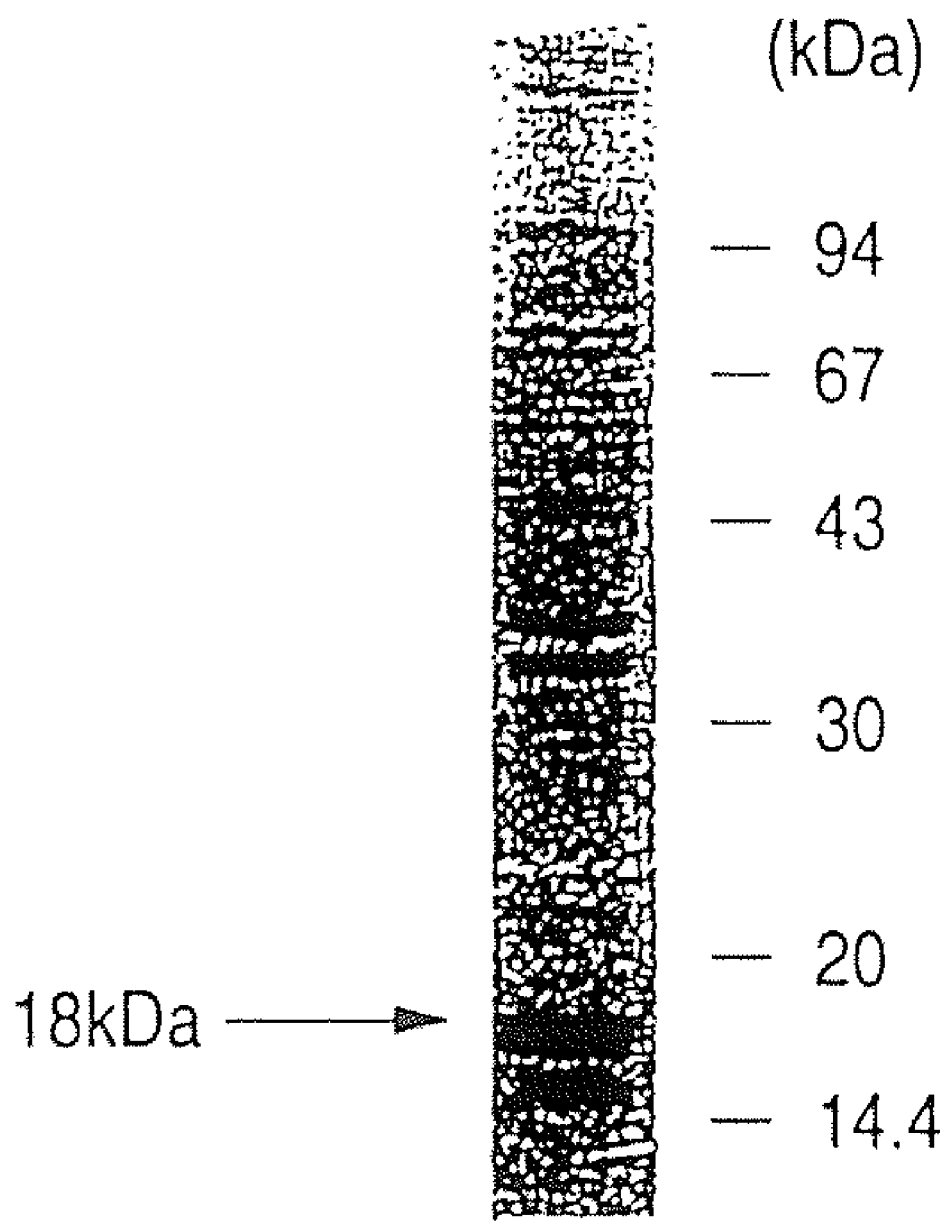

FIG. 41 is an SDS-polyacrylamide electrophoresis pattern of the human-derived aging-suppressing polypeptide C-terminal region (peptide SUHC) produced in *Escherichia coli* harboring pYS202.

FIG. 42 is an electrophoresis pattern depicting the results of Western blot hybridization of murine tissues. The extract solution of the murine membrane type complete length-expressing CHO cells; murine kidney, the membrane fraction and cytoplasmic fraction of liver, and the murine membrane type complete length-expressing CHO cell extract solution were separated by SDS-polyacrylamide electrophoresis, Western blotting was carried out using KM2076, and detection was carried out through exposure to an X-ray film with a chemiluminescent reagent.

FIG. 43 is an electrophoresis pattern showing the results of Western blot hybridization of a murine tissue and the extract solution of the murine membrane type complete length-expressing CHO cells using KM2119 and KM2116; the membrane fractions and cytoplasmic fractions of murine kidney and liver, and the extract solution of murine membrane-type complete length-expressing CHO cells were separated by SDS-polyacrylamide electrophoresis; Western blotting was carried out by means of KM2076 or KM2116, for detection through exposure to an X-ray film with a chemiluminescent reagent.

Figure 44:
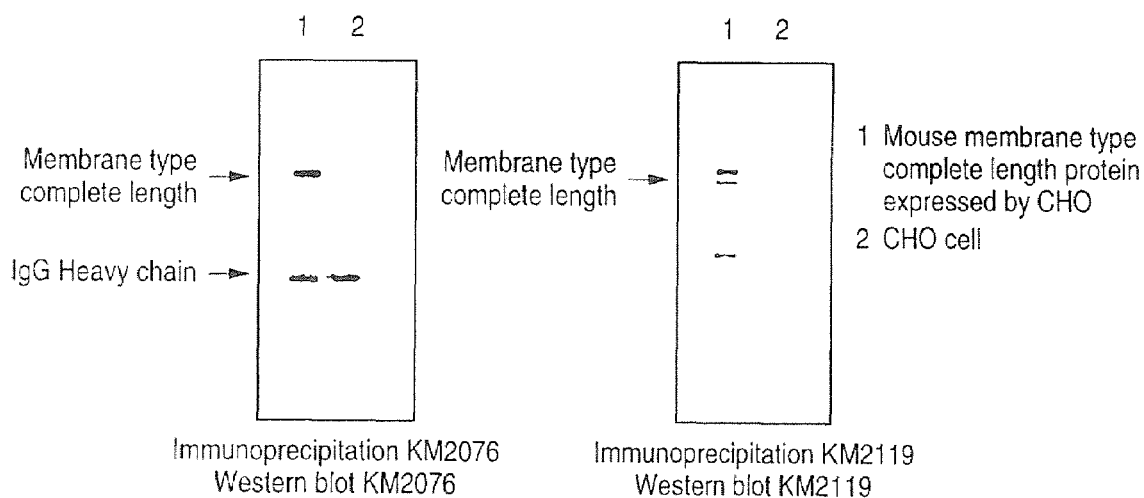

FIG. 44 is an electrophoresis pattern showing the results of Western blot hybridization, comprising preparing a cell extract solution from murine membrane-type complete length-expressing CHO cells, carrying out immunoprecipitation using KM2076, KM2119 and Protein G-Sepharose 4FF for separation by SDS-polyacrylamide electrophoresis, and carrying out Western blotting.

Figure 45:
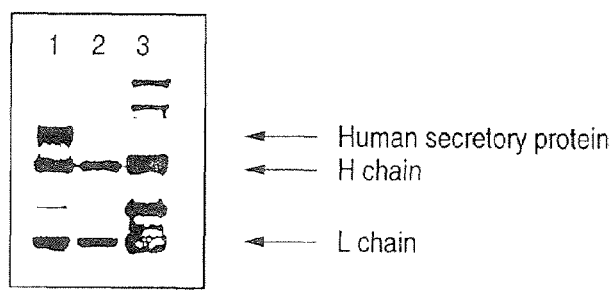

FIG. 45 depicts an electrophoresis pattern showing the results of Western blot hybridization, comprising immune precipitating a culture supernatant of human secretory expressing CHO cells using KM2076 and Protein G-Sepharose 4FF, carrying out SDS-polyacrylamide electrophoresis for separation, and carrying out Western blotting using KM2076; lane 1 represents the results of the immunoprecipitation of the culture supernatant of human secretory CHO cells using KM2076 and Protein G-Sepharose 4FF; lane 2 represents the results of the immunoprecipitation of a serum-free medium using KM2076; and lane 3 represents the results of the immunoprecipitation of the culture supernatant of the human secretory expressing CHO cells using NRIgG.

Figure 46:
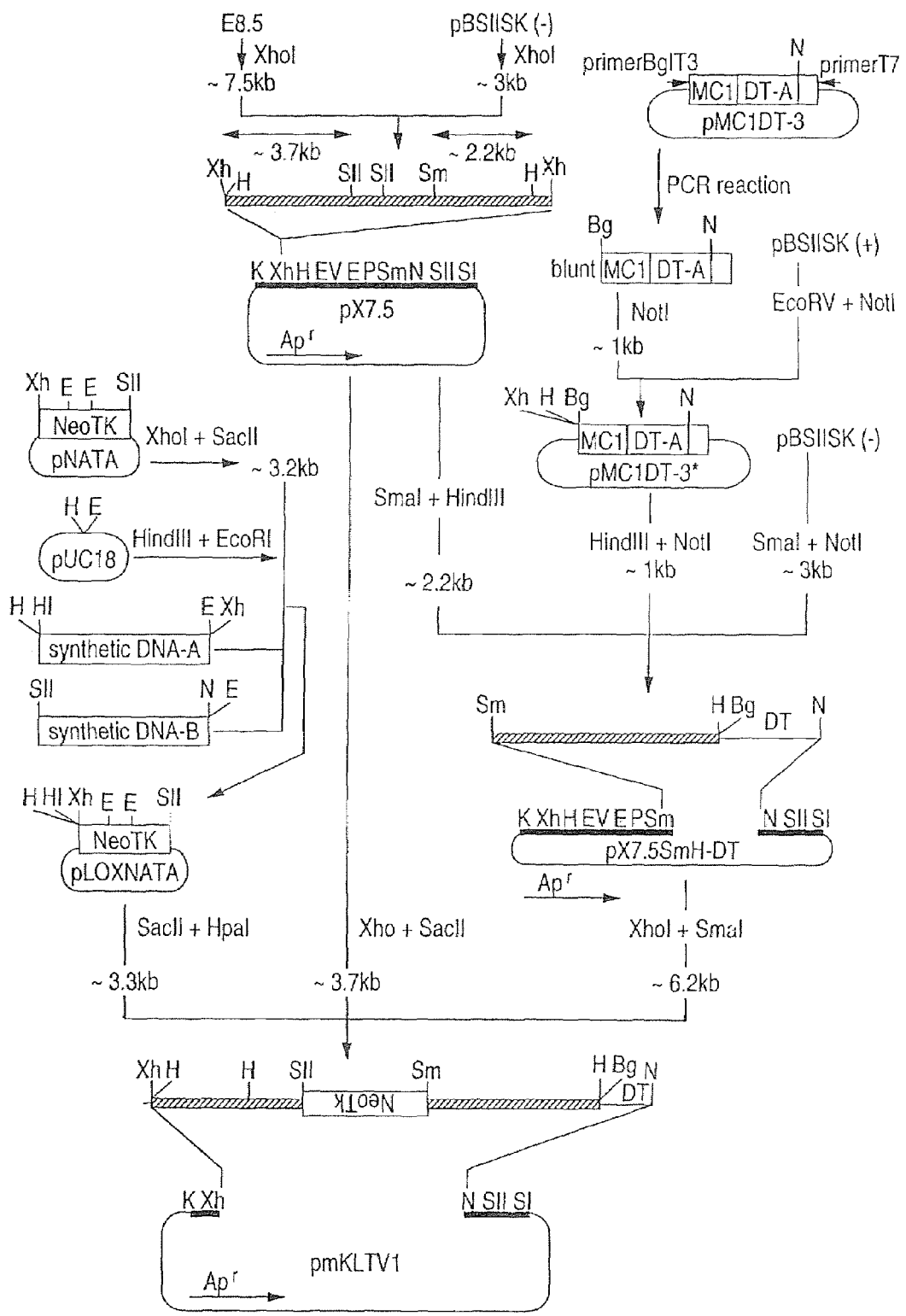

FIG. 46 is a graph showing a construction process of vector pmYLTV1 of interest. In the drawing, restriction enzymes are abbreviated as Bg for BglII, E for EcoRI, EV for EcoRV, H for HindIII, HI for HpaI, K for KpnI, N for NotI, SI for SacI, SII for SacII, Sm for SmaI and Xh for XhoI, and vectors are abbreviated as pBSIISK(+) for pBluescriptIISK(+) and pBSIISK(−) for pBluescriptIISR(−).

Figure 47:
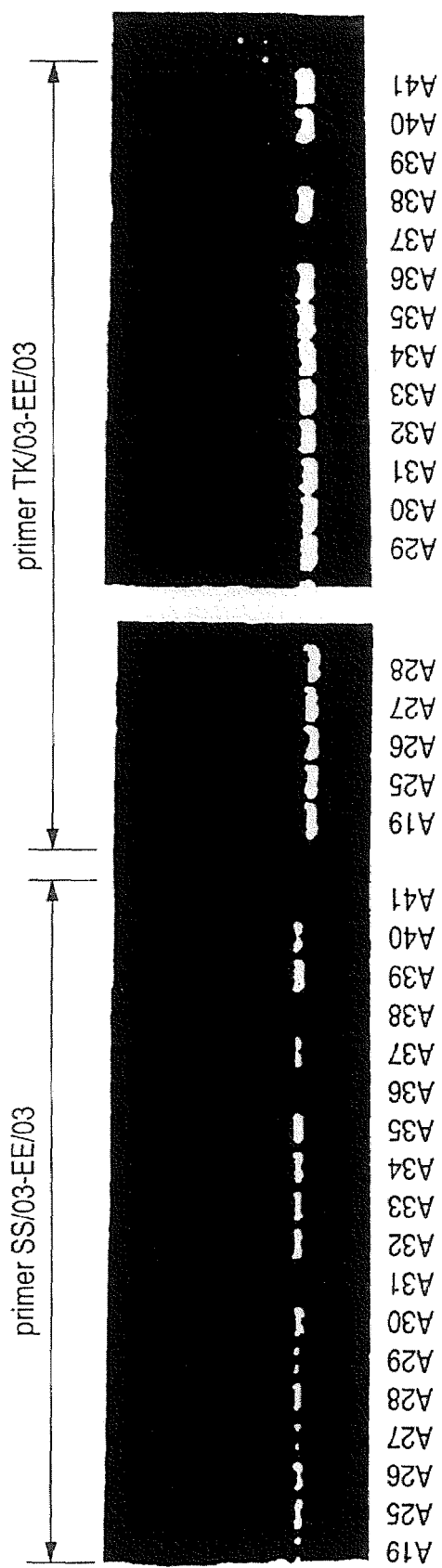

FIG. 47 is a graph showing results of the genotype analysis of mouse individuals obtained by crossbreeding of hetero mice. A DNA fragment of 640 bp is amplified with the primer set of TK/03 and EE/02 in samples obtained from individuals in which the exon 1 moiety of the aging-suppressing gene is destroyed. A fragment of 954 bp of the normal aging-suppressing gene is amplified with the set of SS/03 and EE/02. A19 and A25 to A41 shown in the bottom of the drawing are individual numbers.

DETAILED DESCRIPTION OF THE INVENTION

This application is based on Japanese applications No. 8-347871 filed on Dec. 26, 1996 and No. 9-205815 filed on Jul. 31, 1997, and PCT/JP97/04585 filed on Dec. 12, 1997, the entire contents of which are incorporated hereinto by reference.

The polypeptide of the present invention can be produced by the following processes 1 to 7.

(Process 1)

A mouse showing a distinctive syndrome resembling premature aging is screened out from the homozygotes of the mice using transgenic mice, that is a transgenic mouse into which a foreign gene is introduced, e.g., a Na⁺/H⁺ reverse transporter linked to the known human elongation factor-1α promoter (EF-1α promoter) (Japanese Published Unexamined Patent Application No. 268856/1993). The foreign gene introduced into the transgenic mouse, which functions as a marker, is referred to as "introduction gene" hereinafter. Any gene may be used as such introduction gene, so long as the gene can be detected after the gene is introduced into mice.

Mice showing a syndrome resembling premature aging include mice with higher incidence of short lifespan, juvenile arteriosclerosis, osteoporosis, atrophy of gland tissues, reduction of nerve cells and the like, and more specifically, include a mouse showing a syndrome resembling premature aging as reported at the 18th Annual Meeting of The Molecular Biology Society of Japan (Nabeshima et al., 2K-02, 1995).

As the results of observation, the mouse showing a syndrome resembling premature aging has the properties described below:

OBSERVATION EXAMPLE 1

Apparent Observation

A homozygote of an aged mouse (age 8 to 9 weeks) is of a body length of about 4 cm, which is considerably small, compared with the body length of a wild-type mouse of the same age in weeks (about 6 cm). Additionally, the ratio of the head part to the waist length is large. Although the body size of the aged mouse (male, age 8 weeks) is very small, no abnormality is found in the luster of body hair or the nail of limbs. The performance is normal.

As to longevity, 1) the growth stops around three weeks of age after birth, involving gradual reduction of activity;

2) the longevity is shortened such that mean longevity is 8.0±0.9 weeks (n=13) in males while in females, the mean longevity is 9.3±0.9 weeks (n=13); these mice are characteristic in their syndrome resembling premature aging such that all the mice are dead by 15 weeks of age after birth.

Five homozygous males and 5 homozygous females, around age 8 weeks, and 4 wild-type male mice and 4 female mice as litters from the same mother, were subjected to autopsy, followed by macroscopic observation, and then, these mice were subjected to formalin fixing, paraffin embedding, thin-sectioning procedures and HE staining, for pathological observation by a known method (edited by Kei-ichi Watanabe and Kazuho Nakane, Enzyme Antibody Method, Gakusai Kikaku, 1992, the 3rd revised edition) (up to Observation Example 12, hereinafter, animals were observed by the same procedures).

OBSERVATION EXAMPLE 2

Pathological Examination of Pituitary Gland

Reduction numbers of acidophil cells were observed. The acidophil cells of the pituitary gland are cells that produce growth hormone (GH) or prolactin (PRL). It is known that GH secretion is reduced in aged individuals.

OBSERVATION EXAMPLE 3

Pathological Observation of Gonad

Gonad is distinctively atrophied, which indicates that the animals are infertile. In males, the testicle is prominently atrophied, which can be visualized with the naked eye. The size of the seminiferous tubule is atrophied to an extent as small as about ⅓ the size in the wild-type, so that sperm maturation is advanced only to the pachytene stage of spermacytes, with absolutely no observed sperm. In females, ovary and uterus are markedly atrophied even macroscopically. Egg maturation is advanced only to primary ovarian follicle, with no observed secondary ovarian follicle or corpus luteum.

OBSERVATION EXAMPLE 4

Pathological Examination of Submaxillary Salivary Gland

In normal males, a vast amount of acidophil granules is contained at their striated part, while in homozygotes, the cells at the striated part are short in length, with almost no acidophil granules observed.

OBSERVATION EXAMPLE 5

Pathological Examination of Kidney

Mineralization is observed in the epidermis of uriniferous tubule, the wall of Bowman's capsule and the like. The wall of Bowman's capsule is composed of squamous epidermis.

OBSERVATION EXAMPLE 6

Pathological Examination of Vascular System

Arteriosclerosis was prominent in homozygotes. The size of the thoracic aorta was irregular and a higher degree of mineralization was present on the tunica media. Additionally, hypertrophy of the tunica intima was observed. Arteriosclerosis, primarily involving mineralization of the tunica media and hypertrophy of the tunica intima, was observed in a medium blood vessel such as renal artery to small blood vessel in parenchymatous organs. Particularly, the mineralization of the tunica media of the blood vessel in renal parenchyma was distinctive, but glomerulus and uriniferous tubule were nearly normal. Kossa staining verified that the deposit was certainly $Ca^{2+}$. Mineralization of the tunica media of the aorta was frequently observed in aged individuals.

OBSERVATION EXAMPLE 7

Pathological Observation of Lung Tissue

The damage to the structure, particularly the wall, of alveoli pulmonis was prominent. Mineralization was also observed in the wall of alveoli pulmonis.

OBSERVATION EXAMPLE 8

Observation of Soft Tissue and Cartilage

Mineralization was observed in the tunica mucosa tracheae intrinsic layer, gastric mucosa intrinsic layer and mucosa fascia, and the epidermis of alveoli pulmonis. Mineralization was also observed in fundus ventricule gland cells and submucosal connective tissue and muscle layer. The mineralization of gastric mucosa is similar to the finding observed in rats and mice fed for a prolonged term. Additionally, the mineralization of the mitral ring of the heart was observed in some individuals. The mineralization of the mitral ring is a finding characteristic to aged persons. Furthermore, mineralization was also observed in joint cartilage, tracheal cartilage, and costochondral cartilage. The mineralization of these glass cartilages is a finding frequently observed in aged persons.

OBSERVATION EXAMPLE 9

Pathological Observation and X-Ray Observation of Bone Tissue

An increase in the bone density of the metaphysis of the distal end of the femur was observed, together with chondroepiphyseal hypertrophy. An image of irregular mineralization over cartilage cells was observed in joint cartilage. X-ray transmission of the femur and tibia was escalated, which possibly indicates the reduction of mineral density. Actual mineral density of the diaphyseal area, tibia distal end and femur proximal end was measured and showed reduction at maximum by about ½ the densities in the wild-type. Histologically, cortex bone was prominently reduced. Primary sponge bone proliferated exceptionally on the diaphyses of the tibia proximal end and femur distal end, and the mineral density adversely increased, only on that part.

OBSERVATION EXAMPLE 10

Pathological Observation of Cerebellum

The reduction of the number of Purkinje's cells in the cerebellum nerve cell layer, as well as isolated necrosis and expansion of axon, was observed. It has been known that Purkinje's cells are decreased in the cerebellum following aging, which involves the expansion of axon protrusion.

OBSERVATION EXAMPLE 11

Pathological Observation of Liver

Almost no glycogen granule stained as acidophil is observed. The cytoplasm of liver cells is slightly small, compared with the cytoplasm in normal subjects.

OBSERVATION EXAMPLE 12

Pathological Observation of Thymus

The thymus is prominently atrophied, but cannot be confirmed in some individuals visually with the naked eye.

(Process 2)

The chromosomal part damaged and inactivated by insertion of the introduction gene was isolated from a mouse showing a syndrome resembling premature aging. The DNA present in the chromosal region was then analyzed by cloning techniques.

(Process 3)

After confirming the expression state of the DNA in individual tissues of normal mice, the causative gene of a syndrome resembling premature aging (hereinafter referred to as "aging-suppressing gene"), the expression of which is unlikely to be observed in normal mice, is determined.

(Process 4)

The aging-suppressing gene in humans and the like is determined by cloning a gene with high homology to the murine aging-suppressing gene from a cDNA library of humans and the like.

(Process 5)

A polypeptide encoded by the gene is produced and accumulated by expressing the aging-suppressing gene of mice, humans and the like in suitable host cells such as *Escherichia coli*, insect cells and mammalian cells and the like through conventional methods using genetic recombinant technology.

(Process 6)

By purifying the accumulated polypeptide by a conventional method and using the polypeptide as an immunogen, an antibody against the polypeptide is raised in rats, mice, rabbits, sheep, guinea pigs, horses, cow, monkeys and the like.

(Process 7)

It should be confirmed that the antibody raised recognizes the polypeptide produced and accumulated by *Escherichia coli*, insect cells, mammalian cells and the like through conventional methods using genetic recombinant technology.

The present invention will now be described in detail.

The DNA of the present invention is DNA encoding a polypeptide having an activity of suppressing aging, for example, DNA encoding the polypeptide of an amino acid sequence selected from amino acid sequences represented by SEQ ID NOS:1, 2, 3, 4 and 5; DNA encoding a peptide comprising an amino acid sequence wherein at least one amino acid of the amino acid sequence of a polypeptide comprising an amino acid sequence selected from amino acid sequences represented by SEQ ID NOS:1, 2, 3, 4 and 5 is deleted, substituted or added, and the peptide having an activity of suppressing aging; and DNA which hybridizes with the DNA under stringent conditions.

The DNA which hybridizes under stringent conditions means the DNA obtained by colony hybridization, plaque hybridization or Southern blot hybridization using DNA encoding a polypeptide having an activity of suppressing aging as the probe, specifically including DNA identified after hybridization, using a filter on which colony- or plaque-derived DNA has been immobilized in the presence of 0.7 to 1.0 M NaCl at 65° C. and washing the resulting filter using 0.1 to 2×SSC solutions (the composition of 1×SSC solution comprises 150 mM sodium chloride and 15 mM sodium citrate) at 65° C. Hybridization can be carried out according to a method described, for example, in *Molecular Cloning, A Laboratory Manual*, the 2nd edition [Sambrook, Fritsch, & Maniatis eds., Cold Spring Harbor Laboratory Press, 1989 (hereinafter referred to as "*Molecular Cloning*, 2nd ed.")]. Specific examples of the DNA which hybridizes include DNA having a homology of 60% or more with a nucleotide sequence of the DNA encoding the polypeptide of an amino acid sequence selected from amino acid sequences represented by SEQ ID NOS:1, 2, 3, 4 and 5, preferably DNA having a homology of 80% or more, and more preferably DNA having a homology of 95% or more.

The oligonucleotide of the present invention includes an oligonucleotide comprising a nucleotide sequence which is identical or complementary to a partial nucleotide sequence of the nucleotide sequence of the DNA, for example, an oligonucleotide comprising a nucleotide sequence which is identical or complementary to a nucleotide sequence of continuous 5 to 60 residues, preferably 10 to 50 residues, in the nucleotide sequence of DNA selected from SEQ ID NOS:6 to 10, and derivatives of the oligonucleotide.

The polypeptide of the present invention includes the polypeptide encoded by the DNA, specifically including a polypeptide of an amino acid sequence selected from amino acid sequences represented by SEQ ID NOS:1, 2, 3, 4 and 5, or DNA encoding a peptide comprising an amino acid sequence wherein at least one amino acid of the amino acid sequence of a polypeptide comprising an amino acid sequence selected from amino acid sequences represented by SEQ ID NOS:1, 2, 3, 4 and 5 is deleted, substituted or added and the peptide having an activity of suppressing aging.

The peptide comprising an amino acid sequence in which at least one in the amino acid sequence of the polypeptide is deleted, substituted or added and having an activity of suppressing aging can be prepared according to a method described, for example, in *Nucleic Acids Research*, 10: 6487 (1982); *Proc. Natl. Acad. Sci., USA*, 79: 6409 (1982); *Proc. Natl. Acad. Sci., USA*, 81: 5662 (1984); *Science*, 224: 1431 (1984); PCT WO 85/00817 (1985); *Nature*, 316: 601 (1985); *Gene*, 34: 315 (1985); *Nucleic Acids Research*, 13: 4431 (1985); and *Current Protocols in Molecular Biology, Chapter 8, Mutagenesis of Cloned DNA*, John Wiley & Sons, Inc. (1989).

The antibody of the present invention includes antibodies recognizing the polypeptide described above.

The ligand of the present invention means a molecule specifically binding to the polypeptide of the present invention, and any molecule can be used as the ligand of the present invention, so long as it is capable of specifically binding to the polypeptide of the present invention.

A method for preparing DNA encoding the polypeptide having an activity of suppressing aging in accordance with the present invention is described below.

1) Cloning of Murine Chromosomal DNA Adjacent to the Introduction Site of Gene (i) Detection of Introduction Gene Multiple copies of an introduction gene can be incorporated into a transgenic mouse, but generally, the copies are inserted in succession in tandem into one site of the chromosomal DNA.

To confirm that the insertion site of an introduction gene resides at one site in a transgenic mouse showing a syndrome resembling premature aging, the chromosomal DNAs prepared from the livers of the wild-type, the heterozygote and the homozygote are digested with restriction enzymes (EcoRV, XbaI, etc.) with no cleavage potency of the introduction gene, for Southern blotting using the full length of the introduction gene as the probe.

By confirming that a single signal is detected in the heterozygote and homozygote by Southern blotting, it is indicated that the introduction gene is inserted at only one site in the murine chromosome.

Introduction gene insertion can also be confirmed by fluorescent in situ hybridization (FISH) using the introduction gene as the probe.

(ii) The Cloning of the Murine Chromosomal DNA Adjacent to the Site of Insertion of the Introduction Gene can be Carried out as Follows.

If the introduction gene inserted into a transgenic mouse contains a plasmid vector, such as pUC or the like, the plasmid rescue process can be used.

That is, after the chromosomal DNA of the homozygote is digested with an arbitrary restriction enzyme with no cleavage potency of the plasmid vector, which is capable of self-circularization, the resulting DNA is then transformed into *Escherichia coli*. Only transformed *Escherichia coli* harboring the auto-circularized DNA containing a plasmid expressing a chemical resistance gene (for example, ampicillin resistant gene) derived from the plasmid vector form colonies on a selective medium. The plasmid obtained from the *Escherichia coli* may possibly contain the introduction gene per se and a fragment of the murine chromosomal DNA adjacent to the gene.

Southern blotting is carried out to confirm that the segment adjacent to the introduction gene is derived from the fragment of the murine chromosomal DNA using the fragment of the murine chromosomal DNA segment contained in the rescued plasmid as the probe and the same membrane used for the aforementioned Southern blotting. More specifically, it should be confirmed that only the signal from the wild allele (wild allele is hereinafter sometimes referred to as "+") is observed in the wild-type mouse; only the signal from the mutant allele (mutant allele is hereinafter sometimes referred to as "pg") is observed in the homozygote; and signals from both alleles are observed in the heterozygote.

In addition to the rescue method, common chromosomal DNA cloning may also be used. More specifically, chromosomal DNA is digested with a restriction enzyme, and the resulting digested fragments are cloned using general plasmid vectors or phage vectors to prepare a library. By using the fragments of the introduction gene as the probe and according to a method similar to the rescue method, the cloning of the murine chromosomal DNA adjacent to the site of the introduction gene can be carried out by screening the library.

2) Cloning of Aging-suppressing Gene Derived from Mouse

A phage clone that hybridizes with the probe is obtained by using the fragments of the murine chromosomal DNA segment contained in the plasmid obtained by the chromosomal DNA cloning or rescue method as the probe and screening the wild-type mouse genomic library (Stratagene, murine genomic library, λFIXII) according to known methods.

In order to identify the aging-suppressing gene, the nucleotide sequence is sequentially determined, in which the murine chromosomal DNA contained in the plasmid obtained by centering the chromosomal DNA cloning method or rescue method.

Because it is known that the first exon and second exon of a gene are frequently present in the CpG island (Bruce Alberts et al., *Molecular Biology of the Cell*, Keiko Nakamura and Kenichi Matsubara as responsible translators, Kyoikusha, Apr. 25, 1985), the CpG island region should be identified during the determination of the nucleotide sequence, and then, the murine chromosomal DNA contained in the plasmid obtained by the chromosomal DNA cloning method or rescue method should be digested with an appropriate restriction enzyme, for example, SacII or the like so as to contain the CpG island.

If no CpG island region is observed, an exon region should be predicted by an exon trapping method [for example, using Exon Trapping System (manufactured by GIBCO BRL, CO.)] or by using a computer software for predicting an exon region on a nucleotide sequence [For example, HEXON: Human Genome Center, Baylor College of Medicine, Houston on Internet; available on the address http://dot.imgen.bc-m.tmc.edu:9331/gene-finder/gf.html as TX gene structure analysis site], and thereafter, a DNA fragment possibly containing an exon can be isolated using restriction enzymes.

It can be confirmed by the following method that the DNA fragment is involved in the aging-suppressing gene.

The DNA fragment is labeled with α-[$^{32}$P]-dCTP, for example, using Megaprime DNA Labeling Kit (manufactured by Amersham Co.) or the like.

Northern hybridization is carried out using the labeled DNA as the probe and using a poly(A)$^+$ RNA filter of murine heart, brain, spleen, lung, liver, skeletal muscle, kidney and spleen [Filter of Mouse Multiple Tissue Northern Blots (manufactured by Clontech Co.)] according to the manual conditions for Hybond N$^+$.

Through the Northern hybridization, tissues with bands are identified.

From the wild-type, homozygote and heterozygote mice, the tissues specifically described above are collected, from which poly(A)$^+$ RNAs are prepared using QuickPrep mRNA Purification Kit (manufactured by Pharmacia Co.) or the like.

The RNAs from the individual murine tissues are electrophoresed and transferred on a Hybond N$^+$ filter by a conventional method, and Northern hybridization is carried out using the labeled DNA fragment as the probe.

Based on the bands obtained by the Northern hybridization, it should be confirmed that the expression in the homozygote is different from the expression in the wild-type and heterozygote. Examples of such different expression include absolutely no expression with not any band observed. Based on the confirmation, it can be verified that the restriction cleaved DNA fragment has some relation with the aging-suppressing gene.

Subsequently, the tissue specified above is drawn out from the wild-type mouse, and a cDNA library is prepared from the tissue by a conventional method. For example, a cDNA library can be prepared by synthetically preparing cDNA from the renal poly(A)+ RNA using cDNA Synthesis System (manufactured by GIBCO BRL, CO.) and adding an EcoRI-NotI-SalI adapter (SuperScript Choice System for cDNA Synthesis; manufactured by GIBCO BRL, CO.) to both the termini, and subsequently incorporating the resulting cDNA into the EcoRI site of a cloning vector λ ZAP II [λ ZAP II Cloning Kit (manufactured by STRATAGENE Co.)].

The cloning vector for preparing the cDNA library can be any phage vector or plasmid vector and the like, so long as such vector can autonomously replicate in *Escherichia coli* K12. Specific examples of the vector include ZAP Express [manufactured by STRATAGENE Co., *Strategies*, 5: 58 (1992)], pBlueScript II SK(+) [*Nucleic Acids Research*, 17: 9494 (1989)], λ ZAP II (manufactured by STRATAGENE Co.), λgt10, λgtII [*DNA Cloning, A Practical Approach*, 1: 49 (1985)], λTriplEx (manufactured by CloneTech Co.), λEx-Cell (manufactured by Pharmacia Co.), pT7T318U (manufactured by Pharmacia Co.), pcD2 [H. Okayama and P. Berg; *Mol. Cell. Biol.*, 3: 280 (1983)].

As the host microorganism, any microorganism can be used, so long as it belongs to *Escherichia coli*. Preferred examples include *Escherichia coli* XL1-Blue and the like. Specific examples include *Escherichia coli* XL2-Blue, *Escherichia coli* XL1-Blue MRF' [manufactured by STRATAGENE Co., *Strategies*, 5: 81 (1992)], *Escherichia coli* C600 [R. K. Appleyard; *Genetics*, 39: 440 (1954)], *Escherichia coli* Y1088 [R. A. Young and R. W. Davis; *Science*, 222: 778 (1983)], *Escherichia coli* Y1090 [R. A. Young and R. W. Davis; *Science*, 222: 778 (1983)] *Escherichia coli* NM522 [J. A. Gough and N. E. Murray; *J. Mol. Biol.*, 166: 1 (1983)], *Escherichia coli* K802 [W. B. Wood; *J. Mol. Biol.*, 16: 118 (1966)], *Escherichia coli* JM105 [L. J. Reha-Krantz; *Gene*, 38: 275 (1985)], *Escherichia coli* DH1, *Escherichia coli* MC1000 and the like.

One example of preparation of a cDNA library follows: cDNA is synthesized from the renal poly(A)+ RNA of the wild-type mouse using a cDNA synthesis system (cDNA Synthesis System; manufactured by GIBCO BRL, CO.), an EcoRI-NotI-SalI adapter (SuperScript Choice System for cDNA Synthesis; manufactured by GIBCO BRL, CO.) is added to both the termini, and the resulting cDNA is inserted into the EcoRI site of a cloning vector λ ZAP II [λ ZAP II Cloning Kit (manufactured by STRATAGENE Co.)].

The cDNA library is screened by colony or plaque hybridization using the labeled DNA fragment as the probe according to conventional methods.

From the clone (transformant) obtained through the screening, the aging-suppressing gene is isolated and its DNA sequence determined by conventional methods, for example, the dideoxy method by Sanger et al. [*Proc. Natl. Acad. Sci., USA*, 74: 5463 (1977)] or the like. The nucleotide sequence can be analyzed using an automatic nucleotide sequence analyzer, for example, 373A DNA Sequencer, manufactured by Applied Biosystems Co. or the like.

Examples of an aging-suppressing gene sequence determined following the examples above include DNA comprising a sequence represented by SEQ ID NO:8. *Escherichia coli* ENKM101 harboring plasmid pNKM101 containing the DNA is deposited as FERM BP-5765 on Dec. 5, 1996 at National Instituted of Bioscience and Human Technology, Agency of Industrial Science and Technology, 1-3, Higashi 1 chome, Tsukuba-shi, Ibaraki-ken, Japan (Zip code 305).

The DNA obtained above can be prepared by chemical synthesis based on the nucleotide sequence of DNA using a DNA synthesizer.

Such DNA synthesizer includes a DNA synthesizer according to a thiophosphite method, as manufactured by Shimadzu Corporation; a DNA synthesizer of Model 1392 according to a phosphoramidite method, as manufactured by Perkin Elmer Co. and the like. In the similar manner, the DNA having the sequence determined in the present invention described below can be synthesized using a DNA synthesizer.

The DNA of the present invention can be prepared by PCR using a sense primer DNA having the same sequence of successive 10 to 50 nucleotides in the nucleotide sequence of DNA selected from DNAs represented by SEQ ID NOS:6 to 10, an antisense primer DNA of a complementary sequence to the DNA, and using as a template the cDNA prepared from the mRNA of a cell expressing mRNA complementary to the DNA. As such sense primer and antisense primer, the aforementioned oligonucleotides having similar melting temperatures and nucleotide numbers from each other are preferred.

Examples of the polypeptide encoding the aging-suppressing gene obtained as described above include a polypeptide comprising a sequence represented by SEQ ID NO:3.

3) Cloning of cDNA of Mouse-derived Secretory Aging-suppressing Gene

A mouse-derived secretory aging-suppressing gene can be obtained using the aging-suppressing gene obtained above in 2) or 4). More specifically, the gene can be obtained by the following method.

With reference to the amino acid sequence of the 535th to 549th amino acids in the amino acid sequence represented by SEQ ID NO:2 different from SEQ ID NO:1 in terms of the amino acid sequence of the 535th to 549th amino acids as obtained from human renal poly(A)+ RNA screening from the murine kidney-derived cDNA library is carried out according to a 5' RACE method using a synthetic DNA encoding an amino acid sequence with homology to the sequence. The resulting cDNA fragment is used to isolate a gene in a method similar to the above described, and the nucleotide sequence is determined.

A gene having a high homology to SEQ ID NO:2 is included as the mouse-derived secretory aging-suppressing gene of interest. One example of a gene having high homology to SEQ ID NO:2 is DNA having a sequence represented by SEQ ID NO:9 and the like. An example of the polypeptide encoded by the gene includes a polypeptide comprising a sequence represented by SEQ ID NO:4.

*Escherichia coli* ENKM 112 harboring the plasmid pNKM112 containing the DNA is deposited as FERM BP-6184 on date Nov. 28, 1997 at National Instituted of Bioscience and Human Technology, Agency of Industrial Science and Technology, 1-3, Higashi 1 chome, Tsukuba-shi, Ibaraki-ken, Japan (Zip code 305).

4) Cloning of cDNA of Human-derived Aging-suppressing Gene (i) Aging-suppressing Genes Derived from Other Animals, for Example Humans, can be Obtained Using the Mouse-derived Aging-suppressing Gene Obtained Above by the Following Method.

The DNA fragment containing the mouse-derived aging-suppressing gene obtained above is labeled with α-[$^{32}$P]-dCTP using, for example, Megaprime DNA Labeling Kit (manufactured by Amersham Co.).

From an objective animal tissue, for example, human kidney, human hippocampus tissue or the like, a cDNA library is prepared by a method similar to that mouse described above for mouse.

Colony hybridization or plaque hybridization is carried out using the labeled DNA fragment as the probe for screening the cDNA library.

The gene is isolated from a clone (transformant) obtained by the screening to determine the nucleotide sequence in a method similar to that described above for mouse.

The nucleotide sequence having high homology to the nucleotide sequence of the murine aging-suppressing gene is considered to be the aging-suppressing gene of the animal of interest.

Examples of the gene sequence include DNA comprising a sequence represented by SEQ ID NO:6 or 7 as derived from human kidney. *Escherichia coli* ENKM103 harboring plasmid pNKM103 and *Escherichia coli* ENKH106 harboring plasmid pNKH106 each containing the DNA are deposited individually as FERM BP-5942 and FERM BP-5767, respectively, on date May 15, 1997 and Dec. 5, 1996, respectively, at National Instituted of Bioscience and Human Technology, Agency of Industrial Science and Technology, 1-3, Higashi 1 chome, Tsukuba-shi, Ibaraki-ken, Japan (Zip code 305).

(ii) cDNA of an Aging-suppressing Gene Derived from Other Tissues of the Animal or Derived from Other Animals can be Obtained Using the Animal-derived Aging-suppressing Genes thus Obtained by the Following Method.

By labeling the DNA fragment containing the aging-suppressing gene as obtained above with α-[$^{32}$P] dCTP using, for example, Megaprime DNA Labeling Kit (manufactured by Amersham Co.), the resulting DNA fragment is defined as a probe. By conducting PCR using an appropriate primer set and a template RNA or cDNA from an objective animal tissue, such as human pancreas or the like, and then isotopically labeling the amplified DNA fragment in the same manner as described above or labeling the fragment with digoxigenin (DIG) and the like using, for example, DIG DNA Labeling Kit (manufactured by Boehringer Mannheim Co.), the resulting labeled product is defined as a probe. Specifically as such primer set, preference is given for example to synthetic DNAs with the nucleotide sequences represented by SEQ ID NOS:19 and 20.

Colony hybridization or plaque hybridization is carried out on a cDNA library derived from an objective animal tissue, such as human pancreas or the like, using the labeled DNA fragment as the probe for screening the cDNA library.

The gene is isolated from a clone (transformant) obtained by the screening in a method similar to the mouse and human methods as described above to determine the nucleotide sequence.

The nucleotide sequence having high homology to the nucleotide sequence of the murine aging-suppressing gene is considered to be the aging-suppressing gene of the animal of interest.

Examples of the DNA sequence include DNA with the sequence represented by SEQ ID NO:10 derived from human pancreas and the like. *Escherichia coli* XL1-Blue/pRYHH02 harboring plasmid pRYHH02 containing the DNA is deposited as FERM BP-6193 on date Dec. 4, 1997 at National Instituted of Bioscience and Human Technology, Agency of Industrial Science and Technology, 1-3, Higashi 1 chome, Tsukuba-shi, Ibaraki-ken, Japan (Zip code 305).

5) Production of Aging-suppressing Polypeptide

In order to express the aging-suppressing gene obtained above in a host cell, a DNA fragment containing the aging-suppressing gene is first digested with restriction enzymes or cleaved with DNase to prepare a DNA fragment of an appropriate length containing the DNA encoding the aging-suppressing polypeptide; then the DNA fragment is inserted downstream of a promoter in an expression vector, and finally the expression vector inserted with the DNA is introduced into a host cell suitable to the expression vector.

Any host cell can be used, so long as it can express the gene of interest. Examples include procaryotes belonging to the genus *Escherichia, Serratia, Corynebacterium, Brevibacterium, Pseudomonas, Bacillus, Microbacterium*, and the like; yeasts belonging to the genus *Kluyveromyces, Saccharomyces, Schizosaccharomyces, Trichosporon, Schwanniomyces*, and the like; animal cell hosts, and the like.

Examples of the expression vector include those which can replicate autonomously in the host cell or which can be integrated into chromosomes and have a promoter at such a position that the aging-suppressing gene can be transcribed.

When a procaryote, such as a bacterium or the like, is used as the host cell, it is preferred that the aging-suppressing gene expression vector can replicate autonomously in the procaryote and is a recombinant vector constructed with a promoter, a ribosome binding sequence, the aging-suppressing gene and a transcription termination sequence. A promoter controlling gene may also be contained.

Examples of the expression vector include pBTrp2, pBTac1, pBTac2 (all commercially available from Boehringer Mannheim Co.), pKK233-2 (manufactured by Pharmacia Co.), pSE280 (manufactured by Invitrogen Co.), pGEMEX-1 (manufactured by Promega Co.), pQE-8 (manufactured by QIAGEN Co.), pKYP10 (Japanese Published Unexamined Patent Application No. 110600/1983), pKYP200 [*Agricultural Biological Chemistry*, 48: 669 (1984)], pLSA1 [*Agricul. Bio. Chem.*, 53: 277 (1989)], pGEL1 [*Proc. Natl. Acad. Sci. USA*, 82: 4306 (1985)], pBluescript II SK(–) (manufactured by Stratagene Co.), pGEX (manufactured by Pharmacia Co.), pET-3 (manufactured by Novagen Co.), pTerm2 (U.S. Pat. Nos. 4,686,191, 4,939,094, and 5,160,735), pSupex, pUB110, pTP5, pC194, and the like.

Any promoter can be used, so long as it can be expressed in a host cell, such as *Escherichia coli* or the like. Examples include promoters derived from *Escherichia coli*, phages and the like, such as trp promoter (Ptrp), lac promoter (Plac), $P_L$ promoter, $P_R$ promoter, $P_{SE}$ promoter, and the like; SPO1 promoter, SPO2 promoter, penP promoter, and the like. Additionally, promoters artificially designed and modified may be used, such as a promoter with two Ptrp linked together in series (Ptrp×2), tac promoter, letI promoter, lacT7 promoter, and the like.

With regard to the ribosome binding sequence, any sequence can be used so long as it can be expressed in the host cell, such as *Escherichia coli* or the like. However, it is preferred to use a plasmid in which the space between Shine-Dalgarno sequence and the initiation codon is adjusted to an appropriate distance (for example, 6 to 18 bases).

The transcription termination sequence is not always necessary for the expression of the aging-suppressing gene of the present invention. However, it is preferred to arrange the transcription terminating sequence just downstream of the structural gene.

Examples of the host cell include microorganisms belonging to the genus *Escherichia, Serratia, Corynebacterium, Brevibacterium, Pseudomonas, Bacillus, Microbacterium*, and the like, such as *Escherichia coli* XL1-Blue, *Escherichia coli* XL2-Blue, *Escherichia coli* DH1, *Escherichia coli* MC1000, *Escherichia coli* KY3276, *Escherichia coli* W1485, *Escherichia coli* JM109, *Escherichia coli* HB101, *Escherichia coli* No. 49, *Escherichia coli* W3110, *Escherichia coli* NY49, *Bacillus subtilis, Bacillus amyloliquefacines, Brevibacterium ammoniagenes, Brevibacterium immariophilum* ATCC 14068, *Brevibacterium saccharolyti-* cum ATCC 14066, *Corynebacterium glutamicum* ATCC 13032, *Corynebacterium glutamicum* ATCC 14067, *Corynebacterium glutamicum* ATCC 13869, *Corynebacterium acetoacidophilum* ATCC 13870, *Microbacterium ammoniaphilum* ATCC 15354, and the like.

As the method for introducing the recombinant vector, any method for introducing DNA into the host cell can be used, such as the method using a calcium ion [*Proc. Natl. Acad. Sci. USA*, 69: 2110 (1972)], the protoplast method (Japanese Published Unexamined Patent Application No. 2483942/1988), the methods described in *Gene*, 17: 107 (1982) and *Molecular & General Genetics*, 168: 111 (1979), and the like.

When yeast is used as the host cell, examples of the expression vector include YEp13 (ATCC 37115), YEp24 (ATCC 37051), YCp50 (ATCC 37419), pHS19, pHS15 and the like.

Any promoter can be used, so long as it can drive the expression in yeast. Examples include PHO5 promoter, PGK promoter, GAP promoter, ADH promoter, gal 1 promoter, gal 10 promoter, heat shock protein promoter, MF at promoter, CUP 1 promoter, and the like.

Examples of the host cell include *Saccharomyces cerevisiae*, *Schizosaccharomyces pombe*, *Kluyveromyces lactis*, *Trichosporon pullulans*, *Schwanniomyces alluvius*, and like.

As the method for introducing the recombinant vector, any method for introducing DNA into yeast can be used, such as an electroporation method [*Methods. Enzymol.*, 194: 182 (1990)], a spheroplast method [*Proc. Natl. Acad. Sci. USA*, 75: 1929 (1978)], a lithium acetate method [*J. Bacteriol.*, 153: 163 (1983)], a method described in *Proc. Natl. Acad. Sci. USA*, 75: 1929 (1978), and the like.

When animal cells are used as the host cell, examples of the expression vector include pcDNAI, pcDM8 (commercially available from Funakoshi Co.), pAGE107 [Japanese Published Unexamined Patent Application No. 22979/1991; Cytotechnology, 3: 133 (1990)], pAS3-3 (Japanese Published Unexamined Patent Application No. 227075/1990), pCDM8 [*Nature*, 329: 840 (1987)], pcDNAI/Amp (manufactured by Invitrogen Co.), pREP4 (manufactured by Invitrogen Co.), pAGE103 [*J. Biochem.*, 101: 1307 (1987)], and pAGE210.

Any promoter can be used, so long as it can be expressed in animal cells. Examples include a promoter for the IE (immediate early) gene of cytomegalovirus (human CMV), an early promoter for SV40, a retrovirus promoter, a metallothionein promoter, a heat shock promoter, and SRα promoter. Additionally, these promoters may be used in combination with the enhancer of the IE gene of human CMV.

Examples of the host cell include Namarba cell, HBT5637 (Japanese Published Unexamined Patent Application No. 299/1988), COS1 cell, COS7 cell, CHO cell and the like.

As the method for introducing the recombinant vector into the animal cells, any method to introduce DNA into animal cells can be used, such as an electroporation method [*Cytotechnology*, 3: 133 (1990)], calcium phosphate method (Japanese Published Unexamined Patent Application No. 227075/1990), a lipofection method [*Proc. Natl. Acad. Sci., USA*, 84: 7413 (1987)], a method described in *Virology*, 52: 456 (1973), and the like. According to the method described in Japanese Published Unexamined Patent Application No. 227075/1990 or Japanese Published Unexamined Patent Application No. 257891/1990, transformants can be obtained and cultured.

When insect cells are used as hosts, protein can be expressed according to a method described in, for example, *Baculovirus Expression Vectors, A Laboratory Manual, Current Protocols in Molecular Biology*, Supplement 1-38 (1987-1997), *Bio/Technology*, 6, 47 (1988), and the like.

That is, a recombinant gene transfer vector and baculovirus are simultaneously incorporated into insect cells to obtain a recombinant virus in an insect cell culture supernatant, and then the insect cells are infected with the thus obtained recombinant virus to express the protein.

Examples of the gene-introduced vector for use in the method include pVL1392, pVL1393, and pBlueBacIII (all manufactured by Invitrogen Co.).

Examples of the baculovirus include *Autographa californica* nuclear polyhedrosis virus with which insects of the family Barathra are infected, and the like.

Examples of the insect cell include Sf9 and Sf21 as ovarian cells of *Spodoptera frugiperda* [*Baculovirus Expression Vectors, A Laboratory Manual*, W. H. Freeman and Company, New York, (1992)], High 5 as the ovarian cell of *Trichoplusia ni* (manufactured by Invitrogen Co.), and the like.

Examples of the method for co-introducing the recombinant gene-introduced vector and the baculovirus to prepare a recombinant virus include calcium phosphate method (Japanese Published Unexamined Patent Application No. 227075/1990), a lipofection method [*Proc. Natl. Acad. Sci. USA*, 84: 7413 (1987)], and the like.

As the method for expressing the gene, secretion and generation, fused protein expression and the like can be carried out according to the method described in *Molecular Cloning*, 2nd ed. and the like.

When the gene is expressed in yeast, animal cells or insect cells, a polypeptide to which a sugar or sugar chain has been added can be obtained.

The aging-suppressing polypeptide can be produced by culturing a transformant harboring the recombinant DNA to which the aging-suppressing gene is incorporated in a culture, producing and accumulating the aging-suppressing polypeptide in the culture, and recovering the aging-suppressing peptide from the culture.

The method for culturing the transformant for producing the aging-suppressing polypeptide of the present invention can be carried out according to the conventional method used in culturing of hosts.

If the transformant for producing the aging-suppressing polypeptide of the present invention is a procaryote, such as *Escherichia coli* or the like, or a eucaryote, such as yeast or the like, the medium for culturing these organisms may be any of natural culture media and synthetic culture media, so long as they contain a carbon source, a nitrogen source, inorganic salts and the like which can be assimilated by these organisms and can make the culturing of the transformant effective.

As the carbon source, any such source which can be assimilated by individual organisms can be used. Examples include carbohydrates, such as glucose, fructose, sucrose, molasses, starch, starch hydrolysate, and the like; organic acids, such as acetic acid, propionic acid, and the like; and alcohols, such as ethanol, propanol, and the like.

Examples of the nitrogen source include ammonia, various ammonium salts of inorganic acids or organic acids, such as ammonium chloride, ammonium sulfate, ammonium acetate, ammonium phosphate, and the like; other nitrogen-containing compounds, peptone, meat extract, yeast extract, corn steep liquor, casein hydrolysate, soybean meal and soybean meal hydrolysate, various fermented cells and hydrolysates thereof, and the like.

Examples of inorganic substance include potassium dihydrogen phosphate, dipotassium hydrogen phosphate, magnesium phosphate, magnesium sulfate, sodium chloride, ferrous sulfate, manganese sulfate, copper sulfate, calcium carbonate, and the like.

The culturing is carried out under aerobic conditions by means of shaking, aeration stirring or the like. The culturing temperature is preferably from 15 to 45° C., and the culturing time is generally for 16 to 96 hours. The pH of the medium is maintained at 3.0 to 9.0 during the culturing. Adjustment of the medium pH is carried out using an inorganic or organic acid, an alkali solution, urea, calcium carbonate, ammonia and the like.

Also, antibiotics, such as ampicillin, tetracycline, and the like, may be added to the medium during the culturing as occasion demands.

When a microorganism transformed with an expression vector containing an inducible promoter is cultured, an inducer may be added to the medium as occasion demands. For example, isopropyl-β-D-thiogalactopyranoside (IPTG) or the like may be added to the medium when a microorganism transformed with an expression vector containing lac promoter is cultured, or indoleacrylic acid (IAA) or the like may by added thereto when a microorganism transformed with an expression vector containing trp promoter is cultured.

Examples of the medium for culturing a transformant obtained from animal cells as a host cell include media conventionally used, such as RPMI1640 medium [*The Journal of the American Medical Association,* 199: 519 (1967)], Eagle's MEM medium [*Science,* 122: 501 (1952)], DMEM medium [*Virology,* 8: 396 (1959)], 199 medium [*Proceeding of the Society for the Biological Medicine,* 73: 1 (1950)], and media to which calf fetus serum or the like is added.

The culturing is generally carried out under conditions at pH 6-8 and 30 to 40° C. in the presence of 5% $CO_2$ for 1 to 7 days.

Also, antibiotics, such as kanamycin, penicillin, and the like, may be added to the medium during culturing.

Examples of the medium for culturing the transformant obtained from insect cells as a host cell include media conventionally used, such as TNM-FH medium [manufactured by Pharmingen Co.], Sf-900 II SFM medium [manufactured by GIBCO BRL, CO.], ExCell 400 and ExCell 405 [both manufactured by JRH Biosciences Co.], Grace's Insect Medium [Grace, T. C. C., *Nature,* 195: 788 (1962)], and the like.

The culturing is generally carried out under conditions at pH 6 to 7 and 25 to 30° C. for 1 to 5 days.

Furthermore, antibiotics, such as gentamycin and the like, may be added to the medium during culturing.

In order to isolate and purify the aging-suppressing polypeptide of the present invention from the culture of the transformant for producing the aging-suppressing polypeptide, conventional methods for isolating and purifying enzymes can be used.

For example, when the polypeptide of the present invention is expressed under dissolved conditions inside cells, the cells are recovered by centrifugation after the culturing, suspended in an aqueous buffer, and disrupted with an ultrasonic disrupter, French Press, Manton-Gaulin homogenizer, Dinomill or the like to give a cell-free extract solution. From the supernatant recovered after the centrifugation of the cell-free extract solution, a purified specimen can be obtained by a single conventional method or a combination of conventional methods for isolating and purifying enzymes of a solvent extraction method, a salting-out method using ammonium sulfate, a desalting method, a precipitation method using an organic solvent, an anion exchange chromatography method using a resin, such as diethylaminoethyl (DEAE)-Sepharose, DIAION HPA-75 (manufactured by Mitsubishi Chemical Industry Co.), or the like, a cation exchange chromatography method using a resin, such as S-Sepharose FF (manufactured by Pharmacia Co.) or the like, a hydrophobic chromatography method using a resin, such as butyl Sepharose, phenyl Sepharose, or the like, a gel filtration method using a molecular sieve, an affinity chromatography method, a chromatofocusing method, and an electrophoresis method, such as isoelectric focusing or the like.

When the polypeptide is expressed after the polypeptide forms an insoluble matter inside cells, the cells are similarly recovered and disrupted, and are centrifuged to recover a precipitate fraction. From the precipitate fraction, the polypeptide is recovered according to conventional methods, and the insoluble matter of the polypeptide is solubilized in a polypeptide modifier. The solubilized solution is diluted with or dialyzed against a solution containing no polypeptide modifier or at a concentration of a polypeptide modifier being nearly at a dilution degree such that no modification of the polypeptide does not occur to compose the polypeptide having a normal stereostructure, a purified specimen can be recovered according to an isolation and purification method similar to the above.

When the polypeptide of the present invention or a derivative thereof, such as sugar modified product or the like, is secreted outside cells, the polypeptide or a derivative thereof, such as the sugar chain adduct thereof, can be recovered from the culturing supernatant. More specifically, a soluble fraction is collected by treating the culture in a method similar to the above, such as centrifugation, and a purified specimen is obtained from using an isolation and purification method similar to the above.

The polypeptide expressed by the method can be produced by a chemical synthesis method, such as an Fmoc method (fluorenylmethyloxycarbonyl method), a tBoc method (t-butyloxycarbonyl method), and the like. Additionally, the polypeptide can be produced using a peptide synthesizer produced by, for example, Souwa Trade (manufactured by Advanced ChemTech Co., USA), Perkin Elmer Japan (manufactured by Perkin-Elmer Co.), Pharmacia Biotech (manufactured by Pharmacia Biotech Co., Sweden), Aloka (manufactured by Protein Technology Instrument Co., USA), Kurabo (manufactured by Synthecell-Vega Co., USA), Japan PerSeptive Limited (manufactured by PerSeptive Co., USA), Shimadzu Corporation, and the like.

6) Preparation of Antibody Recognizing Aging-suppressing Polypeptide (i) Preparation of Polyclonal Antibody Along with an appropriate adjuvant [for example, complete Freund's adjuvant or aluminium hydroxide gel together with pertussoid vaccine, or the like], a purified specimen (antigen) of the full length or a partial fragment of the aging-suppressing polypeptide obtained above in 4) or 5) is subcutaneously, intravenously or peritoneally administered at a dose of 50 to 100 μg/animal into rabbits, goat or rats, mice or hamsters of age 3 to 20 weeks.

The antigen is boosted once, and thereafter, the antigen is boosted 3 to 10 times, every 1 to 2 weeks. After each booster, blood is collected from plexus basilaris on day 3 to 7. It is confirmed by enzyme immunoassay [*ELISA,* published by Igaku Shoin, 1976; *Antibodies, A Laboratory Manual,* Cold Spring Harbor Laboratory (1988)] and the like, that the serum reacts with the antigen used for immunization.

From rabbits, goat, mice, rats or hamsters with the sera of sufficient antibody titers against the antigen used for immunization, the sera are collected, and purified antibodies can be obtained using a conventional method, such as a salting-out method using 40 to 50% saturated ammonium sulfate, a caprylic acid precipitation method, a chromatographic method using, such as a DEAE-Sepharose column, a protein A-column, a gel filtration column, and the like.

(ii) Preparation of Monoclonal Antibody (a) Preparation of Antibody-Producing Cell A rat having serum of a sufficiently high antibody titer against the partial fragment of the aging-suppressing polypeptide used for immunization is used as a supply source of antibody-producing cells.

On day 3 to 7 after the final dosing of the antigen substance to the rat showing the antibody titer, the spleen is resected from the rat.

The spleen is cut into pieces in MEM medium (manufactured by Nissui Pharmaceuticals Co.), and the pieces are then loosened with tweezers and centrifuged at 1,200 rpm for 5 minutes to discard the resulting supernatant.

The splenic cells in the resulting precipitate fraction are treated with a Tris-ammonium chloride buffer (pH 7.65) for 1 to 2 minutes to remove the erythrocytes, and the resulting cells are washed with MEM medium three times to use the resulting splenic cells as antibody-producing cells.

(b) Preparation of Myeloma Cell

As myeloma cells, cells of an established cell line obtained from mice or rats are used. Examples include 8-azaguanine resistant mouse (derived from BALB/c) myeloma cell lines P3-X63Ag8-U1 (hereinafter referred to as "P3-U1") [*Curr. Topics Microbiol. Immunol.*, 81: 1 (1978)], [*Europ. J. Immunol.*, 6: 511 (1976)], SP2/0-Ag14 (SP-2) [*Nature*, 276: 269 (1978)], P3-X63-Ag8653 (653) [*J. Immunol.*, 123: 1548 (1979)], P3-X63-Ag8 (X63) [*Nature*, 256: 495 (1975)] and the like. These cell lines are sub-cultured in an azaguanine medium [RPMI-1640 medium supplemented with glutamine (1.5 mM), 2-mercaptoethanol ($5 \times 10^{-5}$ M), gentamycin (10 µg/ml) and fetus calf serum (FCS) (manufactured by CSL Co.; 10%) (hereinafter referred to as "normal medium") and further supplemented with 8-azaguanine (15 µg/ml)]. The cells are cultured in the normal medium for 3 to 4 days before cell fusion, and for the cell fusion, the cells are used at $2 \times 10^7$ or more (c) Preparation of Hybridoma The antibody-producing cells as obtained in (a) and the myeloma cells as obtained in (b) are thoroughly washed with MEM medium or PBS (disodium phosphate (1.83 g), monopotassium phosphate (0.21 g), common salt (7.65 g), and distilled water (1 liter), pH 7.2) to mix to give a final cell number ratio of 5:1 to 10:1 as the ratio of number of the antibody-producing cells:the number of the myeloma cells, the mixture is centrifuged at 1,200 rpm for 5 minutes, and the supernatant is discarded.

The cell population in the resulting precipitate fraction is sufficiently loosened, and to the cell population under stirring is added 0.2 to 1 ml of a mixture solution of polyethylene glycol-1000 (PEG-1000; 2 g), MEM (2 ml) and dimethylsulfoxide (DMSO; 0.7 ml) per $10^8$ antibody-producing cells, and 1 to 2 ml of MEM medium is further added every 1 to 2 minutes.

After addition, MEM medium is added to the resulting mixture to give the final volume of 50 ml.

The prepared solution is centrifuged at 900 rpm for 5 minutes, and the resulting supernatant is discarded.

The cells in the resulting precipitate fraction are gently loosened and gently suspended in HAT medium (100 ml) [a medium prepared by adding hypoxanthine ($10^{-4}$ M), thymidine ($1.5 \times 10^{-5}$ M) and aminopterin ($4 \times 10^{-7}$ M) to the normal medium] through aspiration and blowing by means of a measuring pipette.

The suspension is divided in 100 µl portions into each well of a 96-well culture plate for culturing at 37° C. in a 5% $CO_2$ incubator for 7 to 14 days.

After culturing, a part of the culture supernatant is sampled, and hybridomas which specifically reacts with a partial fragment of the aging-suppressing polypeptide are screened by the enzyme immunoassay described in *Antibodies, A Laboratory manual*, Cold Spring Harbor Laboratory, Chapter 14 (1988) and the like.

Specific examples of the enzyme immunoassay include the following method.

The method comprises coating the partial fragment of the aging-suppressing polypeptide used as the antigen in the immunoziation on an appropriate plate; reacting it with the hybridoma supernatant or the purified antibody obtained in section (d) described above as a first antibody; reacting it with a second antibody anti-rat immunoglobulin antibody labeled with biotin, an enzyme, a chemiluminescent substance or a radioactive compound; carrying out a reaction depending on the labeling substance, and screening a substance having a specific reactivity to the aging-suppressing polypeptide as a hybridoma producing anti-aging-suppressing polypeptide monoclonal antibody.

Specific examples of the hybridoma include a hybridoma KM1902. The hybridoma KM1902 is deposited as FERM BP-5983 on Jun. 17, 1997 at National Institute of Bioscience and Human Technology, Agency of Industrial Science and Technology.

Using the hybridoma, cloning is repeated two times by limiting dilution [for first dilution, HT medium (HAT medium from which aminopterin is excluded) is used; for second dilution, the normal medium is used]. Then, a cell line having a stable strong antibody titer is selected as a hybridoma producing an anti-aging-suppressing polypeptide antibody.

(d) Preparation of Monoclonal Antibody

To a mouse or nude mouse aged 8 to 10 weeks, $5 \times 10^6$ to $20 \times 10^6$ cells of the anti-aging-suppressing polypeptide monoclonal antibody producing hybridoma cells obtained in (c) are injected peritoneally, and treated with Pristane [after peritoneal administration of 0.5 ml of 2,6,10,14-tetramethylpentadecane (Pristane), feeding was continued for 2 weeks]. The hybridoma turns ascites tumor in 10 to 21 days.

From the mouse with the ascites tumor, the ascites is collected, and centrifuged at 3,000 rpm for 5 minutes to remove the solid matters.

By a salting-out method using 40 to 50% saturated ammonium sulfate, a caprylic acid precipitation method [*Antibodies, A Laboratory Manual*, Cold Spring Harbor Laboratory (1988)], a chromatographic method using a DEAE-Sepharose column, a protein A-column or a Cellulofine GSL2000 (manufactured by Biochemical Industry Co.), an IgG or IgM fraction is collected from the resulting supernatant, and the fraction is used as a purified monoclonal antibody.

The subclass of the antibody is determined using a mouse monoclonal antibody typing kit or a rat monoclonal antibody typing kit. The protein level is calculated by the Lowry's method or based on the absorbance at 280 nm.

7) Staining of Immune Cell Using Monoclonal Antibody

For staining immune cells using adhesive cells, preferably, the adhesive cells are preliminarily subjected to the following treatment to tear away the cells from the culture flask.

That is, cultured adhesive cells are washed with a PBS buffer, and a PBS buffer (3 ml) containing 0.05% trypsin and 0.02% EDTA (ethylenediaminetetraacetatic acid) is added thereto. From the resulting mixture, an excess solution is removed, and the cells are tore away from the flask by incubation at 37° C. for 5 minutes (hereinafter this procedure is referred to as "trypsin-EDTA treatment").

As to suspension cells, the cultured cells are used as they are.

The cells for immune cell staining are suspended in an immune cell staining buffer (PBS containing 1% BSA, 0.02% EDTA, and 0.05% sodium azide), and is divided as each portion of $1\times10^5$ to $20\times10^5$ cells into a 96-well round bottom plate.

The culture supernatant of the hybridoma producing an anti-aging-suppressing polypeptide monoclonal antibody obtained in (c), the purified monoclonal antibody obtained in (d) or the monoclonal antibody labeled with biotin according to the known method (*Enzyme Antibody Method*, issued by Gakusai Kikaku, 1985) which is diluted with the immune cell staining buffer or the immune cell staining buffer containing 10% animal serum to give a final concentration of 0.1 to 50 μg/ml is divided into the wells to give a final volume of 20 to 500 μl/well, and the plate is allowed to stand under ice cooling for 30 minutes.

If the culture supernatant of the anti-aging-suppressing polypeptide monoclonal antibody obtained in (c) or the purified monoclonal antibody obtained in (d) is used in the above procedure, the immune cell staining buffer is added to the plate to rinse the cells, and the immune cell staining buffer containing an anti-mouse immunoglobulin antibody or anti-rat immunoglobulin antibody preliminarily labeled with a fluorescent dye, such as FITC, phycoerythrin, or the like, at a concentration of about 0.1 to 50 μg/ml is divided at 50 to 500 μl/well. Then, the resulting plate is allowed to stand in darkness under ice cooling for 30 minutes.

If the monoclonal antibody labeled with biotin is used, streptoavidin is divided into the plate at 50 to 500 μl/well, and the plate is allowed to stand in darkness under ice cooling for 30 minutes.

In both the procedures, after the reaction, an immune cell staining buffer is added to the plates, and the cells are thoroughly washed and analyzed with a cell sorter.

8) Immunoprecipitation of Aging-suppressing Polypeptide

The CHO cells or insect cells expressing the aging-suppressing polypeptide of the present invention is cultured in a culture container such as a Petri dish.

PBS is added to the culture container to rinse the cells.

To the culture container, 100 to 500 μl of a buffer preliminarily cooled in ice which is capable of solubilizing cell membrane, such as a buffer containing 1% Triton X100, 20 mM Tris-HCl, 150 mM NaCl (hereinafter referred to as "Buffer 1"), is added at 100 to 500 μl, and the resulting mixture is allowed to stand in ice for 30 minutes and is then gently vibrated as solubilization treatment.

For preparing a sample from the culture supernatant, the supernatant is concentrated by a method, such as ultrafiltration membrane, freeze-drying, or the like, and then immunoprecipitation reaction is carried out using the sample by the following method.

The solution after the solubilization treatment is recovered in a 1.5 ml centrifuge tube, and centrifuged at 14,000 rpm for 30 minutes.

To the resulting supernatant, 10 to 50 μl of protein G-Sepharose or protein A-Sepharose equilibrated with the buffer is added under stirring at 4° C. for one hour and centrifuged at 5,000 rpm for 2 minutes to recover the supernatant.

To the supernatant, the culture supernatant of the hybridoma producing the anti-aging-suppressing polypeptide monoclonal antibody obtained in (c) or the purified monoclonal antibody obtained in (d) is added to give a final concentration of 0.01 to 50 μg/ml, followed by shaking at 4° C. for one hour or more.

To the shaken solution, 10 to 50 μl of protein G-Sepharose or protein A-Sepharose is added, followed by shaking at 4° C. for one hour or more, and the mixture is centrifuged at 5,000 rpm for 2 minutes.

To the resulting precipitate fraction, 200 μl of the buffer solubilizing the cell membrane as described above is added to suspend the precipitate. The same procedures are repeated 3 times or more to rinse the precipitate fraction.

To the precipitate, a sample buffer for SDS-polyacrylamide gel electrophoresis is added, the mixture is heated using a heat block, and SDS-PAGE is carried out.

After the SDS-PAGE, the polypeptide in the resulting gel is transferred on a PVDF membrane or the like to detect the aging-suppressing polypeptide by Western blotting or the like using an anti-aging-suppressing partial fragment polypeptide polyclonal antibody in accordance with the present invention and the like.

By cutting the detected aging-suppressing polypeptide from the PVDF membrane, the protein can be purified. The structural analysis of the purified polypeptide of the present invention can be carried out according to the method described in, for example, *Protein Structural Analysis for DNA Cloning* (Hisashi Hirano, issued by Tokyo Kagaku Dojin, 1993).

9) Production of Mouse Showing Ameliorated Syndrome Resembling Premature Aging from Mice Showing Syndrome Resembling Premature Aging Using the Aging-suppressing Gene Derived from Mouse (Verification of the Efficacy of the Aging-suppressing Gene for the Treatment of a Syndrome Resembling Premature Aging, Because of the Amelioration of the Syndrome Resembling Premature Aging Owing to the Introduction of the Aging-suppressing Gene)

In order to produce a transgenic mouse excessively expressing the aging-suppressing gene obtained above, DNA containing the aging-suppressing gene to introduce and express the gene in a mouse (hereinafter referred to as "aging-suppressing DNA for introduction") is constructed. The aging-suppressing DNA for introduction is injected into the male pronucleus of a fertilized egg of a wild-type mouse and is then transplanted into a female mouse which is preliminarily induced into a false pregnancy.

A new-born transgenic mouse (+/+) excessively expressing the aging-suppressing gene is mated with a heterozygote (pg/+) obtained from mice showing a syndrome resembling premature aging to produce a mouse expressing the aging-suppressing gene and showing pg/+.

The mouse is mated together or the mouse is mated with a mouse showing pg/+ to obtain a mouse expressing the aging-suppressing gene and showing pg/pg.

By confirming that the mouse does not show a syndrome resembling premature aging, it is verified that the aging-suppressing gene obtained above is effective for the treatment.

By the method described below, for example, a mouse showing an ameliorated syndrome resembling premature aging from mice showing a syndrome resembling premature aging can be obtained.

(i) Construction of Aging-suppressing DNA for Introduction

The aging-suppressing DNA for introduction is preferably composed of a promoter, the aging-suppressing gene and a cassette of SV40 early splicing region & poly adenylation signal (hereinafter referred to as "SV40 cassette").

As the promoter, any promoter can be used, so long as it can cause expression in mice; however, a stronger promoter is preferably used. Examples include a HindIII treated fragment (2.5 kb promoter region containing partially the 1st exon and 2nd exon of 5' UTR) of human elongation factor 1α [pEF321CAT (Kim D W et al., *Gene*, 91: 217, 1990)].

As the aging-suppressing gene, any of the genes obtained above in 2) can be used. Specifically, DNA encoding the amino acid sequence represented by SEQ ID NO:3 is exemplified.

As the SV40 cassette, the nucleotide Nos. 1551-2427 of an expression vector pMAMneo (commercially available from Clontech Co.) can be utilized.

By a conventional method, the promoter, the aging-suppressing gene and the SV40 cassette are ligated together in this order, and then the ligation product is cleaved with an appropriate enzyme, such as NotI or the like, and is then dissolved in a PBS buffer to give a final concentration of about 500 copies/ml for use as an aging-suppressing DNA for introduction.

(ii) Production of Transgenic Mouse

A transgenic mouse can be produced by a routine microinjection method (*Developmental Engineering Experimental Manual—How to Prepare Transgenic Mouse*, Tatsuji Nomura as responsible editor, Motoya Katsuki as editor, Kodansha Scientific, 1987).

More specifically, 7 units of Serotropin (manufactured by Teikoku Hormone Mfg. Co., Ltd.) are administered peritoneally into F1 females (BCF1), aged 8 to 16 weeks, from C57BL/6 and C3H. After 48 hours, 7 units of gonadotropin (manufactured by Teikoku Hormone Mfg. Co., Ltd.) are peritoneally administered into them, and they are mated with males of C3H.

On the next day, a fertilized egg is collected from the ampulla of uterine tube of the mated females. The DNA solution is injected into the male pronucleus of the fertilized egg using a micro-manipulator (manufactured by Narumo Co.) under an erect microscope.

The fertilized egg is transplanted into a female which is mated with a vasoligated male (ICR) on the previous day, so as to induce false pregnancy in the female.

On day 20 after the transplantation, litter mice are born, and their tails are cut when they are at age 4 to 5 weeks to extract the chromosomal DNA for DNA typing using PCR as described below.

(iii) Analysis of Genotype

To the mouse's tail obtained above, 2 ml of a lysis buffer [lysis buffer; a buffer containing 50 mM Tris-HCl (pH 8.0), 100 mM NaCl, 20 mM EDTA, 1% SDS, 0.15 ml/ml Proteinase K (manufactured by SIGMA Co.), and 1 mg/ml Pronase E (manufactured by SIGMA Co.)] is added, and the resulting mixture is allowed to stand at 50° C. overnight.

The buffer is extracted into an equal volume of phenol, and 1 ml of the supernatant is used as a PCR template.

As the PCR primers, the following 5 primers are prepared and are mixed together for use.

From a segment of a nucleotide sequence derived from the aging-suppressing gene obtained in 2) and corresponding to a region with an inserted intron in the sequence of genomic DNA, two primers (primers 1 and 2) are prepared; a primer is prepared from a region present commonly in mutant allele and wild-type allele (primer 3); a primer is prepared from a region present only in mutant allele (primer 4); and a primer is prepared from a region present only in mutant allele (primer 5).

Examples of the primers 1 and 2 include DNA sequence represented by SEQ ID NO:25 or 26.

Examples of the primer 3 include DNA sequence represented by SEQ ID NO:27.

Examples of the primer 4 include DNA sequence represented by SEQ ID NO:28.

Examples of the primer 5 include DNA sequence represented by SEQ ID NO:29.

If the aging-suppressing gene obtained in 2) is present in a mouse, a fragment which can be amplified by PCR with the primers 1 and 2 is produced; a fragment which can be amplified with the primers 3 and 4 is produced in the homozygote (pg/pg); a fragment which can be amplified with the primers 3 and 5 is produced in the wild-type (+/+); two fragments which can be amplified with the primers 3 and 4 and with the primers 3 and 5 are produced in the heterozygote (pg/+). Thus, the genotype of the mice can be analyzed.

PCR can be carried out by a conventional method. Specifically, PCR is carried out in a 50 μl system [1×LA PCR buffer II (Mg plus), dNTP mixture solution of each ingredient at 400 mM, each primer of 0.2 mM, 2.5 U TaKaRa LATaq] by heating at 94° C. for 1.5 minutes using TaKaRa PCR Thermal Cycler 480 and an LA PCR kit (manufactured by Takara Shuzo Co., Ltd.), followed by 30 cycles, each cycle consisting of 94° C. for 30 seconds, 56° C. for 30 seconds, and 72° C. for 1.5 minutes, and subsequent heating at 72° C. for 10 minutes.

(iv) Mating of Transgenic Mouse with Mouse Showing pg/+

The genotype about a litter mouse obtained from the mating of the transgenic mouse obtained in (ii) with a mouse showing pg/+ is analyzed according to the method described in (iii) to confirm that the mouse expressing the aging-suppressing gene and showing pg/pg does not show a syndrome resembling premature aging.

10) Obtaining a Mouse Showing Ameliorated Syndrome Resembling Premature Aging from Mice Showing Syndrome Resembling Premature Aging Using Recombinant Adenovirus Containing the Aging-suppressing Gene Derived from Mice In order to introduce and express the aging-suppressing gene obtained above in a mouse, a recombinant adenovirus containing the aging-suppressing gene is constructed, and the recombinant virus is then dosed to a mouse showing a syndrome resembling premature aging to confirm that the mouse does not show the syndrome resembling premature aging and thereby verify that the aging-suppressing gene obtained above is therapeutically effective.

By the method described below, for example, a mouse showing an ameliorated syndrome resembling premature aging can be obtained from mice showing a syndrome resembling premature aging.

(i) Construction of Recombinant Cosmid Containing Aging-suppressing Gene

Preferably, the introduction aging-suppressing gene DNA contains a promoter, the aging-suppressing gene and a splicing region, and type 5 adenovirus genomic DNA containing a poly(A) additive signal from which E1A, E1B and E3 are deleted.

As a cosmid containing the individual composition elements except for the aging-suppressing gene, pAxCAwt [*Nucl. Acids. Res.*, 23: 3816 (1995)] is included.

As the aging-suppressing gene, any of the genes obtained above in 2) can be used. Specifically, DNA encoding the amino acids represented by SEQ ID NO:3 may be used.

According to a conventional method, the cosmid is digested with an appropriate enzyme, such as SwaI or the like, and ligated with the aging-suppressing gene to prepare a recombinant cosmid.

(ii) Preparation of Recombinant Adenovirus Containing Aging-suppressing Gene

Recombinant viruses can be prepared by the method described by Miyake et al. [*Proc. Natl. Acad. Sci. USA*, 93: 1320 (1996)] and the like.

More specifically, the recombinant cosmid containing the aging-suppressing gene as prepared in (i) is mixed with an EcoT22I-cleaved type 5 adenovirus Ad5dlX DNA with deletion of E3, E1A and E1B [*J. Virology*, 54: 711 (1985)], and the resulting mixture is then introduced into a cell line harboring E1A and E1B genes, for example, human fetus kidney-derived 293 cells using, for example, a potassium phosphate method (Japanese Published Unexamined Patent Application No. 227075/1990) or the like. If the recombination between the cosmid and the adenovirus DNA occurs inside the cells, a recombinant adenovirus is produced, which kills the cells, and therefore, confirms that a recombinant adenovirus containing the aging-suppressing gene is produced and acts as a marker therefor. By recovering the killed cells and by disrupting the cells through repeating freezing and thawing the cells using a cell disrupter, for example, a recombinant adenovirus solution containing the aging-suppressing gene is obtained.

Furthermore, the DNA of the resulting recombinant virus is extracted from the virus by a conventional method, and cleaved with a restriction enzyme, such as XhoI or the like, to confirm the structure thereof.

(iii) Purification of Recombinant Adenovirus

According to the method by Kanegae, et al. [*Jpn. J. Med. Sci. Biol.*, 47: 157 (1994)], for example, the resulting recombinant virus is purified twice on cesium chloride density gradient, and is then suspended in a solution, such as PBS containing 10% glycerol, HEPES-MgCl$_2$ containing 10% glycerol, HEPES-EDTA containing 10% glycerol, or the like, and can be stored at −80° C. prior to appropriate use.

(iv) Dosing of Recombinant Adenovirus Containing Aging-suppressing Gene into Mice Showing Syndrome Resembling Premature Aging The recombinant virus thus obtained is administered at $10^8$ to $10^{10}$ plaque forming units (PFU) through the caudal vein of a mouse showing a syndrome resembling premature aging, preferably aged about 3 to 4 weeks. After the administration of the recombinant virus, elimination of the syndrome resembling premature aging is observed.

11) Screening and Identification of Ligand Specifically Binding to Aging-suppressing Polypeptide of the Present Invention By putting the aging-suppressing polypeptide of the present invention in contact with a test sample, such ligand can be screened and identified.

Examples of the test sample include urine, body fluids, tissue extracts, cell culture supernatant, cell extracts, and the like from mammals (for example, mouse, rat, guinea pig, hamster, pig, sheep, bovine, horse, dog, cat, monkey, humans, and the like).

By appropriately diluting, concentrating and fractionating urine, body fluids, tissue extracts, cell culture supernatants, and cell extracts, subsequently putting them in contact with the aging-suppressing polypeptide of the present invention, and further fractionating them using the cell stimulating activity as an index, a single ligand can be isolated.

More specifically, by putting a test sample in contact with both cells essentially never expressing the aging-suppressing gene and the cells after introduction and expression of the aging-suppressing gene, assaying various cell stimulating activities in the two types of the cells, for example, the change in concentrations of cellular information transmission molecules, such as cellular calcium, cAMP, cGMP, and the like, the phosphorylation of cellular protein, the change of the expression of early transcription factor gene, the change of cell membrane potential, the change of cellular pH, the release of extracellular information transmission molecules, the morphological change of cells, and the like, and comparing and analyzing the difference in the two types of the cells, a ligand is screened and identified.

By labeling naturally occurring or artificially synthesized protein, sugar and lipid, and their modified products and derivatives with radioisotopes and the like, and assaying the binding of the labeled compounds onto the aging-suppressing polypeptide expressing cells, the cell membrane fractions, or the aging-suppressing polypeptide immobilized on microtiter plates and the like in accordance with the present invention, it is possible to identify whether or not the ligand described above is the ligand of the present invention.

By the known method comprising covalently bonding the aging-suppressing polypeptide of the present invention, or a partially modified product or a partial peptide thereof to the sensor chip of BIAcore (manufactured by Pharmacia Biotech Co.) and then putting a test sample in contact with the covalently bonded polypeptide [*Nature*, 368: 558 (1994)], the ligand can be screened and identified.

By using further the aging-suppressing gene polypeptide, labeled or non-labeled, together with a labeled antibody against the polypeptide, a ligand specifically associating with the polypeptide can be screened and identified by the following method.

That is, by appropriately fractionating urine, body fluids, tissue extracts, cell culture supernatants, cell extracts, or the like, further fractionating them by electrophoresis, such as polyacrylamide electrophoresis, agarose electrophoresis, two-dimensional electrophoresis, or the like, column chromatography, such as HPLC or the like, and thin-layer chromatography, thereafter comparing and analyzing in detail the difference between individuals expressing the aging-suppressing gene and individuals never expressing the gene or the difference between the aging-suppressing gene-expressing cells and the gene-non-expressing cells, bands, spots and peaks make appearance (disappearance) with a specific correlation with the expression of the aging-suppressing gene is identified.

The bands, spots and peaks are transferred onto a support, such as nitrocellulose membrane, nylon membrane, PVDF membrane, or the like, from gel or thin-layer plate, using blotting procedures, bands or spots specifically binding to the polypeptide are screened using the aging-suppressing gene polypeptide, labeled or non-labeled, together with a labeled antibody against the polypeptide, and a ligand is extracted from the band or spots and identified.

12) Screening and Identification of Compounds Inhibiting Specific Binding Between Aging-suppressing Polypeptide of the Present Invention and Ligand of the Present Invention By comparing the case when the aging-suppressing polypeptide of the present invention is put in contact with the ligand of the present invention and the case when the aging-suppressing polypeptide, the ligand of the present invention and a test compound are put in contact with each other, a compound inhibiting the specific binding between the aging-suppressing polypeptide and the ligand (for example, protein, peptide, sugar, lipid, non-peptide compounds, synthetic compounds, fermentation compounds, biological components, or the like) can be screened from the test sample. The compound obtained through the screening includes for example a compound (antagonist) inhibiting the specific binding of the ligand to the aging-suppressing polypeptide and inhibiting the activity of the aging-suppressing polypeptide, and a compound (agonist) inhibiting the specific binding but having the same functions as those of the ligand or having an alternative activity.

In addition to synthetic compounds, protein, sugar, and lipid from natural origin or artificially synthesized, their modified products and derivatives thereof, and the like, the test sample includes, for example, urine, body fluids, tissue extracts, cell culture supernatants, and cell extracts of mammals (for example, mouse, rat, guinea pig, hamster, pig, sheep, bovine, horse, dog, cat, monkey, humans, etc.), and additionally includes fermentation products and extracts from plants, other biological organisms, and the like.

The method for screening the compound includes, for example, the following method.

A method for screening and identifying the compound inhibiting the specific binding between the aging-suppressing gene polypeptide of the present invention and the ligand of the present invention is illustrated, comprising putting a cell with the aging-suppressing gene introduced and expressed therein or a cell essentially expressing the aging-suppressing gene in contact with the ligand alone or in combination with a test sample and comparing then the case of the ligand alone with the case of the ligand put in contact with the test sample from the various cell stimulating activities, for example, the change of the concentrations of cellular information transmission molecules, such as cellular calcium, cAMP, cGMP, or the like, the phosphorylation of cellular protein, the change of the expression of early transcription factor gene, the change of cell membrane potential, the change of cellular pH, the release of extracellular information transmission molecules, the morphological change of cells, and the like.

By labeling the ligand of the present invention with radioactivity or the like, and assaying the binding of the labeled ligand onto the aging-suppressing polypeptide-expressing cells, the cell membrane fraction thereof, or the aging-suppressing polypeptide immobilized on a microtiter plate or the like in accordance with the present invention, and then comparing the binding level between the case of the ligand alone and the case of the ligand put in contact with the test sample, a compound inhibiting the binding between the aging-suppressing polypeptide and the ligand can be screened and identified.

13) Screening and Identification of a Compound Induced as a Consequence of Binding of Aging-suppressing Polypeptide of the Present Invention and Ligand of the Present Invention The culture supernatant, cells, cytoplasmic fraction, cell membrane fraction and the like of the cells expressing the polypeptide of the present invention and the polypeptide-non-expressing cells, separately in contact with the ligand of the present invention or not in contact with the ligand, are subjected to electrophoresis, such as polyacrylamide electrophoresis, agarose electrophoresis, two-dimensional electrophoresis or the like, column chromatography, such as HPLC or the like, and thin-layer chromatography to fractionate individual components, and the components are compared with each other. Hence, bands, spots or peaks and the like are identified, which specifically develop or are eliminated on contact to the ligand or which specifically develop or are eliminated with a correlation to the expression of the polypeptide to obtain an objective molecule from the bands, spots, and peaks.

It is believed that the specific binding between the polypeptide and the ligand constantly occurs in individuals expressing the polypeptide of the present invention, and that such interaction does not occur in individuals who do not express the polypeptide (preferable specific examples include the premature aging mouse described in the present specification). Thus, various organs, tissues, body fluids, blood, urine and the like of the normal mouse and the premature aging mouse described in the present specification) are appropriately fractionated, and are then further fractionated using electrophoresis, such as polyacrylamide electrophoresis, agarose electrophoresis, two-dimensional electrophoresis, or the like, column chromatography, such as HPLC or the like, thin-layer chromatography, or the like. Through the comparison between these mice, bands, spots, peaks and the like having a difference in performance between the two types of the mice are screened to collect molecules based on the bands, spots and peaks and identify an objective compound from the bands, spots and peaks.

14) Screening and Identification of a Compound Enhancing Expression of the Aging-suppressing Polypeptide of the Present Invention (Hereinafter Referred to as "Expression Enhancing Compound")

(i) Screening and Identification Using an Antibody Recognizing the Aging-suppressing Polypeptide of the Present Invention After putting cells expressing the aging-suppressing polypeptide of the present invention in contact with a test sample, an expression enhancing compound present in the cell culture supernatant of the cells can be screened and identified using an antibody which recognizes the aging-suppressing polypeptide of the present invention.

The cells expressing the aging-suppressing polypeptide of the present invention include murine kidney-derived uriniferous tubule cells, which can be prepared by a known method, such as a concentration density method, an osmotic pressure-resistant separation method, and a tubular separation method [*Kidney and Dialysis*, Extra issue, 588 (1991)].

In addition to synthetic compounds, protein, peptide, non-peptide compounds, sugar, and lipid from natural origin and lipid artificially synthesized, their modified products and derivatives, and the like, the test compound includes urine, body fluids, tissue extracts, cell culture supernatant, cell extracts of mammalian animals (for example, mice, rats, guinea pigs, hamsters, pigs, sheep, horse, bovine, dogs, cats, monkeys, humans, and the like); and further includes fermentation products, extracts from plants and other biological organisms, and the like; however, it is not limited thereto.

After suspending the cells expressing the aging-suppressing polypeptide of the present invention, for example, in a medium capable of growing the cells, and adding a test sample into the medium to put the cells in contact with the test sample, the content of the aging-suppressing polypeptide expressed by the cells is assayed using the polyclonal antibody or monoclonal antibody described in 6) according to the method described above in 7).

By screening a test sample which could increase the content of the aging-suppressing polypeptide, compared with a system with no addition of the test sample, an expression enhancing compound can be identified.

(ii) Screening and Identification Using an Assay System of the Transcription Product of the Aging-suppressing Gene of the Present Invention After putting the cells expressing the aging-suppressing polypeptide of the present invention in contact with a test sample and assaying the transcription product of the aging-suppressing gene of the present invention, an expression enhancing compound can be screened and identified.

An example of the cells expressing the aging-suppressing polypeptide of the present invention and the test sample is described above in (i).

After suspending the cells expressing the aging-suppressing polypeptide of the present invention, for example, in a medium capable of growing the cells, and adding a test sample into the medium to thereby put the cells in contact with the test sample, the amount of the transcription product of the aging-suppressing polypeptide expressed by the cells is assayed by conventional Northern blot hybridization, RNA dot blot hybridization, RT-PCR, or the like.

The probe which can be used for hybridization and the primer which can be used for RT-PCR include fragments of the aging-suppressing gene of the present invention. Specific examples include DNA fragments comprising DNA sequences selected from DNA sequences represented by SEQ ID NOS:6, 7, 8, 9 and 10.

By screening a test sample which could increase the content of the transcription product of the aging-suppressing polypeptide, compared with a system with no addition of the test sample, an expression enhancing compound can be identified.

(iii) Screening and Identification Using a Reporter Gene

After putting a transformant harboring a plasmid containing DNA with a reporter gene ligated downstream of a region controlling the transcription of the gene encoding the aging-suppressing polypeptide of the present invention (hereinafter referred to as "transcription controlling region") in contact with a test sample and assaying the expression level of the polypeptide encoded by the reporter gene, an expression enhancing compound can be screened and identified.

The transcription controlling region includes a region of about 8 kb present in a site about 6 kb upstream the aging-suppressing gene in which it is observed that the region is deleted in the homozygote described in Example 2 described below. Additionally, a fragment of an appropriate length can also be used as the transcription controlling region. Such a fragment is prepared by excising the region using an appropriate restriction enzyme.

Any reporter gene can be used, so long as the translation product of the reporter gene is stable inside cells and the amount of the translation product present is readily assayed. Examples include chloramphenicol acetyltransferase (CAT), β-galactosidase (β-gal), luciferase (luc), green fluorescent protein (GFP), and the like.

As the test sample, those described above in (i) can be used.

After ligating the reporter gene downstream of the transcription controlling region by a conventional method, a host cell is transformed using the prepared plasmid by a conventional method.

By suspending the transformant for example in a medium capable of growing the cells, adding a test sample into the medium and putting the cells in contact with the test sample, the content of the transcription product of the reporter gene as expressed by the cells is detected and assayed by a method appropriate for the transcription product.

Examples of the detection and assay methods include the method described in *Molecular Cloning*, 2nd ed., Chapter 16, page 60 for CAT, the method described in *Experimental Medicine, Supplementary Volume, Biomanual Series, 4, Gene Introduction and Expression Analysis*, 81 (1994) for luc, and the method described in *Proc. Natl. Acad. Sci. USA*, 94: 4653 (1997) for GFP.

By screening a test sample which could increase the content of the transcription product of the aging-suppressing polypeptide of the present invention, compared with a system with no addition of the test sample, an expression enhancing compound can be identified.

15) Preparation of the Oligonucleotide of the Present Invention

Using the DNA of the present invention and the DNA fragments thereof, oligonucleotides (both antisense and sense oligonucleotides, and the like) containing a partial sequence of the DNA of the present invention can be prepared.

The oligonucleotide includes DNA comprising a sequence which is identical to or complementary to continuous 10 to 50 nucleotides of the DNA sequence. Specific examples include DNA comprising a sequence which is identical to or complementary to continuous 10 to 50 nucleotides in the nucleotide sequence of DNA selected from DNAs represented by SEQ ID NOS:6 to 10.

The oligonucleotide is included as the oligonucleotide of the present invention, and furthermore, the derivatives of such oligonucleotide is also included as the oligonucleotide of the present invention. The derivative DNA includes a derivative DNA prepared in which the phosphate diester bonding in DNA is modified to phosphorothioate bonding, a derivative DNA in which the phosphate diester bonding in DNA is modified to N3'—P5' phosphoramidate bonding, a derivative DNA in which the ribose and phosphate diester bonding in DNA is modified to peptide-nucleic acid bonding, a derivative DNA in which the uracil in DNA is substituted with C-5 propionyluracil, a derivative DNA in which the uracil in DNA is substituted with C-5 thiazole uracil, a derivative DNA prepared in which the cytosine in DNA is substituted with phenoxazine-modified cytosine, a derivative DNA in which the ribose in DNA is substituted with 2'-O-propylribose, or a derivative DNA in which the ribose in DNA is substituted with 2'-methoxyethoxyribose, and the like [*Cell Engineering*, 16: 1463 (1997)]

16) Use of the Aging-suppressing Polypeptide, DNA Encoding the Polypeptide, the Antibody Recognizing the Polypeptide, Oligonucleotide of the Present Invention, the Ligand of the Present Invention, and the Expression Enhancing Compound (i) The aging-suppressing polypeptide can be detected and assayed in samples of blood, some organs, cells, and the like, using the anti-aging-suppressing polypeptide antibody of the present invention. Specific examples of the preferable means include ELISA, a fluorescent antibody method, and Western blotting, and additionally, immune cell staining using pathological tissue sections. Therefore, the antibody is useful for diagnosing the possibility of the occurrence of a syndrome resembling premature aging and various adult diseases due to the decrease in the expression of the aging-suppressing polypeptide. Similarly, the antibody is also useful as a laboratory reagent for research works of the subject peptide.

(ii) Aging can be suppressed by administering the full length or a partial length of the aging-suppressing polypeptide of the present invention into biological organisms. Therefore, the aging-suppressing polypeptide is useful as a therapeutic agent or a preventive agent for various adult diseases occurring in close relation with the progress of aging, for example, arteriosclerosis, hypertension, osteoporosis, and the like. Based on the suppression of aging, additionally, the polypeptide is effectively useful for the prolongation of the life.

(iii) The aging-suppressing gene of the present invention can be used for therapeutic treatment by gene therapy after the aging-suppressing gene of the present invention is incorporated into viral vectors and other vectors, such as retrovirus, adenovirus, and the like.

(iv) According to Northern hybridization or PCR using the aging-suppressing gene or oligonucleotides of the present invention, the expression level of the gene is assayed, and aging and adult diseases are diagnosed. Additionally, the aging-suppressing gene or oligonucleotides can be used for suppressing aging or suppressing the onset of adult diseases. By detecting an individual who is aging and has a higher possibility of adult diseases due to the congenital defect of the aging-suppressing gene, using the aging-suppressing gene or oligonucleotides according to Southern blotting or PCR, gene diagnosis can be carried out based on the information of the sequence of the nucleic acids in the detected individual. Furthermore, the aging-suppressing gene or oligonucleotide is extremely useful as the reagent for genetic research works.

(v) By administering the product of the aging-suppressing gene derived from objective livestock, such as bovine, sheep, goat, pig, horse, chicken, and the like, as provided in accordance with the present invention to an adequate animal or by expressing the gene in an individual using an appropriate vector, such as virus or the like, for gene therapy, the life of the objective livestock can be prolonged or the aging thereof can be suppressed. As a result, the livestock can be raised well for a long term, so that milk, egg and fetus can be harvested for a prolonged term. Furthermore, so-called transgenic livestock may be generated by introducing the gene into a fertilized egg and inserting the gene into the chromosomes of the cells of the whole body for expressing the gene therein, and the same effect can be expected, which may be useful in stock breeding.

Additionally, a mutant clone wherein the aging-suppressing gene on the chromosome in an embryonic stem cell is inactivated or substituted with an appropriate sequence by a known homologous recombinant technique [for example, *Nature*, 326: 6110, 295 (1987); *Cell*, 51: 3, 503 (1987), etc.] can be prepared [for example, *Nature*, 350: 6315, 243 (1991)] using a vector containing the gene. A chimera comprising the embryonic stem cell and normal cells can be prepared using the embryonic stem cell clone thus prepared according to technique, such as an injection chimera method, a coenochimera method, or the like into the blastcyst of a fertilized egg of an animal. Through the mating of the chimera with a normal subject, an individual with an appropriate mutation in the aging-suppressing gene in the cells of the whole body can be prepared, and through the mating of such individuals, a homozygote in which mutations inserted into both the homologous chromosomes can be obtained.

In such a manner, in animal individuals, mutations can be introduced into an appropriate site of the aging-suppressing gene. By introducing mutations, such as substitution, deletion, insertion, or the like, of nucleotides into the translation region of the aging-suppressing gene, the activity of the product can be modified. Additionally, through similar insertion of mutations into the expression controlling region, the extent, timing and tissue specificity and the like of the expression can be modified. Through the combination with the Cre-loxP line, the expression timing, expression site, expression level and the like can be more actively controlled. Known examples of these ideas include the situation wherein an objective gene is deleted in a specific cerebral region using a promoter expressed in the region [*Cell*, 87: 7, 1317 (1996)] and an example wherein an objective gene is deleted at an objective timing in a specific method to organs using an adenovirus expressing Cre [*Science*, 278: 5335 (1997)]. Regarding the aging-suppressing gene of the present invention, an animal individual capable of controlling the expression in an appropriate tissue at an appropriate time or having an appropriate insertion, deletion or substitution in the translation region or expression controlling region can be prepared. In such an animal, a syndrome of aging and various diseases, such as adult diseases based on aging and the like, can be induced at an appropriate site and at an appropriate time. Thus, the animal serves as an extremely useful model for therapeutically treating or preventing aging or various diseases such as adult diseases. In particular, the animal is very useful as an assessment model of the therapeutic agents and preventive agents thereof, functional foods, health food, and the like.

(vi) The aging-suppressing polypeptide of the present invention is useful as a reagent for screening and determining a ligand specifically binding to the polypeptide.

(vii) The aging-suppressing polypeptide of the present invention is used, together with the ligand of the present invention, to screen and identify a compound inhibiting the specific binding between the polypeptide and the ligand.

(viii) A molecule induced as the consequence of the binding of the polypeptide to the ligand can be screened and identified using the aging-suppressing polypeptide of the present invention and the ligand of the present invention.

(ix) It is possibly suggested that a compound inhibiting the specific binding between the aging-suppressing polypeptide of the present invention and the ligand of the present invention as well as the molecule induced as the consequence of the binding between the polypeptide and ligand of the present invention serves as an alternative to the aging-suppressing functions of the aging-suppressing gene polypeptide or supplement the functions, and therefore, pharmaceutical agents containing such molecules are useful as therapeutic agents of a syndrome resembling premature aging, therapeutic agents of adult diseases, and aging-suppressing agents.

(x) A compound enhancing the expression of the aging-suppressing gene encoding the aging-suppressing polypeptide of the present invention (expression enhancing compound), which is useful as a therapeutic agent for a syndrome resembling premature aging, a therapeutic agent for adult diseases and an aging-suppressing agent, is useful for suppressing aging and therapeutically treating or preventing adult diseases, like the aging-suppressing polypeptide.

The present invention can provide a polypeptide having an activity of suppressing aging; a therapeutic agent for a syndrome resembling premature aging, a therapeutic agent for adult diseases or an aging-suppressing agent, each comprising the polypeptide; DNA encoding the polypeptide; a therapeutic agent for a syndrome resembling premature aging, a therapeutic agent for adult diseases or an aging-suppressing agent, each comprising the DNA; a method for improving livestock by using the DNA; a recombinant DNA prepared by incorporating the DNA into a vector; a transformant harboring the recombinant; a method for producing the polypeptide of the present invention using the transformant; an antibody recognizing the polypeptide; a method for assaying the polypeptide of the present invention or a method for diagnosing aging, using the antibody; a method for screening a ligand for the polypeptide of the present invention; the ligand; a method for screening a compound inhibiting the specific binding between the polypeptide and ligand of the present invention; a compound obtained by the screening method; a method for screening a compound enhancing the expression of the aging-suppressing gene encoding the aging-suppressing polypeptide of the present invention; and a compound obtained by the screening method.

Examples are shown hereinafter. Unless otherwise stated, genetic manipulation is carried out according to the known method described in *Molecular Cloning*, 2nd ed.

EXAMPLE 1

Cloning of Murine Chromosomal DNA Adjacent to Gene-Introduced Site (1) Detection of Introduction Gene A transgenic mouse into which a foreign gene with a $Na^+/H^+$ reverse transmitter ligated to human elongation factor 1α promoter (EF-1α promoter) was introduced was produced (Japanese Published Unexamined Patent Application No. 268856/1993), the resulting heterozygotes were mated to each other to obtain a homozygote showing a syndrome resembling premature aging. From the homozygote, a mouse showing a prominent syndrome resembling premature aging [18th Annual Meeting of The Molecular Biology Society of Japan (Nabeshima et al., 2K-02, 1995)], and a heterozygote used for obtaining the homozygote were used in the following experiments.

From the livers of the heterozygote, homozygote and a wild-type mouse, chromosomal DNAs were prepared. Each 10 μg of the chromosomal DNAs was completely digested with EcoRV and XbaI.

The digested DNA fragments were subjected to 0.8% agarose gel electrophoresis, and blotted on a Hybond $N^+$ filter (manufactured by Amersham Co.).

The labeled plasmid pEFNaH (Japanese Published Unexamined Patent Application No. 268856/1993), which was used for preparing the transgenic mouse with α-[$^{32}$P]-dCTP using Megaprime DNA Labeling Kit (manufactured by Amersham Co.), was also used as a probe for hybridization with the blotted Hybond $N^+$ filter according to the attached manual of the Hybond $N^+$ filter.

The results are shown in FIG. 1. Because only a single band was detected around about 150 kb in the heterozygote and homozygote, it was indicated that the introduction gene was inserted at only one site on the murine chromosome. The results were also confirmed by FISH using the introduction gene as a probe. More specifically, a single signal was detected on the telomere of the 6th chromosomal long arm (6G2-3).

(2) Cloning of Murine Chromosomal DNA Adjacent to Gene-Introduced Site (1)

Ten μg of the chromosomal DNA of the homozygote described in (1) was completely digested with EcoRI or KpnI, and ligation reaction was carried out at a concentration of 10 ng/ml at 16° C. for 30 minutes using a DNA ligation kit (manufactured by Takara Shuzo Co., Ltd.).

*Escherichia coli* XL1-Blue MRF' (Epicurian Coli, manufactured by STRATAGENE Co.) was transformed using 10 μl of the reaction solution, and then cultured at 37° C. for 18 hours, and the plasmids were recovered from the resulting colonies.

When the chromosome was digested with EcoRI, two types of plasmids, namely E50 and E70, were rescued as plasmids harboring a fragment of murine genomic DNA. When the chromosome was digested with KpnI, K8 plasmid was rescued as such plasmid.

FIG. 2 depicts restriction maps of the introduction gene and the actually rescued plasmids. All three types of plasmids contain DNA fragments different from the introduction gene, and it was indicated that these DNA fragments might possibly be chromosomal fragments adjacent to the introduction gene.

After preparing an EcoRI-PvuII fragment of the murine chromosomal DNA region contained in the rescued plasmid E50 and subsequently labeling the fragment with a radioisotope by a method similar to that in (1) Southern blotting was carried out using the filter used in (1) after dehybridization and the labeled product as a probe.

The results are shown in FIG. 3. A single band from only the wild allele was observed in the wild-type mouse; a single band from only the mutant allele was observed in the homozygote; bands from both the alleles were observed in the heterozygote, whereby it was confirmed that the chromosome-derived DNA fragment contained in the rescued plasmid was a region adjacent to the introduction gene.

EXAMPLE 2

Cloning of Murine Aging-suppressing Gene

The genomic library of a wild-type mouse (manufactured by STRATAGENE Co., murine genomic library, λFIXII) was screened using the probe of Example 1(2) (according to the attached manual) to obtain three independent phage clones hybridizable with the probe (E8.5, E2.6, E11.1) (FIG. 4).

In comparison with the genomic DNA rescued from the homozygote in Example 1(2), deletion over about 8 kb was present in the region inside the aging-suppressing gene of the homozygote.

In order to identify a gene transcribed from the region, the nucleotide sequence over the center of the deletion part was sequentially determined with a sequencer Model 14000L manufactured by Li-Cor Co. (the same sequencer used hereinafter). It was demonstrated that a CpG island was present by about 6 kb apart from the deletion part.

By excising out a 450 bp fragment with SacII from the deletion part and subsequently labeling the fragment by a method similar to that in Example 1(1), the labeled product was used as a probe for Northern hybridization under the conditions according to the manual for Hybond $N^+$ filter using a poly(A)$^+$ RNA filter of murine heart, brain, spleen, lung, liver, skeletal muscle, kidney and pancreas [Mouse Multiple Tissue Northern Blots' filters; manufactured by Clontech Co.].

The results are shown in FIG. 5. A band of about 5.3 kb was observed in kidney, and it was confirmed that an exon was contained in the SacII-digested fragment of 450 bp.

Poly(A)$^+$ RNAs were prepared separately from the murine kidneys of the wild-type, homozygote and heterozygote using QuickPrep mRNA Purification Kit (manufactured by Pharmacia Co.), and 5 μg of each RNA was subjected to 0.8% agarose gel electrophoresis, and then transferred on a Hybond $N^+$ filter (manufactured by Amersham Co.).

In the same manner as described above, Northern hybridization was carried out using the SacII digestion fragment of 450 bp as the probe.

The results are shown in FIG. 6. A band was observed individually for the wild-type and heterozygote, which establishes confirmation that the aging-suppressing gene was expressed, while no band was detected for the homozygote, which apparently indicates absolutely no expression of the gene.

Similarly, poly(A)+ RNA was prepared from murine kidney at each stage after birth for Northern hybridization using as a probe the SacII-digested fragment of 450 bp. As shown in FIG. 6, almost no expression of the aging-suppressing gene was observed until one to two weeks after birth; but the expression level was elevated gradually from the new born stage and was likely to be stronger on week 3 to 4 after birth.

EXAMPLE 3

Cloning of cDNA of Murine Aging-suppressing Gene

A cDNA library was prepared by synthesizing cDNA from the poly(A)+ RNA of the kidney of a wild-type mouse using a cDNA synthesis system (cDNA Synthesis System, manufactured by GIBCO BRL, CO.), adding an EcoRI-NotI-SalI adapter (SuperScript Choice System for cDNA Synthesis; manufactured by GIBCO BRL, CO.) onto both the termini, inserting then the resulting cDNA into the EcoRI site of a cloning vector λZAP II (λZAP II Cloning Kit; manufactured by STRATAGENE Co.) for in vitro packaging (Gigapack II Gold manufactured by STRATAGENE Co.).

Plaque hybridization of $5 \times 10^5$ clones of the cDNA library was carried out using the SacII-digested fragment of 450 bp in Example 2 as a probe. During the hybridization, the filter was washed twice under the conditions that the filter was immersed in a buffer containing 2×SSPE [1×SSPE composition contains 180 mM sodium chloride, 10 mM sodium dihydrogen phosphate, and 1 mM ethylenediaminetetraacetate (EDTA) (pH 7.4)], washed twice under conditions that the filter was immersed in a buffer containing 0.1% SDS at 65° C. for 10 minutes, washed once under conditions that the filter was immersed in a buffer of 1×SSPE and 0.1% SDS at 65° C. for 15 minutes, and washed twice under conditions that the filter was immersed in a buffer of 0.2×SSPE and 0.1% SDS at 65° C. for 10 minutes.

Through the hybridization, 40 independent hybridizable clones were obtained. From the clones, plasmids were recovered through in vivo excision, and analyzed with restriction enzymes and nucleotide sequencing.

It was indicated from the nucleotide sequencing that plasmid pNKM101 contains cDNA of about 5 kb represented by SEQ ID NO:8, and that an open reading frame (hereinafter referred to as "ORF") of 3042 bp was present in the cDNA. In the ORF, a novel protein of 1014 amino acid residues was encoded, having a signal sequence of 35 amino acids at the N terminus and a transmembrane region of 19 amino acids at the C terminus, as shown in SEQ ID NO:3 (FIG. 7). The structure of pNKM101 is shown in FIG. 8.

EXAMPLE 4

Isolation of Mouse-derived Secretory Aging-suppressing Gene

In order to isolate a clone containing the genome region of the murine aging-suppressing gene from the library containing the murine genomic DNA (Bacterial artificial chromosome, BAC), PCR was carried out using as the primers the sequences of two regions in the murine aging-suppressing gene cDNA obtained in Example 3, the regions represented by SEQ ID NOS:11 and 12, along with the murine chromosomal DNA as the template. It was confirmed that a DNA fragment of 127 bp was amplified.

By using DNA Thermal Cycler 480 manufactured by Perkin Elmer Co., PCR was carried out for 30 cycles, each cycle being composed of a process of 94° C. for one minute, 56° C. for one minute and 72° C. for one minute.

From the BAC library containing the murine chromosomal DNA of 100 kb on average a BAC clone was selected wherein a DNA fragment of 127 bp was amplified using the primers and amplification conditions described above by PCR.

After adding a sample of 10 μg of the resulting BAC clone to 50 μl of the buffer B, 3 units of Sau3AI were added to the sample and reacted at 37° C. for 10 minutes.

Phenol-chloroform extraction and ethanol precipitation were carried out using the reaction solution to recover about 5 μg of the DNA fragment.

Cosmid vector pWE15 (manufactured by Clontech Co.) of 5 μg was added to 30 μl of buffer C, and 30 units of BamHI were added thereto to react at 37° C. for 2 hours. Phenol-chloroform extraction and ethanol precipitation using the reaction solution were carried out to recover about 2 μg of the DNA fragment.

The Sau3AI treated BAC clone fragment (1 μg) and the BamHI treated pWE 15 fragment (100 ng) were dissolved in a T4-DNA ligase buffer (20 μl), and one unit of T4 DNA ligase was added thereto for ligation at 16° C. for 18 hours. The reaction solution was treated for in vitro packaging using Gigapack II Gold Extract (manufactured by STRATAGENE CO.) to prepare a cosmid library.

A clone in which the 127 bp fragment was amplified was obtained from the library using the primers and under the amplification conditions for the selection of the BAC clone by PCR.

The nucleotide sequence corresponding to the C terminus of the human-derived secretory aging-suppressing polypeptide obtained in Example 5 below was compared with the DNA sequence of the corresponding region of the murine aging-suppressing gene sub-cloned in the cosmid, and consequently, a DNA sequence encoding a sequence with homology to the polypeptide sequence from the 535th amino acid to the 549th amino acid of the human-derived secretory aging-suppressing polypeptide represented by SEQ ID NO:2 was found.

Gene amplification was carried out by PCR using a template Mouse Kidney Marathon Ready cDNA kit (manufactured by Clontech Co.), after adding a library-derived adapter primer represented by SEQ ID NO:13 and a primer corresponding to a mouse-derived region homologous to the C terminus of the human secretory aging-suppressing polypeptide represented by SEQ ID NO:14.

PCR reaction was carried out for 30 cycles using DNA Thermal Cycler 480 manufactured by Perkin Elmer Co., each cycle being composed of a process of 94° C. for one minute, 55° C. for 30 seconds, and 72° C. for one minute.

The resulting reaction product was analyzed by agarose gel electrophoresis, an amplified fragment of about 2 kb was observed, and the fragment was incorporated into pCR2.1 vector (manufactured by Invitrogen Co.).

A nucleotide sequence was determined, and a sequence represented by SEQ ID NO:9 was obtained. This result indicates that the cDNA is a murine secretory aging-suppressing gene of 1650 bp containing an ORF encoding 550 amino acid residues.

The gene was further subjected to PCR using synthetic DNA represented by SEQ ID NOS:15 and 16, HindIII and BamHI digestion sites were added on both the termini of the gene, which was then inserted into the HindIII and BamHI cleavage sites of plasmid vector pUC118, to prepare pNKM112 (FIG. 9).

In order to examine the expression of the gene in murine tissues, a reverse transcription reaction with a primer random 9-mer was carried out using TaKaRa RNA LA PCR kit (AMV) Ver. 1.1 (manufactured by Takara Shuzo Co., Ltd.) with a template poly(A)$^+$ mRNA (500 ng) prepared from various organs using the primers represented by SEQ ID NOS:17 and 18 and using QuickPrep mRNA Purification Kit (manufactured by Pharmacia Co.), followed by PCR reaction using LA-TaqDNA polymerase (manufactured by Takara Shuzo Co., Ltd.).

The PCR reaction was carried out for 30 cycles using a DNA Thermal Cycler 480 manufactured by Perkin Elmer Co., each cycle being composed of a process of 94° C. for 20 seconds, 60° C. for 30 seconds, and 72° C. for one minute.

The resulting reaction products were analyzed by agarose gel electrophoresis, and the results are shown in FIG. 10. Expression was observed in kidney, brain, pituitary gland, ovary, spermary, and pancreas.

EXAMPLE 5

Cloning of cDNA for a Human Aging-suppressing Gene (1) Preparation of Aging-suppressing Gene Derived from Human Kidney A human kidney cDNA library was constructed using human kidney poly(A)$^+$ RNA (manufactured by Clontech Co.) by a method similar to that in Example 3. Plaque hybridization of about 1,000,000 clones of the library was carried out using a 4.2 kb fragment excised out with the NotI site derived from the 5' terminal adapter in the murine cDNA of Example 2 and the NotI site present in the cDNA.

Through the hybridization, six independent strongly hybridizing clones were obtained. From the clones, plasmids were recovered by in vivo excision, and restriction analysis and nucleotide sequencing were carried out.

It was indicated from the nucleotide sequencing that a plasmid obtained from two clones harbored cDNA of about 3.2 kb having high homology over the full length to the murine sequence represented by SEQ ID NO:6, and that an ORF of about 3,036 bp was present in the cDNA, the ORF encoding the 1,012 amino acid residues represented by SEQ ID NO:1.

It was concluded that the amino acid sequence was a human homologue because the sequence had homology as high as 86% to mouse (FIG. 7).

The structure of the plasmid pNKM103 harboring the cDNA is shown in FIG. 11.

It was indicated that the plasmid obtained from the remaining four clones contained cDNA of about 3.4 kb represented SEQ ID NO:7 and an ORF of 1647 bp was present in the cDNA, the ORF encoding the polypeptide represented by SEQ ID NO:2.

Compared with the polypeptide represented by SEQ ID NO:1, the polypeptide represented by SEQ ID NO:2 does not contain the transmembrane region around the C terminus, and therefore, it is indicated that the polypeptide is a secretory protein (FIG. 7).

The structure of plasmid pNKH106 containing the cDNA is shown in FIG. 12.

(2) Aging-suppressing Gene Derived from Human Pancreas

Using a phage solution (1 µl; containing 1×10$^8$ phages) of human pancreas cDNA library (manufactured by Clontech Co.) as a template, 1 µl each of 10 µM sense primer represented by SEQ ID NO:19 (RYHH-02-5') and 10 µM antisense primer represented by SEQ ID NO:20 (RYHH-02-3'-2), 4 µl of 10×PCR buffer (using the buffer attached to the enzyme), and 3.2 µl of 2.5 mM dNTP were mixed together, and the resulting mixture was set on a thermal cycler. After reaction at 97° C. for 5 minutes, the mixture was rapidly cooled in ice for 5 minutes, and 0.5 µl of Taq DNA polymerase (manufactured by Takara Shuzo Co., Ltd.; 5 units/µl) was mixed, followed by PCR for 30 cycles, each cycle being composed of a process of 95° C. for 60 seconds, 65° C. for one minute, and 72° C. for one minute. Then, it was confirmed by agarose gel electrophoresis that a band of about 400 bp was amplified.

The amplified fragment of 0.2 kb was purified from the agarose gel, which was then incorporated into pT7Blue T-vector (Novagen Co.), using a DNA ligation kit ver. 2 (manufactured by Takara Shuzo Co., Ltd.). The method followed the kit instruction. *Escherichia coli* XL1-Blue was transformed in the solution to obtain an ampicillin resistant strain. From the transformant, a plasmid was recovered using a plasmid extruder PI-100 (manufactured by Kurabo Co.), and the nucleotide sequence of two clones was determined using a DNA sequencer 377 [manufactured by Perkin Elmer Co.]. pT7-02 with a sequence homologous to the aging-suppressing gene was detected.

An insertion fragment of the plasmid pT7-02 was labeled with digoxigenin (DIG) using a DIG DNA labeling kit (manufactured by Boehringer Mannheim Co.), and was used as a probe. The labeling method followed the kit instruction.

Human pancreas cDNA library was cultured in five plates each of a diameter of 15 cm, so that about 2×10$^5$ plaques might appear per one dish, which were then blotted on a nylon membrane filter Hybond N+ (manufactured by Amersham Co.). According to the protocol by Boehringer Mannheim Co. (DIG Luminescent Detection Kit for Nucleic Acids), denaturation and immobilization of DNA and probe hybridization and filter washing were carried out. As the hybridizing solution, solution containing 5×SSC, 1% blocking solution [DIG Luminescent Detection Kit for Nucleic Acids (Boehringer Mannheim Co.)], 0.1% Sarcosyl, and 0.02% SDS was used for overnight hybridization at 68° C. Under shaking, the solution was washed twice with 2×SSC containing 0.1% SDS at room temperature for 10 minutes, and twice in 1×SSC containing 0.1% SDS at 68° C. for 15 minutes, and then, a positive plaque was detected using a DIG detection kit (manufactured by Boehringer Mannheim Co.) with anti-DIG antibody. The plaque was scooped out together with the agar medium, and was then placed in 500 µl of an SM buffer (0.1 M NaCl, 0.008 M MgSO$_4$.7H$_2$O) to elute the phage into the buffer solution at room temperature overnight. Using 1 µl of the buffer as a template, PCR was carried out in the same manner as described above. It was confirmed on the basis of the amplification of a fragment of 0.4 kb that the objective cDNA was contained in the positive clone, and by subsequently cleaving out an insertion sequence of about 3.5 kb with EcoRI from the positive clone, the sequence was then sub-cloned in the EcoRI site of pBluescript II SK(+). The plasmid was recovered from the transformant using a plasmid extruder PI-100 (manufactured by Kurabo Co.), and the nucleotide sequence of one clone was determined using a DNA sequencer 377 [manufactured by Perkin Elmer Co.]. Plasmid pRYH02 harboring the nucleotide sequence represented by SEQ ID NO:10 was observed. It was demonstrated that an ORF capable of encoding the protein of 1,015 amino acids represented by SEQ ID NO:5 was present in the gene. Because the amino acid sequence possibly deduced from the nucleotide sequence showed over its whole region about 45% homology to the aging-suppressing gene, it was demonstrated that the gene was one of the aging-suppressing gene family.

The 100 amino acids from the N terminus of the amino acid sequence represented by SEQ ID NO:10 were analyzed using Signal P ver. 2 *[Protein Engineering*, 10: 1 (1997)] and SPScan (Genetics Computer Group Inc.) as signal sequence cleavage site prediction software. Consequently, the signal sequence cleavage sites predicted by the two types of software agreed with each other, which were present between the 23rd Gly and the 24th Phe. Therefore, it was concluded that the 1st to 23rd amino acids of the amino acid sequence of the polypeptide formed a signal sequence and the amino acids at position 24 and thereafter formed a maturation peptide.

EXAMPLE 6

Construction of Plasmid pYT102 for Expressing Partial Fragments of Murine Aging-suppressing Polypeptide in *Escherichia coli*

The expression of partial fragments of the murine aging-suppressing polypeptide in *Escherichia coli* was carried out by inserting a DNA fragment containing cDNA encoding a murine aging-suppressing polypeptide fragment into expression vector pSupex for *Escherichia coli*, as shown below, to prepare pYT102, and introducing pYT102 into *Escherichia coli*.

pSupex was prepared through the following 5-step process by combining pGHA2 (Japanese Published Unexamined Patent Application No. 221091/1985), pTerm2 (Japanese Published Unexamined Patent Application No. 22979/1991) and pGKAA2 (Japanese Published Unexamined Patent Application No. 221091/1985) previously reported, as shown in FIG. 13.

(Process 1) Construction of Plasmid pTerm4

After adding 3 μg of plasmid pGHA2 into 30 μl of a buffer containing 10 mM Tris-HCl (pH 7.5), 10 mM magnesium chloride, 50 mM sodium chloride and 1 mM DTT (hereinafter referred to as "Tris A buffer"), 10 units of HindIII was added to the buffer, for reaction at 37° C. for 4 hours.

Phenol-chloroform extraction and ethanol precipitation were carried out using the reaction solution to recover DNA fragments. After adding the DNA to 30 μl of a buffer containing 10 mM Tris-HCl (pH 7.5), 10 mM magnesium chloride, 100 mM sodium chloride and 1 mM DTT (hereinafter referred to as "Tris B buffer"), 10 units of PstI were added to the buffer to react at 37° C. for 4 hours.

The treated DNA fragments in the reaction solution were fractionated using agarose gel electrophoresis to recover about 0.3 μg of an about 0.94 kb PstI/HindIII treated fragment of pGHA2 containing the letI promoter.

To 30 μl of Tris A buffer, 3 μg of the plasmid pTerm2 was added, and 10 units of HindIII were added to the buffer to react at 37° C. for 4 hours.

DNA fragments were then recovered by ethanol precipitation from the reaction solution. The DNA was added to 30 μl of Tris B buffer, and 10 units of PstI were added to the buffer to react at 37° C. for 4 hours.

The treated DNA fragments in the reaction solution were fractionated using agarose gel electrophoresis to recover an about 1.1 kb PstI/HindIII treated fragment of pTerm at a yield of about 0.8 μg, the fragment containing an origin of replication and a translation termination codon.

The PstI/HindIII treated fragment (100 ng) of the pGHA2 and the PstI/HindIII treated fragment (50 ng) of pTerm2 were dissolved in 20 μl of a T4 DNA ligase buffer, 100 units of T4 DNA ligase (manufactured by Takara Shuzo Co., Ltd.) were added to the solution, and a ligation was carried out at 16° C. for 18 hours.

*Escherichia coli* JM109 was transformed using the recombinant plasmid obtained through the reaction to obtain plasmid pTerm4 shown in FIG. 13.

(Process 2) Construction of Plasmid pGBZ2

To 30 μl of a buffer containing 10 mM Tris-HCl (pH 7.5), 70 mM magnesium chloride, 150 mM potassium chloride, 0.01% bovine serum albumin and 7 mM 2-mercaptoethanol (abbreviated as Tris C buffer hereinafter), 3 μg of pGKA2 was added, and 10 units of NruI were added to the buffer to react at 37° C. for 4 hours.

Phenol-ethanol extraction and ethanol precipitation were carried out using the reaction solution to recover NruI treated fragments of pGKA2.

BglII linker (5'-pCAGATCTG-3') was synthesized, and 50 ng of the linker and the NruI treated fragments of the pGKA2 were dissolved in 20 μl of a T4 DNA ligase buffer, 100 units of T4 DNA ligase to the solution were added, and a ligation was carried out at 16° C. for 18 hours.

*Escherichia coli* JM109 was transformed using the recombinant DNA thus obtained through the reaction to obtain plasmid pGBZ2 shown in FIG. 13.

(Process 3) Construction of Plasmid pTerm5

To 30 μl of Tris B buffer, 3 μg of plasmid pTerm4 was added, and 10 units of PstI and 10 units of BglII were added to the buffer to react at 37° C. for 4 hours.

The treated DNA fragments in the reaction solution were fractionated using agarose gel electrophoresis to recover a 1.15 kb PstI/BglII treated fragment of pTerm4 at a yield of about 0.8 μg, the fragment containing letI promoter and a translation termination codon.

To 30 μl of Tris B buffer, 3 μg of plasmid pGBZ2 was added, 10 units each of PstI and BglII were added to the buffer to react at 37° C. for 4 hours.

The treated DNA fragments in the reaction solution were fractionated using agarose gel electrophoresis to recover an about 2.63 kb PstI/BglII treated fragment of pGBZ2 at a yield of about 0.3 μg, the fragment containing the origin of replication, an ampicillin resistant gene and a rop gene.

In 20 μl of a T4 DNA ligase buffer, 100 ng of the PstI/BglII treated fragment of pTerm and 50 ng of the PstI/BglII treated fragment were dissolved, 100 units of T4 DNA ligase were added to the solution, and a ligation was carried out at 16° C. for 18 hours.

*Escherichia coli* JM109 was transformed using the recombinant plasmid obtained through the reaction to obtain plasmid pTerm5 shown in FIG. 13.

(Process 4) Construction of Plasmid pTerm6

To 30 μl of Tris C buffer, 3 μg of plasmid pTerm5 was added, and 10 units of NruI were added to react at 37° C. for 4 hours.

Phenol/chloroform extraction and ethanol precipitation were carried out using the reaction solution to recover DNA fragments. The DNA was added to 30 μl of Tris A buffer, and 10 units of ClaI were added to the buffer to react at 37° C. for 4 hours.

The treated DNA fragments in the reaction solution were fractionated using agarose gel electrophoresis to recover an about 3.7 kb NruI/ClaI treated fragment of pTerm5 at a yield of about 0.3 µg, the fragment containing the origin of replication, ampicillin resistant gene, letI promoter and rop gene.

Synthetic DNAs having the nucleotide sequences represented by SEQ ID NOS:21 and 22 were dissolved at 1 µg each in 10 µg of distilled water and heated at 95° C. for 5 minutes, and the resulting solution was cooled over 30 minutes to room temperature for annealing (hereinafter referred to as "synthetic DNA-1").

In 20 µl of T4 DNA ligase buffer, 50 ng of the NruI/ClaI treated fragment of pTerm5 and 50 ng of the synthetic DNA-1 were dissolved, 100 units of T4 DNA ligase were added, and a ligation was carried out at 16° C. for 18 hours.

*Escherichia coli* JM109 was transformed using the recombinant plasmid DNA thus obtained through the reaction to obtain plasmid pTerm6 shown in FIG. 13.

(Process 5) Construction of Plasmid pSupex

To 30 µg of a buffer containing 50 mM potassium phosphate, 3 µg of plasmid pTerm6, 20 mM Tris-acetic acid (pH 7.9), 10 mM magnesium acetate and 1 mM DTT, and 10 units of NsiI were added to the buffer to react at 37° C. for 4 hours.

Phenol-chloroform extraction and ethanol precipitation were carried out using the reaction solution to recover DNA fragments. The DNA was added to 30 µl of Tris A buffer, and 10 units of HindIII were added to the buffer to react at 37° C. for 4 hours.

The treated DNA fragments in the reaction solution were fractionated using agarose gel electrophoresis to recover an about 3.7 kb NsiI/HindIII treated fragment of pTerm6 at a yield of about 0.3 µg, the fragment containing the origin of replication, ampicillin resistant gene, letI promoter and rop gene.

Synthetic DNAs having the nucleotide sequences represented by SEQ ID NOS:23 and 24 were dissolved at 1 µg each in 10 µg of distilled water and heated at 95° C. for 5 minutes, and the resulting solution was cooled over 30 minutes to room temperature for annealing (hereinafter referred to as "synthetic DNA-2").

In 20 µl of T4 DNA ligase buffer, 50 ng of the NsiI/HindIII treated fragment of pTerm6 and 50 ng of the synthetic DNA-2 were dissolved, 100 units of T4 DNA ligase were added thereto, and a ligation was carried out at 16° C. for 18 hours.

*Escherichia coli* JM109 was transformed using the recombinant plasmid DNA thus obtained through the reaction to obtain plasmid pSupex shown in FIG. 13.

(Process 6) Construction of Plasmid pYT102

To 30 µl of a buffer containing 50 mM Tris-HCl (pH 7.5), 10 mM magnesium chloride, 100 mM sodium chloride and 1 mM DTT, 3 µg of plasmid pNKM101 obtained in Example 3 was added, and 10 units of Eco47III were added to the buffer to react at 37° C. for 4 hours.

Phenol-chloroform extraction and ethanol precipitation were carried out using the reaction solution to recover DNA fragments. The DNA was added to 30 µl of a buffer containing 10 mM Tris-HCl (pH 7.5), 10 mM magnesium chloride and 1 mM DTT, and 10 units of KpnI were added to the buffer to react at 37° C. for 4 hours.

The treated DNA fragments in the reaction solution were fractionated using agarose gel electrophoresis to recover an about 0.7 kb Eco47III/KpnI treated fragment (FIG. 14) of pNKM101 at a yield of about 0.3 µg, the fragment containing DNA encoding a fragment containing the amino acid residues from $Ala^{35}$ to $Tyr^{267}$ of the aging-suppressing polypeptide represented by SEQ ID NO:3.

To 30 µl of Tris A buffer, 3 µg of expression vector pSupex for *Escherichia coli* obtained in Process 5 was added, and 10 units of StuI were added to the buffer to react at 37° C. for 4 hours.

Phenol-chloroform extraction and ethanol precipitation were carried out using the reaction solution to recover DNA fragments. The DNA was added to 30 µl of a buffer containing 10 mM Tris-HCl (pH 7.5), 10 mM magnesium chloride and 1 mM DTT, and 10 units of KpnI were added to the buffer to react at 37° C. for 4 hours.

The treated DNA fragments in the reaction solution were fractionated using agarose gel electrophoresis to recover about 0.3 µg of an about 3.8 kb StuI/KpnI treated fragment of pSupex.

In 20 µl of T4 DNA ligase buffer, 50 ng of the Eco47III/KpnI treated fragment of pNKM101 and 100 ng of the StuI/KpnI treated fragment of pSupex were dissolved, 100 units of T4 DNA ligase were added thereto, and a ligation was carried out at 16° C. for 18 hours.

*Escherichia coli* JM109 was transformed using the recombinant plasmid DNA thus obtained through the reaction to obtain plasmid pYT102 shown in FIG. 14.

EXAMPLE 7

Expression of Aging-suppressing Partial Fragment Polypeptide in *Escherichia coli* pYT102 obtained in Example 6 was introduced into *Escherichia coli* NY49. The *Escherichia coli* was cultured in 400 ml of an M9 minimal medium (the medium described in *Molecular Cloning, A Laboratory Manual*) supplemented with 75 µg/ml ampicillin and 2 mg/ml casaminoic acid at 37° C. for 2 hours, and 50 µg/ml indole acrylic acid was added thereto, followed by culturing at 37° C. for 18 hours.

A 400 ml portion of the culture was centrifuged at 3,000×g for 15 minutes, the precipitate containing the *Escherichia coli* was then suspended in 7 ml of Buffer 1 [buffer containing 10 mM Tris-HCl (pH 8.0), 1 mM EDTA, and 150 mM sodium chloride], and the *Escherichia coli* was disrupted by ultrasonic treatment.

The treated solution was centrifuged at 10,000×g for 30 minutes, and the resulting precipitate was dissolved in a sample buffer for SDS-polyacrylamide gel electrophoresis [buffer containing 6 mM Tris-HCl (pH 6.8), 2% SDS, 10% glycerol, and 5% 2-mercaptoethanol]. The solution was fractionated by SDS-polyacrylamide electrophoresis, and the gel was stained with Coomassie Brilliant Blue. The results are shown in FIG. 15. It was confirmed that an aging-suppressing partial fragment polypeptide of a molecular weight of about 27 kDa was produced. During the electrophoresis, phosphorylase b (97,400), bovine serum albumin (66,200), ovalbumin (45,000), carbonic anhydrase (31,000), soybean trypsin inhibitor (21,500), and lysozyme (14,400) were used as molecular weight markers.

EXAMPLE 8

Production of Anti-Murine Aging-suppressing Polypeptide Antibody Reacting with Murine Aging-suppressing Partial Fragment Polypeptide (1) The murine aging-suppressing partial fragment polypeptide expressed in *Escherichia coli* as a host in Example 7 was fractionated by SDS-polyacrylamide gel electrophoresis using a 2-mm thick gel under reductive conditions by a conventional method.

The gel was stained with an aqueous 0.1% Coomassie Brilliant Blue solution, and decolored in water, and a band of about 27 kDa corresponding to the aging-suppressing partial fragment polypeptide was cut out.

The gel was ground and crushed, which was then used to extract and recover the aging-suppressing polypeptide partial fragment at 4° C. overnight using 0.1% SDS-PBS. The protein concentration was determined by SDS-polyacrylamide gel electrophoresis using BSA as a standard for assaying protein concentration.

(2) A rat was immunized using the aging-suppressing partial fragment polypeptide obtained in (1) by a conventional method.

That is, the aging-suppressing partial fragment polypeptide with addition of adjuvant (2 mg of aluminum hydroxide, and pertussoid vaccine at $1 \times 10^9$ cells/animal) for a first dosage was intraperitoneally administered at a concentration of 50 μg/animal into a rat, and on weeks 2 and 3 from the first dosing, only the aging-suppressing partial fragment polypeptide was administered intraperitoneally.

Three days after the final immunization, blood was drawn locally to assay the blood antibody titer by the ELISA described below.

[ELISA]

The aging-suppressing partial fragment polypeptide described above was prepared to a concentration of 10 μg/ml in PBS buffer [buffer prepared by dissolving disodium hydrogen phosphate (1.83 g), potassium dihydrogen phosphate (0.21 g) and sodium chloride (7.65 g) in distilled water to a final volume of one liter (pH 7.2)]. The prepared solution was divided at 50 μl/well into a 96-well EIA plate (manufactured by Gleiner Co.), and allowed to stand at 4° C. overnight.

After washing the plate in a PBS buffer, a PBS buffer containing 1% BSA (hereinafter referred to as "BSA-PBS") was divided at 100 to 200 μl/well, and the plate was allowed to stand at room temperature for one to two hours or at 4° C. for one to two nights. After allowing the plate to stand, the BSA-PBS was discarded, and the resulting plate was thoroughly washed with PBS buffer.

The collected anti-serum was diluted in BSA-PBS, which was then added at 20 to 100 μl/well into the plate, and the plate was allowed to stand at room temperature for 2 hours.

After allowing the plate to stand, the plate was washed with a PBS buffer containing 0.05% Tween 20 (hereinafter referred to as "PBS-0.05 Tween"), and then peroxidase-labeled anti-rat immunoglobulin or peroxidase-labeled anti-murine immunoglobulin (manufactured by DAKO CO.) was added at 50 to 100 μl/well into the plate, and the plate was allowed to stand at room temperature for one hour.

After allowing the plate to stand alone, the plate was washed with PBS-0.05 Tween, and then, an ABTS substrate solution [solution prepared by dissolving 2,2-azinobis(3-ethylbenzothiazole-6-sulfonic acid) ammonium (550 mg) in one liter of a 0.1 M citrate buffer (pH 4.2) and adding 1 μl/ml hydrogen peroxide to the resulting solution just prior to use] was added to the plate for chromogenic reaction to determine the absorbance at $OD_{415}$ nm (NJ2001; Nippon Intermed Co.).

(3) By Western blotting, it was confirmed that the serum reacted with the above murine aging-suppressing partial fragment polypeptide.

According to the method described in Example 7, the bacterial protein of *Escherichia coli*, where the expression of the aging-suppressing partial fragment polypeptide fragment was confirmed, was fractionated by polyacrylamide gel electrophoresis.

The protein fractionated on the gel was transferred onto a transfer membrane (Immobilon Transfer Membranes, manufactured by Millipore Co.). The transfer was continued under conditions of 2 $mA/cm^2$ constant current for 2 hours using a transfer membrane immersed in 100% methanol for 20 seconds and then immersed in a solution containing 10 mM CAPS (3-cyclohexylaminopropane sulfonic acid), 10% methanol and 0.03% SDS (pH 11.0) for 30 minutes.

The transfer membrane was shaken in 200 ml of BSA-PBS for one hour, and was then washed once with a PBS buffer.

The transfer membrane and serum (2 ml) collected from a rat, which serum was preliminarily diluted by 1/25000-fold in a PBS buffer, were placed in a vinyl bag, and the bag was then sealed and gently shaken at 4° C. overnight.

The transfer membrane was immersed twice in PBS-0.05 Tween for 5 minutes, followed by washing, and then the resulting membrane was immersed in a PBS buffer for 5 minutes and was then washed.

The transfer membrane and 3 ml of an anti-rat IgG antibody labeled with 0.5 mg/ml peroxidase (anti-rat immunoglobulin, manufactured by Amersham Co.) were placed in a vinyl bag, sealed, and shaken at room temperature for one hour.

After shaking, the transfer membrane was immersed twice in PBS-0.05 Tween for 5 minutes, and the resulting membrane was washed, and immersed in PBS buffer for 5 minutes, followed by washing.

By a luminescent method (ECL Western blotting detection reagents, manufactured by Amersham Co.) protein present on the transfer membrane and observed to have cross reactivity with the antibody in the rat serum was detected.

The results are shown in FIG. 16.

A band was detected on the same position of the band of about 27 kDa as obtained in Example 7, and it was indicated that the antibody in the rat serum collected in Example 8(2) recognized the murine aging-suppressing polypeptide fragment as the antigen and the polypeptide fragment is usable for Western blotting.

The antibody in the rat serum is referred to as "anti-aging-suppressing polypeptide antibody" hereinafter.

EXAMPLE 9

Preparation of Anti-Aging-suppressing Polypeptide Monoclonal Antibody (1) Preparation of Antibody-Producing Cell Spleens were resected from three rats having sufficient serum antibody titers, as obtained in Example 8(2)

The spleens were cut into pieces in MEM medium (manufactured by Nissui Pharmaceutical Co.) and the pieces were loosened with a pair of tweezers, and centrifuged at 1,200 rpm for 5 minutes, and the resulting supernatant was discarded.

The splenic cells in the resulting precipitate fraction were treated with a Tris-ammonium chloride buffer (pH 7.65) for 1 to 2 minutes to remove erythrocytes, and the resulting cells were washed three times with MEM medium. The resulting splenic cells were used as antibody-producing cells.

(2) Preparation of Murine Myeloma Cell

8-Azaguanine resistant murine myeloma cell line P3-U1 preliminarily sub-cultured in the 8-azagunine medium was cultured in the normal medium for use as myeloma cells for cell fusion. For the cell fusion, cells of $2 \times 10^7$ or more were used.

(3) Preparation of Hybridoma

The antibody-producing cells obtained in (1) and the myeloma cells obtained in (2) were thoroughly washed with MEM medium and were then mixed together, so that the cell numbers should be 10:1 as the ratio of antibody-producing cells:myeloma cells, and the resulting mixture was centrifuged at 1,200 rpm for 5 minutes to remove the supernatant.

The cell population in the resulting precipitate fraction was thoroughly loosened, and to the cell population, 0.2 to 1 ml of a mixture solution of polyethylene glycol-1000 (PEG-1000) 2 g, MEM 2 ml and dimethyl sulfoxide (DMSO) (0.7 ml) was added per 108 antibody-producing cells, 1 to 2 ml of MEM medium was added thereto several times every 1 to 2 minutes.

After addition, MEM medium was further added to the culture to give a final total volume of 50 ml.

The prepared solution was centrifuged at 900 rpm for 5 minutes to discard the supernatant.

The cells in the resulting precipitate fraction were loosened and were then suspended gently in 100 ml of HAT medium under aspiration and blowing using a measuring pipette.

The suspension was divided at 100 µl/well into a 96-well culture plate, and then cultured in a 5% $CO_2$ incubator at 37° C. for 7 to 14 days.

After culturing, a part of the culture supernatant was sampled, and about 1000 hybridomas specifically reacting with the aging-suppressing partial fragment polypeptide produced in *Escherichia coli* were screened according to the enzyme immunoassay described in Example 8(2).

Cloning was carried out using the hybridomas by limited dilution, firstly in HT medium and secondly in the normal medium, to obtain hybridoma KM1902 producing anti-aging-suppressing polypeptide antibody.

It was determined by an enzyme immunoassay using a subtype typing kit that the antibody class of the monoclonal antibody KM1902 produced by the hybridoma KM1902 was IgG2a.

(4) Purification of Monoclonal Antibody

Into a Pristane-treated female nude mouse (Balb/c) of age 8 weeks, the hybridoma obtained in (3) at 5 to $20 \times 10^6$ cells/animal was intraperitoneally injected the hybridoma turned ascites tumor in 10 to 21 days.

From the mouse having ascites tumor, ascites (1 to 8 ml/animal) was collected, and then centrifuged at 3,000 rpm for 5 minutes to remove the solids.

The resulting supernatant was purified by a caprylic acid precipitation method [*Antibodies, A Laboratory Manual*, Cold Spring Harbor Laboratory (1988)] and IgG was obtained and used as a purified monoclonal antibody.

EXAMPLE 10

Construction of Plasmid pYT103 for Expressing Murine Aging-suppressing Polypeptide in Animal Cell (Process 1) Construction of Expression Vector pAGE210 for Animal Cell (FIG. 17)

pAGE207 (Japanese Published Unexamined Patent Application No. 46841/1994) and pAGE148 (Japanese Published Unexamined Patent Application No. 205694/1994), expression vector pAGE210 for animal cells was constructed using expression vectors for animal cells as follows.

In 30 µl of Tris A buffer, 3 µg of pAGE207 or pAGE148 was dissolved, 10 units each of ClaI and KpnI were added to the solution to react at 37° C. for 4 hours.

The treated DNA fragments in the reaction solution were fractionated by agarose gel electrophoresis to recover an about 4.7 kb ClaI/KpnI treated fragment of pAGE207 at a yield of about 0.5 µg from pAGE207, the fragment containing the early promoter and enhancer of SV40 (hereinafter referred to as "$P_{SE}$"), hygromycin resistant gene and ampicillin resistant gene (hereinafter referred to as "Ap"), while an about 4.3 kb ClaI/KpnI treated fragment containing dehydrofolic acid reductase gene (hereinafter referred to as "dhfr") was recovered at a yield of about 0.5 µg from pAGE148.

In 20 µl of a T4 DNA ligase buffer, 50 ng of the aforementioned ClaI/KpnI treated fragment of pAGE207 and 50 ng of the aforementioned ClaI/KpnI treated fragment of pAGE148 were dissolved, 200 units of T4 DNA ligase were added, and a ligation was carried out at 12° C. for 16 hours.

*Escherichia coli* JM109 was transformed using the recombinant plasmid obtained through the reaction to obtain plasmid pAGE210 shown in FIG. 17.

(Process 2)

By ligating together the XbaI fragment of pAGE210 as obtained in the above Process 1 and the XbaI fragment of pNKM101 described in Example 6 (Process 6), the fragment containing the DNA encoding the aging-suppressing polypeptide, expression vector pYT1103 for the murine aging-suppressing polypeptide was constructed as follows (FIG. 18).

In 30 µl of Tris A buffer, 3 µg of pAGE210 was dissolved, 10 units of XbaI were added to the buffer to react at 37° C. for 4 hours.

Phenol-chloroform extraction and ethanol precipitation were carried out using the reaction solution to recover DNA fragments. The DNA was solubilized in 50 µl of 1M Tris-HCl buffer (pH 8.0), and one unit of alkali phosphatase was added to the solution to react at 37° C. for one hour.

Phenol-chloroform extraction and ethanol precipitation were carried out using the reaction solution to recover about 0.5 µg of the XbaI-dephosphorylated fragment of pAGE210 from the extract solution.

To 30 µl of Tris A buffer containing 0.01% BSA, 3 µg of pNKM101 was added, 10 units of XbaI were added to the buffer to react at 37° C. for 4 hours.

The reaction solution was fractionated by agarose electrophoresis to recover about 0.3 µg of a 3.2 kb XbaI treated fragment of pNKM101.

In 20 µl of T4 DNA ligase buffer, 50 ng of the aforementioned XbaI treated fragment of pNKM101 and 300 ng of the above XbaI-dephosphorylated fragment of pAGE210 were dissolved, one unit of T4 DNA ligase was added to the solution, and a ligation was carried out at 16° C. for 18 hours.

*Escherichia coli* JM109 was transformed using the recombinant plasmid DNA obtained through the reaction to obtain plasmid pYT103 shown in FIG. 18.

EXAMPLE 11

Expression of Murine Aging-suppressing Polypeptide in Animal Cell

The introduction of plasmid into animal cells was carried out using electroporation according to the method by Miyaji et al. [*Cytotechnology*, 3: 133 (1990)].

pYT103 obtained in Example 10 (Process 2) was introduced at a ratio of 4 µg per $4 \times 10^6$ cells into CHO cells by deleting dhfr gene [*Proc. Natl. Acad. Sci.*, 77: 4216 (1980)], and was then suspended in 10 ml of MEMα2000-dFCS (5) [MEMα2000 medium (manufactured by GIBCO, CO.) containing dFCS at 5%, 7.5% NaHCO$_3$ at a volume of ¼₀, 200 mM L-glutamine solution (manufactured by GIBCO, CO.) at 3%, and penicillin-streptomycin solution (manufactured by GIBCO, Co; containing 5000 units/ml penicillin and 5000 µg/ml streptomycin) at 0.5%], and was then placed in a 10 cm plate (manufactured by Iwaki Glass Co.).

After 24 hour culturing in a 5% CO$_2$ incubator at 37° C., hygromycin (manufactured by GIBCO, CO.) was added to the culture to a final concentration of 0.3 mg/ml, followed by culturing for 1 to 2 weeks.

When the transformant growing through the culturing reached the confluent state, the cells of the transformant were obtained.

After suspending the cells in MEMα2000-dFCS (5) medium containing 0.3 mg/ml hygromycin and 50 nM methotrexate (hereinafter referred to as "MTX") at a final concentration of 1 to 2×10$^5$ cells/ml and dividing then 2 ml thereof into an F75 flask (manufactured by Gliner Co.), the cells were cultured in a CO$_2$ incubator at 37° C. for 1 to 2 weeks to induce 50 mM MTX resistant clone.

The clone was suspended in MEMα2000-dFCS (5) medium containing 0.3 mg/ml hygromycin and 100 nM MTX to 1 to 2×10$^5$ cells/ml, and 2 ml of the resulting suspension was divided in an F75 flask, followed by culturing in a CO$_2$ incubator at 37° C. for 1 to 2 weeks to induce 100 nM MTX resistant clone.

The clone was suspended in MEMα2000-dFCS (5) medium containing 0.3 mg/ml hygromycin and 500 nM MTX to 1-2×10$^5$ cells/ml, and 2 ml of the resulting suspension was divided in an F75 flask, followed by culturing in a CO$_2$ incubator at 37° C. for 1 to 2 weeks to induce 500 nM MTX resistant clone.

The 500 nM MTX resistant clone was suspended in MEMα2000-dFCS (5) medium containing 500 nM MTX to 1 to 2×10$^5$ cells/ml, and 15 ml of the resulting suspension was divided in an F75 flask, followed by culturing in a CO$_2$ incubator at 37° C. for 5 to 7 days, until the resistant clone reached 80 to 100% confluency, and then the medium was exchanged to 15 ml of a serum-free medium for CHO cells, namely CHO-S-SFMII medium (manufactured by GIBCO, CO.), for further culturing for 3 days.

The cells obtained through culturing were treated with trypsin and EDTA, and the resulting cells were suspended into 10 ml of MEMα2000 medium.

The suspension was centrifuged at 1,500×g for 5 minutes to collect the cells.

After adding 7 ml of a PBS buffer into the cells for washing the cells, the cells were centrifuged at 1,500×g for 5 minutes to collect the cells.

The cells can be stored at −20° C. and thawed for use, if necessary.

Western blotting was carried out using the whole protein of the cells (1×10$^5$ cells per one lane) by a method similar to that in Example 8(3).

The results are shown in FIG. 19. A band crossing with the anti-aging-suppressing polypeptide antibody was confirmed, and it was indicated that the aging-suppressing polypeptide was prominently expressed using the animal cells.

Additionally, the N-terminal amino acid sequence of the murine membrane-bound aging-suppressing polypeptide was determined by a conventional method.

More specifically, from CHO cells (CHO dhfr−/pYT103) which expressed the aging-suppressing polypeptide and grown to confluency at a volume of 20 Petri dishes of a 10 cm diameter, as described in Example 10, was purified an aging-suppressing polypeptide of about 140 kDa according to the immunoprecipitation described in Example 25 below, and the sequence of 9 amino acid residues at the N terminus of the polypeptide was analyzed using a gas-phase protein sequencer (PPSQ-10, manufactured by Shimadzu Corporation) according to the method recommended by the manufacturer.

As the results of the analysis, the sequence agreed with the sequence of 9 amino acid residues starting from the 36th residue from the N-terminus of the amino acid sequence represented by SEQ ID NO:3.

EXAMPLE 12

Preparation of Recombinant Virus for Expressing Aging-suppressing Polypeptide in Insect Cell For producing protein in insect cells, a recombinant virus incorporating an objective gene should necessarily be prepared, and the preparation requires (Process 1) a process of incorporating DNA encoding the objective protein into a specific plasmid and (Process 2) a process of co-transfecting a wild-type virus and a transfer vector into insect cells to obtain a recombinant virus by homologous recombination.

In order to conduct the processes, the following procedures were carried out according to the manual of BaculoGold Starter Kit manufactured by Pharmingen Co. (Product No. PM-21001K).

(Process 1) Preparation of Transfer Vector (FIG. 20)

To 30 µl of Tris B buffer to which 0.01% bovine serum albumin and 0.01% Triton X-100 had been added (hereinafter referred to as "Tris D buffer"), 3 µg of pNKM101 was added, 10 units of NotI were added to the buffer to react at 37° C. for 4 hours.

Phenol-chloroform extraction and ethanol precipitation were carried out using the reaction solution to recover DNA fragments. Into the DNA was added 30 µl of a buffer containing 10 mM Tris-HCl (pH 7.5), 10 mM magnesium chloride, 0.01% bovine serum albumin and 1 mM DTT (hereinafter referred to as "Tris E buffer"), and 10 units of XbaI were added to the buffer to react at 37° C. for 4 hours.

The treated DNA fragments in the reaction solution were fractionated using agarose gel electrophoresis to recover about 0.3 µg of an about 3.2 kb NotI-XbaI treated fragment of pNKM101 containing the DNA encoding the murine aging-suppressing polypeptide fragment.

To Tris D buffer, 3 µg of plasmid pVL392 contained the BaculoGold Starter Kit manufactured by Pharmingen Co. was added, and 10 units of NotI were added to react at 37° C. for 4 hours.

Phenol-chloroform extraction and ethanol precipitation were carried out using the reaction solution to recover DNA. Into the DNA was added 30 µl of Tris E buffer, and 10 units of XbaI were added to the buffer to react at 37° C. for 4 hours.

The treated DNA fragments in the reaction solution were fractionated using agarose gel electrophoresis to recover about 0.9 µg of an about 9.6 kb NotI-XbaI treated fragment of pVL1392.

In 20 µl of a T4 DNA ligase buffer, 200 ng of the NotI-XbaI treated fragment of the pVL1392 and 50 ng of the NotI-XbaI treated fragment of the pNKM101 were dissolved, 1 unit of T4 DNA ligase was added thereto, a ligation was carried out at 16° C. for 18 hours.

*Escherichia coli* JM109 was transformed using the recombinant plasmid DNA thus obtained through the reaction to obtain plasmid pAS104 (FIG. 20).

(Process 2) Preparation of Recombinant Virus

By introducing linear baculovirus DNA [BaculoGold baculovirus DNA, manufactured by Pharmingen Co.] and the plasmid pAS104 into insect cells Sf9 (manufactured by Pharmingen Co.) cultured using TMN-FH insect medium (manufactured by Pharmingen Co.) [*Protein, Nucleic Acids and Enzymes*, 37: 2701 (1992)], a recombinant baculovirus was prepared by the following method.

In 12 µl of distilled water, 1 µg of pAS104 and 20 ng of linear baculovirus DNA were dissolved, an intimate mixture of 6 µl of lipofectin and 6 µl of distilled water was added thereto, and then the resulting mixture was allowed to stand at room temperature for 15 minutes.

In 2 ml of Sf900-II medium (manufactured by GIBCO, CO.), $1\times10^6$ cells of Sf9 cells were suspended, and the resulting suspension was placed in a plastic Petri dish of a 35-mm diameter for cell culture, the total volume of an intimate mixture solution of the plasmid DNA, linear baculovirus DNA and lipofectin was added, followed by culturing at 27° C. for 3 days.

From the culture, 1 ml of the culture supernatant containing the recombinant virus was collected. Into the Petri dish from which the culture supernatant was recovered was added fresh Sf900-II medium, followed by culturing at 27° C. for 3 days, and in the same manner, the culture supernatant containing the recombinant virus was obtained additionally at 1.5 ml.

EXAMPLE 13

Expression of Murine Aging-suppressing Polypeptide in Insect Cell (Process 1) Proliferation of Recombinant Virus In 10 ml of Sf900-II medium, $2\times10^7$ cells of Sf9 cells were suspended, and the resulting suspension was placed in a 175 cm² flask (manufactured by Gliner Co.), and allowed to stand at room temperature for one hour to attach the cells onto the flask.

After allowing the cells to stand, the supernatant was removed, and 15 ml of TMN-FH insect medium and 1 ml of the culture supernatant containing the recombinant virus obtained in Example 12 were added to the flask, followed by culturing at 27° C. for 3 days.

After culturing, the supernatant was centrifuged at 1,500×g for 10 minutes to obtain a recombinant virus solution from which the Sf9 cells had been removed.

The virus titer of the recombinant virus solution was calculated by the following method [Manual of BaculoGold Starter Kit manufactured by Pharmingen Co.].

In 4 ml of Sf900-II medium, $6\times10^6$ cells of Sf9 cells were suspended, and the suspension was then placed in a plastic Petri dish of a 60-mm diameter for cell culturing, and then allowed to stand at room temperature for one hour to attach the cells onto the Petri dish.

After allowing the solution to stand, the supernatant was removed, and then 400 µl of the Sf900-II medium and the recombinant virus solution after dilution by 10,000 fold with Sf900-II medium were added to the dish, and then allowed to stand at room temperature for one hour.

After allowing the solution to stand, the medium was removed from the dish, 5 ml of a medium [prepared by intimately mixing together 1 ml of an aqueous 5% Agarplaque plus agarose solution and 4 ml of TMN-FH insect medium and keeping the resulting solution at 42° C.] containing 1% low melting agarose [Agarplaque Agarose, manufactured by Pharmingen Co.] was poured into the Petri dish, and then allowed to stand at room temperature for 15 minutes.

After allowing the Petri dish to stand, vinyl tape was wound around the Petri dish, the Petri dish was placed in a plastic container which could be sealed, followed by culturing the recombinant virus therein at 27° C. for 6 days.

After adding 1 ml of a PBS buffer containing 0.01% Neutral Red into the Petri dish, followed by further culturing for one day, the number of the developed plaques was counted.

It was indicated from the above procedures that the recombinant virus solution contained the virus at about $1\times10^8$ plaque forming units (PFU)/ml virus.

(Process 2) Expression of Aging-suppressing Polypeptide in Insect Cell

According to the manual attached to the BaculoGold Starter Kit manufactured by Pharmingen Co., the murine aging-suppressing polypeptide was expressed by the following procedures.

In 45 ml of Grace's Insect Medium, $6\times10^6$ cells of Sf9 cells were suspended, manufactured by GIBCO, CO. containing 10% FCS in a 225 cm² flask (manufactured by Gliner Co.), followed by culturing at 27° C. for 3 to 4 days.

After culturing, the culture supernatant was removed, and 30 ml of Grace's Insect Medium containing 10% FCS and 1 ml of a solution containing the recombinant virus from pAS104 at a concentration of about $1\times10^8$ PFU/ml were added freshly into the flask, followed by culturing at 27° C. for one day.

After culturing, the supernatant was removed, and 45 ml of Sf900-II medium was added freshly into the flask, followed by culturing for 2 to 3 days.

After culturing, the supernatant was removed after centrifugation at 1,500×g for 5 minutes, and the resulting cells were peeled off with trypsin-EDTA treatment.

The resulting cell fraction was suspended in 10 ml of Sf900-II medium, and centrifuged at 1,500×g for 5 minutes to collect the cells.

To the cell fraction, 7 ml of a PBS buffer was added for washing, and centrifuged at 1,500×g for 5 minutes to collect the cells.

The cells can be stored at −20° C., and the cells were used after thawing, if necessary.

(Process 3) Verification of Expression

By a method similar to that in Example 7, SDS-PAGE was carried out using the total protein of the cells obtained at the above Process 2 ($1\times10^5$ cells per lane).

The results are shown in FIG. 21. A specific band was confirmed around 120 kDa.

Also, by a method similar to that in Example 8(3), Western blotting was carried out using the whole protein of the cells obtained at the above Process 2 ($1\times10^5$ cells per one lane).

The results are shown in FIG. 22. By Western blotting, a specific band having cross reactivity with the anti-aging-suppressing polypeptide antibody was confirmed at the same position as by SDS-PAGE.

It was thus indicated that a prominent level of the aging-suppressing polypeptide having cross reactivity with the anti-aging-suppressing polypeptide antibody can be expressed using the insect sell.

Additionally, from the inset cells, the aging-suppressing polypeptide was obtained according to the method in Example 8(1).

EXAMPLE 14

Construction of Plasmid pYS110 for Expressing Human Membrane-Bound Aging-suppressing Polypeptide in Animal Cell By ligating together the (KpnI blunt ended)-BamHI fragment of pAGE210 obtained in Example 10 (Process 1) and the BamHI-HpaI fragment of pNKM103 described in Example 5, the fragment containing DNA encoding the human membrane-bound aging-suppressing polypeptide, vector pYS110 expressing the human membrane-bound aging-suppressing polypeptide was constructed as follows (FIG. 23).

To 30 µl of a buffer containing Tris-HCl (pH 7.5), 10 mM magnesium chloride and 1 mM DTT, 5 µg of pAGE210 was added, and 20 units of KpnI were added to the buffer to react at 37° C. for 2 hours.

Phenol-chloroform extraction and ethanol precipitation were carried out using the reaction solution to recover about 3 µg of DNA fragments. After subjecting the DNA to blunt end treatment using a DNA blunting kit (manufactured by Takara Shuzo Co., Ltd.), phenol-chloroform extraction and ethanol precipitation were carried out, and then the precipitate was dissolved in 50 µl of a buffer containing 20 mM Tris-HCl (pH 7.5), 10 mM magnesium chloride, 1 mM DTT, and 100 mM potassium chloride, and 20 units of BamHI into the buffer were added to react at 37° C. for 2 hours.

The reaction solution was fractionated by agarose gel electrophoresis to cut out a 9.0 kb BamHI-(KpnI blunt ended) fragment from the gel, and the fragment was purified by a glass powder method [Gene Clean II, manufactured by Bio101 Co.] to recover about 1 µg.

To 50 µl of a buffer containing 20 mM Tris-HCl (pH 8.5), 10 mM magnesium chloride, 1 mM DTT, and 100 mM potassium chloride, 10 µg of pNKM103 was added, and 30 units of BamHI and 30 units of HpaI were added to the buffer to react at 37° C. for 2 hours.

The reaction solution was fractionated by agarose gel electrophoresis to recover about 0.5 µg of a 3.2 kb BamHI-HpaI fragment.

In 20 µl of a T4 DNA ligase buffer, 100 ng of the BamHI-HpaI fragment of the pNKM103 and 100 ng of the BamHI-(KpnI blunt ended) fragment of the pAGE210 were dissolved, one unit of T4 DNA ligase was added, and a ligation was carried out at 16° C. for 18 hours.

*Escherichia coli* JM109 was transformed using the recombinant plasmid DNA obtained through the reaction to obtain plasmid pYS110 shown in FIG. 23.

EXAMPLE 15

Expression of Human Membrane-Bound Aging-suppressing Polypeptide in Animal Cell

The introduction of plasmid into animal cells was carried out using electroporation according to the method by Miyaji et al. [*Cytotechnology*, 3: 133 (1990)].

pYS110 obtained in Example 14 was introduced at a ratio of 4 µg per $4 \times 10^6$ cells into CHO cells by deleting dhfr gene [*Proc. Natl. Acad. Sci.*, 77: 4216 (1980)], and was then suspended in 10 ml of MEMα2000-dFCS (5) [MEMα2000 medium (manufactured by GIBCO, CO.) containing dFCS at 5%, 7.5% $NaHCO_3$ at a volume of ¹/₄₀, 200 mM L-glutamine solution (manufactured by GIBCO, CO.) at 3%, and a penicillin-streptomycin solution (manufactured by GIBCO, CO; containing 5000 units/ml penicillin and 5000 µg/ml streptomycin) at 0.5%] and was placed in a 10 cm plate (manufactured by Iwaki Glass Co.). The following procedures were carried out by a method similar to that in Example 11 to induce 500 nM MTX resistant clone.

After suspending the 500 M MTX resistant clone in an MEMα2000-dFCS (5) medium containing MTX of 500 nM to $1 \times 10^5$ to $2 \times 10^5$ cells/ml and dividing then 15 ml of the suspension in an F75 flask, and culturing the clone in a $CO_2$ incubator at 37° C. for 5 to 7 days until the resistant clone reached 80 to 100% confluency, the culturing was terminated to remove the culture and to recover the cells through trypsin-EDTA treatment.

The resulting cells were suspended in 10 ml of MEMa2000 medium, and the resulting suspension was centrifuged at 1,500×g for 5 minutes to collect the cells.

To the cells, 7 ml of a PBS buffer was added for washing, and the mixture was centrifuged at 1,500×g for 5 minutes to collect the cells.

The cells can be stored at −20° C., and can be used after thawing if necessary.

By a method similar to that in Example 8(3), Western blotting was carried out using the whole protein of the cells ($1 \times 10^5$ cells per one lane). Herein, the monoclonal antibody KM1902 described in Example 9 was used as a primary antibody.

The results are shown in FIG. 24. A band having cross reactivity with the anti-aging-suppressing polypeptide antibody was confirmed, and it was indicated that the human membrane-bound aging-suppressing polypeptide was expressed at a higher level using the animal cells.

Additionally, the N-terminal amino acid sequence of the human membrane-bound aging-suppressing polypeptide was determined by a conventional method in the field of protein chemistry.

That is, a human membrane-bound aging-suppressing polypeptide having about 140 kDa which was purified according to immunoprecipitation from CHO cells (CHO dhfr−/pYS110) grown to confluency at a volume of 20 Petri dishes of a 10 cm diameter, as described in Example 14, which expressed the human membrane-bound aging-suppressing polypeptide, was then subjected to SDS-PAGE under 2-mercaptoethanol reduction conditions to transfer the reduced product in an electric manner on a PVDF membrane (ProBlott, PERKIN ELMER Co.) according to the method by P. Matsudaira et al. [*J. B. C.*, 262: 10035 (1987)].

The transferred membrane was stained with Coomassie Blue, and a band around 140 kDa which was positive by Western blotting described in the present Example was cut out. Analysis of the sequence of the N-terminal 10 amino acid residues was determined using a gas-phase protein sequencer (PPSQ-10, manufactured by Shimadzu) according to the method recommended by the manufacturer.

As the results of the analysis, the sequence was identical to the sequence of 10 amino acid residues starting from the 34th residue from the N-terminus of the amino acid sequence represented by SEQ ID NO:1.

Additionally, the human membrane-bound aging-suppressing polypeptide was obtained from the animal cells by the method in Example 8(1).

EXAMPLE 16

Preparation of Plasmid Pys111 for Expressing Human Secretory Aging-suppressing Polypeptide in Animal Cell By ligating together the BamHI-(KpnI blunt ended) fragment of pAGE210 obtained in Example 10 (Process 1) and the BamHI-HpaI fragment of pNKM106 described in Example 5, the fragment containing DNA encoding the human membrane-bound aging-suppressing polypeptide, vector pYS111 expressing the human membrane-bound aging-suppressing polypeptide was constructed as follows (FIG. 25).

To 30 μl of a buffer containing Tris-HCl (pH 7.5), 10 mM magnesium chloride and 1 mM DTT, 5 μg of pAGE210 was added, and 20 units of KpnI were added to the buffer to react at 37° C. for 2 hours.

Phenol-chloroform extraction and ethanol precipitation were carried out using the reaction solution to recover about 3 μg of a DNA fragment.

After subjecting the DNA to blunt end treatment using a DNA blunting kit (manufactured by Takara Shuzo Co., Ltd.), phenol-chloroform extraction and ethanol precipitation were carried out, and then the precipitate was dissolved in 50 μl of a buffer containing 20 mM Tris-HCl (pH 7.5), 10 mM magnesium chloride, 1 mM DTT, and 100 mM potassium chloride, and 20 units of BamHI were added to the buffer to react at 37° C. for 2 hours. The reaction solution was fractionated by agarose gel electrophoresis to cut out a 9.0 kb BamHI-(KpnI blunt ended) fragment of pAGE210 from the gel, and the fragment was then purified by a glass powder method to recover about 1 μg.

To 50 μl of a buffer containing 20 mM Tris-HCl (pH 8.5), 10 mM magnesium chloride, 1 mM DTT, and 100 mM potassium chloride, 10 μg of pNKH106 was added, and 30 units of BamHI were added to the buffer to react at 37° C. for 2 hours.

Phenol-chloroform extraction and ethanol precipitation were carried out using the reaction solution, and the resulting precipitate was dissolved in 50 μl of a buffer containing 50 mM potassium acetate, 20 mM Tris-acetic acid (pH 7.9), 10 mM magnesium acetate, and 1 mM DTT, and 30 units of MscI were added thereto to react at 37° C. for 2 hours.

The reaction solution was fractionated by agarose electrophoresis to recover about 0.5 μg of a 1.9 kb BamHI-MscI treated fragment of pNKH106.

In 20 μl of a T4 DNA ligase buffer, 100 ng of the BamHI-MscI treated fragment of the pNKH106 and 100 ng of the BamHI-(KpnI blunt ended) fragment of the pAGE210 were dissolved, one unit of T4 DNA ligase was added thereto, and a ligation was carried out at 16° C. for 18 hours.

*Escherichia coli* JM109 was transformed using the recombinant plasmid DNA obtained through the reaction to obtain plasmid pYS111 shown in FIG. 25.

EXAMPLE 17

Expression of Human Membrane Secretory Aging-suppressing Polypeptide in Animal Cell The introduction of plasmid into animal cells was carried out using electroporation according to the method by Miyaji, et al. [*Cytotechnology*, 3: 133 (1990)].

pYS111 obtained in Example 16 was introduced at a ratio of 4 μg per $4\times10^6$ cells into CHO cells by deleting dhfr gene [*Proc. Natl. Acad. Sci.*, 77: 4216 (1980)], and was then suspended in 10 ml of MEMa2000-dFCS (5) [MEMa2000 medium containing dFCS at 5%, 7.5% NaHCO$_3$ at a volume of 1/40, 200 mM L-glutamine solution (manufactured by GIBCO, CO.) at 3%, and penicillin-streptomycin solution (manufactured by GIBCO, Co; containing 5000 units/ml penicillin and 5000 μg/ml streptomycin) at 0.5%] and was placed in a 10 cm plate (manufactured by Iwaki Glass Co.).

The following procedures were carried out by a method similar to that in Example 11 to induce 500 nM MTX resistant clone.

After suspending the 500 nM MTX resistant clone in MEMa2000-dFCS (5) medium containing MTX of 500 nM to a final concentration of $1\times10^5$ to $2\times10^5$ cells/ml, and dividing then 15 ml of the suspension in an F75 flask, and culturing the clone in a CO$_2$ incubator at 37° C. for 5 to 7 days, until the resistant clone reached 80 to 100% confluency, the medium was exchanged to 15 ml of a serum-free medium for CHO cells, namely CHO-S-SFMII medium (manufactured by GIBCO, CO.), followed by further culturing for 3 days.

After termination of the culturing, acetone of 1.5 ml was added to the culture of 0.5 ml, and the resulting culture was allowed to stand at 20° C. for 30 minutes. The sample was centrifuged at −10° C. under conditions of 15,000×g for 10 minutes to obtain a precipitate fraction, 70% ethanol was added thereto, followed by centrifugation at 4° C. for 5 minutes.

The resulting precipitate was subsequently dried to obtain an acetone-concentrated sample of the culture supernatant.

The culture supernatant can be stored at −20° C. and may be used after thawing, if necessary.

The products were analyzed using the recombinant plasmid DNA obtained through the reaction by Western blotting.

The results are shown in FIG. 26.

A band having cross reactivity with the anti-aging-suppressing polypeptide antibody was confirmed, and it was indicated that the human secretory aging-suppressing polypeptide was expressed at a prominent level using the animal cells.

According to the method described in Example 15, the human secretory aging-suppressing polypeptide after concentration from 300 ml of the culture supernatant by immunoprecipitation was determined of the N-terminal amino acid sequence. The resulting amino acid sequence agreed with the sequence of 9 amino acid residues from the 34th residue from the N-terminus of the amino acid sequence represented by SEQ ID NO:2.

Additionally, the human secretory aging-suppressing polypeptide was obtained from the animal cell culture according to the method in Example 8(1).

EXAMPLE 18

Preparation of Recombinant Virus for Expressing Human Secretory Aging-suppressing Polypeptide in Insect Cell The preparation of a recombinant virus for expressing the human secretory aging-suppressing polypeptide in insect cells was carried out according to the method described in Example 12.

More specifically, 10 μg of pNKH106 was dissolved in 50 μl of a buffer containing 20 mM Tris-HCl (pH 8.5), 10 mM magnesium chloride, 1 mM DTT and 100 mM potassium chloride, and 30 units of BamHI were added to the buffer to react at 37° C. for 2 hours. The reaction solution passed through phenol-chloroform extraction and ethanol precipitation, and was then dissolved in 50 μl a buffer containing 50 mM potassium acetate, 20 mM Tris-HCl (pH 7.9), 10 mM magnesium chloride, and 1 mM DTT, and 30 units of MscI was added to react at 37° C. for 2 hours.

The reaction solution was fractionated by agarose gel electrophoresis, and a 1.9 kb BamHI-MscI fragment of pNKH106 was cut out from the gel and then purified by the glass powder method to recover about 0.5 μg.

To 50 μl of Tris B buffer, 5 μg of the plasmid pVL1393 contained in the BaculoGold Starter Kit manufactured by Pharmingen Co. was added, and 30 units of EcoRI were added to react at 37° C. for 4 hours.

Phenol-chloroform extraction and ethanol precipitation were carried out using the reaction solution to recover DNA fragments. The DNA was subjected to blunt end treatment using a DNA blunting kit (manufactured by Takara Shuzo Co., Ltd.), followed by phenol-chloroform extraction and ethanol precipitation. The resulting DNA was dissolved in 50 μl of a buffer containing 20 mM Tris-HCl (pH 8.5), 10 mM magnesium chloride, 1 mM DTT and 100 mM potassium chloride, and 20 units of BamHI were added to the solution to react at 37° C. for 2 hours.

The resulting reaction solution was fractionated by agarose gel electrophoresis, and a 9.6 kb (EcoRI blunt ended)-BamHI fragment of pVL1393 was cut out from the gel and then purified by the glass powder method to recover about 1 μg.

In 20 μl of T4 DNA ligase, 200 ng of the (EcoRI blunt ended)-BamHI fragment of the pVL1393 and 50 ng of the BamHI-MscI treated fragment of the pNRH106 were dissolved, one unit of T4 DNA ligase was added thereto, and a ligation was carried out at 16° C. for 18 hours.

*Escherichia coli* JM109 was transformed using the recombinant DNA obtained through the reaction to obtain plasmid pYS150 (FIG. 27).

The recombinant virus was prepared using 1 μg of pYS150, introducing the plasmid, together with 20 ng of linear baculovirus, into Sf21 cells by lipofection method and then culturing the cells at 27° C. for 3 days. The culture supernatant containing the recombinant virus was collected at a volume of 1.0 ml from the culture.

EXAMPLE 19

Expression of Human Secretory Aging-suppressing Polypeptide in Insect Cell (Process 1) Proliferation of Recombinant Virus In 10 ml of Sf900-II medium, $2 \times 10^7$ cells of Sf21 cells were suspended, which was then placed in a 175 cm$^2$ flask (manufactured by Gliner Co.) and allowed to stand at room temperature for one hour to attach the cells onto the flask. After allowing the cells to stand, the supernatant was removed, and 15 ml of TMN-FH insect medium and 1 ml of the culture supernatant containing the recombinant virus obtained in Example 17 were added thereto, followed by culturing at 27° C. for 3 days.

After culturing, the supernatant was centrifuged at 1,500×g for 10 minutes to obtain a recombinant virus solution from which the Sf21 cells had been removed.

The virus titer of the recombinant virus solution was calculated by the method described in Example 13, and it was indicated that the recombinant virus solution contained about $2 \times 10^8$ plaque forming units (PFU)/ml virus.

(Process 2) Expression of Aging-suppressing Polypeptide in Insect Cell

According to the manual attached to BaculoGold Starter Kit manufactured by Pharmingen Co., the murine aging-suppressing polypeptide was expressed by the following procedures.

In 45 ml of Grace's Insect Medium, manufactured by GIBCO, CO., containing 10% FCS in a 225 cm$^3$ flask, $6 \times 10^6$ cells of Sf21 cells were suspended, followed by culturing at 27° C. for 3 to 4 days.

After culturing, the culture supernatant was removed, 30 ml of the Grace's Insect Medium containing 10% FCS and 0.5 ml of a solution containing the recombinant virus derived from pSY150 as obtained in the above Process 1 at a concentration of about $2 \times 10^8$ PFU/ml were further added, followed by culturing at 27° C. for one day.

After culturing, the supernatant was removed, and 45 ml of Sf900-II medium was further added, followed by culturing for 2 to 3 days.

After culturing, the culture was centrifuged at 1500×g for 5 minutes to obtain the culture supernatant. The culture supernatant can be stored at −20° C., and was used after thawing, if necessary.

(Process 3) Verification of Expression

By a method similar to that in Example 17, 0.5 ml of the culture supernatant was used, followed by concentration in acetone, and the resulting culture supernatant was electrophoresed by SDS-PAGE and was then Western blotted.

The results are shown in FIG. 28. By Western blotting, a specific band having cross reactivity with the anti-aging-suppressing polypeptide antibody was confirmed.

It was thus indicated that a marked amount of the human secretory aging-suppressing polypeptide having cross reactivity with the anti-aging-suppressing polypeptide antibody could be expressed using insect cells.

Additionally, the human secretory aging-suppressing polypeptide was obtained from the culture supernatant of the insect cells according to the method in Example 8(1).

EXAMPLE 20

Construction of Plasmid pYS112 for Expressing Murine Secretory Aging-suppressing Polypeptide in Animal Cell By ligating together the HindIII-BamHI fragment of pAGE210 obtained in Example 10 (Process 1) and the HindIII-BamHI fragment of pNKM112, the fragment containing DNA encoding the aging-suppressing polypeptide, as described in Example 4, vector pYS112 expressing the murine secretory aging-suppressing polypeptide was constructed as follows (FIG. 29).

To 30 μl of a buffer containing 20 mM Tris-HCl (pH 8.5), 10 mM magnesium chloride, 1 mM DTT and 100 mM potassium phosphate, 5 μg of pAGE210 was added, and 20 units of BamHI and 20 units of HindIII were added to the buffer to react at 37° C. for 2 hours.

The reaction solution was fractionated by agarose gel electrophoresis, and a 9.0 kb HindIII-BamHI fragment of pAGE210 was cut out from the gel and then purified by glass powder method to recover about 1 μg.

To 50 μl of a buffer containing 20 mM Tris-HCl (pH 8.5), 10 mM magnesium chloride, 1 mM DTT, and 100 mM potassium chloride, 10 μg of pNKM112 was added, and 30 units of BamHI and 30 units of HindIII were added to the buffer to react at 37° C. for 2 hours.

The reaction solution was fractionated by agarose gel electrophoresis to recover about 0.5 μg of a 1.6 kb HindIII-BamHI fragment of pNKM112.

In 20 μl of a T4 DNA ligase buffer, 100 ng of the HindIII-BamHI fragment of the pNKM112 and 100 ng of the HindIII-BamHI fragment of the pAGE210 were dissolved, one unit of T4 DNA ligase was added, and a ligation was carried out at 16° C. for 18 hours.

*Escherichia coli* JM109 was transformed using the recombinant plasmid DNA obtained through the reaction to obtain plasmid pYS112 shown in FIG. 29.

EXAMPLE 21

Expression of Murine Secretory Aging-suppressing Polypeptide in Animal Cell

The introduction of plasmid into animal cells was carried out using electroporation according to the method by Miyaji et al [*Cytotechnology*, 3: 133 (1990)].

pYS112 obtained in Example 20 was introduced at a ratio of 4 μg per $4 \times 10^6$ cells into CHO cells with deletion of dhfr gene [*Proc. Natl. Acad. Sci.*, 77: 4216 (1980)], and was then suspended in 10 ml of MEMa2000-dFCS (5) [MEMa2000 medium (manufactured by GIBCO, CO.) containing dFCS at 5%, 7.5% $NaHCO_3$ at a volume of 1/40, 200 mM L-glutamine solution (manufactured by GIBCO, CO.) at 3%, and penicillin-streptomycin solution (manufactured by GIBCO, Co; containing 5000 units/ml penicillin and 5000 μg/ml streptomycin) at 0.5%], and was then placed in a 10 cm plate (manufactured by Iwaki Glass Co.).

The following procedures were carried out by a method similar to that in Example 11 to induce 500 nM MTX resistant clone.

After suspending the 500 nM MTX resistant clone in an MEMa2000-dFCS (5) medium containing MTX of 500 nM to a final concentration of $1 \times 10^5$ to $2 \times 10^5$ cells/ml and dividing then 15 ml of the suspension in an F75 flask, and culturing the clone in a $CO_2$ incubator at 37° C. for 5 to 7 days, until the resistant clone reached 80 to 100% confluency, the medium was just then exchanged to 15 ml of a serum-free medium for CHO cells, namely CHO-S-SFMII medium (manufactured by GIBCO, CO.), followed by culturing for 3 days.

The culture supernatant can be stored at −20° C., and the supernatant may be used after thawing, if necessary.

The product was concentrated using 1 ml of the culture supernatant by immunoprecipitation described below in Example 25, and was analyzed by Western method.

The results are shown in FIG. 30. It was confirmed that a band having cross reactivity with the anti-aging-suppressing polypeptide antibody was confirmed, and it was indicated that a marked amount of the murine secretory aging-suppressing polypeptide was expressed using the animal cells.

By the method described in Example 15, the N-terminal amino acid sequence of the murine secretory aging-suppressing polypeptide which was prepared through concentration from 45 ml of the culture supernatant of the animal cells by immunoprecipitation was determined. The resulting amino acid sequence corresponded to the sequence of the 13 amino acid residues starting from the N-terminal 36th residue of the amino acid sequence represented by SEQ ID NO:4.

The murine secretory aging-suppressing polypeptide was obtained from the culture supernatant of animal cells according to the method in Example 8(1).

EXAMPLE 22

Preparation of Recombinant Virus for Expressing Murine Secretory Aging-suppressing Polypeptide in Insect Cell Preparation of a recombinant virus for expressing the murine secretory aging-suppressing polypeptide in insect cells followed the method described in Example 12.

More specifically, 10 μg of the aging-suppressing polypeptide encoding DNA of pNKM112 was dissolved in 50 μl of a buffer containing 20 mM Tris-HCl (pH 8.5), 10 mM magnesium chloride, 1 mM DTT and 100 mM potassium chloride, 30 units of HindIII were added to react at 37° C. for 2 hours.

Phenol-chloroform extraction and ethanol precipitation were carried out using the reaction solution to recover DNA fragments. The DNA was subjected to blunt end treatment using a DNA blunting kit (manufactured by Takara Shuzo Co., Ltd.), followed by phenol-chloroform extraction and ethanol precipitation. The resulting precipitate was dissolved in 50 μl of a buffer containing 20 mM Tris-HCl (pH 8.5), 10 mM magnesium chloride, 1 mM DTT and 100 mM potassium chloride, and 20 units of BamHI were added to the solution to react at 37° C. for 2 hours.

The reaction solution was fractionated by agarose electrophoresis, and a 1.6 kb (HindIII blunt ended)-BamHI fragment was cut out from the gel and then purified by glass powder method to obtain about 0.5 μg.

To 50 μl of Tris B buffer, 5 μg of plasmid pVL1392 contained in BaculoGold Starter Kit manufactured by Pharmingen Co. was added, and 30 units of EcoRI were added to react at 37° C. for 4 hours.

Phenol-chloroform extraction and ethanol precipitation were carried out using the reaction solution to recover DNA fragments. The DNA was subjected to blunt end treatment using a DNA blunting kit, followed by phenol-chloroform extraction and ethanol precipitation. The resulting precipitate was dissolved in 50 μl of a buffer containing 20 mM Tris-HCl (pH 8.5), 10 mM magnesium chloride, 1 mM DTT and 100 mM potassium chloride, and 20 units of BamHI were added to the solution to react at 37° C. for 2 hours.

The reaction solution was fractionated by agarose electrophoresis, and a 9.6 kb (EcoRI blunt ended)-BamHI fragment of pVL1393 was cut out from the gel and then purified by glass powder method to obtain about 1 μg.

In 20 μl of a T4 DNA ligase buffer, 100 ng of the (EcoRI blunt ended)-BamHI fragment of the pVL1392 and 100 ng of the (HindIII blunt ended)-BamHI fragment of the pNKM112 were dissolved, one unit of T4 DNA ligase was added thereto, and a ligation was carried out at 16° C. for 18 hours.

*Escherichia coli* JM109 was transformed using the recombinant plasmid DNA thus obtained through the reaction to obtain plasmid pYS151 (FIG. 31).

A recombinant virus was prepared using 1 μg of pYS151 and introducing the plasmid together with 20 ng of linear baculovirus into Sf21 cells by lipofection method, followed by culturing at 27° C. for 3 days. From the culture, the supernatant of 1.0 ml containing the recombinant virus was collected.

EXAMPLE 23

Expression of Murine Secretory Aging-suppressing Polypeptide in Insect Cell (Process 1) Proliferation of Recombinant Virus In 10 ml of Sf900-II medium, $2 \times 10^7$ cells of Sf21 cells were suspended, and the resulting suspension was placed in a 175 cm³ flask (manufactured by Gliner Co.) and was then allowed to stand at room temperature to attach the cells on the flask.

After allowing the cells to stand, the supernatant was removed, 15 ml of TMN-FH insect medium and 1 ml of the culture supernatant containing the recombinant virus obtained in Example 12 were added to the flask, followed by culturing at 27° C. for 3 days.

After culturing, the supernatant was centrifuged at 1,500×g for 10 minutes to obtain a recombinant virus solution from which the Sf21 cells had been removed.

The virus titer of the recombinant virus solution was calculated by the method described in Example 13, and it was indicated that the recombinant virus solution contained about $1 \times 10^8$ plaque forming units (PFU)/ml virus.

(Process 2) Expression of Murine Secretory Aging-suppressing Polypeptide in Insect Cell According to the manual attached to BaculoGold Starter Kit manufactured by Pharmingen Co., the murine aging-suppressing polypeptide was expressed by the following procedures.

In 45 ml of Grace's insect medium (manufactured by GIBCO, CO.) containing 10% FCS in a 225 cm² flask, $6 \times 10^6$ cells of Sf21 cells were suspended, followed by culturing at 27° C. for 3 to 4 days.

After culturing, the culture supernatant was removed, and 30 ml of the Grace's insect medium containing 10% FCS and 1 ml of a solution containing the recombinant virus derived from pSY151 at a concentration of about $1 \times 10^8$ PFU/ml as obtained in the above Process 1 were further added, followed by culturing at 27° C. for one day.

After culturing, the culture supernatant was removed, 45 ml of SF900-II medium was further added, followed by culturing for 2 to 3 days.

After culturing, the mixture was centrifuged at 1,500×g for 5 minutes, the culture supernatant was obtained. The culture supernatant could be stored at −20° C., and was used after thawing, if necessary.

(Process 3) Confirmation of Expression

By a method similar to that in Example 21, 1 ml of the culture supernatant was used for immunoprecipitation, and the resulting product was analyzed by Western method.

The results are shown in FIG. 32.

A specific band having cross reactivity with the anti-aging-suppressing polypeptide antibody was confirmed by the Western method.

It was thus indicated that the murine secretory aging-suppressing polypeptide having cross reactivity with the anti-aging-suppressing polypeptide antibody could be exerted at a prominent level using the insect cells.

The murine secretory aging-suppressing polypeptide was obtained from the culture supernatant of the insect cells according to the method in Example 8(1).

EXAMPLE 24

Staining of Immune Cell Using Monoclonal Antibody

The aging-suppressing polypeptide-expressing CHO cells (CHO dhfr⁻/pYT103) prepared in Example 11 was suspended in a buffer for immune cell staining at a final concentration of $5 \times 10^6$ cells/ml, and the resulting suspension was divided at 100 μl/well into a 96-well round bottom plate.

As a control, the CHO cells used as host in Example 11 was subjected to the same procedures.

The plate was centrifuged at 4° C. and 350×g for one minute to remove the supernatant.

A 5 ml portion of the culture supernatant of the anti-aging-suppressing polypeptide monoclonal antibody producing hybridoma KM1902 obtained in Example 9(3) was concentrated by 20-fold using MabTrapGII (manufactured by Pharmacia Biotech Co.), and then added at 50 μl/well into the plate, and the plate was allowed to stand at 4° C. for 30 minutes.

After allowing the plate to stand, a buffer for immune cell staining was added at 200 μl/well into the plate, and then centrifuged at 4° C. and 350×g for one minute to remove the supernatant and, and the cells were washed.

After additionally carrying out the rinse procedure twice, a buffer for immune cell staining containing FITC-labeled anti-rat immunoglobulin antibody (manufactured by Wako Pure Chemical Co.), after 30-fold dilution, was added at 50 μl/well into the plate, and then allowed to stand in darkness under ice cooling for 30 minutes. After allowing the plate to stand and subsequently carrying out the same rinse procedure three times, analysis with FLOW CYTOMETER (manufactured by Coulter Co.) was carried out.

The results are shown in FIG. 33.

The monoclonal antibody KM1902 did not react with the CHO cells; however, it specifically recognized the aging-suppressing polypeptide expressing CHO cells.

EXAMPLE 25

Immunoprecipitation of Aging-suppressing Polypeptide

As a sample of the aging-suppressing polypeptide for immunoprecipitation, the aging-suppressing polypeptide expressing CHO cells (CHO dhfr⁻/pYT103) described in Example 11 was used.

PBS was added to a 6 cm Petri dish where the CHO cells grew until confluency, and the CHO cells were washed once.

To the Petri dish, 360 μl of ice-cold Buffer 1 was added, and allowed to stand in ice for 30 minutes, and then the dish was gently shaken at an interval of 5 minutes for solubilization treatment.

The treated solution was recovered into a 1.5-ml centrifugation tube, and centrifuged at 14,000 rpm for 30 minutes.

To the culture supernatant, 25 μl of protein G-Sepharose (50% v/v) equilibrated with Buffer 1 was added and shaken at 4° C. for one hour, and the mixture was centrifuged at 5,000 rpm for 2 minutes to recover the supernatant.

The purified monoclonal antibody obtained in Example 9(4) was added to the supernatant at a final concentration of 10 μg/ml, followed by shaking at 4° C. for one hour.

To the shaken solution, 25 μl of protein G-Sepharose (50% v/v) was added, followed by shaking at 4° C. for one hour, and the mixture was centrifuged at 5,000 rpm for 2 minutes.

To the resulting precipitate fraction, 200 μl of Buffer 1 was added to suspend the precipitate. The same procedure was repeated three times to rinse the precipitate fraction.

To the precipitate, 15 μl of a sample buffer for SDS-polyacrylamide gel electrophoresis [buffer containing 6 mM Tris-HCl (pH 6.8), 2% SDS, 10% glycerol, and 5% 2-mercaptoethanol] was added, and the mixture was heated using a heat block and electrophoresed using a commercially available gradient gel for SDS-PAGE (manufactured by Atoh Co.). After the electrophoresis, the polypeptide in the resulting gel was transferred onto a PVDF membrane (manufactured by Millipore Co.).

According to the method of Example 8, Western blotting was carried out using a PVDF membrane and the anti-aging-suppressing partial fragment peptide polyclonal antibody to detect an aging-suppressing polypeptide at the position of about 140 kDa.

The results are shown in FIG. 34.

The monoclonal antibody KM1902 immunologically precipitated the aging-suppressing polypeptide.

EXAMPLE 26

Production of Murine Showing Ameliorated Syndrome Resembling Premature Aging from Mice Showing a Syndrome Resembling Premature Aging Using Aging-suppressing Gene Derived from Mouse (1) Construction of Aging-suppressing DNA for Introduction As a DNA fragment containing a promoter, a HindIII fragment of pEF321CAT, containing human elongation factor 1α [*Gene,* 91: 217 (1990)] was utilized. In the HindIII fragment of about 2.5 kb, parts of the first exon and second exon of the 5'-non-translation region of the human elongation factor 1α, a promoter, a HindIII linker at the 5' terminus and EcoRI and HindIII linkers at the 3' terminus were present.

By ligating a NotI fragment (4.2 kb) of pNKM101 containing the aging-suppressing gene and the cassette of SV40 early splicing region & polyadenylation signal [nucleotide number 1551-2427 in plasmid pMAMneo (Clontech Co.)] to the downstream of the HindIII fragment, the resulting product was used as aging-suppressing DNA for introduction.

The construction method of the aging-suppressing DNA for introduction is shown in FIGS. 35 and 36.

More specifically, as follows.

(i) By cleaving pEF321CAT with HindIII, the resulting 2.5 kb HindIII fragment was blunt ended using a DNA Blunting Kit (manufactured by Takara Shuzo Co., Ltd.). An XbaI linker (4693P, manufactured by Takara Shuzo Co., Ltd.) was added to the blunt ended fragment using a DNA ligation kit (manufactured by Takara Shuzo Co., Ltd.), and the fragment was cleaved with XbaI to obtain an XbaI cleaved linker.

(ii) By cleaving pMAMneo (manufactured by Clontech Co.) with BamHI and SmaI, the resulting 870-bp BamHI/SmaI fragment containing the poly(A) cassette was subcloned into the BamHI/EcoRV site of pBluescript II SK(−) (manufactured by STRATAGENE Co.).

After subcloning, the product was cleaved with BamHI, an XhoI linker (4694 bp, manufactured by Takara Shuzo Co., Ltd.) was added, and cleaved with XhoI and HindIII to cut out a poly(A) cassette (both the termini work as the ends for XhoI and HindIII).

(iii) The poly(A) cassette obtained in (ii) was subcloned into the HindIII/XhoI site of pBluescript II SK(−) to obtain a plasmid containing the poly(A) cassette.

(iv) The XbaI cleavage fragment obtained in (i) was subcloned into the XbaI site of the plasmid obtained in (iii). The resulting plasmid is referred to as "pEFSA" hereinafter.

(v) pNKM101 was cleaved with NotI, and the resulting 4.2 kb NotI fragment was blunt ended and was then subcloned into the EcoRV site of pBluescript II SK(−).

After subcloning, the product was cleaved with EcoRI and HindIII to cut out a 4.2 kb EcoRI/HindIII fragment.

(vi) The fragment obtained in (v) was subcloned into the EcoRI/HindIII site of pEFSA to obtain plasmid pRES.

The pRES was cleaved with NotI, linearlized, and dissolved in PBS at a final concentration of 5.7 ng/ml (about 500 copies/ml) to prepare a DNA solution for micro-injection.

(2) Production of Transgenic Mouse

A transgenic mouse was produced by a common microinjection method (*Developmental Engineering Experimental Manual-Preparation of Transgenic Mouse,* Tatsuji Nomura as responsible editor, Motoya Katsuki as editor, Kodansha Scientific, 1987).

More specifically, as follows.

(i) Into a F1 (BCF1) female (age 8 to 16 weeks) of C57BL/6 and C3H, 7 units of Serotropin (manufactured by Teikoku Zoki Co.) were intraperitoneally administered. After 48 hours of the administration, 7 units of gonadotropin (manufactured by Teikoku Hormone Mfg. Co., Ltd.) were administered into the female, and mated with a C3H male.

(ii) On the next day, a fertilized egg was collected from the oviduct ampulla of the female after copulation. The DNA solution for micro-injection as prepared in (1) was injected into the male pronucleus of the fertilized egg using a micromanipulator under an erect microscope.

(iii) On the day before the practice of (i), the fertilized egg prepared in (i) was transplanted into the oviduct of a female (ICR, age 8 to 16 weeks) who had been mated with a vasoligated male (ICR) so that the female had been fallen into false pregnancy.

(iv) The tail of a litter mouse on birth on the 20th day after the transplantation was cut at the age 4 to 5 weeks to extract the chromosomal DNA, and the genotype was analyzed using PCR according to the method described in (3).

(3) Analysis of Genotype (i) To the murine tail obtained above, 2 ml of a lysis buffer was added, and the resulting mixture was allowed to stand at 50° C. overnight.

(ii) An equal volume of phenol was added to the solution standing alone described in (i) for phenol extraction, and the resulting supernatant of 1 ml was used as a PCR template.

As the primers of PCR, 5 types of DNAs, represented by SEQ ID NOS:25 to 29, were used.

Since the DNAs having SEQ ID NOS:25 and 26 were synthesized on the basis of the nucleotide sequence of the cDNA of pNKM101, a fragment of 339 bp can be amplified if the cDNA is present. Because an intron is present between both the primers of DNA from chromosome, any DNA fragment from chromosomal DNA cannot be amplified.

The DNA having the nucleotide sequence represented by SEQ ID NO:27 was synthesized from a region present in common to the mutant allele (pg) and wild-type allele (+); the DNA having the nucleotide sequence represented by SEQ ID NO:28 was synthesized from a region present in the mutant allele alone; and the DNA having the nucleotide sequence represented by SEQ ID NO:29 was synthesized from a region present in the wild-type allele alone.

Therefore, a 920 bp fragment amplified between the DNA having the nucleotide sequence represented by SEQ ID NO:27 and the DNA having the nucleotide sequence represented by SEQ ID NO:28 was produced from pg/pg; and a 458 bp fragment amplified between the DNA having the nucleotide sequence represented by SEQ ID NO:27 and the DNA having the nucleotide sequence represented by SEQ ID NO:29 was produced from +/+; and both the fragments were produced from pg/+.

PCR was carried out in a system in a total volume of 50 μl [1×LA PCR buffer II (Mg plus), a mixture solution of 400 mM each component of dNTP, 0.2 mM each component of primers, TaKaRa LATaq of 2.5 U] using LA PCR kit (manufactured by Takara Shuzo Co., Ltd.) under the following conditions.

That is, the system was heated at 94° C. for 1.5 minutes, and then, the system was subjected to 30 cycles of heating, each cycle consisting of heating at 94° C. for 30 seconds, 56° C. for 30 seconds, and 72° C. for 1.5 minutes, followed by further heating at 72° C. for 10 minutes.

(4) Mating of Transgenic Mouse with Mouse Showing pg/+

As a result that screening according to the method in (3) was carried out for 161 litter mice obtained in (2), 37 animals were transgenic mice having the aging-suppressing gene.

A transgenic mouse of the genotype of pg/+ and having the aging-suppressing gene was obtained at F1 by mating the transgenic mouse with a mouse showing pg/+.

The anti-aging gene for introduction to the F1 could be transmitted by 31 lines.

By mating between pg/+ animals both having the aging-suppressing gene or mating between pg/+ and pg/+ having the aging-suppressing gene, 3 lines of pg/pg animals having the aging-suppressing gene were obtained at F2.

The results are shown in Table 1.

TABLE 1

| Individual No. | Sex | Genotype | Aging-suppressing gene | Phenotype[*1] |
|---|---|---|---|---|
| 1 | male | pg/+ | − | − |
| 2 | male | +/+ | − | − |
| 3 | male | pg/+ | − | − |
| 4 | male | pg/+ | − | − |
| 5 | female | +/+ | + | − |
| 6 | male | pg/pg | + | −[*2] |
| 7 | male | pg/+ | + | − |
| 8 | male | pg/pg | + | −[*2] |
| 9 | male | pg/pg | + | −[*2] |
| 10 | female | pg/+ | + | − |
| 11 | female | pg/+ | + | − |
| 12 | female | pg/pg | − | + |

[*1]+ showing a syndrome resembling premature aging;
− showing no syndrome resembling premature aging
[*2]mouse from which a syndrome resembling premature aging was eliminated.

TABLE 2

| Individual No. | Sex | Genotype | Aging-suppressing gene | Phenotype[*1] |
|---|---|---|---|---|
| 13 | male | +/+ | + | − |
| 14 | male | +/+ | + | − |
| 15 | female | pg/+ | + | − |
| 16 | female | +/+ | + | − |
| 17 | male | pg/pg | + | −[*2] |
| 18 | female | pg/+ | − | − |

[*1]+ showing a syndrome resembling premature aging;
− showing no syndrome resembling premature aging.
[*2]mouse from which a syndrome resembling premature aging is eliminated.

It was confirmed that the pg/pg mouse showing a syndrome resembling premature aging did not show the syndrome if the mouse acquired the aging-suppressing gene.

Therefore, it was demonstrated that the gene is the causative gene of a syndrome resembling premature aging in a premature aging mouse, and it was thus indicated that the expression of the gene in individuals showing a syndrome resembling premature aging could suppress the syndrome resembling premature aging.

EXAMPLE 27

Preparation of Mouse Showing Ameliorated Syndrome Resembling Premature Aging from Mice Showing a Syndrome Resembling Premature Aging Using Recombinant Adenovirus Containing Aging-suppressing Gene Derived from Mouse A recombinant virus containing a mouse-derived aging-suppressing gene was prepared according to the method by Miyake et al. [*Proc. Natl. Acad. Sci. USA*, 93: 1320 (1996)].

More specifically, plasmid pNKM101 containing a mouse-derived aging-suppressing gene was cleaved with NotI and XbaI to obtain a 3.1 kb fragment containing the gene, and the fragment was blunt ended using a DNA blunting kit (manufactured by Takara Shuzo Co., Ltd.).

In 20 μl of a T4 DNA ligase buffer, 3 μg of the fragment and 1 μg of a SwaI fragment of cosmid pAxCAwt containing Type 5 adenovirus genome from which E3, E1A and E1B were deleted, a cytomegarovirus enhancer, and a chimera promoter of a chicken β-actin promoter (CAG promoter) [Kanegae et al., *Nucl. Acids. Res.*, 23: 3816 (1995)] were dissolved, one unit of T4 DNA ligase was added to the solution, and a ligation was carried out at 16° C. for 18 hours.

In vitro packaging was carried out using the ligase reaction solution and Gigapack II XL Packaging Extract (manufactured by Stratagene Co.), and then the resulting phage was infected into *Escherichia coli* DH5a to obtain a recombinant cosmid.

The orientation of the mouse-derived aging-suppressing gene toward the promoter in the recombinant cosmid was confirmed by cleaving the cosmid with BamHI to detect a 1.6 kb fragment.

A 8 μg portion of the cosmid thus obtained and 1 μg of Type 5 adenovirus Ad5dIX DNA [*J. Virology*, 54: 711 (1985)] from which E3, E1A and E1B were deleted by cleavage of EcoT22I were mixed together, and the resulting mixture was transfected into the 293 cells in a 6 cm Petri dish by a calcium phosphate method using CellPhect Transfection Kit (Pharmacia Biotech Co.).

According to the method by Kanegae et al. [*BioManual Series*, 4: 43-58, Yodosha (1994)], the following procedures were carried out to obtain a recombinant virus.

According to the method by Kanegae et al. [*Jpn. J. Med. Sci. Biol.*, 47: 157 (1994)], the recombinant virus was purified twice by a cesium chloride density gradient, suspended in PBS containing 10% glycerol, and stored at −80° C. for appropriate use.

The titer of the virus in the recombinant virus solution was calculated according to the method by Kanegae et al. [*Jpn. J. Med. Sci. Biol.*, 47: 157 (1994)], and it was found that the solution contained $1 \times 10^{10}$ pfu/ml virus.

To the caudal vein of a mouse aged 4 weeks showing a syndrome resembling premature aging, $5 \times 10^8$ pfu of the recombinant virus thus obtained were inoculated, and the course was observed.

The results are shown in FIG. 37.

The mouse inoculated having the virus had body weight gain and prolonged life expectancy, and it was found that the syndrome resembling premature aging is eliminated.

EXAMPLE 28

Construction of Plasmid pYS201 for Expressing N-terminal Region of Human Aging-suppressing Polypeptide in *Escherichia coli*

By ligating together the (KpnI blunt ended)-EcoRV fragment of pSupex prepared in Example 6 and a 623 bp SacII fragment containing DNA encoding the human-derived aging-suppressing polypeptide of pNKM103 obtained in Example 5, vector pYS201 for expressing the N-terminal region of the human aging-suppressing polypeptide was constructed as follows (FIG. 38).

To 30 μl of a buffer containing 33 mM Tris-acetic acid (pH 7.9), 10 mM magnesium acetate, 66 mM potassium acetate, 0.01% BSA and 0.5 mM DTT, 10 μg of pNKM103 obtained in Example 5 was added, and 20 units of SacII were added to the buffer to react at 37° C. for 4 hours. Phenol-chloroform extraction and ethanol precipitation were carried out using the reaction solution to recover DNA fragments, and the DNA fragments were blunt ended using a DNA blunting kit (manufactured by Takara Shuzo Co., Ltd.).

The treated DNA fragments in the reaction solution were fractionated by agarose gel electrophoresis to recover about 0.3 μg of a blunt ended SacII fragment of about 0.6 kb containing DNA encoding a fragment containing the amino acid residues from $Gly^{55}$ to $Pro^{261}$ in the aging-suppressing polypeptide represented by SEQ ID NO:1.

To 30 μl of a buffer containing Tris-HCl (pH 7.5), 10 mM magnesium chloride and 1 mM DTT, 3 μg of expression vector pSupex for *Escherichia coli* obtained in Example 6, Process 5 was added, and 10 units of KpnI were added thereto at 37° C. for 4 hours. Phenol-chloroform extraction and ethanol precipitation were carried out using the reaction solution to recover DNA fragments, and they were subjected to blunt end treatment using a DNA blunting kit (manufactured by Takara Shuzo Co., Ltd.).

Additionally, phenol-chloroform extraction and ethanol precipitation were carried out, and the DNA was added to 30 μl of a buffer containing 50 mM Tris-HCl (pH 7.5), 10 mM magnesium chloride, 100 mM sodium chloride and 1 mM DTT, and 10 units of EcoRV were added to the buffer to react at 37° C. for 4 hours.

The treated DNA fragments in the reaction solution were fractionated by agarose gel electrophoresis to recover about 2 μg of an about 3.8 kb (blunt ended KpnI)-EcoRV treated fragment of pSupex.

The resulting fragment was dissolved in 44 μl of $H_2O$, and 5 μl of a solution containing 0.5 M Tris-HCl (pH 8.5), 1 mM EDTA and one unit of alkali phosphatase (manufactured by Boehringer Mannheim Co.) was added thereto, and allowed to stand at 37° C. for 30 minutes.

Phenol-chloroform extraction and ethanol precipitation were carried out using the reaction solution to recover DNA fragments.

In 20 μl of a T4 DNA ligase buffer, 50 ng of the blunt ended SacII fragment of pNKM103 and 100 ng of (blunt ended KpnI)-EcoRV treated fragment of pSupex after alkali phosphatase treatment were dissolved, 100 units of T4 DNA ligase (manufactured by Takara Shuzo Co., Ltd.) were added thereto, and a ligation was carried out at 16° C. for 18 hours.

*Escherichia coli* JM109 was transformed to obtain plasmid pYS201 (FIG. 38) using the recombinant plasmid obtained through the reaction.

EXAMPLE 29

Expression of N-terminal Region of Human-derived Aging-suppressing Polypeptide in *Escherichia coli* pYS201 obtained in Example 28 was introduced into *Escherichia coli* NY49. The N-terminal region of a human-derived aging-suppressing polypeptide was expressed using *Escherichia coli* by a method similar to that in Example 7.

That is, the above *Escherichia coli* was cultured in 400 ml of an M9 minimal medium to which 75 μg/ml ampicillin and 2 mg/ml casaminoic acid were added (the medium described in *Molecular Cloning, A laboratory manual*) at 37° C. for 2 hours, and 50 μg/ml indole acrylic acid was added thereto, followed by further culturing at 37° C. for 18 hours.

A 400 ml portion of the resulting culture was centrifuged at 3,000×g for 15 minutes, and the precipitate containing the *Escherichia coli* was suspended in 7 ml of Buffer 1 [buffer containing 10 mM Tris-HCl (pH 8.0), 1 mM EDTA and 150 mM sodium chloride], and the *Escherichia coli* was disrupted by ultrasonic treatment.

The treated solution was centrifuged at 10,000×g for 30 minutes, and the resulting precipitate was dissolved in a sample buffer for SDS-polyacrylamide gel electrophoresis [buffer containing 6 mM Tris-HCl (pH 6.8), 2% SDS, 10% glycerol, and 5% 2-mercaptoethanol].

The solution was fractionated by SDS-polyacrylamide gel electrophoresis, and the gel was then stained with Coomassie Brilliant Blue.

The results are shown in FIG. 39.

It was confirmed that the N-terminal region of human-derived aging-suppressing polypeptide (hereinafter referred to as "peptide SUHN") having a molecular weight of about 26 kDa was produced. In the electrophoresis, phosphorylase b (94,000), bovine serum albumin (67,000), ovalbumin (43,000), carbonic anhydrase (30,000), soybean trypsin inhibitor (20,000) and lysozyme (14,400) were used as molecular markers.

EXAMPLE 30

Construction of Vector pYS202 for Expressing C-Terminal Region of Human Aging-suppressing Polypeptide By ligating together the (KpnI blunt ended)-EcoRV fragment of pSupex prepared in Example 28 and a 467 bp KpnI-ApaI fragment containing DNA encoding the human-derived aging-suppressing polypeptide of pNKM103 described in Example 5, vector pYS202 for expressing the C-terminal region of the human aging-suppressing polypeptide was constructed as follows (FIG. 40).

To 30 µl of a buffer containing 10 mM Tris-HCl (pH 7.5), 10 mM magnesium chloride and 1 mM DTT, 10 µg of the pNKM103 obtained in Example 5 was added, and 20 units each of ApaI and KpnI were added to the buffer to react at 37° C. for 4 hours.

Phenol-chloroform extraction and ethanol precipitation were carried out using the reaction solution to recover DNA fragments, and they were subjected to blunt end treatment using a DNA blunting kit (manufactured by Takara Shuzo Co., Ltd.).

The treated DNA fragments in the reaction solution were fractionated by agarose gel electrophoresis to recover about 0.3 µg of a blunt ended ApaI-KpnI fragment of about 0.5 kb of pNKM103 containing DNA encoding a fragment containing the amino acid residues from $Phe^{801}$ to $Pro^{954}$ in the aging-suppressing polypeptide represented by SEQ ID NO:1.

In 20 µl of a T4 DNA ligase buffer, 50 ng of the blunt ended ApaI-KpnI fragment of pNKM103 and 100 ng of (blunt ended KpnI)-EcoRV treated fragment of pSupex after alkali phosphatase treatment described in Example 28 were dissolved, 100 units of T4 DNA ligase (manufactured by Takara Shuzo Co., Ltd.) were added thereto, and a ligation was carried out at 16° C. for 18 hours.

*Escherichia coli* JM109 was transformed using the recombinant plasmid DNA obtained by the reaction to obtain plasmid pYS202 (FIG. 40).

EXAMPLE 31

Expression of C-Terminal Region of Human-derived Aging-suppressing Polypeptide in *Escherichia coli* pYS202 obtained in Example 30 was introduced into *Escherichia coli* NY49. The C-terminal region of human-derived aging-suppressing polypeptide was expressed using the *Escherichia coli* by a method similar to that in Example 7.

That is, the *Escherichia coli* was cultured in 400 ml of an M9 minimal medium to which 75 µg/ml ampicillin and 2 mg/ml casaminoic acid were added at 37° C. for 2 hours, and 50 µg/ml indole acrylic acid was added thereto, followed by culturing at 37° C. for 18 hours.

A 400 ml portion of the resulting culture was centrifuged at 3,000×g for 15 minutes, the precipitate containing the *Escherichia coli* was suspended in 7 ml of Buffer 1, and the *Escherichia coli* was disrupted by ultrasonic treatment.

The treated solution was centrifuged at 10,000×g for 30 minutes, and the resulting precipitate was dissolved in a sample buffer for SDS-polyacrylamide gel electrophoresis. The resulting solution was fractionated by SDS-polyacrylamide gel electrophoresis, and the gel was then stained with Coomassie Brilliant Blue.

The results are shown in FIG. 41.

It was confirmed that the C-terminal region of human-derived aging-suppressing polypeptide (hereinafter referred to as "peptide SUHC") having a molecular weight of about 18 kDa was produced. In the electrophoresis, the molecular weight markers the same as those in Example 29.

EXAMPLE 32

Generation of Monoclonal Antibody Reacting with Partial Fragment of Human Aging-suppressing Polypeptide Peptides SUHN and SUHC produced in host *Escherichia coli* in Examples 29 and 31, respectively, were purified by a method similar to that in Example 8.

The molecular weights of the purified peptides SUHN and SUHC were about 26 kDa and about 18 kDa, respectively.

According to the method described in Example 8, rats were immunized, and monoclonal antibodies were prepared by a method similar to that in Example 9.

A list of the monoclonal antibodies produced is shown in Table 3.

Hybridoma KM2070, hybridoma KM2076, hybridoma KM 2105, hybridoma KM 2116, and hybridoma KM 2119 were deposited as FERM BP-6196, FERM BP-6197, FERM BP-6198, FERM BP-6199 and FERM BP-6200, respectively, on Dec. 9, 1997 at National Instituted of Bioscience and Human Technology, Agency of Industrial Science and Technology, 1-3, Higashi 1 chome, Tsukuba-shi, Ibaraki-ken, Japan (Zip code 305).

TABLE 3

| Immunogen | Monoclonal antibody | Animal species | Subclass |
| --- | --- | --- | --- |
| Human N-terminal region (SUHN) | KM2070 | rat | IgM |
| Human N-terminal region (SUHN) | KM2076 | rat | IgG2a |
| Human extra-membrane C-terminal region (SUHN) | KM2105 | rat | IgG1 |
| Human extra-membrane C-terminal region (SUHN) | KM2116 | rat | IgG2b |
| Human extra-membrane C-terminal region (SUHN) | KM2119 | rat | IgG2b |

EXAMPLE 33

Detection of Aging-suppressing Polypeptide Using Monoclonal Antibody Reacting with Partial Fragment of Human Aging-suppressing Polypeptide (1) Western Blotting of Murine Complete Length Protein Expressed by CHO and Murine Tissue The kidney and liver of a wild-type ICR mouse and the kidney and liver of a homozygote ICR mouse (aged mouse) were ground in a homogenizing buffer [20 mM Tris-HCl (pH 7.5), 0.25 M Sucrose, 1 mM EDTA, 10 mM EGTA, 10 mm 2-mercaptoethanol], and ultra-centrifugation (100,000×g, 4° C., one hour) was carried out to separate and recover the membrane fraction (precipitate) and the cytoplasm fraction (supernatant).

The resulting membrane fraction was dissolved in a dissolution buffer [1% Triton-X100, 20 mM Tris-HCl (pH 7.5), 150 mM NaCl]. Additionally, the murine membrane type complete length-expressing CHO cells as described in Example 11 were washed with PBS, and then solubilized in a dissolution buffer. SDS-polyacrylamide gel electrophoresis was carried out using the membrane fraction and cytoplasm fraction (20 µg) of each tissue and the cell lysate (2 µg) of the murine membrane type complete length-expressing CHO cells, and the culture supernatant (15 µl) of the murine membrane type complete length-expressing CHO cells to transfer the protein from the gel onto a PVDF membrane.

After the transfer, blocking was carried out in PBS-Tween containing 5% skim milk for 20 minutes, and the culture supernatant of each of hybridoma KM2076, hybridoma KM2116 and hybridoma KM2119 was allowed to react at room temperature for one hour. After washing in PBS-Tween for one hour, a peroxidase-labeled anti-rat immunoglobulin antibody (Amersham Co., 4000-fold dilution) was allowed to react as the second antibody at room temperature for 30 minutes.

After the reaction, the membrane was washed with PBS-Tween for one hour, an ECL Western blotting detection reagent (Amersham Co.) was allowed to react, and the membrane was exposed to an X-ray film to detect bands.

The results are shown in FIGS. 42 and 43.

RM2076 recognized a band of about 130 kDa specifically to the wild-type in the kidney membrane fraction. Because the band of about 130 kDa is close to the molecular weight estimated on the basis of the amino acid sequence and is almost equal to the size of the murine membrane type complete length protein expressed in CHO cells, the band would be derived from the membrane type complete length protein. Additionally, KM2076 recognized a band of about 70 kDa in the culture supernatant of the murine membrane type complete length-expressing CHO cells.

In the kidney membrane fraction, KM2119 recognized a band of about 130 kDa of the membrane type complete length and a band of about 60 kDa in a manner specific to the wild-type. Because the band of about 60 kDa was not detected with KM2076 (human N-terminal recognizing antibody) but detected only with KM2119 (human C-terminal recognizing antibody), it is suggested that the band would be a fragment on the side of the C terminus of the complete length protein remaining after cleavage of the side of the N-terminus. Then, the band of about 70 kDa in the culture supernatant of the murine membrane type complete length-expressing CHO cells as recognized with KM2076 would be a cleavage fragment on the side of the N-terminus. Additionally, KM2119 recognized a non-specific band of about 66 kDa, which reacted with the cytoplasm fractions of kidney and liver from the wild-type and homozygote. Alternatively, KM2116 recognized the complete length protein in the kidney membrane fraction in a manner specific to the wild-type, and also detected the non-specific band of about 70 kDa.

(2) Immunoprecipitation of Murine Complete Length Protein Expressed by CHO and Human Secretory Protein Expressed by CHO The murine membrane type complete length protein-expressing CHO cells described in Example 11 and CHO cells were solubilized in a dissolution buffer [1% Triton-X100, 20 mM Tris-HCl (pH 7.5), 150 mM NaCl]. An immunoprecipitation buffer [20 mM Tris-HCl (pH 7.5), 150 mM NaCl] of 8001 was added to 200 µl of the resulting solution to a final total volume of 1 ml, 25 µl of Protein G-Sepharose 4FF (Pharmacia Co.) was added to react at 4° C. for one hour. The culture supernatant was recovered by centrifugation (1000×g, 4° C., 5 minutes), 1 µg each of purified KM2076 and KM2119 antibodies was added thereto prior to reaction at 4° C. for one hour. Furthermore, 25 µl of Protein G-Sepharose 4FF was added to the resulting mixture to react at 4° C. for one hour. Still furthermore, 1 ml of the culture supernatant of the human secretory protein-expressing CHO cells was allowed to react with KM2076 preliminarily bound to Protein G-Sepharose at 4° C. for one hour in the same manner as described above. After washing these reaction products in a buffer for immunoprecipitation, the precipitate was recovered by centrifugation (10,000×g, 4° C., 5 minutes), and then separated by SDS-polyacrylamide gel electrophoresis to transfer the protein from the gel onto a PVDF membrane. Blocking was carried out in PBS-Tween containing 5% skim milk, and Western blotting was carried out using KM2076 and KM2119. Consequently, as shown in FIG. 44, the membrane type complete length protein was recovered by immunoprecipitation using KM2076, and the membrane type complete length protein and the C-terminal fragment protein were recovered by immunoprecipitation using KM2119. As shown in FIG. 45, similarly, the human secretory protein was recovered by immunoprecipitation using KM2076.

(3) Immune Tissue Staining Using Human Tissue Section

Formalin-immobilized paraffin-embedded tissues of two samples of human kidney and two samples of human liver were thinly cut to 4 mm, and fixed on a slide glass. The sections were deparaffinated with xylene, the hydrophilicity of the sections was increased with alcohol-water, and the sections were treated with methanol containing an aqueous 1% hydrogen peroxide solution for 15 minutes to block the endogenous peroxidase. The sections were washed with PBS and were blocked with diluted normal horse serum for 20 minutes, and were allowed to react with either KM2070 or KM2116 (10 mg/ml) at room temperature for 30 minutes. After thorough washing, a biotin-labeled anti-rat immunoglobulin antibody (Vector Co., 200-fold dilution) was allowed to react as the second antibody at room temperature for 30 minutes. After washing, ABC reagent (manufactured by Vector Co.) was allowed to react at room temperature for 30 minutes. After washing with PBS, color development was carried out in a diaminobenzidine substrate solution [produced by dissolving 50 mg of diaminobenzidine in 150 ml of a 0.1 M Tris-HCl buffer (pH 7.2), followed by filtration, and 50 ml of hydrogen peroxide was added thereto] for about one minute, and then the reaction was terminated under ice cooling. The nucleus was stained with hematoxylene, the sections were dehydrated with alcohol-water and xylene and sealed with Enteran New for microscopic observation. As a result, as shown in Table 4, KM2070 was allowed to react with the renal uriniferous tubule and vascular smooth muscle of the human kidney, and KM2116 was allowed to specifically react with the distal uriniferous tubule of the human kidney. As to human liver, both KM2070 and KM2116 were allowed to react with liver cells. It is demonstrated that KM2116 is useful for the analysis of human pathological sections, additionally because a band was detected in the kidney membrane fraction of wild-type ICR mouse but not detected in the kidney membrane fraction of homozygote mouse (aged mouse) by Western blotting with KM2116 (FIG. 43).

(4) Immune Tissue Staining Using Murine Tissue Section

Formalin-immobilized paraffin-embedded tissues of two samples of kidney and liver of wild-type ICR mouse and two samples of kidney and liver of homozygote ICR mouse (aged mouse) were thinly cut to 4 mm, and fixed on a slide glass. In the same manner as for KM2070 and KM2116 in (1), immune tissues were stained with KM2070 and KM2105 (10 mg/ml). Consequently, as shown in Table 4, both KM2070 and KM2105 were allowed to react with renal uriniferous tubule in a manner specific to the wild-type. However, KM2070 was allowed to react with vascular smooth muscle from both wild-type and homozygote. Furthermore, KM2070 and KM2105 were allowed to react with the liver cells from both wild-type and homozygote.

TABLE 4

| Monoclonal antibody | KM2070 | KM2105 | KM2116 |
|---|---|---|---|
| Human kidney | uriniferous tubule, vascular smooth | — | distal uriniferous tubule |

TABLE 4-continued

| Monoclonal antibody | KM2070 | KM2105 | KM2116 |
|---|---|---|---|
| Human liver | muscle liver cell | — | liver cell |
| Wild-type murine kidney | uriniferous tubule, vascular smooth muscle | uriniferous tubule | — |
| Wild-type murine liver | liver cell | liver cell | — |
| Homozygote murine kidney | uriniferous tubule | — | — |
| Homozygote murine liver | liver cell | liver cell | — |

EXAMPLE 34

Preparation of Aging-suppressing Gene Knockout Mouse

[1] Preparation of Targeting Vector for Homologous Recombination (1) Preparation of pX7.5

Plasmid pX7.5 was prepared by subcloning an exon 1-containing XhoI fragment of about 7.5 kb (FIG. 4) obtained from the murine chromosomal gene clone E8.5 isolated in Example 2 into the XhoI site of pBluescript II SK(−).

(2) Preparation of pMC1DT-3*

The whole DT-A expression unit was amplified by PCR using pMC1DT-3 [Yagi, T. et al., *Analytical Biochemistry*, 214: 77 (1993)] as a template, a primer BglT3 (SEQ ID NO:30) prepared by adding a BglII cleavage site to a sequence corresponding to a vicinity of the transcription initiation point of T3 promoter of a vector and a primer T7 (SEQ ID NO:30) having a sequence corresponding to a vicinity of the T7 promoter. The thus obtained fragments were digested with NotI to recover a fragment of about 1 kb containing MC1 promoter and DT-A. The plasmid pBluescript II SK(+) was digested with EcoRV and NotI to recover a fragment of about 3 kb. The above fragment of about 1 kb containing MC1 promoter and DT-A moiety was ligated with the fragment of pBluescript II SK(+) thus cleaved with EcoRV and NotI to obtain pMC1DT-3*.

(3) Preparation of pX7.5SmH-DT

A fragment of about 2.2 kb containing a chromosomal gene fragment obtained by digesting pX7.5 with SmaI and HindIII and another fragment of about 1 kb containing MC1 promoter and DT-A obtained by digesting pMC1DT-3* with HindIII and NotI were fractionated and recovered by agarose gel electrophoresis. These two fragments were ligated with pBluescript II SK(−) digested with SmaI and NotI to obtain plasmid pX7.5SmH-DT.

(4) Preparation of pLOXNATA

Plasmid pNATA [Gondo, Y. et al., *Biochemical and Biophysical Research Communications*, 202: 830 (1994)] was digested with XhoI and SacII to recover a fragment of about 3.2 kb containing MC1 promoter-Neo (neomycin resistant gene) and MC1 promoter-TK (herpes simplex virus thymidine kinase gene). The following synthetic DNA fragments A and B containing loxP sequence were prepared. The sequences of A-1, A-2, B-1 and B-2 of these synthetic DNA fragments are represented by SEQ ID NOS:32, 33, 34 and 35, respectively.

```
A   A-1  5'-AGCTTGTTAACGGATCCATAACTTCGTATAATGTATGC
             TATACGAAGTTATGAATTCC-3'
    A-2  3'-ACAATTGCCTAGGTATTGAAGCATATTACATACGATAT
             GCTTCAATACTTAAGGAGCT-5'

B   B-1  5'-GGATAACTTCGTATAATGTATGCTATACGAAGTTATGT
             CGACGCGGCCGCG-3'
    B-2  3'-CGCCTATTGAAGCATATTACATACGATATGCTTCAATA
             CAGCTGCGCCGGCGCTTAA-5'
```

The XhoI-SacII fragment of pNATA and synthetic DNA fragments A and B were connected to pUC18 digested with HindIII and EcoRI to obtain pLOXNATA.

(5) Preparation of Targeting Vector pmKLTV1 pX7.5SmH-DT was digested with XhoI and SmaI, and a fragment of about 6.2 kb was recovered in the same manner as described above. Separately from this, a fragment of about 3.7 kb containing a portion of the chromosomal gene fragment obtained by digesting pX7.5 with SacII and XhoI and another fragment of about 3.3 kb containing neomycin resistant gene and thymidine kinase gene obtained by digesting pLOXNATA with SacII and HpaI (hereinafter referred to as "Neo-Tk") each was fractionated and recovered by agarose gel electrophoresis. These XhoII-SmaI fragment of about 6.2 kb obtained from pX7.5SmH-DT, SacII-XhoI fragment of about 3.7 kb obtained from pX7.5 and SacII-HpaI fragment of about 3.3 kb obtained from pLOXNATA were connected to obtain a targeting vector pmKLTV1. Construction steps of the targeting vector pmKLTV1 are shown in FIG. 46.

[2] Preparation of Homologous Recombination Embryonic Stem Cell Line

The pmKLTV1 prepared in the above step [1] was digested with NotI, and 40 μg of the digest was dissolved in HBS (25 mM HEPES, 137 mM NaCl, 5 mM KCl, 0.7 mM $NaH_2PO_4.2H_2O$, and 6 mM dextrose, pH 7.05) and mixed with $1.14 \times 10^7$ TT2 cells [Yagi, T. et al., *Analytical Biochemistry*, 214(1): 70-76 (1993)] which had been suspended in 0.4 ml of HBS. The mixture was subjected to electroporation using Gene Pulser II manufactured by Bio-Rad under conditions of 250 V and 950 μF to introduce the gene into the cells.

On the second day, selection of gene-introduced cells was carried out by adding 200 μg/ml of G418. A total of 240 colonies were isolated 7 to 9 days after commencement of the selection. Chromosomal DNA fragments were prepared from these cells and amplified by PCR by a method described in Example 26(3) using primers TK/03 (SEQ ID NO:36) and EE/02 (SEQ ID NO:37). A DNA fragment of 640 bp was amplified in the case of cells in which the exon 1 of aging-suppressing gene is destroyed by producing homologous recombination of the aging-suppressing gene with the targeting vector. As a result, amplification of the fragment of 640 bp was confirmed in 8 of the 240 clones, so that it was concluded that the aging-suppressing gene was destroyed as intended in these clones.

[3] Preparation of Aging-suppressing Gene Knockout Mouse

The homologous recombination embryonic stem cell line obtained in the above step [2] was injected into fertilized eggs. A total of 170 ICR 8 cell stage fertilized eggs (available from CLEA Japan) were injected, cultured for one day and then transplanted into the uteri of pseudopregnant mice. A total of 38 pups were obtained as a result, and 7 of them were found to be chimeras judging from the hair color. These chimera mice were crossbred with normal C57BL/6J mice to obtain hetero mice, the hetero-mice were mutually crossbred to obtain pups, and then DNA was extracted from the tail of each mice by the method described in Example 26(3) to carry out inspection of genotypes by PCR. In addition to the set of TK/03 (SEQ ID NO:36) and EE/02 (SEQ ID NO:37) used in the above step [2], a set of SS/03 (SEQ ID NO:38) and EE/02 was also used as the primers. When the set of SS/03 and EE/02 was used, a 954 bp fragment of normal aging-suppressing gene was amplified. As shown in FIG. 47, when samples obtained from 18 mice were analyzed, the gene was not amplified with TK/03-EE/02 but only with SS/03-EE/02 in samples of two mice, so that they have only normal aging-suppressing gene. In the case of 4 animals, the gene was amplified with TK/03-EE/02 but not with SS/03-EE/02, so that they are homo mice having only mutated gene. In samples of the remaining 12 animals, the gene was amplified with both TK/03-EE/02 and SS/03-EE/02, so that they are hetero-mice having both normal and mutated aging-suppressing genes. It was concluded on the basis of these results that homo mice in which both alleles of the aging-suppressing gene were destroyed were obtained.

It has been observed that these aging-suppressing gene knockout homo mice show almost the same characters of the mice having a syndrome resembling premature aging described in Observation Examples of the present specification, both in appearance and by macroscopic anatomical findings.

While the invention has been described in detail and with reference to specific examples thereof, it will be apparent to one skilled in the art that various changes and modifications can be made therein without departing from the spirit and scope thereof.

---

What is claimed is:

1. An isolated antibody which recognizes a polypeptide comprising the amino acid sequence of SEQ ID NO: 1.

2. A hybridoma, which is selected from the group consisting of KM1902 (FERM BP-5983), KM2070 (FERM BP-6196), KM2076 (FERM BP-6197), KM2105 (FERM BP-6198), KM2116 (FERM BP-6199) and KM2119 (FERM BP-6200).

3. The isolated antibody according to claim 1, which is produced by a hybridoma selected from the group consisting of KM 1902 (FERM BP-5983), KM2070 (FERM BP-6196), KM2076 (FERM BP-6197), KM2105 (FERM BP-6198), KM2116 (FERM BP-6199) and KM2119 (FERM BP-6200).

* * * * *

UNITED STATES PATENT AND TRADEMARK OFFICE
CERTIFICATE OF CORRECTION

PATENT NO. : 7,667,005 B2
APPLICATION NO. : 12/046718
DATED : February 23, 2010
INVENTOR(S) : Youichi Nabeshima et al.

It is certified that error appears in the above-identified patent and that said Letters Patent is hereby corrected as shown below:

ON THE TITLE PAGE [56] REFERENCES CITED:

> Other Publications, after "Sambrook, et al.": ""Molecular Cloning: A Laboratory"" should read --"Molecular Cloning: A Laboratory Manual"--.

SHEET 5:

> Figure 5, "kedney" should read --kidney--.

SHEET 8:

> Figure 10, "brain medura" should read --brain medulla--.

COLUMN 3:

> Line 58, "PYT103." should read --pYT103.--.

COLUMN 6:

> Line 20, "pmYLTV1" should read --pmKLTV1--; and
> Line 25, "pBluescriptIISR(-)." should read --pBluescriptIISK(-).--.

COLUMN 12:

> Line 62, "include absolutely no expression with not" should read --include those with absolutely no expression and without--.

Signed and Sealed this

Eighth Day of June, 2010

David J. Kappos
*Director of the United States Patent and Trademark Office*

COLUMN 13:

Line 31, "778 (1983)]" should read --778 (1983)],--; and
    Line 62, "Instituted" should read --Institutes--.

COLUMN 14:

Line 49, "Instituted" should read --Institutes--.

COLUMN 15:

Line 18, "Instituted" should read --Institutes--.
    Line 26, "α-[$^{32}$P]dCTP" should read --α-[$^{32}$P]-dCTP--; and
    Line 57, "Instituted" should read --Institutes--.

COLUMN 17:

Line 19, "MF at promoter," should read --MF α1 promotor,--; and
    Line 23, "like." should read --the like.--.

COLUMN 22:

Line 2, "reacts" should read --react--;
    Line 11, "immunoziation" should read --immunization--;
    Line 23, "Instituted" should read --Institutes--; and
    Line 67, "tore" should read --torn--.

COLUMN 24:

Line 51, "The mouse is" should read --Those mice are--.

COLUMN 30:

Line 12, "specification)" should read --specification,--.

COLUMN 32:

Line 25, "derivatives" should read --derivative--; and
    Line 60, "works" should read --work--.

COLUMN 33:

Line 23, "works." should read --work.--; and
    Line 49, "blastcyst" should read --blastocyst--.

COLUMN 34:

Line 40, "supplement" should read --supplements--.

COLUMN 36:

Line 12, "(1)" should read --(1),--.

COLUMN 37:

Line 9, "new born" should read --newborn--.

COLUMN 47:

Line 12, "108 antibody-producing cells," should read --$10^8$ antibody-producing cells,--; and
Line 41, "injected the" should read --injected. The--.

COLUMN 52:

Line 67, "sell." should read --cell.--.

COLUMN 53:

Line 1, "inset" should read --insect--.

COLUMN 55:

Line 7, "Plasmid Pys111" should read --Plasmid pYS111--.

COLUMN 57:

Line 3, "a buffer" should read --of a buffer--.

COLUMN 62:

Line 25, "supernatant and," should read --supernatant,--.

COLUMN 64:

Line 12, "linearlized," should read --linearized,--.

COLUMN 66:

Line 41, "cytomegarovirus" should read --cytomegalovirus--; and
Line 49, "Escherichia coli DH5a" should read --Escherichia coli DH5α--.

CERTIFICATE OF CORRECTION (continued)
U.S. Pat. No. 7,667,005 B2

COLUMN 70:

Line 13, "Instituted" should read --Institutes--; and
    Line 44, "10 mm" should read --10mM--.

COLUMN 71:

Line 9, "RM2076" should read --KM2076--; and
    Line 47, "8001" should read --800 μl--.

COLUMN 75:

Line 2, "hetero mice," should read --hetero-mice--; and
    Line 4, "mice" should read --mouse--.

COLUMN 77:

SEQ ID No. 1

"Thr Gln Gly Gly Gln Val Ser Ile Ala Leu Ser Ser His Trp Ile Asn
  290                        295                300                         "

should read

--Thr Gln Gly Gly Gln Val Ser Ile Ala Leu Ser Ser His Trp Ile Asn
    290                       295                300                     --.

COLUMN 91:

SEQ ID No. 4

"Met Tyr Tyr Leu Lys Lys Phe Ile Met Glu Thr Leu Lys Ala Ile Arg
    435                    440                   445               "

should read

--Met Tyr Tyr Leu Lys Lys Phe Ile Met Glu Thr Leu Lys Ala Ile Arg
      435                   440                  445             --.

COLUMN 131:

SEQ ID 11, "(ii) MOLECULE TYPE: other nucleic acid" should read
        --(ii) MOLECULE TYPE: synthetic DNA--;

CERTIFICATE OF CORRECTION (continued)
U.S. Pat. No. 7,667,005 B2

COLUMN 131:

SEQ ID 12, "(ii) MOLECULE TYPE: other nucleic acid" should read
--(ii) MOLECULE TYPE: synthetic DNA--;

SEQ ID 13, "(ii) MOLECULE TYPE: other nucleic acid" should read
--(ii) MOLECULE TYPE: synthetic DNA--; and SEQ ID 14, "(ii) MOLECULE TYPE: other nucleic acid" should read
--(ii) MOLECULE TYPE: synthetic DNA--.

COLUMN 133:

SEQ ID 15, "(ii) MOLECULE TYPE: other nucleic acid" should read
--(ii) MOLECULE TYPE: synthetic DNA--;

SEQ ID 16, "(ii) MOLECULE TYPE: other nucleic acid" should read
--(ii) MOLECULE TYPE: synthetic DNA--;

SEQ ID 17, "(ii) MOLECULE TYPE: other nucleic acid" should read
--(ii) MOLECULE TYPE: synthetic DNA--;

SEQ ID 18, "(ii) MOLECULE TYPE: other nucleic acid" should read
--(ii) MOLECULE TYPE: synthetic DNA--;

SEQ ID 19, "(ii) MOLECULE TYPE: other nucleic acid" should read
--(ii) MOLECULE TYPE: synthetic DNA--; and SEQ ID 20, "(ii) MOLECULE TYPE: other nucleic acid" should read
--(ii) MOLECULE TYPE: synthetic DNA--.

COLUMN 135:

SEQ ID 21, "(ii) MOLECULE TYPE: other nucleic acid" should read
--(ii) MOLECULE TYPE: synthetic DNA--;

SEQ ID 22, "(ii) MOLECULE TYPE: other nucleic acid" should read
--(ii) MOLECULE TYPE: synthetic DNA--;

SEQ ID 23, "(ii) MOLECULE TYPE: other nucleic acid" should read
--(ii) MOLECULE TYPE: synthetic DNA--;

SEQ ID 24, "(ii) MOLECULE TYPE: other nucleic acid" should read
--(ii) MOLECULE TYPE: synthetic DNA--; and SEQ ID 25, "(ii) MOLECULE TYPE: other nucleic acid" should read
--(ii) MOLECULE TYPE: synthetic DNA--.

COLUMN 137:

SEQ ID 26, "(ii) MOLECULE TYPE: other nucleic acid" should read
--(ii) MOLECULE TYPE: synthetic DNA--;

SEQ ID 27, "(ii) MOLECULE TYPE: other nucleic acid" should read
--(ii) MOLECULE TYPE: synthetic DNA--;

SEQ ID 28, "(ii) MOLECULE TYPE: other nucleic acid" should read
--(ii) MOLECULE TYPE: synthetic DNA--;

SEQ ID 29, "(ii) MOLECULE TYPE: other nucleic acid" should read
--(ii) MOLECULE TYPE: synthetic DNA--; and SEQ ID 30, "(ii) MOLECULE TYPE: other nucleic acid" should read
--(ii) MOLECULE TYPE: synthetic DNA--.

COLUMN 139:

SEQ ID 31, "(ii) MOLECULE TYPE: other nucleic acid" should read
--(ii) MOLECULE TYPE: synthetic DNA--;

SEQ ID 32, "(ii) MOLECULE TYPE: other nucleic acid" should read
--(ii) MOLECULE TYPE: synthetic DNA--;

SEQ ID 33, "(ii) MOLECULE TYPE: other nucleic acid" should read
--(ii) MOLECULE TYPE: synthetic DNA--;

SEQ ID 34, "(ii) MOLECULE TYPE: other nucleic acid" should read
--(ii) MOLECULE TYPE: synthetic DNA--;

SEQ ID 35, "(ii) MOLECULE TYPE: other nucleic acid" should read
--(ii) MOLECULE TYPE: synthetic DNA--; and SEQ ID 36, "(ii) MOLECULE TYPE: other nucleic acid" should read
--(ii) MOLECULE TYPE: synthetic DNA--.

COLUMN 141:

SEQ ID 37, "(ii) MOLECULE TYPE: other nucleic acid" should read
--(ii) MOLECULE TYPE: synthetic DNA--; and SEQ ID 38, "(ii) MOLECULE TYPE: other nucleic acid" should read
--(ii) MOLECULE TYPE: synthetic DNA--.